(12) United States Patent
Bughrara

(10) Patent No.: US 8,088,970 B2
(45) Date of Patent: Jan. 3, 2012

(54) **INTROGRESSION OF *FESTUCA MAIREI* DROUGHT TOLERANT GENOME INTO *LOLIUM PERENNE* PLANTS**

(75) Inventor: Suleiman Bughrara, East Lansing, MI (US)

(73) Assignee: Board of Trustees of Michigan State University, East Lansing, MI (US)

(*) Notice: Subject to any disclaimer, the term of this patent is extended or adjusted under 35 U.S.C. 154(b) by 546 days.

(21) Appl. No.: 12/069,091

(22) Filed: Feb. 6, 2008

(65) Prior Publication Data

US 2009/0210957 A1    Aug. 20, 2009

Related U.S. Application Data

(60) Provisional application No. 60/899,837, filed on Feb. 6, 2007.

(51) Int. Cl.
*A01H 5/00* (2006.01)
*A01H 1/00* (2006.01)
*A01H 1/02* (2006.01)

(52) U.S. Cl. .................. 800/260; 800/320; 800/298
(58) Field of Classification Search .................. None
See application file for complete search history.

(56) References Cited

OTHER PUBLICATIONS

Wang et al., Crop Sci., 2003, vol. 43, pp. 2154-2161.*

* cited by examiner

*Primary Examiner* — Medina A Ibrahim
(74) *Attorney, Agent, or Firm* — Medlen & Carroll, LLP

(57) ABSTRACT

The present inventions relate to compositions and methods for providing drought resistant grass plants comprising *Festuca mairei* plant germplasm. Specifically, the inventions relate to providing compositions and methods for introgressing *Festuca mairei* germplasm and/or specific *Festuca mairei* genes into grass plants, such as *Lolium perenne* plants. Further, the invention relates to methods of grass plant breeding comprising genetic markers for identifying the preferred *Festuca mairei* germplasm introgressed into grass plants, and providing commercially desirable drought resistant cultivars of grass plants.

13 Claims, 54 Drawing Sheets

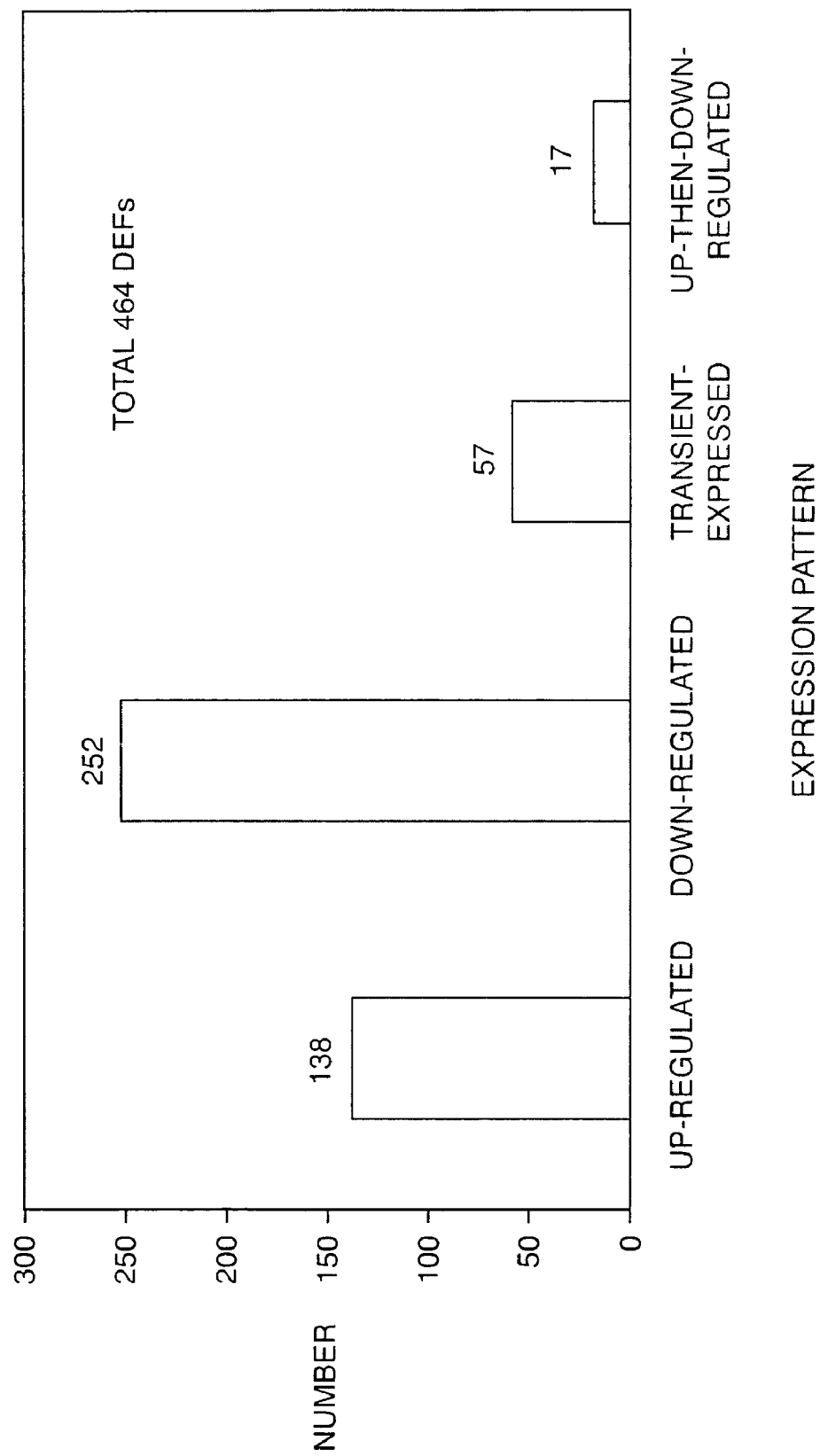

SEQ ID NO:1 SSBI082604_A12 catgcataggacccagtaatggactgtagagtaagttgtcccgcgtgcgacggcgtgtacgcgtgttcgtgacacactgacatc
g

SEQ ID NO:2
SSBI082604_A02

Catgcgctgttatttgccaaagctcgctggccattgttttccaccattgcccattcttggcacctcgcatcctgtcgtcactgagatt
ggaaagcgaaatcagggccgaccgacggacacctccgacaacaacaacctcaccaatcttgcacatcaagtcgtgacattcaa
tagacgtaagctttcg

SEQ ID NO:3 SSBI082604_A03 catgccgtgctacaggaggtagataatcagggtgcctaattttggatggtgttttgtatgcaatatggcgtttgtgttagcatcaca
gattaatgagggaatctctggatgatttattcg

SEQ ID NO:4 SSBI082604_A06 catgcaccggagataggcactgcggaagccctgtaggagacgccctgcctccgaattggcatcaacgcctggaggtagaaca
tgagctggcgttgatgaagtgacaccaaagctttccatggtcgcccttcg

SEQ ID NO:5 SSBI082604_C01 catgtatcatgaaacaacgcatggcagtgttccttcttttaggttatagcttcactggcttcgctagctccaggtctccaaaactcat
catcttttttcg

SEQ ID NO:6 SSBI082604_C03 catgcgctctgacaaagggccgtggaaggaccctgaaatcctaaaggttaatggttactctccgaagattttggagttcatgcatg
acctgtgggaaaatgtagtgcagacttgccactgaactgaaggaagtagcagtactactacagctaaactcctgagcacaggtc
cattaacatttcctggtttgatcttcagatggtgcaatgtggaatgggagatgcggaatgaacagctcggaccttatatgcaggt
attatatggccttttcgccatattttctgaacattgccgtctgatttcatacgcagaagcaagattcg

SEQ ID NO:7 SSBI082604_C08 cgattccggttaaaggacgctgggtgctgggaaagcaggtcggcctctttatggctgcctgcgatggccacgaaggccccagc
ctgattcctccccagattttggtcttgctgtgctggtgtcatgtaactcatgtttggatgccgttcaacaacttggtgaatgagcaagt
tctgagctcaagtttccatgtgtatgagtttccatgcgtacgagtgtctgttacggttccgttataccggtatttattgtctgtgttggttt
cttctgcatg

SEQ ID NO:8 SSBI082604_E01 catgtttcagaactactctatgaaaagcaatgtgaaactctgggagttgaacacaaacatcacagagaagtttctgagaatgcttct
gtttagttttatgtgaagatattcccgtttccaaagacatcttcggagaggtccacatttccacttgcagattccacaaaaagggagt

FIG. 7A ttcaacactgctctatccataggagggttcaactctgtgagttgaatgcaatcatcacagagaagtttcagagaaggcttctgtcta
gattttatgcgaagatataccccgtttcg SEQ ID NO:9 SSBI082604_E05
catgtgcaaatctggcttgcacccgttgtatgcacacgttgaatctatcacacacgatcatcacgtgatgcttcg SEQ ID NO:10 SSBI082604_F11
cgatgatgccgccgcaggaggcgtactcgcagcaggggcagtcaatgcagcagtggtcgccgtcgtacctgtacatg

SEQ ID NO:11 SSBI082604_F03 catgccaggtaatagccctgttgaaacacccagggcattgtgtacttgtttatttttcttttgcttgtaaatgctacagcccctcggat
gaatcacaaccaccgtggttgctatgtgtggtggtaatgaccagtctattggttgagcccagcataaattcg

SEQ ID NO:12 SSBI082604_F07 catgccccccacaggtgttgtcggtggtacatttgtcggagatgctaatctaactgtaacagcgggtattacaccgtcgtatatcct
acaagagggtgatcttactgccgactggactattacatttgggcagaacgatcaatttggtcgtcccgtcctagacggagctagttt
tagaatctatcg

SEQ ID NO:13 SSBI082604_F08 cgattagatcgtgggaggaatgtcttttccaattttggaagggcttaatcatattaccgacccggcaatattttcggatcggaggga
gtactgatcttttcaccgcgcatg SEQ ID NO:14 SSBI082604_G01
cgaaacggcgcgcagtaaactccttcgtttacgcgcaagtggagaaaatgggccgggcgcaccgattccttcctccacatg

SEQ ID NO:15 SSBI082604_G11 catgtgtaaaggtgcatacaaatctgaaccaagaattacttttaatgcatgaactgtgaacatctaccggatggtaggtatcattttc
gtgctaagcgcaaatcttcgtaaaccatgtagtcgttcaggactcatcg SEQ ID NO:16 SSBI082604_G02
catgcagaggattgaacgacactagtatatgggtgtcctcgtagtgttttcctttgcacgtgggtgtccacttattcg SEQ ID NO:17 SSBI082604_G03
cgaatagcaaatggccgaggtccctgctgcatgaacctgatctgctgcgaaatgagagctgggcgcatg

SEQ ID NO:18 SSBI082604_G04 cgatggcagctagggcgctaggcagcgcgctacggcagctggcagccagcaggctcaaggtgcgtggacgggctaatcag
ggcgtgcgggcgtgcgttgcaagcaggaggccggaggctggcgttcaggcggatgacgcgcagaaggctgggccgaaag
gtgcatg

SEQ ID NO:19 SSBI082604_G07

FIG. 7B catgcctagctgtgcgcacctgttcgccgatgagtacgccaccacgggcaaccaaacaataccccgtcacgctgccgcgcctat
ggcagccatcggatggctattggggtattatcg

SEQ ID NO:20 SSBI082604_G08 catgtacactggtataccaccggatacgtacattgaattaagaacaccgccatcagacgcaactactttaacagaactattgatac
catcggctgcccgaacaccgtcatagcagaaatgtccagtatggttaccgtacgtgtcgccaccaataataccaccgatataagc
ggacttaacgttggcacccaggtataccgcacaggcattatctccggtatagtagttactgttgttgtagtctttaatatcggtaacg
atcattacacgacgagcattttcaagccagacggggattgcctacaaatgtagacatttgcccgccagtccaactaatagagttcac
agacccattagtggcggtagaacctttgtcactaatagctcagtagttattaccctgacccagggctgaacaacccgtaaagtgga
ttgaagctacttgtccacttgtatcttcattttcaaaacgaatacaagcatcattagtgccgataccgcatggatcaaatgtactgttga
caaaattcaagtcttgaatgatcg

SEQ ID NO:21 SSBI082604_H11 catgcatgaatgccacatgaatgcaagaaaggtaaaaagggtctaggtgttactcttgggatgttacacgtagtgtggtgcgacc
atgaacttggcgaaggcctggcggccaagcacgcagtggaacgggctgtggaagctgacgacctcgttcaggactcatcg

SEQ ID NO:22 SSBI082604_H09 catgcatatatgcagacatgacacataacacagccgccaccggcgacatggctgacagtactcatctagctcatccgtacatcg
gctataagtacatcggctataagcggtagcataattacagttgtgtagagaactggtgagcactatcagtatgtactatctactcacc
agtagctagttcggttcggctagagcgccttacagatcg

SEQ ID NO:23 SSBII082604_A10 catgtatgtgttggacaccatgtatagggggcggatgggcggttatgtagggatctcatatcagctatgatctggttgctgttccgtat
ctttggatgaccaccaggagggggctcagcacccgctcg

SEQ ID NO:24 SSBII082604_A09 cgagtcaactcaaaggttaattttttgctggccttgctgtagagaagctagtgatgaaattaagcaaggtagcttgttgattaagttgta
atcaagacagtaactagtataggtagccccacacactactttgcaggttcagtttagatgcatg SEQ ID NO:25 SSBII082604_B10
catgtacaagtataacacccaccagatcgcctcctctgcttcggatcaggagctcatgaaagcgctcg

SEQ ID NO:26 SSBII082604_B11 cgatggcattggcgttcatgtccaggaaggcaaggtgccatctcagagagctagcagaccagcaaacgggaggagcccgtcg
ccgagctacaacatg
SEQ ID NO:27 SSBII082604_B03 catgtgtacatttcctctgtactcctccctactccgacgctagactgaatcgctgatcacatatatccacggtcaaaacacttgcttca
ctcttcctcctgcgcgtgaatccgatggaccctgatggggaggcccttggggaagtcg

SEQ ID NO:28 SSBII082604_B07 catgtgctaaataaaacatttlggatatgctagtacaaatgtggtctggatgctcgcatatagaagcaaggtccataagagcgaca
attggaagatcaagctagcattgtgtggtctcg

SEQ ID NO:29 SSBII082604_B09 cgagttcccggccttctgatccaatccaatccaaggagtcgtgtcatgccttcctgattcctagctattcatttgctcttcccttacaga
ataaactgtgggagcatg
SEQ ID NO:30 SSBII082604_C04 cgaccgtagggctagtaatacaattgtgtggagccacttggcttgtgagcatactatacactcccctacacatttatcatcccttact
agaagtgcacatg
SEQ ID NO:31 SSBII082604_C05 catgctcaccacagggccaaggaagaggccaaagtgcccctgaacgagtccaccctgctgctggatccatccatccatctcctc
ctcaacggacctacggcaccctgcctaattgcctagatgtgttctcgtgtagcttccctctgctcctgctagttagttttttttttttttgaa
caggctagttagctagtgtgatgcgtattgtctgttggattcgcgtgctgtacgtgcctgaagctacgtatatgttgtcgttgtcagctt
gtaagagtaatgttctgctagccaggatcgtcg

SEQ ID NO:32 SSBII082604_C06 catgcgcaacacggaaattacacacatacggagtataatttacagatacaatcaacactgcgttcgtgcgaacatatatgtgaattt
atcggtggaacgctcctcggaatcttgaaacgatcaagcgccggaaaccaccgccgccgcaggctgatcgccgggaacgtcg SEQ ID NO:33 SSBII082604_C09
catgctactttggggcctccaacgcactctcgatctgctggattagctgatcagcaggcaacgctcactcg

SEQ ID NO:34 SSBII082604_D06 catgttttggtttccagataattaacttgtgccggagtacgaatacgtcgtcaccccacccaggataggtcctagtattgataatct
agccggatgcaatgcgctagtcgtatttaattagccactgttctctcgttgtgctgcagaattgtaaagatgtgtaagctgtagtgca
catggagcagcttcagtaccagttctcg

SEQ ID NO:35 SSBII082604 E08 catgttagcgtaaaacacgttcttgatcggcttgcgcttaatcccgataaggtctgcgttttcctggtgagggtcatggccctctgtg
tagaatcgcttgcccagttcgggattcggcagaaagtgagcgaaacatcgcatctgagcggccgcagcatcgtagccgaccag
tactcg

SEQ ID NO:36 SSBII082604_F09

FIG. 7D catgcccgttccaggcttccagcagatctgttgtcatctactcatctgtcagtgccgggtgcgaaccaaggcctcccacccgaact
cg

SEQ ID NO:37 SSBII082604_G05 catgctaggatgatgacgttggcaacagcgtcgcgttagagtggggccgggcgcgtggactgccgttagtaatgcgagctcgt
acaacatctacgagaagctacccgtggcgacgacgatggtcctcctccgtggtcgtcacgatctcctccaggtcgtcg

SEQ ID NO:38 SSBII082604_H01 cgacaacgaggcaacgtggcttgatttgagaggaccaagcctggtgtgctggccaggtagaagtgctactcgttttgctcactgg
taaggcacgtcgcccagatattttagctaatgcctaagcggcgggcggcaagatattttacacagtttgagcggctagattttag
ctgacttgggaaccgacgttgagcacctatatatagatagccttgccgcttctgcggctgctaacatcagtagactgcaaatagag
ctggacctaccaaacgagagtgagagagtagagaaagagagcgagagaagggccggtgaagatcattcatgcgcatg SEQ ID NO:39
SSBII082604_E10
cgagggaacgcgtctacaacatg

FIG. 7E

SEQ ID NO:40
SSBI082604_A12 Predicted Protein: 3'5' Frame 1:
RCQCVTNTRTRRRTRDNLLYSPLLGPMH SEQ ID NO:41
SSBI082604_A12 Predicted Protein: 3'5' Frame 2:
DVSVSRTRVHAVARGTTYSTVHYWVLCM SEQ ID NO:42
SSBI082604_A12 Predicted Protein: 3'5' Frame 3:
MSVCHEHAYTPSHAGQLTLQSITGSYA SEQ ID NO:43
SSBI082604_A02 Predicted Protein: 5'3' Frame 3:
CAVICQSSLAIVFPPLPILGTSHPVVTEIGKRNQGRPTDTSDNNNLTNLAHQVVTF
NRRKLS SEQ ID NO:44
SSBI082604_A02 Predicted Protein: 3'5' Frame 1:
RKLTSIECHDLMCKIGEVVVVGGVRRSALISLSNLSDDRMRGAKNGQWWENNG
QRALANNSA SEQ ID NO:45
SSBI082604_A06 Predicted Protein: 3'5' Frame 1:
RRATMESFGVTSSTPAHVLPPGVDANSEAGRLLQGFRSAYLRCM SEQ ID NO:46
SSBI082604_A06 Predicted Protein: 3'5' Frame 2:
EGRPWKALVSLHQRQLMFYLQALMPIRRQGVSYRASAVPISGA SEQ ID NO:47
SSBI082604_E01 Predicted Protein: 5'3' Frame 2:
MFQNYSMKSNVKLWELNTNITEKFLRMLLFSFYVKIFPFPKTSSERSTFPLADSTK
REFQHCSIHRRVQLCELNAHTEKFQRRLLSRFYAKIYPF SEQ ID NO:48
SSBI082604_E01 Predicted Protein: 3'5' Frame 3:
KRVYLRIKSRQKPSLKLLCDDCIQLTELNPPMDRAVLKLPFCGICKWKCGPLRRC
LWKREYLHIKTKQKHSQKLLCDVCVQLPEFHIAFHRVVLKH SEQ ID NO:49
SSBI082604_E05 Predicted Protein: 5'3' Frame 2:
MCKSGLHPLYAHVESITHDHHVML

SEQ ID NO:50

FIG. 8A

SSBI082604_E05 Predicted Protein: 3'5' Frame 3:
KHHVMIVCDRFNVCIQRVQARFAH

SEQ ID NO:51
SSBI082604_F11 Predicted Protein: 5'3' Frame 2:
DDAAAGGVLAAGAVNAAVVAVVPVH SEQ ID NO:52
SSBI082604_F11 Predicted Protein: 5'3' Frame 3:
MMPPQEAYSQQGQSMQQWSPSYLYM SEQ ID NO:53
SSBI082604_F11 Predicted Protein: 3'5' Frame 2:
MYRYDGDHCCIDCPCCEYASCGGII SEQ ID NO:54
SSBI082604_F11 Predicted Protein: 3'5' Frame 3:
CTGTTATTAALTAPAASTPPAAASS SEQ ID NO:55
SSBI082604_F07 Predicted Protein: 5'3' Frame 2:
MPPTGVVGGTFVGDANLTVTAGITPSYILQEGDLTADWTITFGQNDQFGRPVLD
GASFRIY SEQ ID NO:56
SSBI082604_F08 Predicted Protein: 5'3' Frame 1:
RLDRGRNVFFQFWKGLIILPTRQYFRIGGSTDLFHRA SEQ ID NO:57
SSBI082604_G01 Predicted Protein: 5'3' Frame 2:
ETARSKLLRLRASGENGPGAPIPSST SEQ ID NO:58
SSBI082604_G01 Predicted Protein: 5'3' Frame 3:
KRRAVNSFVYAQVEKMGRAHRFLPPH SEQ ID NO:59
SSBI082604_G01 Predicted Protein: 3'5' Frame 1:
HVEEGIGAPGPFSPLARKRRSLLRAVS SEQ ID NO:60
SSBI082604_G01 Predicted Protein: 3'5' Frame 2:
MWRKESVRPAHFLHLRVNEGVYCAPF

SEQ ID NO:61

FIG. 8B

SSBI082604_G11 Predicted Protein: 3'5' Frame 3:
MSPERLHGLRRFALSTKNDTYHPVDVHSSCIKSNSWFRFVCTFTH SEQ ID NO:62
SSBI082604_G02 Predicted Protein: 3'5' Frame 3:NKWTPTCKGKHYEDTHILVSFNPLH SEQ ID NO:63
SSBI082604_G03 Predicted Protein: 5'3' Frame 1: RIANGRGPCCMNLICCEMRAGRM SEQ ID NO:64
SSBI082604_G03 Predicted Protein: 5'3' Frame 3: NSKWPRSLLHEPDLLRNESWAH SEQ ID NO:65
SSBI082604_G03 Predicted Protein: 3'5' Frame 1: HAPSSHFAADQVHAAGTSAICYS SEQ ID NO:66
SSBI082604_G03 Predicted Protein: 3'5' Frame 2: MRPALISQQIRFMQQGPRPFAI SEQ ID NO:67
SSBI082604_G03 Predicted Protein: 3'5' Frame 3: CAQLSFRSRSGSCSRDLGHLLF SEQ ID NO:68
SSBI082604_G04 Predicted Protein: 5'3' Frame 3:
MAARALGSALRQLAASRLKVRGRANQGVRACVASRRPEAGVQADDAQKAGPKGA SEQ ID NO:69
SSBI082604_G07 Predicted Protein: 5'3' Frame 2:
MPSCAHLFADEYATTGNQTIPVTLPRLWQPSDGYWGII SEQ ID NO:70
SSBI082604_G07 Predicted Protein: 5'3' Frame 3:
CLAVRTCSPMSTPPRATKQYPSRCRAYGSHRMAIGVLS SEQ ID NO:71
SSBII082604_B10 Predicted Protein: 5'3' Frame 2: MYKYNTHQIASSASDQELMKAL SEQ ID NO:72
SSBII082604_B10 Predicted Protein: 3'5' Frame 2: ERFHELLIRSRGGDLVGVILVH SEQ ID NO:73
SSBII082604_B11 Predicted Protein: 5'3' Frame 2:
DGIGVHVQEGKVPSQRASRPANGRSPSPSYNM

SEQ ID NO:74

FIG. 8C

SSBII082604_B11 Predicted Protein: 5'3' Frame 3:
MALAFMSRKARCHLRELADQQTGGARRRATT SEQ ID NO:75
SSBII082604_B11 Predicted Protein: 3'5' Frame 1:
HVVARRRAPPVCWSASSLRWHLAFLDMNANAI SEQ ID NO:76
SSBII082604_B09 Predicted Protein: 5'3' Frame 3:
SSRPSDPIQSKESCHAFLIPSYSFALPLQNKLWEH SEQ ID NO:77
SSBII082604_C04 Predicted Protein: 5'3' Frame 2:
DRRASNTIVWSHLACEHTIHSPTHLSSLTRSAH SEQ ID NO:78
SSBII082604_C04 Predicted Protein: 5'3' Frame 3:
TVGLVIQLCGATWLVSILYTPLHIYHPLLEVHM SEQ ID NO:79
SSBII082604_C04 Predicted Protein: 3'5' Frame 3:
CALLVRDDKCVGECIVCSQAKWLHTIVLLALRS SEQ ID NO:80
SSBII082604_C09 Predicted Protein: 5'3' Frame 1:
HATLGPPTHSRSAGLADQQATLT SEQ ID NO:81
SSBII082604_E10 Predicted Protein: 5'3' Frame 1: RGNASTT SEQ ID NO:82
SSBII082604_E10 Predicted Protein: 5'3' Frame 2: EGTRLQH SEQ ID NO:83
SSBII082604_E10 Predicted Protein: 5'3' Frame 3: RERVYNM SEQ ID NO:84
SSBII082604_E10 Predicted Protein: 3'5' Frame 1: HVVDAFP SEQ ID NO:85
SSBII082604_E10 Predicted Protein: 3'5' Frame 3: CCRRVPS SEQ ID NO:86
SSBII082604_E08 Predicted Protein: 5'3' Frame 1:
HVSVKHVLDRLALNPDKVCVFLVRVMALCVESLAQFGIRQKVSETSHLSGRSIV
ADQYS

FIG. 8D

SEQ ID NO:87
SSBII082604_E08 Predicted Protein: 3'5' Frame 1:
RVLVGYDAAAAQMRCFAHFLPNPELGKRFYTEGHDPHQENADLIGIKRKPIKNV
FYANM SEQ ID NO:88
SSBII082604_E08 Predicted Protein: 3'5' Frame 2:
EYWSATMLRPLRCDVSLTFCRIPNWASDSTQRAMTLTRKTQTLSGLSASRSRTCF
TLT SEQ ID NO:89
SSBII082604_F09 Predicted Protein: 5'3' Frame 1:
HARSRLPADLLSSTHLSVPGANQGLPPEL SEQ ID NO:90
SSBII082604_F09 Predicted Protein: 5'3' Frame 2:
MPVPGFQQICCHLLICQCRVRTKASHPNS SEQ ID NO:91
SSBII082604_F09 Predicted Protein: 5'3' Frame 3:
CPFQASSRSVVIYSSVSAGCEPRPPTRT

FIG. 8E

SEQ ID NO: 93
embl|DW248995
Fm1 Festuca mairei EST Festuca mairei c
DNA clone SSBI082604_A10 3', mRNA sequence.

catgcacagaggacactccatggttgcagccaccggatgccaagctgttccccgagaaggcaggctacaacgagctgaatc
agatggctgaagaggcaaaacggagagctgaaattgcaaggctcagggagcttcacactctcaaggggcacgtagagtcggt
tgtgaagctgaagggcctggacattgacaccattcagcaatcttacacagtgtgatcg SEQ ID NO: 94
embl|DW248996
Fm2 Festuca mairei EST Festuca mairei
cDNA clone SSBI082604_A04 3', mRNA sequence.

catgttcgtcaacgaggtttacacggttctgaccgatccggtgcagcgtgccgtgtatgatgagctccatggctacgcagcaacg
gccgccaacccttctttaatgacagtgcgcccaaggatcacgtctttgttgacgagtttacctgtataggatgcaagatttgtgcca
atgtgtgccccaatgtgttcg SEQ ID NO: 95
embl|DW248997
Fm3 Festuca mairei EST Festuca mairei
cDNA clone SSBI082604_A05 3', mRNA sequence.

catgcgcctctaaatcttcagcatggcctccaacgcgcgaagtacgtcatcacgggtaactatacctatcacttggttgtcctgatttt
actattggtaatctgtggatcttcttcttgagcatcagagctgcggcatcggtcactgttctatcacatgatagcgtgatcgctggag
aggtcatcacttgtgcaatctttgtccttgacccatatgaagcccttgttcg SEQ ID NO: 96
embl|DW248998
Fm4 Festuca mairei EST Festuca mairei
cDNA clone SSBI082604_A07 3', mRNA sequence.

catgttccttctacgttgataggtacggtgcatacacacacaattatatgtggaaataaaagtaaaacccggaaagcggagttgtc
atcaaaaactaaaccaagagactccatatggattcctagctcgcagcttatgccttgccggactcctcacagcctggtggcttgaa
ggcgatgaagctgacgcactgcacctgacggatgttatcg SEQ ID NO: 97
embl|DW248999
Fm5 Festuca mairei EST Festuca mairei
cDNA clone SSBI082604_A08 3', mRNA sequence.

Catgcgctttacaataatcatgatgtatcagtagaaatcggctcttgtacaaattattacacgaatgacagacgccacaaggcgcg
taacgtggggtactctttccaaaataggcgcagtactttctagcatcgggtaattaatccttatcg

SEQ ID NO: 98

Figure 9A embl|DW249000
Fm6 Festuca mairei EST Festuca mairei
cDNA clone SSBI082604_B01 3', mRNA sequence.

catgtactacagagtatgcgattccagcctgtttccgaaacctgccttacagaacagcacatggaagtttatgtacctcttccaaat
atcatctcctcaaactgaaccaggcttgcctaatattccatataacccatgatcctaccgtaattgctgactgaaccaactagtatttc
catcttacagcttgccagcaaatacctgcagtaaaacttttgtctatctgcatctgaagatccaggcctcccatgcaagtagtcatca
aaattgtacccgagatcgtcagcagctcactggtcaactgagttaaccagttttgacaaaaacgaattccaattacgctctgtccac
attactgcacaatgcgcttccttttcg SEQ ID NO: 99
embl|DW249001
Fm7 Festuca mairei EST Festuca mairei
cDNA clone SSBI082604_B02 3', mRNA sequence.

catgcgcgttccaccagctcccacagcgcattgggtatgccagttctattgaaaccatccaccgttatgaacatcccgcagaaga
agatcaacagcgagtaggatacctttcg SEQ ID NO: 100
embl|DW249002
Fm8 Festuca mairei EST Festuca mairei
cDNA clone SSBI082604_B03 3', mRNA sequence.

catgcccttaaaccaccattaataatgccattattctcagcaaaaacaaacgcctgctcttccaaccctcacccgggcacaaaaca
taacaaatcctccgcctagacagactgtaagataatgcaaaaaaaaaaggatagttgacaattcg SEQ ID NO: 101
embl|DW249003
Fm9 Festuca mairei EST Festuca mairei
cDNA clone SSBI082604_B05 3', mRNA sequence.

cgaactcgcggttcttggcgaaggtctcggggtcggcggacagcccagcggtgtcccagccatagtcgccggggaactcgcc
ggtgaggtagctcgggggctcgccggagagcgggccgaggtagagcacgcggtcggagccgtaccacgggctgccggac
gcggccaccttgggcttgccggccgtcttgcgcatg SEQ ID NO: 102
embl|DW249004
Fm10 Festuca mairei EST Festuca mairei
cDNA clone SSBI082604_B06 3', mRNA sequence.

Cgaagttgtggttccccggcttgtcgctgacataaatcgggcagccgccgatcgcccttgcggcgccgtggtactccgccgcc
gggtgcaagctatgaaacatatcccagtcgggctgcatgaactcgccgaggaagagggtgttgtaagccacggaggagatgt
ggatggtatgcgacgccgggtcgtgcgggtagaagtcgtcggaggcgcgcacgacggctgtctgcctggcgctgtagagcat
g

SEQ ID NO: 103

Figure 9B embl|DW249005
Fm11 Festuca mairei EST Festuca mairei
cDNA clone SSBI082604_B07 3', mRNA sequence.

catgtcctgagttgataaactggttgggttttgagcagcagcctggtatttctgtacaaccgcgccaagctgactaacctgcggtat
tattgacctccgtggaataagttcctcatgacgcctagcacagaactcccaagatgcgatcttgaggtctggattaaaaattatcct
cagatgccctcacgtacgacacgcaattgatcaaagacactttcttgaattgcttttgtatagtccagaacaatctgaccagatac
attcttggactcacgtggcatatcg SEQ ID NO: 104
embl|DW249118
Fm12 Festuca mairei EST Festuca mairei
cDNA clone SSBI082604_B08 3', mRNA sequence.

catgcggctcacaggcatggccgtagtggatgccttacttgccgggaacaaagttggtggcgaacgcccttgcgttgttgttgac
agggtcagcgaggtggtcggcgaggttatcg SEQ ID NO: 105
embl|DW249006
Fm13 Festuca mairei EST Festuca mairei
cDNA clone SSBI082604_B09 3', mRNA sequence.

cgatcagcggtgtgacgagcgtggccgtgaacccgaagatgagcaggtgacggtgacggggtacgtggagccgcgcaag
gtgctggagaaggttaagagcacggggaaggcggcagagatgtggccgtacgtgccctacaccatggccacctaccccac
gtcggcggcgcctacgacaagaaggcaccggcgggcttcatccggagcgcgccgcaggccatggccgcccccggggcgc
cagaggtccagtacatgaacatg SEQ ID NO: 106
embl|DW249007
Fm14 Festuca mairei EST Festuca mairei
cDNA clone SSBI082604_B10 3', mRNA sequence.

cgatcacgttgctgacccagtcaacaacaacgcatgggctttcgccaccaacttcgctcctggaagttaaatgagttagccatcc
gtccgaccaccggccgggcgagatatgcatg SEQ ID NO: 107
embl|DW249008
Fm15 Festuca mairei EST Festuca mairei
cDNA clone SSBI082604_B11 3', mRNA sequence.

catgcgcggagcacgcgtacaaatttacatttcacacccacacccttgcatatatacctctcgcacgcacacaggtataccatgc
acaggacgacgatgcttttggcctagtggaacttgaggctggtgaggatgttgttgttgacggggtcggggaggtgatcg SEQ ID NO: 108
embl|DW249009
Fm16 Festuca mairei EST Festuca mairei cDNA clone SSBI082604_B12 3', mRNA sequence.

Catgctaaagattgggtgagttaggtaggggctgtcgcgcacaaggctgctaggaatggagcttgagacttcaggtgcaatgg
attcagctgtgaagcccactggctttccaccagagaacaccttgaacagctggtcaacatcctccaaggtggtggtctcatcg SEQ ID NO: 109
embl|DW249010
Fm17 Festuca mairei EST Festuca mairei
cDNA clone SSBI082604_C02 3', mRNA sequence.

cgaataaggaagcattaaagtcaggctgaactccatgtgtgcaatatatggtttgcctagtccagcgaaatcaagttgtagcagat
gttggcacttatgcggttgtcctagagaagtagaagaagcttagataacgagttctccggttagctacactcctctcagtcttgact
gtgttcttacaagagatggctgcagcgcgtcatagtgcccataaccgtcgtagagaacacggactggattatccttggcatactc
ctgaccatattctgctatgatcctggggccatcagacccccttggtgtacatg SEQ ID NO: 110
embl|DW249011
Fm18 Festuca mairei EST Festuca mairei
cDNA clone SSBI082604_C04 3', mRNA sequence.

cgaacaaggcctgcatctctctttgcttcacatctgacgaccctgctccaatcactatgtctatgattatcacctttcccccatcctctc
ttgaaggaatagctttcttgcagttctttagtatcttgacacactcttggtcgccccagtcatgcataacccacttgaggaagacaac
gtttgccggaggaacgctctcaaacatg SEQ ID NO: 111
embl|DW249012
Fm19 Festuca mairei EST Festuca mairei
cDNA clone SSBI082604_C05 3', mRNA sequence.

cgaagaagagtacctgcacgatgacacgcagagggagacgctcattctgagcggcgtgggtgcaagcctccagggagagttt
ctggcagtccattacacggcaaagttcttccttctctgactccggggagatggggatgcgccttcagatagatgtcaacagcacga
taaagtccatcgtctattggccgagcataatctggtatggcagcagccaaagacttgaactttggcaactttaggttggcatctggc
gcaacttcagctaggtagccgtcaatcaacttagcaaccatagttaccggcattagagatggagaagctaatagttgcccatcgt
cgccaaggccaggggaagttccaccagtttcttgatccattgccaagaagtgtccaagaatcctatggacgcaatccacatcgta
gagcgtttcatcagattcagacatg SEQ ID NO: 112
embl|DW249013
Fm20 Festuca mairei EST Festuca mairei
cDNA clone SSBI082604_C06 3', mRNA sequence.

catgcttgtccaggagcaggacaatgttaagcgtgtgcagcttgctgacacttacatgagccaggcagctctgggtgatgctaac
caggatgccacgaagactggttccttctacggttagaacactcttcatacacccaccatctctagctgcataggaggaggtaaag
gagcacaacaaagaactttgcctgtgccggaaggttgtaccgaccgggaagccaagaacttcg

SEQ ID NO: 113

Figure 9D embl|DW249014
Fm21 Festuca mairei EST Festuca mairei
cDNA clone SSBI082604_C07 3', mRNA sequence.

cgaacaaggcctgcatctctctttgcttcacatctgacgaccctgctccaatcactatgtctatgattatcacctttcccccatcctctc
ttgaaggaatagctttcttgcagttctttagtatcttgacacactcttggtcgccccagtcatgcataacccacttgaggaagacaac
gtttgccggaggaacgctctcaaacatg SEQ ID NO: 114
embl|DW249015
Fm22 Festuca mairei EST Festuca mairei
cDNA clone SSBI082604_C09 3', mRNA sequence.

catgttgaacagcctttgccgcgacaagaacaacatggtcttgctcgctagcacgaagactcgggcgatgttaagcgaatggttt
tcgccatgtgagaacctagggctggctgctgagcacggctatttcctcaggctgagaggagatgcagagtgggagacgtgcgc
tcctgcgcctgactctggctggaagcagattgtggagcctgtgatgaaaacctacacggagacaaccgacgggtcaacgatcg SEQ ID NO: 115
embl|DW249016
Fm23 Festuca mairei EST Festuca mairei
cDNA clone SSBI082604_C10 3', mRNA sequence.

catgctatccgatcagagcagcaactcatttggctctaccgactttgggtgggatgatgaggccatgacaccggactacacatcc
gtcttcgttccaaatgctgccatgccagcatatggcgggcccgcttacctgcaaggcggagcgccaaagaggatgaggaacaa
tttcggtgtagctgtgcttcctcagggaaatgatgcgccacaagatgtctgtgcttttgaccatgagatgaagtattcactgccttac
gttgagagtagctcagacggatcg SEQ ID NO: 116
embl|DW249017
Fm24 Festuca mairei EST Festuca mairei
cDNA clone SSBI082604_C11 3', mRNA sequence.

catgtacttaccagctagctgttggtccggtcgtcgttaagaagcaattaaccacagcttaattgaagtgatcgtgacgagtaacta
aaccaaactagggtaggtagacggacgggtccgggacgtccgtccagcagctcccggcgttccagtacgcggccggcgacg
cgtcgtccccgagctcgttcaggactcatcg SEQ ID NO: 117
embl|DW249018
Fm25 Festuca mairei EST Festuca mairei
cDNA clone SSBI082604_D02 3', mRNA sequence.

Catgtgtggtctctagaggaacttgaacagcaggcctccgtacgtggcaaagaacggcgcaaacacaagggattcg

SEQ ID NO: 118
embl|DW249019
Fm26 Festuca mairei EST Festuca mairei

Figure 9E cDNA clone SSBI082604_D03 3', mRNA sequence.

Catgcgacaggtagtagtacaaaccaacagactacaagattagtcaggacaacagctacagagcgtattcctactatgtacaca
tatatggcaccatctatacgtagtagtaacttaatgtgtgcaatgcatgtccacatcaccagccatatacagggtgctgtacctggg
gaggcagcaggcccatatcagcacggtgttgttcatcgtagtcacgtgtaccaggaatcgcgcctgtagccaacctgaggacct
cactagaggtcaggcaacgatgcgcaaatgccgatccactgtccacgacattcg SEQ ID NO: 119
embl|DW249020
Fm27 Festuca mairei EST Festuca mairei
cDNA clone SSBI082604_D04 3', mRNA sequence.

catgtggtatccagggtccatttatccacacaaatgcacaatcggcaatacatacgtaagcacagactggtcactgggttcagcg
atgaatactgatcactgggtttcaaggctggggcatttgttcagtgcttgtgttttggcttcttcacaatcatcaccgtgcagtgcgcg
tgatgggtgcagtaatcgctcacacttccaagaacagcccttttaattgctccatagccatggttgcccacaaccaacatctccgc
gtgatgccgttcg SEQ ID NO: 120
embl|DW249021
Fm28 Festuca mairei EST Festuca mairei
cDNA clone SSBI082604_D05 3', mRNA sequence.

catgtggtgctgtctctccacgaagtgaaggtgaagctgaagccaaagcgcttttgacatggaagtctactttgatgttctccgac
gtcaacggctcttctccgctctcgtcatgatcaccggccaactccctctgcaattcttggtctggcatcacgtgcaacacggctgg
ccatatcgtggagctcacggttcccggagctggtgtcgcaggcacgctggacgccttcg SEQ ID NO: 121
embl|DW249022
Fm29 Festuca mairei EST Festuca mairei
cDNA clone SSBI082604_D06 3', mRNA sequence.

cgcagggcaaactgcaagcagatgcaaaggatcctgagacagcactggccccaagcattgtagagatctctccagcaccaag
tttgtctctgagtaactcaacactctggtcataggaagcgagcatg SEQ ID NO: 122
embl|DW249023
Fm30 Festuca mairei EST Festuca mairei
cDNA clone SSBI082604_D09 3', mRNA sequence.

catgttaaggcttatagcaatgtgaacaagtatctacttactggtaggtacagaaacatcatggacatgaacgcaggctttggggg
tttcgctgcagcgatcg SEQ ID NO: 123
embl|DW249024
Fm31 Festuca mairei EST Festuca mairei
cDNA clone SSBI082604_D10 3', mRNA sequence.

Figure 9F

Catgctaagcgcactgtttcataaatataatgttgtgcagacgatgataaatacagtagatgcaaccagaggcgactggtaaccc
agcttcattatccagggaagtgggcgaaccettggtcctaaagcagtcgctcactgcttaggagagtgccaaggatcaatctgat
ctcacaggagatgcagaaccggataagctcttgctagggcttctgctcactgattttccaggagaggccgaagaaactggggat
cg SEQ ID NO: 124
embl|DW249025
Fm32 Festuca mairei EST Festuca mairei
cDNA clone SSBI082604_D11 3', mRNA sequence.

ccatgatgctgaagggatggtgaatgttatatctgagaaggaaactgacagaatcctcggcgtacacattatgtcccctggcgcg
ggagagatcatccatgaggctgtgcttgcgcttcagtatggagcttccagcgaggacattgcccgtacatg SEQ ID NO: 125
embl|DW249026
Fm33 Festuca mairei EST Festuca mairei
cDNA clone SSBI082604_D12 3', mRNA sequence.

cgacagcaacggacagggtgtacagcggggccaccttatagtcaactaccagttcgtcaactgcggcgacaacgagctgctg
ctccagcgcgaagagaaataagaagctaccagtacatg SEQ ID NO: 126
embl|DW249027
Fm34 Festuca mairei EST Festuca mairei
cDNA clone SSBI082604_E02 3', mRNA sequence.

cgaatgagaacgcggcatcctccgtcgccaagaccatctccggtcagcccccactgaagataccgatcaggagcgacaacgc
cgggtcctggctgctcacaacctaccttgatgacgagcttagaatctccagaggagatggcagcagcatctttgtgctgttcaag
gaagggagcactctcttaatataggcttacgtgtatctcttctcagagtagaatttgggcgaatccaatagatagttgtggctatgtg
tttgttttgttagcccgtgcgtttatagttcgttcttgtgtgttgtgcatg SEQ ID NO: 127
embl|DW249028
Fm35 Festuca mairei EST Festuca mairei
cDNA clone SSBI082604_E03 3', mRNA sequence.

catgcgtagaattcttcgcgaagtaaacacgacatgatacgtacgtaaagcatcacgtatacgtagctaatctcggttgattctgtc
ctcgcaacctacataaactggctgcaaggacgcggtactagttaatttcgcaaaaagtatatcggccacgtgtacgattcg SEQ ID NO: 128
embl|DW249029
Fm36 Festuca mairei EST Festuca mairei
cDNA clone SSBI082604_E04 3', mRNA sequence.

Figure 9G cgaactcgtgccgcagcgtggcgacccagaacccgacggtggcgatggcgagcgacttgccggggcagctccgcctgccc
gacccgaacggcgccagcctgaggtctgagcccgttatggagaactcggcggcgccggcgtgatcccgcgacggtccggc
gaggaaccggtcaggcctgaactctgccggctcggtccagacggccgggtcgtgcgttatggcccacatg SEQ ID NO: 129
embl|DW249030
Fm37 Festuca mairei EST Festuca mairei
cDNA clone SSBI082604_E06 3', mRNA sequence.

cgaagggaagagatagacaaatgtatccataaagccgatggcttcattcagagtattcaaagaagtgacggttcatggtacggct
cctggggtgtttgtttcacatatgggacatggtatgcagtgaggggattagttgccgctggaaggacattcaagaactgtcctgct
atcaggaaggcatg SEQ ID NO: 130
embl|DW249031
Fm38 Festuca mairei EST Festuca mairei
cDNA clone SSBI082604_E07 3', mRNA sequence.

cgataattgctcttatcgtctgcataccaccagcagttattattgaaggtccccaacttatgcagtatggattaaatgacgcaattgca
aaagtaggtctgacaaagtttgtttcagaccttttcctggtcggactgttctaccatctgtataaccagcttgctacaaacacattgga
gcgggtggcccctctgacacatg SEQ ID NO: 131
embl|DW249032
Fm39 Festuca mairei EST Festuca mairei
cDNA clone SSBI082604_E08 3', mRNA sequence.

catgcgtgaagatggaggttttgaagtgattaagaaagcaatcctgaacctttcacttcgtcacgacttgcacataagtgaatatgg
tgaaggaaatgaacggaggttgacagggttacatgagacagctagcatatcagacttttcatggggtgtagcaaaccgtggttgc
tctattcggtgtggggcgagacactgaggcaaaagggaaaggatacctggaagaccgtcgtccggcctcaaacatggacccat
acactgtgacggccctactggctgaaaccacaattctctgggagccgacccttgaagcagaggctcttgctgccaagaagctgg
cgatgaacgtatgaaggactgaaaaggatgaatttctggggaaaataaatcg SEQ ID NO: 132
embl|DW249033
Fm40 Festuca mairei EST Festuca mairei
cDNA clone SSBI082604_E09 3', mRNA sequence.

catgttcggcggcggcaagttcaagaagtggaagtaatctgccagtagctttccatagctgatggatcg

SEQ ID NO: 133
embl|DW249034
Fm41 Festuca mairei EST Festuca mairei
cDNA clone SSBI082604_E10 3', mRNA sequence.

Figure 9H catgcccgccaacaaccggaacactgacttctctaggatcaactccaagcacttcagccacaaaggtgttagccctcgctacatc
aagagttgtcactccaaggagacgtttggggcagtaagttccagccctcttgaaaactttcgccgcaatggggacagttgagttc
acagggttgctgatcaaattcataattgcattagggcagctcttggcaacgccctcacagattgatcg SEQ ID NO: 134
embl|DW249035
Fm42 Festuca mairei EST Festuca mairei
cDNA clone SSBI082604_E11 3', mRNA sequence.

catgtacacgcaagcccccctaatacaggtcgccttccttgtgggtgtggatgatgcagtcagacttgggggtatgagacgcaggt
cagcacgtagccttcctcctgctggttgtcatcg SEQ ID NO: 135
embl|DW249036
Fm43 Festuca mairei EST Festuca mairei
cDNA clone SSBI082604_E12 3', mRNA sequence.

catgtaccacactgagcacgagcttctccgttacctacacaagttgcaaaccaaggatctctcactgtgccacagtatgattcctct
tggttcttgcaccatgaaactaaatgctactgtcg SEQ ID NO: 136
embl|DW249037
Fm44 Festuca mairei EST Festuca mairei
cDNA clone SSBI082604_F01 3', mRNA sequence.

cgaaacggggngatttcttttctttttatggaggaaaagaacattcaagtgaacaacatcccagcagaagatggggagaaagag
agatgaataagaattattccgatcaggggaggaacaaacaagctcccttcttaattatgatgacatg SEQ ID NO: 137
embl|DW249038
Fm45 Festuca mairei EST Festuca mairei
cDNA clone SSBI082604_F02 3', mRNA sequence.

cgaatcctggctgtgcaatacccggaccgaatctattgacagatcatccatccttggtttcttgggagaaggctgcatg

SEQ ID NO: 138
embl|DW249039
Fm46 Festuca mairei EST Festuca mairei
cDNA clone SSBI082604_F05 3', mRNA sequence.

Catgcatccttaccagcttcctcagttgtcctgttgctctccaatgtaacaactgctgatttatccccttcctccaaacctgcgacccc
tttaatctcattgctatgccaagactcagcattagcatcacaagctaactgaggctgagaattttcagtcttcattttcacccgccgac
cattctgttcatgcttatcagcaagcacaggagatgaagatctactcccagtgacagatgggtcgtcaaatgagccaccactcac
acttctagcaggactacgacttggatttgaaaagcgaactatcaatctatggctattaccattatcaggaggtgtatcacctactttct
cagacaccattccaggttgtgatgcttttcctggaatgaggaccgatcaagtgaagtagatcttcccacggtagcttctttctttacc
ccagaaccaagacgggcactgtttgcccttcg

Figure 9I

SEQ ID NO: 139
embl|DW249040
Fm47 Festuca mairei EST Festuca mairei
cDNA clone SSBI082604_F06 3', mRNA sequence.

cgacttcaccgggggcatctcatcctacccgctcctcgtcgcccaggtgacccacttcaagtgcggaggcgtggccctcggca
taggcatg SEQ ID NO: 140
embl|DW249041
Fm48 Festuca mairei EST Festuca mairei
cDNA clone SSBI082604_F09 3', mRNA sequence.

cgatccggtgaagcaatccctccgccgcttcgccgaagaaaggagaaaagccattggtgaagagatagcccggctgctcgca
gccggctttatcatggaagtgctgcccccagactggttggctaacccagtcctggtcttgaagaagaatgacacctggcacatg SEQ ID NO: 141
embl|DW249042
Fm49 Festuca mairei EST Festuca mairei
cDNA clone SSBI082604_F10 3', mRNA sequence.

cgatcgccgtctccgcactgcagcagctaccatggcgtccaccgcgctctccaccgcctccaaccctacccagctctgcaggt
ccagagcttcgccgtgcaagcccatcaagggcctgggcatcggccgggagcgcgtcccgaggaacatcacatgcatggccg
gcagcatctccgccgaccgcgtgccggacatgagcaagagggagacgatgaacctcctcctgctcggcgccatctcgctccc
caccttcggcatg SEQ ID NO: 142
embl|DW249043
Fm50 Festuca mairei EST Festuca mairei
cDNA clone SSBI082604_F12 3', mRNA sequence.

catgttctcttttgcaggaagttaggacaggagcgaagccgaacgtctttagcttgataaaaaagatgaagcaaaggaagacgc
cgcatcctgagacggggtccttgtgggttaacgagcaatccgggacccagtgtgcggcgtatgtcttgaagttcaagcagaagc
acggcgagagctccaacccagaggccgaggattttgacgttgaggttgcggtgcttgcgggagaaggcatgaagcatggccg
cctatggcttggtgatgggtgtgtcg SEQ ID NO: 143
embl|DW249044
Fm51 Festuca mairei EST Festuca mairei
cDNA clone SSBI082604_G05 3', mRNA sequence.

cgaagaggttattcgtgataaggaggcccagttcagcagccccaacctcaatgttgtttaccgcatgaatgtgcgggagtacca
ggcactaaccccctatgcctccatgctggaggagaactggggcaaggcacctgggcatctcaattctgatggcgagaacctcc
ttgtctatgggaagcagtatggaaacatcttcatcggagtgcagcccactttggttatgaaggtgatcctatgcggctcctgttctc
aaaatctgccagccctcaccatggatttgcagcatactacacctatgttgagaagatcttcaaggcagatgctgttctgcatttcgg
cacacacggatcccttgagttcatgcccgggaaacaagtcgggacgagtgatgcatg

Figure 9J

SEQ ID NO: 144
embl|DW249045
Fm52 Festuca mairei EST Festuca mairei
cDNA clone SSBI082604_G06 3', mRNA sequence.

catgtatacaaaacctggacctcagaatacaacacatccagtaataaggtaaaaacaaattaactcttaacaggatggaaaacat
catctatctagctcttggggatgttcttgccaacgatcttggcaggtgtgatgcggagaaggttcccctgcttcccaggaatggctc
ccttgatcatcacaactttaagatcgttatcg SEQ ID NO: 145
embl|DW249046
Fm53 Festuca mairei EST Festuca mairei
cDNA clone SSBI082604_G09 3', mRNA sequence.

cgatcggactatcctcaccaccaattgcatgaataaccaccgggatgtcgctcaggtagcgtatcaccaggggcagagccgct
ggggcaacatcagctttcactacgtcatcgctcagcaaaactgaatcggcagcagcgggaccgccagcctctattgctcctggt
tcatctttgtcttcagataacattaactcggatgggttcaccaccactgcgacttcctcaattgctatgctacatttgaactggcttccc
ctcctttgggcaggcttgttcctgcatg SEQ ID NO: 146
embl|DW249047
Fm54 Festuca mairei EST Festuca mairei
cDNA clone SSBI082604_G10 3', mRNA sequence.

catgccggcgtgcccttgtaatagccacattcatgagcctgctgtcacccatgaaccctacagctcctagagggtttgatcg SEQ ID NO: 147
embl|DW249048
Fm55 Festuca mairei EST Festuca mairei
cDNA clone SSBI082604_H01 3', mRNA sequence.

cgaaatcatacttaacctccttcccttgcttgtttatttctttcaaccccttcctgaaaaagatcatggctccacgtggtccacggagt
gacttgtgagtagtggtagtaacaacatctgcatactcaaaaggagatggaatgacaccagcagcaactaggccactgatatgt
gccatgtctgcgagaagtattgccttctgcttgttacagatcttccgcatg SEQ ID NO: 148
embl|DW249049
Fm56 Festuca mairei EST Festuca mairei
cDNA clone SSBI082604_H02 3', mRNA sequence.

cgaattccataatgaaatatgttgtaattgctcatgtgaacgaatggagaacaggagacctccatgggcggcccagaaattcagc
aatgacgcggacctgcgcttccgcctccaagcatg SEQ ID NO: 149
embl|DW249050
Fm57 Festuca mairei EST Festuca mairei

Figure 9K cDNA clone SSBI082604_H03 3', mRNA sequence.

catgtttgaaggaaatgacgtgtcagatggtatgggtttcggaatgctaaccgagggtgagagatccctggttgagcgtgtaagg
caagagctgaagcacgagcttaaacaggggtacagagaaaagcttgtggacattagggaagagatacttcggaagcgaagag
ccggaaagctcccaggagacacagcgtctactctgaaagcctggtggcaagctcatgcaaaatggccatacccgactgagga
ggacagggcccgcctggtgcaggaaacagggctgcaactgaagcagatcaacaattggttcatcaaccaacgcaagcgcaa
ctggcacagcaaccccacctcatcctcatcagacaagagcaagagaaaaagaaacaatgcaggtgatggcaacgccgagcg
gtcttggtaggacatggttggagaagaacacgcgtgtgtaaacagttcg SEQ ID NO: 150
embl|DW249051
Fm58 Festuca mairei EST Festuca mairei
cDNA clone SSBI082604_H04 3', mRNA sequence.

ccaaccgctcataccagcatgatgatttggaggccttgctgatgatatctctccccccccttcctgttcatataggaaggatttagtgt
acctattgcccgaatagtgtatttctggtgcacctgccggttccctgggtactggcttgaatatgtgaatactgtgcatatggggcat
g SEQ ID NO: 151
embl|DW249052
Fm59 Festuca mairei EST Festuca mairei
cDNA clone SSBI082604_H05 3', mRNA sequence.

catgcatgcagcctggggcgtacagattgacaggcctatgtgtagctcagccctcatcaggtagcgatacatggtggtaattaag
tagtgatgcaagcggccagatcatagctcgttgactgatgatctagcaggtgcagcaggagcagccacagctggtgctgcagtt
gcacttgctgcaggggcagccgccgttctccgcctccgcggccatgtccatcccaccggcgctcgccttgtgggtggcggcg
gcgacgaggaagacgttgccgttgccggcggcttcg SEQ ID NO: 152
embl|DW249053
Fm60 Festuca mairei EST Festuca mairei
cDNA clone SSBI082604_H06 3', mRNA sequence.

cgataagaaggacagcgaggaggccaagcaggcgctagaccagctgaaggagctcggctgggccaagcgatggagctcg
cagccctacatg SEQ ID NO: 153
embl|DW249054
Fm61 Festuca mairei EST Festuca mairei
cDNA clone SSBI082604_H07 3', mRNA sequence.

Catgccggggctggggaaggagcacgtcaaggtgtgggcggagcagaacagcctggtgatcaagggcgagggcgagaa
ggactccgaggaggagggcgtcgccgccccgaggtacagcggccgtatcg SEQ ID NO: 154
embl|DW249055

Figure 9L

Fm62 Festuca mairei EST Festuca mairei
cDNA clone SSBI082604_H08 3', mRNA sequence.

catgtagccgatctttgttccaagagatggtaaagctttgctttcatagatgcacctatatgacctcttcccaggtggtagtcatccca
ggcggcgacgaggtgttcaggggagaggcccttggcgcgatcg SEQ ID NO: 155
embl|DW249056
Fm63 Festuca mairei EST Festuca mairei
cDNA clone SSBII082604_A02 3', mRNA sequence.

catgcggcaaacaatcttcccactccttcaagttcttcttgatcatggatctcaacagttgtgacaatgttctattcaccacctcagttt
gaccatcagtttggggatgacaagtagtgttgaaaagtagcttcgtccccagctttctccaaagcgtcttccagaagtagctcatg
aacttcacgtcacgatcagaaacaatagtcttcgggactccatgtcg SEQ ID NO: 156
embl|DW249057
Fm64 Festuca mairei EST Festuca mairei
cDNA clone SSBII082604_A03 3', mRNA sequence.

cgacttgcgccacaccacctgcgtgtagtgcccgcacaccttgccggcgtcgcaggtgttgctgctgaggtggtagttcttcttct
cgtccacccacatg SEQ ID NO: 157
embl|DW249058
Fm65 Festuca mairei EST Festuca mairei
cDNA clone SSBII082604_A04 3', mRNA sequence.

catgttagccccgagcaggaagcccacggcgagcggcccgatggtgcccacgtggcccctcttggggtcg

SEQ ID NO: 158
embl|DW249059
Fm66 Festuca mairei EST Festuca mairei
cDNA clone SSBII082604_A05 3', mRNA sequence.

catgttgttggccagaacttggcaccacggagccacgccgcagggaacgcggcgtactccctggagtatggcttagtccatgc
gtcactcatcaggagttgggtgggtggggagcgcccttcaggacattgttgttcacatctgctacgccatttctacctgtgcaat
ttcttccctgatggaaataagggcatcacagaacctgtctagttcagccttgctttcactttcagtgggttcaatcataagtgtcctg
gaacaggccatgacatggttggtccatggaacccatagtccatcaagcgcttcgccacatcctcaggctctataccagcagtcg
ccttgagccctcttaaatcaatgatgaattcatgggcaacagttccattgactccacggaaaagaactgggtagtgtttctccagac
gctttgccatgtagtttgcattcaagatcgcaatctttgaagcatcagtgagtccctgagacccatcatggctatgtatgtatagga
aattggaagaatcaaagcagatccccatggagcagcagaaatggaacccaggaggtcggtttc SEQ ID NO: 159
embl|DW249060
Fm67 Festuca mairei EST Festuca mairei

Figure 9M cDNA clone SSBII082604_A06 3', mRNA sequence.

catgccgctgtactgatctaccggaagctgcagctggttgcagaacaagctgctgctggatctcctcctcttcatcccattatactt
gttaccagtagcgtaatcacggtcatctaactgcggcacgtcg SEQ ID NO: 160
embl|DW249061
Fm68 Festuca mairei EST Festuca mairei
cDNA clone SSBII082604_A07 3', mRNA sequence.

catgtggcatcaattttacatcaacctgccgcagctgtcctgatcatacgactaattagccggagaaggtctggatgatggtgttgt
gccacgggtcagacaagtgctggaacaggttctcg SEQ ID NO: 161
embl|DW249062
Fm69 Festuca mairei EST Festuca mairei
cDNA clone SSBII082604_A08 3', mRNA sequence.

catgcggcagcatccatcagcaatgaagttgtcggccaagcacgcgcgcgcacgcccgcgctactgctagagagctgacaaa
gctcactttccggggacgaagttggtggcgaaggcccaggcgttgttgttgacggggtcggcgaggtggtcggcgaggttctc
g SEQ ID NO: 162
embl|DW249063
Fm70 Festuca mairei EST Festuca mairei
cDNA clone SSBII082604_A11 3', mRNA sequence.

cgacaaagaacacggccggcgaccatggcagcagcggttttggaactgctatactttgaagtttgaacagcgccttgacctcag
atgctggtggaattagctatttgcgtgccaaatgtagcgggtaaaaaatagctgtggtggttccaggattgtgtattcggtaccgtg
ccacatg SEQ ID NO: 163
embl|DW249064
Fm71 Festuca mairei EST Festuca mairei
cDNA clone SSBII082604_B01 3', mRNA sequence.

catgcggtacctcccatccatggggctggaagacacactgaacgggtgccactgcaagaacgacagctcccgcacttgaaca
aagatgaagctgagagcactgtaccggaggcttgctggctttgaggagactagctccacagttccgcaggggcggcaggcag
cagaaacaatgtcg SEQ ID NO: 164
embl|DW249065
Fm72 Festuca mairei EST Festuca mairei
cDNA clone SSBII082604_B02 3', mRNA sequence.

catgtgtctctttgtccaaatcagtttcttgaagaggtgctttctcagtggtcttgctttcttcacaaagctgctgtggcgtcaccgttg
gatcaacaggtaaggcagtgcagcttccatctttctctaatttctcatctgctgcatcggtagcgacaggttcttcatcagtgacagc
agcagcagaagcggatacatcttcagactcttgtttctcagctggagctgcctgcttgttcttgccatgcattgccttgtaggtggc
gacggcgtggtcg SEQ ID NO: 165
embl|DW249066
Fm73 Festuca mairei EST Festuca mairei
cDNA clone SSBII082604_B04 3', mRNA sequence.

catgtgtctctttgtccaaatcagtttcttgaagaggtgctttctcagtggtcttgctttcttcacaaagctgctgtggcgtcaccgttg
gatcaacaggtaaggcagtgcagcttccatctttctctaatttctcatctgctgcatcggtagcgacaggttcttcatcagtgacagc
agcagcagaagcggatacatcttcagactcttgtttctcagctggagctgcctgcttgttcttgccatgcattgccttgtaggtggc
gacggcgtggtcg SEQ ID NO: 166
embl|DW249067
Fm74 Festuca mairei EST Festuca mairei
cDNA clone SSBII082604_B06 3', mRNA sequence.

cgacgtactttaatatccgtaaaggcctagacggctccctagacaaggcaattaatgctctttgtgaagaagctgacgctgctgtg
cggagtggttctcaacttctggtcctttctgatcgttctgaagcacttgaaccaacacggcctgccatcccaatacttctagccgttg
gtgccatccaccagcatctgattcaaaatggcctccgcatg SEQ ID NO: 167
embl|DW249068
Fm75 Festuca mairei EST Festuca mairei
cDNA clone SSBII082604_B08 3', mRNA sequence.

catgtaccaacaacgaggcctgcaacgacgccattgtccctgccagcccaaccggcaaagacgaagagtcctatcttgccata
gttataacccatgttgatatcggtaagccctgtcccataggaattggcgaatccaagcatgggggcgacgacataggctataacc
acgtagtaccatttcacctgtcggaacattattggcgtggtaaccactgcaacagcacttaacaaggcatacccggtgtacgcca
accaagaggggatatggcccttccggaagatctcgtcgcgctgcagatcctcaagtgagaccgtattgtccacatctttcactcg SEQ ID NO: 168
embl|DW249069
Fm76 Festuca mairei EST Festuca mairei
cDNA clone SSBII082604_C01 3', mRNA sequence.

cgacacgctcactgatatctgatggaggtgaattcagcttgacaaatgagcaggaaaagtgggttgtagacattatgctctcagta
acgctggtgaaacttgctctagctttatattgccgcacattcaccaatgaaattgtcaaggcttatgcgcaggatcacatg SEQ ID NO: 169
embl|DW249070
Fm77 Festuca mairei EST Festuca mairei
cDNA clone SSBII082604_C02 3', mRNA sequence.

Figure 9O catgcggagggaaggatatgaatttatgattggacctccaaaggtcataaacaagagtgtagatgggaagctactggagccgta
tgagatagctgctatagaggtaccagaggaatatatgtgatcagctgtcg SEQ ID NO: 170
embl|DW249071
Fm78 Festuca mairei EST Festuca mairei
cDNA clone SSBII082604_C03 3', mRNA sequence.

cgactgcggcgtctccatcggaacgatctttgggatttacatgatcaagaactttgacaccgtgacccttgaggaagtgccgctg
cctgggaaggacatgattgctgctggatactgcatg SEQ ID NO: 171
embl|DW249072
Fm79 Festuca mairei EST Festuca mairei
cDNA clone SSBII082604_C07 3', mRNA sequence.

catgcatatgctgcaaatgtttcttcccacctagtgtttcttttttccttttaccccgcaattgaaccgtgcaaagctcaaggctccgat
catatatacgccttcgtatctagcgacaagagtgaatgagcgcggtaagctgttatggaatctccttggcacgtctgatcaatgtac
atactgacactcgcatttgtctcg SEQ ID NO: 172
embl|DW249073
Fm80 Festuca mairei EST Festuca mairei
cDNA clone SSBII082604_C08 3', mRNA sequence.

cgagtcgcagtcgcagaccaacgatctggagtcggacagtctgcaggtgtacagcttctccgggctgttcctcatctgcggcgt
ggcgtgcgtgatcaccctcgccatacatg SEQ ID NO: 173
embl|DW249074
Fm81 Festuca mairei EST Festuca mairei
cDNA clone SSBII082604_C10 3', mRNA sequence.

catgtcgttggacggcagcaccatcaccacatggagagaaaggagccgttggacaatctgtgcaggagctcgccgaggcaca
ggatggcgtagaccagcaggatgaacttgaagaggaacgggaagtagtgcgagagcccggcgctcg SEQ ID NO: 174
embl|DW249075
Fm82 Festuca mairei EST Festuca mairei catgcacccatttgcccctattgatcaggctgcaggctatcatgaaatgtttgacaacttgggtgatctgttgaacacgatcaccgg
ttttgattccttctctctgcaaccaaatgctggtgcttcaggagagtatgctggactgatggttattcgggcccaccacagggcaag
aggagaccatcaccgaaatgtctgcatcattcctgtctcggcacacggtacaaatcctgcaagtgctgctatgtgtggaatgaag
attattactgtcggaactgactccaaaggtaacattaacattgcggagttgaagaaagctgctgaagcaaacaaggacaacctgt
ctgctctgatggttacctatccttcaacccatggagtctatgaagaaagcatcg

Figure 9P

SEQ ID NO: 175
embl|DW249076
Fm83 Festuca mairei EST Festuca mairei
cDNA clone SSBII082604_D01 3', mRNA sequence.

cgacattatgcacaggcagaggaagctgaagaggatgatgaaattgagcggctctttagtagtaagaaagagaagaagaatga
tcggccacgagcagatattggtcttatcgttgagcagttcattgccgagtttgaagtagcgtctgaagaagatgcaaacctaaata
ggcaatccaaaccggccattaacaaacttatgaagcttccactgctcatagaggttctctcaaagaagaatctccagcaggaattc
cttgatcatggaattctcactcttctgaaaaactggcttgaacctttacctgattgaagcatg SEQ ID NO: 176
embl|DW249077
Fm84 Festuca mairei EST Festuca mairei
cDNA clone SSBII082604_D02 3', mRNA sequence.

catgtacgtgcttcgttgcatcttctgaacagcctcggtgacctccttacgtacgccaagccatcgcactgagctgagctcagtcg SEQ ID NO: 177
embl|DW249078
Fm85 Festuca mairei EST Festuca mairei
cDNA clone SSBII082604_D03 3', mRNA sequence.

catgcatatctcgcccggccggtggtcggacggatggctaactcatttaacatccaggagcgaagttggtggcgaaagcccat
gcgttgttgttgactgggtcagcaacgcagtcg SEQ ID NO: 178
embl|DW249079
Fm86 Festuca mairei EST Festuca mairei
cDNA clone SSBII082604_D04 3', mRNA sequence.

cgaccataaacgccccgtgatcggcggcaaggagcaccccctaccctcgccgatgccgcaccggtcgccctaaaaccatcatt
gactcagagacggagaagaggagctcaccagtgtatgtgccacgtgacgagcagttctcggacattaaagggcagacattca
gcgcgacgacactgcggtctggattgcatg SEQ ID NO: 179
embl|DW249080
Fm87 Festuca mairei EST Festuca mairei
cDNA clone SSBII082604_D05 3', mRNA sequence.

cgacgacctaaaggctcacgcagaatcaaatgtgactgataagatgatgtcaaatgcaaagttcatctacccacacaacaccccc
gacaacaaaggaggcatactgttacagaacgatctttgagaggttcttcccccagaactcggcgatcctgacagtgccaggtgg
accaagcgtcgcatgcagcacggcgaaggcggtagagtgggatgctcagtggtcggggaacctggatccctcagggagagc
agcgcttggagtccatctctcagcctatgaacaagagcatg SEQ ID NO: 180
embl|DW249081

Figure 9Q

Fm88 Festuca mairei EST Festuca mairei
cDNA clone SSBII082604_D07 3', mRNA sequence.

Catgcacgtacggggttcgtaacactactctagcttaattaatctagacgttgacaaagggcgtgccggtgatgaactcggtgac
ggcgagcgcgacgagtccgagcatggcgaagcggccgttccagagctcggcgtcggcgctccagacgccgctggacttgct
ctcg SEQ ID NO: 181
embl|DW249082
Fm89 Festuca mairei EST Festuca mairei
cDNA clone SSBII082604_D08 3', mRNA sequence.

Catgttggtgcttacaaatatggcagctggggacgaattaagcaaggaagctgtaatggatgttattgttcctcacagatcagatc
gcatcaagccatcttttgtggtcaactttctgcagagcaaggacgaacaattgagagttgcatctttgtggtgcattcttaacttagct
tacccaaaaagtgatgcttcatctactcg SEQ ID NO: 182
embl|DW249083
Fm90 Festuca mairei EST Festuca mairei
cDNA clone SSBII082604_D09 3', mRNA sequence.

catgcttgggaataggtgtgtcatcttcaatcacctcgcattcgtagtcatcaggaacgccccagggatcccactcg

SEQ ID NO: 183
embl|DW249084
Fm91 Festuca mairei EST Festuca mairei
cDNA clone SSBII082604_E01 3', mRNA sequence.

catgctgtcgttcaggactcatcgtgactgtagactgcgttcccatgctttctcctccaaagtgagttgcacatccttcatctcacact
ggactgatgccatttccccgtgtcg SEQ ID NO: 184
embl|DW249085
Fm92 Festuca mairei EST Festuca mairei
cDNA clone SSBII082604_E02 3', mRNA sequence.

catgttccttctacgttgatatgtacggtgcatacacaaacaattatacgtggaactaaaagtaaaacccggaaagcggagttgtc
atcaaaaactaaaccaagagactccacatggattcctagctcgcggcttatgccttgccggactcctcacagcctggtggcttga
aggcgatgaagctgacgcactgcacctgacggatgttgtcaaaaccgatgatgcggacataggcgtcagggtactccttcttga
cctcctccacctccttgaggacctgggtggcgtctgtgcagccgaacatgggcagcttccacattgtccagtacctgccgtcgta
gtatccgggagtgctgccgtgctcacggaagatgaagccaaccttgctgaactccaggcagggaacccatttggagcggatca
agaagtcg SEQ ID NO: 185
embl|DW249086
Fm93 Festuca mairei EST Festuca mairei cDNA clone SSBII082604_E03 3', mRNA sequence.

catgcagtggaatgtcttctgataaacgtaggggagaacatgactggggaaggacttcggtggaagctattttcttgccagtcg SEQ ID NO: 186
embl|DW249087
Fm94 Festuca mairei EST Festuca mairei
cDNA clone SSBII082604_E04 3', mRNA sequence.

catgcttgcgcacatagttcatctctactggctcgtccagctcagcaaccatctttactgcccggtccagcagattcatctggttgat
gaaaagacctctgaacacgcccgagcagttgacgacgacatcaaccctaggacgtccaagctcctcaatgctgacaggctcca
cacggttgacacggccaaggccatcagtaaccggctccacaccaagcatccaaaacacctgggccagggactcgccgtaggt
cttgatgttgtcagtaccccacaagacaagagcaattgtctcaggatacttgccaccattgtcagccttttgccgctccagcagac
gttccacaacaaccttggcactcttcgtggccgctgcggtcgggattgactgcgggtcg SEQ ID NO: 187
embl|DW249088
Fm95 Festuca mairei EST Festuca mairei
cDNA clone SSBII082604_E05 3', mRNA sequence.

cgacgtccagcgctctcttctccttcttcaccttgggctgcgtgatcacagtggcatcacccggcccagagaccgccttggcgcc
gacgtctgtgcctggagccgccgtggaggccatcatcgcccggcgcgccttccgctgcctgatgccacaagcgttgcaaagtg
acttggggccacatggaccactcctccacaaggggggttttggtggtgttgcagtcggagcatg SEQ ID NO: 188
embl|DW249089
Fm96 Festuca mairei EST Festuca mairei
cDNA clone SSBII082604_E06 3', mRNA sequence.

catgttcaaactagattgatacgacaccaggtccacatgatcactgcggttccgaagagctgaagatcctacagtgccttgagga
tctcctcagcaccagagattgtgaactggccgccctcctcaatgtttgcaacagtgaccttgaggtcatcagcaaggagagcaaa
ccgtctcg SEQ ID NO: 189
embl|DW249090
Fm97 Festuca mairei EST Festuca mairei
cDNA clone SSBII082604_E07 3', mRNA sequence.

cgagagtactttgggcttcaattttgggtcattcaatagagaatctagttcaccttcattcagtacaggacttgatagagtaacctggt
cagcattttcagggccaacctccaagatgttgcctcgtttaccaatattaacttcaagagacatgactaaaccttctcggagtggat
caattgcagggtttgtaacctgtgcaaatcgctgcttgaaataatcaaagagcatg SEQ ID NO: 190
embl|DW249091
Fm98 Festuca mairei EST Festuca mairei
cDNA clone SSBII082604_E09 3', mRNA sequence.

Figure 9S catgccacttgcccttgtaggcagggttctgcttcgttggcttcttccattcaccacatccaggtgcctcttcgcacttggggttgtca
atcttcggtgcctcccattcaccatcctcctcatcatcccagtctttaggcttagcagcctcaggatcgtcaatttcatcaggctcatc
atccagccatcctcctggcttggtggcctcctcatccacaatctctattggggcatcctcatcccagtcgtcaggcttagtagcatct
ggatcagggatcttagctctctcgtcccagtcctctggcttcttgtcgtcagggtcaggaatcgtctttgatggaataagtgctgact
cg SEQ ID NO: 191
embl|DW249092
Fm99 Festuca mairei EST Festuca mairei
cDNA clone SSBII082604_F01 3', mRNA sequence.

catgccttcatatctgcaacaactggtcagtagggcaatcacatcagaagataaattcgttgatgatgttggtccctccaggcaaa
caataagcaagggtgtcccatcagacaacaatgtcg SEQ ID NO: 192
embl|DW249093
Fm100 Festuca mairei EST Festuca mairei
cDNA clone SSBII082604_F02 3', mRNA sequence.

cgactccagcagcaacccgagaagatcgtcgctcgttgcttcgccagcttttaaggcgttctctcttttggtgatgatcctcttagg
atcctcccaatctccgcagcaatctgcttcatccttctgttggctttggttggcaagaacaggtaaccagggatatgtatcttgttcat
ggcctgcatgacgagcaggatctgctcccctgaagctggaatatcctcacgccctcaaggtagctgctgccgaatgcggcgc
gggagatgacatcccctgtcaggttctgcatatcaggccagacatctacctcgcatggcaggtcaccggtgactaaaccttccca
tctgtgtaccagctccgtgcaacattcggcgaaagccggcaacatg SEQ ID NO: 193
embl|DW249094
Fm101 Festuca mairei EST Festuca mairei
cDNA clone SSBII082604_F03 3', mRNA sequence.

catgctgtcaaagtggcagctgatggctgaacaagctaggcagaagcgagcaccagtacagaggccagcacatggatctgga
aaaggttcggcagaacagaatgaagcttcaaagaggagccattttgcagccttcggaactggaggcacgaaaaggcaaggca
agggttcattcgctacgcgtcactcgcatgggccacaacgaactgtttccgtgaaggatgtaatctgcgtcctggagagggagc
ctcagatgacgaaatcacggctaatttatcggctgtacgagcgattgcctggagatttcaccacagattaggctgaattatgtagtg
taacttatagcgtgtaactgtttgttgatgcacagcccgtcgctcagactgacgtgttccagtcg SEQ ID NO: 194
embl|DW249095
Fm102 Festuca mairei EST Festuca mairei
cDNA clone SSBII082604_F04 3', mRNA sequence.

cgacccatgccgtgagcgggtcgcggaagtccttgagcccgatcccgggtggcgggaagaggatggggttggcggggtgct
tgatccagctgcggaggagcgggtcggatgggtcggcgggcacggccaggcactggacctgcgcgaaggtgtcagtgttcc
ccgtgtcgagcaggatcacgcgcccgtcag

SEQ ID NO: 195

Figure 9T embl|DW249096
Fm103 Festuca mairei EST Festuca mairei
cDNA clone SSBII082604_F05 3', mRNA sequence.

catgctattggagaacggtcccaacgaggcccaggcaaagaaggcccgccaggtcctgcaggcctgcggcgataggaaag
acggctaccagctgaactacgacttcaggaacccgttcgttgtgtgcggggcgacctttgtcccgatctaccgcgggcagaag
gacgtctcctgcccctactgcacttcccggttcgtgccctccgtcg SEQ ID NO: 196
embl|DW249097
Fm104 Festuca mairei EST Festuca mairei
cDNA clone SSBII082604_F06 3', mRNA sequence.

cgagatagacgagcagaccttcctgaccaacagggagagggcggtggactacctcaactccctggacaaggtgttcgtgaac
gaccagttcctcaactgggacccggagaaccgcatcaaggtgcgcatcatctccgccagggcctaccactcgctcttcatgcac
aacatg SEQ ID NO: 197
embl|DW249098
Fm105 Festuca mairei EST Festuca mairei
cDNA clone SSBII082604_F07 3', mRNA sequence.

cgagagaatcacggagcaagctggtgtagtgctcactcttgacccaaaaccaatccagggtgactggaatggagctggctgcc
acacaaattacagcacaaagagcatg SEQ ID NO: 198
embl|DW249099
Fm106 Festuca mairei EST Festuca mairei
cDNA clone SSBII082604_F08 3', mRNA sequence.

Cgagtcagcgccactactgtgccattacagttggagaggatgctgtcgtttcagcatataggttatcagaagacagaggcaggt
cattagttggagcaattttgtcaaggggtgtagctgcaacattttcaacaatatcatctttgtccaaaattctatggcggagtgaacc
atcaccaactaagaagccacggccaaaacctcaatcctttgcaaaacttcacctctgacatg SEQ ID NO: 199
embl|DW249100
Fm107 Festuca mairei EST Festuca mairei
cDNA clone SSBII082604_F10 3', mRNA sequence.

cgaggttcgcgttttggagttggagaaacctggtggacgttgggagacaaggtccactattccaatgcaaccatttgaaaatgct
ctgactgtgcgcattgttacattacataacacaaccaccaaggaaaatgaaaccctgatggccatcgggactgcttatgtccaag
gagaggatgtagctgctagaggacgggtgcttctgttctctttcacgaaaagtgaaaattctcaaaatctggtgacagaagtctac
tcaaaagagagtaaaggtgctgtatcagctgttgcatcgcttcaaggtcatcttgtgatagcttctggcccaaaaatcacattgaac
aaatggtccggttctgaattgacagctgttgcattctatgatgccccttttgcatg

SEQ ID NO: 200

Figure 9U embl|DW249101
Fm108 Festuca mairei EST Festuca mairei
cDNA clone SSBII082604_G01 3', mRNA sequence.

catgcctcatctataggcaagaaggcagtagcctttgactggatgtccataaatgcgccatttgaagtagtcatgaatactgttcctt
taatgagtgagccgatttcagtgtcg SEQ ID NO: 201
embl|DW249102
Fm109 Festuca mairei EST Festuca mairei
cDNA clone SSBII082604_G02 3', mRNA sequence.

catgttcacgcctagctggatctgaacccttactgtgcctggaagcaggaggtctacttccccgaatccagcagcagatgatcgc
agtcg SEQ ID NO: 202
embl|DW249103
Fm110 Festuca mairei EST Festuca mairei
cDNA clone SSBII082604_G03 3', mRNA sequence.

catgcttccatctgcaagtgaggattccacaacactgcatctgaccaatttgtatttgagatgacaattttgtcacccaatccattgtc
cagggtaagctcactcggtgcgccaaggtaaacgcagtcg SEQ ID NO: 203
embl|DW249104
Fm111 Festuca mairei EST Festuca mairei
cDNA clone SSBII082604_G04 3', mRNA sequence.

catgccatgtgaccatcacacaggatgcggatgctgatcagatgcttgacaaggtcattgggtacatcaaggcagagtacaaca
tcagtcatgtgaccattcaggtcg SEQ ID NO: 204
embl|DW249105
Fm112 Festuca mairei EST Festuca mairei
cDNA clone SSBII082604_G06 3', mRNA sequence.

cgagacactggctacagtgccctcaagctgctcaaggcgctactagcactctctccataggtagatataagatagctcgccggc
caatggatcagtagctgtagttcttgacgaacatg SEQ ID NO: 205
embl|DW249106
Fm113 Festuca mairei EST Festuca mairei
cDNA clone SSBII082604_G07 3', mRNA sequence.

Figure 9V cgagaagtccgggcacaggttcctgtgggtgctgcgtgcgcctcctgccttcgctgcggccgccgctgaacggatgcggcg
ctttctctcctcccagaggggttcttggcacggaccgcagacaggggcctcgtggtgaccgcgtcctgggtgccgcaggtgga
cgtgcggcgtcacgcctccactggtgccttcgtaacgcactgcggatggaactcaacactggaggcaggcgaccggcatg SEQ ID NO: 206
embl|DW249107
Fm114 Festuca mairei EST Festuca mairei
cDNA clone SSBII082604_G08 3', mRNA sequence.

cgagtcacgatgagtcctgaacgagtgttttcatcttcataatggatatgttgcatggcattttcaaagcttttccctcaatttgcttcc
cggccaatgcgacagaactggtacaacaaatttgttaagagcagcccatatgatatcttgtcccagtggatgtggacagtacaga
tcctccttagcacattggttccgagccttgtcccaatcaacctcatcataggggtactttatagagctccttccgtaagttcaatacaac
tggtgtaattgggccaacaaacctctttccatatacgtaagacatgggaaagtataccattcggcaatgggaccacatg SEQ ID NO: 207
embl|DW249108
Fm115 Festuca mairei EST Festuca mairei
cDNA clone SSBII082604_G09 3', mRNA sequence.

cgagttacaattatatgagtactactgaccagacctgtgtatactggaaagaactgggtcgctaagaggctgctgagaaagaatta
cctacaagccgtggattacatggtgaagattgcttttatggagagagaaaaaaggagaaaaatcagagatatgtgtatgttatat
gtactctcagcaggggaacaacaaaaacgcagcctccctgtggatcctcctattctctaccagtatgatcttgtccagcttcgcctt
gcaccactgcagctgctcgctggtgatcctcggcatccgcagcacccgcgccaccagccgcatg SEQ ID NO: 208
embl|DW249109
Fm116 Festuca mairei EST Festuca mairei
cDNA clone SSBII082604_G10 3', mRNA sequence.

catgcacccggagtggcaagagcaggcaagaaaggaagtgttgcaccacttcggaagaatcacaccagactttgagaactag
agtcggctgaagatagtaacgatggttctatatgaggttcttaggttgtacccgccagcaatctttgttaccagaagaacatacaag
acaatggagcttggtggcatcacatatccggcaggagtgaaccttatgttgcccattctctttatccaccatgaccccaatatatgg
ggaaaagatgcaagcgagttcaatccacagaggtttgctgatggcatctcaagtgccgtgaagcatccggctgcgttcttcccatt
tggagggggtcctcg SEQ ID NO: 209
embl|DW249110
Fm117 Festuca mairei EST Festuca mairei
cDNA clone SSBII082604_H02 3', mRNA sequence.

cgactgtccatgcgattgaaatcggtttgtaacctgaccatggattttctgaattccacttcttcaatccatgatccatcaaagtatgtc
cggtgcaaatgccctgggtctcaactctcacaacacccttcttaaatgtgaagtactcaggatgaactaaggccgtaaagctcaca
ggatcatggaggaaaatcccatggaagccgtcagacttggtatgccaatctctgtagaacttgcacatg SEQ ID NO: 210
embl|DW249111

Figure 9W

Fm118 Festuca mairei EST Festuca mairei
cDNA clone SSBII082604_H03 3', mRNA sequence.

catgccataaaggctcatatatcctactactctacaacttgagctgcctatacaaacgtattacatctgtggtctagtctggactacgt
agatcttcccatccttcactactccctcaacgtcctgtggtgacccatagagctcctcaatggcatggccagcccgtgcaatgctt
gagagaattgagcttcggaatccagagtctgtgatgagagcgtcggtcgtgtagtcg SEQ ID NO: 211
embl|DW249112
Fm119 Festuca mairei EST Festuca mairei
cDNA clone SSBII082604_H05 3', mRNA sequence.

catgcctgacatggcgaacccatccaaattgcaaagaggatttgggaagtttctgacaacctttcctgcaaatatcttggtagcca
caatgctcaggggccccaatattgtttgattcttcaaagcacctgctaacagttcatgagactccaaggaacgctcagcttgcttga
tcatctcatctaaacatgctttctcctccaaagtgagttgcacatccttcatctcacactggactgatgccatttcccgcgtcg SEQ ID NO: 212
embl|DW249113
Fm120 Festuca mairei EST Festuca mairei
cDNA clone SSBII082604_H06 3', mRNA sequence.

catgtgatccaggcgccaccctttatgtccaccttgtaacgaggaggaaggctccgcatgagcttcacacgtaagcaaaggcca
ataatagtcgccatactgcaatgctccactgttggggtgaaagtaacccgcacatgactaagatcatcgctgatctcg SEQ ID NO: 213
embl|DW249114
Fm121 Festuca mairei EST Festuca mairei
cDNA clone SSBII082604_H07 3', mRNA sequence.

Cgagatctgcagtctattgtgttgtatgatcaaaatggtaagtttgtgggggttcgtcggccaagctcaaaactccccattgaaatc
aatggtaatgaaatactaattgaagacgctattggcagtactggtctggatcttaagaccgatccaggaattcctgtcgtgtatgct
ggatttggcgcgctcatgttgacgacctgcattagctatctttcgcatg SEQ ID NO: 214
embl|DW249115
Fm122 Festuca mairei EST Festuca mairei
cDNA clone SSBII082604_H08 3', mRNA sequence.

catgtgctctggatgtaccagtgtcgctggcgaagggaatgcaggccaagcttatcggtgatttcagcagcgttcatggcattag
gaagatcttgtttgtttgcaaacaccagaagcacagcatcacgcaactcatcctcattgagcattcggtgaagctcatctctggcct
caacaacacgctctctgtcgttgctgtccaccacaaaaataaggccctgggtgttctggaagtagtgcctccacaggggcctgat
cttgtcctgaccccgacatcccaaactgtgaaactaatgttcttgtactcg SEQ ID NO: 215
embl|DW249116
Fm123 Festuca mairei EST Festuca mairei

Figure 9X cDNA clone SSBII082604_H09 3', mRNA sequence.

catgtacttaccagctaggtgttggttcggtcgtcgttaagaagcatttaaccacagcttaattgaagtgatcgtgatgagaaagta
agccaaactagggtaggtagacggatggatccgggacgtccgtccagcagctcccggcgttccagtacgcggccggcgacg
cgtcgtcgccgagctcg SEQ ID NO: 216
embl|DW249117
Fm124 Festuca mairei EST Festuca mairei
cDNA clone SSBII082604_H10 3', mRNA sequence.

Ccagggtttgcacccaatgtacgacgaacgtgtgagagacctccttgatttcagcatctacttagacatcagcaatgaggttaagt
ttgcatggaaaattcagagagacatggcagagcgtgggcacagccttgaaagcatcaaggctagcattgaagccaggaaacc
aaattttgatgcatttattcgtagtgccttttgccatctgaaaacaataattgtttgccataaacccaacttaacatggggcatg

Figure 9Y

| Group 1 | Group 2 | Group 3 | Group 4 |
|---|---|---|---|
| Tall fescue cultivar ('Kentucky 31') | Perennial ryegrass cultivar ('Citation') | F1 hybrid (Atlas fescue x 'Calypso') | Backcross progeny G24 |
| Atlas fescue selection | Perennial ryegrass cultivar ('Calypso') | Backcross progeny (G15) | |
| F1 hybrid ('Calypso' x Atlas fescue) | Backcross progeny (G11a) | Backcross progeny (G30a) | |
| Amphiploid (from F1 hybrid, Atlas fescue x 'Citation II') | Backcross progeny (G16) | | |
| Backcross progeny (G6) | Backcross progeny (G26) | | |
| Backcross progeny (G11b) | Backcross progeny (G27a) | | |
| Backcross progeny (G14) | | | |
| Backcross progeny (G27b) | | | |
| Backcross progeny (G30b) | | | |

Figure 15

SEQUENCE LISTING

```
<160> NUMBER OF SEQ ID NOS: 306

<210> SEQ ID NO 1
<211> LENGTH: 85
<212> TYPE: DNA
<213> ORGANISM: Festuca mairei

<400> SEQUENCE: 1
catgcatagg acccagtaat ggactgtaga gtaagttgtc ccgcgtgcga cggcgtgtac      60
gcgtgttcgt gacacactga catcg                                           85

<210> SEQ ID NO 2
<211> LENGTH: 188
<212> TYPE: DNA
<213> ORGANISM: Festuca mairei

<400> SEQUENCE: 2
catgcgctgt tatttgccaa agctcgctgg ccattgtttt cccaccattg cccattcttg      60
gcacctcgca tcctgtcgtc actgagattg gaaagcgaaa tcagggccga ccgacggaca     120
cctccgacaa caacaacctc accaatcttg cacatcaagt cgtgacattc aatagacgta     180
agctttcg                                                             188

<210> SEQ ID NO 3
<211> LENGTH: 122
<212> TYPE: DNA
<213> ORGANISM: Festuca mairei

<400> SEQUENCE: 3
catgccgtgc tacaggaggt agataatcag ggtgcctaat tttggatggt gttttgtatg      60
caatatggcg tttgtgtgtt agcatcacag attaatgagg gaatctctgg atgatttatt     120
cg                                                                   122

<210> SEQ ID NO 4
<211> LENGTH: 132
<212> TYPE: DNA
<213> ORGANISM: Festuca mairei

<400> SEQUENCE: 4
```

```
catgcaccgg agataggcac tgcggaagcc ctgtaggaga cgccctgcct ccgaattggc      60
atcaacgcct ggaggtagaa catgagctgg cgttgatgaa gtgacaccaa agcttttcat     120
ggtcgccctt cg                                                         132

<210> SEQ ID NO 5
<211> LENGTH: 101
<212> TYPE: DNA
<213> ORGANISM: Festuca mairei

<400> SEQUENCE: 5
catgtatcat gaaacaacgc atggcagtgt tccttctttt taggttatag cttcactggc      60
ttcgctagct ccaggtctcc aaaactcatc atctttttc g                         101

<210> SEQ ID NO 6
<211> LENGTH: 328
<212> TYPE: DNA
<213> ORGANISM: Festuca mairei

<400> SEQUENCE: 6
catgcgctct gacaagggc cgtggaagga ccctgaaatc ctaaaggtta atggttactc       60
tccgaagatt ttggagttca tgcatgacct gtgggaaaat gtagtgcaga cttgccactg    120
aactgaagga agtagcagta ctactacagc taaactcctg agcacaggtc cattaacatt    180
ttcctggttt gattcttcag atggtgcaat gtggaatggg gagatgcgga atgaacagct    240
cggaccttat atgcaggtat tatatggcct ttttcgccat attttctga acattgccgt     300 ctgatttcat acgcagaagc aagattcg                                       328

<210> SEQ ID NO 7
<211> LENGTH: 275
<212> TYPE: DNA
<213> ORGANISM: Festuca mairei

<400> SEQUENCE: 7
cgattccggt taaaggacgc tgggtgctgg gaaagcaggt cggcctcttt atggctgcct      60
gcgatggcca cgaaggcccc agcctgattc ctccccagat ttttggtctt gctgtgctgg    120
tgtcatgtaa ctcatgtttg gatgccgttc aacaacttgg tgaatgagca agttctgagc    180
tcaagtttcc atgtgtatga gtttccatgc gtacgagtgt ctgttacggt tccgttatac    240
cggtatttat tgtctgtgtt ggtttcttct gcatg                               275

<210> SEQ ID NO 8
<211> LENGTH: 291
<212> TYPE: DNA
<213> ORGANISM: Festuca mairei

<400> SEQUENCE: 8
catgtttcag aactactcta tgaaaagcaa tgtgaaactc tgggagttga acacaaacat      60
cacagagaag tttctgagaa tgcttctgtt tagtttttat gtgaagatat tcccgtttcc    120
aaagacatct tcggagaggt ccacatttcc acttgcagat tccacaaaaa gggagtttca    180
acactgctct atccatagga gggttcaact ctgtgagttg aatgcaatca tcacagagaa    240
gtttcagaga aggcttctgt ctagatttta tgcgaagata tacccgtttc g             291

<210> SEQ ID NO 9
<211> LENGTH: 75
<212> TYPE: DNA
<213> ORGANISM: Festuca mairei
```

```
<400> SEQUENCE: 9
catgtgcaaa tctggcttgc acccgttgta tgcacacgtt gaatctatca cacacgatca    60
tcacgtgatg cttcg                                                     75

<210> SEQ ID NO 10
<211> LENGTH: 77
<212> TYPE: DNA
<213> ORGANISM: Festuca mairei

<400> SEQUENCE: 10
cgatgatgcc gccgcaggag gcgtactcgc agcaggggca gtcaatgcag cagtggtcgc    60
cgtcgtacct gtacatg                                                   77

<210> SEQ ID NO 11
<211> LENGTH: 162
<212> TYPE: DNA
<213> ORGANISM: Festuca mairei

<400> SEQUENCE: 11
catgccaggt aatagccctg ttgaaacacc cagggcattg tgtacttgtt tattttctt     60 tttgcttgta aatgctacag cccctcggat gaatcacaac caccgtggtt gctatgtgtg   120
gtggtaatga ccagtctatt ggttgagccc agcataaatt cg                      162

<210> SEQ ID NO 12
<211> LENGTH: 186
<212> TYPE: DNA
<213> ORGANISM: Festuca mairei

<400> SEQUENCE: 12
catgcccccc acaggtgttg tcggtggtac atttgtcgga gatgctaatc taactgtaac    60
agcgggtatt acaccgtcgt atatcctaca agagggtgat cttactgccg actggactat   120
tacatttggg cagaacgatc aatttggtcg tcccgtccta gacggagcta gttttagaat   180
ctatcg                                                              186

<210> SEQ ID NO 13
<211> LENGTH: 113
<212> TYPE: DNA
<213> ORGANISM: Festuca mairei

<400> SEQUENCE: 13
cgattagatc gtgggaggaa tgtctttttc caattttgga agggcttaat catattaccg    60
acccggcaat attttcggat cggagggagt actgatcttt ttcaccgcgc atg          113

<210> SEQ ID NO 14
<211> LENGTH: 81
<212> TYPE: DNA
<213> ORGANISM: Festuca mairei

<400> SEQUENCE: 14
cgaaacggcg cgcagtaaac tccttcgttt acgcgcaagt ggagaaaatg ggccgggcgc    60
accgattcct tcctccacat g                                              81

<210> SEQ ID NO 15
<211> LENGTH: 138
<212> TYPE: DNA
<213> ORGANISM: Festuca mairei

<400> SEQUENCE: 15
```

```
catgtgtaaa ggtgcataca aatctgaacc aagaattact tttaatgcat gaactgtgaa        60
catctaccgg atggtaggta tcattttcg tgctaagcgc aaatcttcgt aaaccatgta        120
gtcgttcagg actcatcg                                                    138

<210> SEQ ID NO 16
<211> LENGTH: 78
<212> TYPE: DNA
<213> ORGANISM: Festuca mairei

<400> SEQUENCE: 16
catgcagagg attgaacgac actagtatat gggtgtcctc gtagtgtttt cctttgcacg        60
tgggtgtcca cttattcg                                                    78

<210> SEQ ID NO 17
<211> LENGTH: 69
<212> TYPE: DNA
<213> ORGANISM: Festuca mairei

<400> SEQUENCE: 17
cgaatagcaa atggccgagg tccctgctgc atgaacctga tctgctgcga aatgagagct        60
gggcgcatg                                                              69

<210> SEQ ID NO 18
<211> LENGTH: 166
<212> TYPE: DNA
<213> ORGANISM: Festuca mairei

<400> SEQUENCE: 18
cgatggcagc tagggcgcta ggcagcgcgc tacggcagct ggcagccagc aggctcaagg        60
tgcgtggacg ggctaatcag ggcgtgcggg cgtgcgttgc aagcaggagg ccggaggctg        120
gcgttcaggc ggatgacgcg cagaaggctg ggccgaaagg tgcatg                     166

<210> SEQ ID NO 19
<211> LENGTH: 116
<212> TYPE: DNA
<213> ORGANISM: Festuca mairei

<400> SEQUENCE: 19
catgcctagc tgtgcgcacc tgttcgccga tgagtacgcc accacgggca accaaacaat        60
acccgtcacg ctgccgcgcc tatggcagcc atcggatggc tattggggta ttatcg           116

<210> SEQ ID NO 20
<211> LENGTH: 545
<212> TYPE: DNA
<213> ORGANISM: Festuca mairei

<400> SEQUENCE: 20
catgtacact ggtataccac cggatacgta cattgaatta agaacaccgc catcagacgc        60
aactacttta acagaactat tgataccatc ggctgcccga acaccgtcat agcagaaatg       120
tccagtatgg ttaccgtacg tgtcgccacc aataatacca ccgatataag cggacttaac      180
gttggcaccc aggtataccg cacaggcatt atctccggta tagtagttac tgttgttgta      240
gtctttaata tcggtaacga tcattacacg acgagcattt tcaagccaga cgggattgcc      300
tacaaatgta gacatttgcc cgccagtcca actaatagag ttcacagacc cattagtggc      360
ggtagaacct ttgtcactaa tagctcagta gttattaccc tgacccaggg ctgaacaacc      420
cgtaaagtgg attgaagcta cttgtccact tgtatcttca ttttcaaaac gaatacaagc      480
```

```
atcattagtg ccgataccgc atggatcaaa tgtactgttg acaaaattca agtcttgaat    540
gatcg                                                                545

<210> SEQ ID NO 21
<211> LENGTH: 165
<212> TYPE: DNA
<213> ORGANISM: Festuca mairei

<400> SEQUENCE: 21
catgcatgaa tgccacatga atgcaagaaa ggtaaaaagg gtctaggtgt tactcttggg    60
atgttacacg tagtgtggtg cgaccatgaa cttggcgaag gcctggcggc caagcacgca    120
gtggaacggg ctgtggaagc tgacgacctc gttcaggact catcg                   165

<210> SEQ ID NO 22
<211> LENGTH: 211
<212> TYPE: DNA
<213> ORGANISM: Festuca mairei

<400> SEQUENCE: 22
catgcatata tgcagacatg acacataaca cagccgccac cggcgacatg gctgacagta    60
ctcatctagc tcatccgtac atcggctata agtacatcgg ctataagcgg tagcataatt    120
acagttgtgt agagaactgg tgagcactat cagtatgtac tatctactca ccagtagcta    180
gttcggttcg gctagagcgc cttacagatc g                                  211

<210> SEQ ID NO 23
<211> LENGTH: 126
<212> TYPE: DNA
<213> ORGANISM: Festuca mairei

<400> SEQUENCE: 23
catgtatgtg ttggacacca tgtatagggg cggatgggcg gttatgtagg gatctcatat    60
cagctatgat ctggttgctg ttccgtatct ttggatgacc accaggaggg gctcagcacc    120
cgctcg                                                              126

<210> SEQ ID NO 24
<211> LENGTH: 153
<212> TYPE: DNA
<213> ORGANISM: Festuca mairei

<400> SEQUENCE: 24
cgagtcaact caaaggttaa tttttgctgg ccttgctgta gagaagctag tgatgaaatt    60
aagcaaggta gcttgttgat taagttgtaa tcaagacagt aactagtata ggtagcccca    120
cacactactt tgcaggttca gtttagatgc atg                                153

<210> SEQ ID NO 25
<211> LENGTH: 68
<212> TYPE: DNA
<213> ORGANISM: Festuca mairei

<400> SEQUENCE: 25
catgtacaag tataacaccc accagatcgc ctcctctgct tcggatcagg agctcatgaa    60
agcgctcg                                                            68

<210> SEQ ID NO 26
<211> LENGTH: 97
<212> TYPE: DNA
<213> ORGANISM: Festuca mairei
```

```
<400> SEQUENCE: 26
cgatggcatt ggcgttcatg tccaggaagg caaggtgcca tctcagagag ctagcagacc    60
agcaaacggg aggagcccgt cgccgagcta caacatg                             97

<210> SEQ ID NO 27
<211> LENGTH: 147
<212> TYPE: DNA
<213> ORGANISM: Festuca mairei

<400> SEQUENCE: 27
catgtgtaca tttcctctgt actcctccct actccgacgc tagactgaat cgctgatcac    60
atatatccac ggtcaaaaca cttgcttcac tcttcctcct gcgcgtgaat ccgatggacc   120
ctgatgggga ggcccttggg gaagtcg                                       147

<210> SEQ ID NO 28
<211> LENGTH: 119
<212> TYPE: DNA
<213> ORGANISM: Festuca mairei

<400> SEQUENCE: 28
catgtgctaa ataaaacatt ttggatatgc tagtacaaat gtggtctgga tgctcgcata    60
tagaagcaag gtccataaga gcgacaattg gaagatcaag ctagcattgt gtggtctcg   119

<210> SEQ ID NO 29
<211> LENGTH: 108
<212> TYPE: DNA
<213> ORGANISM: Festuca mairei

<400> SEQUENCE: 29
cgagttcccg gccttctgat ccaatccaat ccaaggagtc gtgtcatgcc ttcctgattc    60
ctagctattc atttgctctt cccttacaga ataaactgtg ggagcatg               108

<210> SEQ ID NO 30
<211> LENGTH: 101
<212> TYPE: DNA
<213> ORGANISM: Festuca mairei

<400> SEQUENCE: 30
cgaccgtagg gctagtaata caattgtgtg gagccacttg gcttgtgagc atactataca    60
ctcccctaca catttatcat cccttactag aagtgcacat g                       101

<210> SEQ ID NO 31
<211> LENGTH: 299
<212> TYPE: DNA
<213> ORGANISM: Festuca mairei

<400> SEQUENCE: 31
catgctcacc acagggccaa ggaagaggcc aaagtgcccc tgaacgagtc caccctgctg    60
ctggatccat ccatccatct cctcctcaac ggacctacgg caccctgcct aattgcctag   120
atgtgttctc gtgtagcttc cctctgctcc tgctagttag ttttttttttt tttgaacagg   180 ctagttagct agtgtgatgc gtattgtctg ttggattcgc gtgctgtacg tgcctgaagc   240
tacgtatatg ttgtcgttgt cagcttgtaa gagtaatgtt ctgctagcca ggatcgtcg    299

<210> SEQ ID NO 32
<211> LENGTH: 169
<212> TYPE: DNA
<213> ORGANISM: Festuca mairei
```

```
<400> SEQUENCE: 32
catgcgcaac acggaaatta cacacatacg gagtataatt tacagataca atcaacactg      60
cgttcgtgcg aacatatatg tgaatttatc ggtggaacgc tcctcggaat cttgaaacga     120
tcaagcgccg gaaaccaccg ccgccgcagg ctgatcgccg ggaacgtcg                 169

<210> SEQ ID NO 33
<211> LENGTH: 71
<212> TYPE: DNA
<213> ORGANISM: Festuca mairei

<400> SEQUENCE: 33
catgctactt tggggcctcc aacgcactct cgatctgctg gattagctga tcagcaggca      60
acgctcactc g                                                          71

<210> SEQ ID NO 34
<211> LENGTH: 204
<212> TYPE: DNA
<213> ORGANISM: Festuca mairei

<400> SEQUENCE: 34
catgttttgg tttccagata attaacttgt gccggagtac gaatacgtcg tcaccccac       60 ccaggatagg tcctagtatt gataatctag ccggatgcaa tgcgctagtc gtatttaatt     120
agccactgtt ctctcgttgt gctgcagaat tgtaaagatg tgtaagctgt agtgcacatg     180
gagcagcttc agtaccagtt ctcg                                            204

<210> SEQ ID NO 35
<211> LENGTH: 177
<212> TYPE: DNA
<213> ORGANISM: Festuca mairei

<400> SEQUENCE: 35
catgttagcg taaaacacgt tcttgatcgg cttgcgctta atcccgataa ggtctgcgtt      60
ttcctggtga gggtcatggc cctctgtgta gaatcgcttg cccagttcgg gattcggcag     120
aaagtgagcg aaacatcgca tctgagcggc cgcagcatcg tagccgacca gtactcg        177

<210> SEQ ID NO 36
<211> LENGTH: 88
<212> TYPE: DNA
<213> ORGANISM: Festuca mairei

<400> SEQUENCE: 36
catgcccgtt ccaggcttcc agcagatctg ttgtcatcta ctcatctgtc agtgccgggt      60
gcgaaccaag gcctcccacc cgaactcg                                        88

<210> SEQ ID NO 37
<211> LENGTH: 161
<212> TYPE: DNA
<213> ORGANISM: Festuca mairei

<400> SEQUENCE: 37
catgctagga tgatgacgtt ggcaacagcg tcgcgttaga gtggggccgg gcgcgtggac      60
tgccgttagt aatgcgagct cgtacaacat ctacgagaag ctacccgtgg cgacgacgat    120
ggtcctcctc cgtggtcgtc acgatctcct ccaggtcgtc g                        161

<210> SEQ ID NO 38
<211> LENGTH: 335
```

```
<212> TYPE: DNA
<213> ORGANISM: Festuca mairei

<400> SEQUENCE: 38
cgacaacgag gcaacgtggc ttgatttgag aggaccaagc ctggtgtgct ggccaggtag    60
aagtgctact cgttttgctc actggtaagg cacgtcgccc agatattttt agctaatgcc   120
taagcggcgg gcggcaagat attttacaca gtttgagcgg ctagattttt agctgacttg   180
ggaaccgacg ttgagcacct atatatagat agccttgccg cttctgcggc tgctaacatc   240
agtagactgc aaatagagct ggacctacca aacgagagtg agagagtaga gaaagagagc   300
gagagaaggg ccggtgaaga tcattcatgc gcatg                              335

<210> SEQ ID NO 39
<211> LENGTH: 23
<212> TYPE: DNA
<213> ORGANISM: Festuca mairei

<400> SEQUENCE: 39
cgagggaacg cgtctacaac atg                                            23

<210> SEQ ID NO 40
<211> LENGTH: 28
<212> TYPE: PRT
<213> ORGANISM: Festuca mairei

<400> SEQUENCE: 40

Arg Cys Gln Cys Val Thr Asn Thr Arg Thr Arg Arg Thr Arg Asp
1               5                   10                  15

Asn Leu Leu Tyr Ser Pro Leu Leu Gly Pro Met His
            20                  25

<210> SEQ ID NO 41
<211> LENGTH: 28
<212> TYPE: PRT
<213> ORGANISM: Festuca mairei

<400> SEQUENCE: 41

Asp Val Ser Val Ser Arg Thr Arg Val His Ala Val Ala Arg Gly Thr
1               5                   10                  15

Thr Tyr Ser Thr Val His Tyr Trp Val Leu Cys Met
            20                  25

<210> SEQ ID NO 42
<211> LENGTH: 27
<212> TYPE: PRT
<213> ORGANISM: Festuca mairei

<400> SEQUENCE: 42

Met Ser Val Cys His Glu His Ala Tyr Thr Pro Ser His Ala Gly Gln
1               5                   10                  15

Leu Thr Leu Gln Ser Ile Thr Gly Ser Tyr Ala
            20                  25

<210> SEQ ID NO 43
<211> LENGTH: 62
<212> TYPE: PRT
<213> ORGANISM: Festuca mairei

<400> SEQUENCE: 43

Cys Ala Val Ile Cys Gln Ser Ser Leu Ala Ile Val Phe Pro Pro Leu
1               5

-continued

Pro Ile Leu Gly Thr Ser His Pro Val Val Thr Glu Ile Gly Lys Arg
            20                  25                  30

Asn Gln Gly Arg Pro Thr Asp Thr Ser Asp Asn Asn Leu Thr Asn
            35                  40                  45

Leu Ala His Gln Val Val Thr Phe Asn Arg Arg Lys Leu Ser
 50                  55                  60

<210> SEQ ID NO 44
<211> LENGTH: 62
<212> TYPE: PRT
<213> ORGANISM: Festuca mairei

<400> SEQUENCE: 44

Arg Lys Leu Thr Ser Ile Glu Cys His Asp Leu Met Cys Lys Ile Gly
 1               5                  10                  15

Glu Val Val Val Gly Gly Val Arg Ser Ala Leu Ile Ser Leu
            20                  25                  30

Ser Asn Leu Ser Asp Asp Arg Met Arg Gly Ala Lys Asn Gly Gln Trp
            35                  40                  45

Trp Glu Asn Asn Gly Gln Arg Ala Leu Ala Asn Asn Ser Ala
 50                  55                  60

<210> SEQ ID NO 45
<211> LENGTH: 44
<212> TYPE: PRT
<213> ORGANISM: Festuca mairei

<400> SEQUENCE: 45

Arg Arg Ala Thr Met Glu Ser Phe Gly Val Thr Ser Thr Pro Ala
 1               5                  10                  15

His Val Leu Pro Pro Gly Val Asp Ala Asn Ser Glu Ala Gly Arg Leu
            20                  25                  30

Leu Gln Gly Phe Arg Ser Ala Tyr Leu Arg Cys Met
            35                  40

<210> SEQ ID NO 46
<211> LENGTH: 43
<212> TYPE: PRT
<213> ORGANISM: Festuca mairei

<400> SEQUENCE: 46

Glu Gly Arg Pro Trp Lys Ala Leu Val Ser Leu His Gln Arg Gln Leu
 1               5                  10                  15

Met Phe Tyr Leu Gln Ala Leu Met Pro Ile Arg Arg Gln Gly Val Ser
            20                  25                  30

Tyr Arg Ala Ser Ala Val Pro Ile Ser Gly Ala
            35                  40

<210> SEQ ID NO 47
<211> LENGTH: 96
<212> TYPE: PRT
<213> ORGANISM: Festuca mairei

<400> SEQUENCE: 47

Met Phe Gln Asn Tyr Ser Met Lys Ser Asn Val Lys Leu Trp Glu Leu
 1               5                  10                  15

Asn Thr Asn Ile Thr Glu Lys Phe Leu Arg Met Leu Leu Phe Ser Phe
            20                  25                  30

Tyr Val Lys Ile Phe Pro Phe Pro Lys Thr Ser Ser Glu Arg Ser Thr
            35                  40                  45

```
Phe Pro Leu Ala Asp Ser Thr Lys Arg Glu Phe Gln His Cys Ser Ile
    50                  55                  60

His Arg Arg Val Gln Leu Cys Glu Leu Asn Ala Ile Ile Thr Glu Lys
65                  70                  75                  80

Phe Gln Arg Arg Leu Leu Ser Arg Phe Tyr Ala Lys Ile Tyr Pro Phe
                85                  90                  95

<210> SEQ ID NO 48
<211> LENGTH: 96
<212> TYPE: PRT
<213> ORGANISM: Festuca mairei

<400> SEQUENCE: 48

Lys Arg Val Tyr Leu Arg Ile Lys Ser Arg Gln Lys Pro Ser Leu Lys
1               5                   10                  15

Leu Leu Cys Asp Asp Cys Ile Gln Leu Thr Glu Leu Asn Pro Pro Met
            20                  25                  30

Asp Arg Ala Val Leu Lys Leu Pro Phe Cys Gly Ile Cys Lys Trp Lys
        35                  40                  45

Cys Gly Pro Leu Arg Arg Cys Leu Trp Lys Arg Glu Tyr Leu His Ile
    50                  55                  60

Lys Thr Lys Gln Lys His Ser Gln Lys Leu Leu Cys Asp Val Cys Val
65                  70                  75                  80

Gln Leu Pro Glu Phe His Ile Ala Phe His Arg Val Val Leu Lys His
                85                  90                  95

<210> SEQ ID NO 49
<211> LENGTH: 24
<212> TYPE: PRT
<213> ORGANISM: Festuca mairei

<400> SEQUENCE: 49

Met Cys Lys Ser Gly Leu His Pro Leu Tyr Ala His Val Glu Ser Ile
1               5                   10                  15

Thr His Asp His His Val Met Leu
            20

<210> SEQ ID NO 50
<211> LENGTH: 24
<212> TYPE: PRT
<213> ORGANISM: Festuca mairei

<400> SEQUENCE: 50

Lys His His Val Met Ile Val Cys Asp Arg Phe Asn Val Cys Ile Gln
1               5                   10                  15

Arg Val Gln Ala Arg Phe Ala His
            20

<210> SEQ ID NO 51
<211> LENGTH: 25
<212> TYPE: PRT
<213> ORGANISM: Festuca mairei

<400> SEQUENCE: 51

Asp Asp Ala Ala Ala Gly Gly Val Leu Ala Ala Gly Ala Val Asn Ala
1               5                   10                  15

Ala Val Val Ala Val Val Pro Val His
            20                  25

<210> SEQ ID NO 52
<211> LENGTH: 25

<212> TYPE: PRT
<213> ORGANISM: Festuca mairei

<400> SEQUENCE: 52

Met Met Pro Pro Gln Glu Ala Tyr Ser Gln Gln Gly Gln Ser Met Gln
1               5                   10                  15

Gln Trp Ser Pro Ser Tyr Leu Tyr Met
            20                  25

<210> SEQ ID NO 53
<211> LENGTH: 25
<212> TYPE: PRT
<213> ORGANISM: Festuca mairei

<400> SEQUENCE: 53

Met Tyr Arg Tyr Asp Gly Asp His Cys Cys Ile Asp Cys Pro Cys Cys
1               5                   10                  15

Glu Tyr Ala Ser Cys Gly Gly Ile Ile
            20                  25

<210> SEQ ID NO 54
<211> LENGTH: 25
<212> TYPE: PRT
<213> ORGANISM: Festuca mairei

<400> SEQUENCE: 54

Cys Thr Gly Thr Thr Ala Thr Thr Ala Ala Leu Thr Ala Pro Ala Ala
1               5                   10                  15

Ser Thr Pro Pro Ala Ala Ala Ser Ser
            20                  25

<210> SEQ ID NO 55
<211> LENGTH: 61
<212> TYPE: PRT
<213> ORGANISM: Festuca mairei

<400> SEQUENCE: 55

Met Pro Pro Thr Gly Val Val Gly Gly Thr Phe Val Gly Asp Ala Asn
1               5                   10                  15

Leu Thr Val Thr Ala Gly Ile Thr Pro Ser Tyr Ile Leu Gln Glu Gly
            20                  25                  30

Asp Leu Thr Ala Asp Trp Thr Ile Thr Phe Gly Gln Asn Asp Gln Phe
        35                  40                  45

Gly Arg Pro Val Leu Asp Gly Ala Ser Phe Arg Ile Tyr
    50                  55                  60

<210> SEQ ID NO 56
<211> LENGTH: 37
<212> TYPE: PRT
<213> ORGANISM: Festuca mairei

<400> SEQUENCE: 56

Arg Leu Asp Arg Gly Arg Asn Val Phe Phe Gln Phe Trp Lys Gly Leu
1               5                   10                  15

Ile Ile Leu Pro Thr Arg Gln Tyr Phe Arg Ile Gly Gly Ser Thr Asp
            20                  25                  30

Leu Phe His Arg Ala
        35

<210> SEQ ID NO 57
<211> LENGTH: 26
<212> TYPE: PRT

```
<213> ORGANISM: Festuca mairei

<400> SEQUENCE: 57

Glu Thr Ala Arg Ser Lys Leu Leu Arg Leu Arg Ala Ser Gly Glu Asn
1               5                   10                  15
Gly Pro Gly Ala Pro Ile Pro Ser Ser Thr
            20                  25

<210> SEQ ID NO 58
<211> LENGTH: 26
<212> TYPE: PRT
<213> ORGANISM: Festuca mairei

<400> SEQUENCE: 58

Lys Arg Arg Ala Val Asn Ser Phe Val Tyr Ala Gln Val Glu Lys Met
1               5                   10                  15
Gly Arg Ala His Arg Phe Leu Pro Pro His
            20                  25

<210> SEQ ID NO 59
<211> LENGTH: 27
<212> TYPE: PRT
<213> ORGANISM: Festuca mairei

<400> SEQUENCE: 59

His Val Glu Glu Gly Ile Gly Ala Pro Gly Pro Phe Ser Pro Leu Ala
1               5                   10                  15
Arg Lys Arg Arg Ser Leu Leu Arg Ala Val Ser
            20                  25

<210> SEQ ID NO 60
<211> LENGTH: 26
<212> TYPE: PRT
<213> ORGANISM: Festuca mairei

<400> SEQUENCE: 60

Met Trp Arg Lys Glu Ser Val Arg Pro Ala His Phe Leu His Leu Arg
1               5                   10                  15
Val Asn Glu Gly Val Tyr Cys Ala Pro Phe
            20                  25

<210> SEQ ID NO 61
<211> LENGTH: 45
<212> TYPE: PRT
<213> ORGANISM: Festuca mairei

<400> SEQUENCE: 61

Met Ser Pro Glu Arg Leu His Gly Leu Arg Arg Phe Ala Leu Ser Thr
1               5                   10                  15
Lys Asn Asp Thr Tyr His Pro Val Asp Val His Ser Ser Cys Ile Lys
            20                  25                  30
Ser Asn Ser Trp Phe Arg Phe Val Cys Thr Phe Thr His
        35                  40                  45

<210> SEQ ID NO 62
<211> LENGTH: 25
<212> TYPE: PRT
<213> ORGANISM: Festuca mairei

<400> SEQUENCE: 62

Asn Lys Trp Thr Pro Thr Cys Lys Gly Lys His Tyr Glu Asp Thr His
1               5                   10                  15
```

Ile Leu Val Ser Phe Asn Pro Leu His
            20                  25

<210> SEQ ID NO 63
<211> LENGTH: 23
<212> TYPE: PRT
<213> ORGANISM: Festuca mairei

<400> SEQUENCE: 63

Arg Ile Ala Asn Gly Arg Gly Pro Cys Cys Met Asn Leu Ile Cys Cys
1               5                   10                  15

Glu Met Arg Ala Gly Arg Met
            20

<210> SEQ ID NO 64
<211> LENGTH: 22
<212> TYPE: PRT
<213> ORGANISM: Festuca mairei

<400> SEQUENCE: 64

Asn Ser Lys Trp Pro Arg Ser Leu Leu His Glu Pro Asp Leu Leu Arg
1               5                   10                  15

Asn Glu Ser Trp Ala His
            20

<210> SEQ ID NO 65
<211> LENGTH: 23
<212> TYPE: PRT
<213> ORGANISM: Festuca mairei

<400> SEQUENCE: 65

His Ala Pro Ser Ser His Phe Ala Ala Asp Gln Val His Ala Ala Gly
1               5                   10                  15

Thr Ser Ala Ile Cys Tyr Ser
            20

<210> SEQ ID NO 66
<211> LENGTH: 22
<212> TYPE: PRT
<213> ORGANISM: Festuca mairei

<400> SEQUENCE: 66

Met Arg Pro Ala Leu Ile Ser Gln Gln Ile Arg Phe Met Gln Gln Gly
1               5                   10                  15

Pro Arg Pro Phe Ala Ile
            20

<210> SEQ ID NO 67
<211> LENGTH: 22
<212> TYPE: PRT
<213> ORGANISM: Festuca mairei

<400> SEQUENCE: 67

Cys Ala Gln Leu Ser Phe Arg Ser Arg Ser Gly Ser Cys Ser Arg Asp
1               5                   10                  15

Leu Gly His Leu Leu Phe
            20

<210> SEQ ID NO 68
<211> LENGTH: 54
<212> TYPE: PRT
<213> ORGANISM: Festuca mairei

<400> SEQUENCE: 68

```
Met Ala Arg Ala Leu Gly Ser Ala Leu Arg Gln Leu Ala Ala Ser
1               5                   10                  15

Arg Leu Lys Val Arg Gly Arg Ala Asn Gln Gly Val Arg Ala Cys Val
            20                  25                  30

Ala Ser Arg Arg Pro Glu Ala Gly Val Gln Ala Asp Asp Ala Gln Lys
                35                  40                  45

Ala Gly Pro Lys Gly Ala
            50
```

<210> SEQ ID NO 69
<211> LENGTH: 38
<212> TYPE: PRT
<213> ORGANISM: Festuca mairei

<400> SEQUENCE: 69

```
Met Pro Ser Cys Ala His Leu Phe Ala Asp Glu Tyr Ala Thr Thr Gly
1               5                   10                  15

Asn Gln Thr Ile Pro Val Thr Leu Pro Arg Leu Trp Gln Pro Ser Asp
            20                  25                  30

Gly Tyr Trp Gly Ile Ile
            35
```

<210> SEQ ID NO 70
<211> LENGTH: 38
<212> TYPE: PRT
<213> ORGANISM: Festuca mairei

<400> SEQUENCE: 70

```
Cys Leu Ala Val Arg Thr Cys Ser Pro Met Ser Thr Pro Pro Arg Ala
1               5                   10                  15

Thr Lys Gln Tyr Pro Ser Arg Cys Arg Ala Tyr Gly Ser His Arg Met
            20                  25                  30

Ala Ile Gly Val Leu Ser
            35
```

<210> SEQ ID NO 71
<211> LENGTH: 22
<212> TYPE: PRT
<213> ORGANISM: Festuca mairei

<400> SEQUENCE: 71

```
Met Tyr Lys Tyr Asn Thr His Gln Ile Ala Ser Ser Ala Ser Asp Gln
1               5                   10                  15

Glu Leu Met Lys Ala Leu
            20
```

<210> SEQ ID NO 72
<211> LENGTH: 22
<212> TYPE: PRT
<213> ORGANISM: Festuca mairei

<400> SEQUENCE: 72

```
Glu Arg Phe His Glu Leu Leu Ile Arg Ser Arg Gly Gly Asp Leu Val
1               5                   10                  15

Gly Val Ile Leu Val His
            20
```

<210> SEQ ID NO 73
<211> LENGTH: 32
<212> TYPE: PRT
<213> ORGANISM: Festuca mairei

<400> SEQUENCE: 73

Asp Gly Ile Gly Val His Val Gln Glu Gly Lys Val Pro Ser Gln Arg
1               5                   10                  15

Ala Ser Arg Pro Ala Asn Gly Arg Ser Pro Ser Pro Tyr Asn Met
            20                  25                  30

<210> SEQ ID NO 74
<211> LENGTH: 31
<212> TYPE: PRT
<213> ORGANISM: Festuca mairei

<400> SEQUENCE: 74

Met Ala Leu Ala Phe Met Ser Arg Lys Ala Arg Cys His Leu Arg Glu
1               5                   10                  15

Leu Ala Asp Gln Gln Thr Gly Gly Ala Arg Arg Ala Thr Thr
            20                  25                  30

<210> SEQ ID NO 75
<211> LENGTH: 32
<212> TYPE: PRT
<213> ORGANISM: Festuca mairei

<400> SEQUENCE: 75

His Val Val Ala Arg Arg Ala Pro Pro Val Cys Trp Ser Ala Ser
1               5                   10                  15

Ser Leu Arg Trp His Leu Ala Phe Leu Asp Met Asn Ala Asn Ala Ile
            20                  25                  30

<210> SEQ ID NO 76
<211> LENGTH: 35
<212> TYPE: PRT
<213> ORGANISM: Festuca mairei

<400> SEQUENCE: 76

Ser Ser Arg Pro Ser Asp Pro Ile Gln Ser Lys Glu Ser Cys His Ala
1               5                   10                  15

Phe Leu Ile Pro Ser Tyr Ser Phe Ala Leu Pro Leu Gln Asn Lys Leu
            20                  25                  30

Trp Glu His
        35

<210> SEQ ID NO 77
<211> LENGTH: 33
<212> TYPE: PRT
<213> ORGANISM: Festuca mairei

<400> SEQUENCE: 77

Asp Arg Arg Ala Ser Asn Thr Ile Val Trp Ser His Leu Ala Cys Glu
1               5                   10                  15

His Thr Ile His Ser Pro Thr His Leu Ser Ser Leu Thr Arg Ser Ala
            20                  25                  30

His

<210> SEQ ID NO 78
<211> LENGTH: 33
<212> TYPE: PRT
<213> ORGANISM: Festuca mairei

<400> SEQUENCE: 78

Thr Val Gly Leu Val Ile Gln Leu Cys Gly Ala Thr Trp Leu Val Ser
1               5                   10                  15

Ile Leu Tyr Thr Pro Leu His Ile Tyr His Pro Leu Leu Glu Val His
            20                  25                  30

Met

<210> SEQ ID NO 79
<211> LENGTH: 33
<212> TYPE: PRT
<213> ORGANISM: Festuca mairei

<400> SEQUENCE: 79

Cys Ala Leu Leu Val Arg Asp Asp Lys Cys Val Gly Glu Cys Ile Val
1               5                   10                  15

Cys Ser Gln Ala Lys Trp Leu His Thr Ile Val Leu Leu Ala Leu Arg
            20                  25                  30

Ser

<210> SEQ ID NO 80
<211> LENGTH: 23
<212> TYPE: PRT
<213> ORGANISM: Festuca mairei

<400> SEQUENCE: 80

His Ala Thr Leu Gly Pro Pro Thr His Ser Arg Ser Ala Gly Leu Ala
1               5                   10                  15

Asp Gln Gln Ala Thr Leu Thr
            20

<210> SEQ ID NO 81
<211> LENGTH: 7
<212> TYPE: PRT
<213> ORGANISM: Festuca mairei

<400> SEQUENCE: 81

Arg Gly Asn Ala Ser Thr Thr
1               5

<210> SEQ ID NO 82
<211> LENGTH: 7
<212> TYPE: PRT
<213> ORGANISM: Festuca mairei

<400> SEQUENCE: 82

Glu Gly Thr Arg Leu Gln His
1               5

<210> SEQ ID NO 83
<211> LENGTH: 7
<212> TYPE: PRT
<213> ORGANISM: Festuca mairei

<400> SEQUENCE: 83

Arg Glu Arg Val Tyr Asn Met
1               5

<210> SEQ ID NO 84
<211> LENGTH: 7
<212> TYPE: PRT
<213> ORGANISM: Festuca mairei

<400> SEQUENCE: 84

His Val Val Asp Ala Phe Pro
1               5

<210> SEQ ID NO 85
<211> LENGTH: 7
<212> TYPE: PRT
<213> ORGANISM: Festuca mairei

<400> SEQUENCE: 85

Cys Cys Arg Arg Val Pro Ser
1               5

<210> SEQ ID NO 86
<211> LENGTH: 59
<212> TYPE: PRT
<213> ORGANISM: Festuca mairei

<400> SEQUENCE: 86

His Val Ser Val Lys His Val Leu Asp Arg Leu Ala Leu Asn Pro Asp
1               5                   10                  15

Lys Val Cys Val Phe Leu Val Arg Val Met Ala Leu Cys Val Glu Ser
            20                  25                  30

Leu Ala Gln Phe Gly Ile Arg Gln Lys Val Ser Glu Thr Ser His Leu
        35                  40                  45

Ser Gly Arg Ser Ile Val Ala Asp Gln Tyr Ser
    50                  55

<210> SEQ ID NO 87
<211> LENGTH: 59
<212> TYPE: PRT
<213> ORGANISM: Festuca mairei

<400> SEQUENCE: 87

Arg Val Leu Val Gly Tyr Asp Ala Ala Ala Gln Met Arg Cys Phe
1               5                   10                  15

Ala His Phe Leu Pro Asn Pro Glu Leu Gly Lys Arg Phe Tyr Thr Glu
            20                  25                  30

Gly His Asp Pro His Gln Glu Asn Ala Asp Leu Ile Gly Ile Lys Arg
        35                  40                  45

Lys Pro Ile Lys Asn Val Phe Tyr Ala Asn Met
    50                  55

<210> SEQ ID NO 88
<211> LENGTH: 58
<212> TYPE: PRT
<213> ORGANISM: Festuca mairei

<400> SEQUENCE: 88

Glu Tyr Trp Ser Ala Thr Met Leu Arg Pro Leu Arg Cys Asp Val Ser
1               5                   10                  15

Leu Thr Phe Cys Arg Ile Pro Asn Trp Ala Ser Asp Ser Thr Gln Arg
            20                  25                  30

Ala Met Thr Leu Thr Arg Lys Thr Gln Thr Leu Ser Gly Leu Ser Ala
        35                  40                  45

Ser Arg Ser Arg Thr Cys Phe Thr Leu Thr
    50                  55

<210> SEQ ID NO 89
<211> LENGTH: 29
<212> TYPE: PRT
<213> ORGANISM: Festuca mairei

<400> SEQUENCE: 89

His Ala Arg Ser Arg Leu Pro Ala Asp Leu Leu Ser Ser Thr His Leu

```
                1               5                  10                 15
Ser Val Pro Gly Ala Asn Gln Gly Leu Pro Pro Glu Leu
                20                 25

<210> SEQ ID NO 90
<211> LENGTH: 29
<212> TYPE: PRT
<213> ORGANISM: Festuca mairei

<400> SEQUENCE: 90

Met Pro Val Pro Gly Phe Gln Gln Ile Cys Cys His Leu Leu Ile Cys
1               5                  10                 15

Gln Cys Arg Val Arg Thr Lys Ala Ser His Pro Asn Ser
                20                 25

<210> SEQ ID NO 91
<211> LENGTH: 28
<212> TYPE: PRT
<213> ORGANISM: Festuca mairei

<400> SEQUENCE: 91

Cys Pro Phe Gln Ala Ser Ser Arg Ser Val Val Ile Tyr Ser Ser Val
1               5                  10                 15

Ser Ala Gly Cys Glu Pro Arg Pro Pro Thr Arg Thr
                20                 25

<210> SEQ ID NO 92

<400> SEQUENCE: 92

000

<210> SEQ ID NO 93
<211> LENGTH: 222
<212> TYPE: DNA
<213> ORGANISM: Festuca mairei

<400> SEQUENCE: 93
catgcacaga ggacactcca tgggttgcag ccaccggatg ccaagctgtt ccccgagaag     60
gcaggctaca cgagctgaa tcagatggct gaagaggcaa acggagagc tgaaattgca     120 aggctcaggg agcttcacac tctcaagggg cacgtagagt cggttgtgaa gctgaagggc    180
ctggacattg acaccattca gcaatcttac acagtgtgat cg                        222

<210> SEQ ID NO 94
<211> LENGTH: 194
<212> TYPE: DNA
<213> ORGANISM: Festuca mairei

<400> SEQUENCE: 94
catgttcgtc aacgaggttt acacggttct gaccgatccg gtgcagcgtg ccgtgtatga     60
tgagctccat ggctacgcag caacggccgc caacccttc tttaatgaca gtgcgcccaa    120
ggatcacgtc tttgttgacg agtttacctg tataggatgc aagatttgtg ccaatgtgtg    180
ccccaatgtg ttcg                                                       194

<210> SEQ ID NO 95
<211> LENGTH: 228
<212> TYPE: DNA
<213> ORGANISM: Festuca mairei

<400> SEQUENCE: 95
```

```
catgcgcctc taaatcttca gcatggcctc caacgcgcga agtacgtcat cacgggtaac    60 tataccatc acttggttgt cctgatttac tattggtaat ctgtggatct tcttcttgag    120
catcagagct gcggcatcgg tcactgttct atcacatgat agcgtgatcg ctggagaggt   180
catcacttgt gcaatctttg tccttgaccc atatgaagcc cttgttcg                228
```

<210> SEQ ID NO 96
<211> LENGTH: 212
<212> TYPE: DNA
<213> ORGANISM: Festuca mairei

<400> SEQUENCE: 96

```
catgttcctt ctacgttgat aggtacggtg catacacaca caattatatg tggaaataaa    60
agtaaaaccc ggaaagcgga gttgtcatca aaaactaaac caagagactc catatggatt   120
cctagctcgc agcttatgcc ttgccggact cctcacagcc tggtggcttg aaggcgatga   180
agctgacgca ctgcacctga cggatgttat cg                                  212
```

<210> SEQ ID NO 97
<211> LENGTH: 152
<212> TYPE: DNA
<213> ORGANISM: Festuca mairei

<400> SEQUENCE: 97

```
catgcgcttt acaataatca tgatgtatca gtagaaatcg gctcttgtac aaattattac    60
acgaatgaca gacgccacaa ggcgcgtaac gtggggtact cttccaaaaa taggcgcagt   120
actttctagc atcgggtaat taatccttat cg                                  152
```

<210> SEQ ID NO 98
<211> LENGTH: 378
<212> TYPE: DNA
<213> ORGANISM: Festuca mairei

<400> SEQUENCE: 98

```
catgtactac agagtatgcg attccagcct gtttccgaaa cctgccttac agaacagcac    60
atggaagttt atgtacctct tccaaatatc atctcctcaa actgaaccag gcttgcctaa   120
tattccatat aacccatgat cctaccgtaa ttgctgactg aaccaactag tatttccatc   180
ttacagcttg ccagcaaata cctgcagtaa aacttttgtc tatctgcatc tgaagatcca   240
ggcctcccat gcaagtagtc atcaaaattg tacccgagat cgtcagcagc tcactggtca   300
actgagttaa ccagttttga caaaaacgaa ttccaattac gctctgtcca cattactgca   360
caatgcgctt ccttttcg                                                 378
```

<210> SEQ ID NO 99
<211> LENGTH: 114
<212> TYPE: DNA
<213> ORGANISM: Festuca mairei

<400> SEQUENCE: 99

```
catgcgcgtt ccaccagctc ccacagcgca ttgggtatgc cagttctatt gaaaccatcc    60
accgttatga acatcccgca gaagaagatc aacagcgagt aggataccctt ttcg         114
```

<210> SEQ ID NO 100
<211> LENGTH: 151
<212> TYPE: DNA
<213> ORGANISM: Festuca mairei

<400> SEQUENCE: 100

```
catgccctta aaccaccatt aataatgcca ttattctcag caaaaacaaa cgcctgctct    60
tccaaccctc acccgggcac aaaacataac aaatcctccg cctagacaga ctgtaagata   120
atgcaaaaaa aaaaggatag ttgacaattc g                                  151
```

<210> SEQ ID NO 101
<211> LENGTH: 197
<212> TYPE: DNA
<213> ORGANISM: Festuca mairei

<400> SEQUENCE: 101

```
cgaactcgcg gttcttggcg aaggtctcgg ggtcggcgga cagcccagcg gtgtcccagc    60
catagtcgcc ggggaactcg ccggtgaggt agctcggggg ctcgccggag agcgggccga   120
ggtagagcac gcggtcggag ccgtaccacg ggctgccgga cgcggccacc ttgggcttgc   180
cggccgtctt gcgcatg                                                  197
```

<210> SEQ ID NO 102
<211> LENGTH: 248
<212> TYPE: DNA
<213> ORGANISM: Festuca mairei

<400> SEQUENCE: 102

```
cgaagttgtg gttccccggc ttgtcgctga cataaatcgg gcagccgccg atcgcccttg    60
cggcgccgtg gtactccgcc gccgggtgca agctatgaaa catatcccag tcgggctgca   120
tgaactcgcc gaggaagagg gtgttgtaag ccacggagga gatgtggatg gtatgcgacg   180
ccgggtcgtg cgggtagaag tcgtcggagg cgcgcacgac ggctgtctgc ctggcgctgt   240
agagcatg                                                            248
```

<210> SEQ ID NO 103
<211> LENGTH: 286
<212> TYPE: DNA
<213> ORGANISM: Festuca mairei

<400> SEQUENCE: 103

```
catgtcctga gttgataaac tggttgggtt ttgagcagca gcctggtatt tctgtacaac    60
cgcgccaagc tgactaacct gcggtattat tgacctccgt ggaataagtt cctcatgacg   120
cctagcacag aactcccaag atgcgatctt gaggtctgga ttaaaaatta tcctcagatg   180
cccctcacgt acgacacgca attgatcaaa gacactttct tgaattgctt ttgtatagtc   240
cagaacaatc tgaccagata cattcttgga ctcacgtggc atatcg                  286
```

<210> SEQ ID NO 104
<211> LENGTH: 116
<212> TYPE: DNA
<213> ORGANISM: Festuca mairei

<400> SEQUENCE: 104

```
catgcggctc acaggcatgg ccgtagtgga tgccttactt gccgggaaca aagttggtgg    60
cgaacgccct tgcgttgttg ttgacagggt cagcgaggtg gtcggcgagg ttatcg       116
```

<210> SEQ ID NO 105
<211> LENGTH: 263
<212> TYPE: DNA
<213> ORGANISM: Festuca mairei

<400> SEQUENCE: 105

```
cgatcagcgg tgtgacgagc gtggccgtga acccgaagat gagcagggtg acggtgacgg    60
```

```
ggtacgtgga gccgcgcaag gtgctggaga aggttaagag cacggggaag gcggcagaga      120
tgtggccgta cgtgccctac accatggcca cctaccccca cgtcggcggc gcctacgaca      180
agaaggcacc ggcgggcttc atccggagcg cgccgcaggc catggccgcc cccggggcgc      240
cagaggtcca gtacatgaac atg                                              263

<210> SEQ ID NO 106
<211> LENGTH: 116
<212> TYPE: DNA
<213> ORGANISM: Festuca mairei

<400> SEQUENCE: 106
cgatcacgtt gctgacccag tcaacaacaa cgcatgggct ttcgccacca acttcgctcc      60
tggaagttaa atgagttagc atccgtccg accaccggcc gggcgagata tgcatg          116

<210> SEQ ID NO 107
<211> LENGTH: 165
<212> TYPE: DNA
<213> ORGANISM: Festuca mairei

<400> SEQUENCE: 107
catgcgcgga gcacgcgtac aaatttacat ttcacaccca cacccttgca tatataccctc     60 tcgcacgcac acaggtatac catgcacagg acgacgatgc ttttggccta gtggaacttg     120
aggctggtga ggatgttgtt gttgacgggg tcggggaggt gatcg                     165

<210> SEQ ID NO 108
<211> LENGTH: 166
<212> TYPE: DNA
<213> ORGANISM: Festuca mairei

<400> SEQUENCE: 108
catgctaaag attgggtgag ttaggtaggg gctgtcgcgc acaaggctgc taggaatgga      60
gcttgagact tcaggtgcaa tggattcagc tgtgaagccc actggctttc caccagagaa     120
caccttgaac agctggtcaa catcctccaa ggtggtggtc tcatcg                    166

<210> SEQ ID NO 109
<211> LENGTH: 310
<212> TYPE: DNA
<213> ORGANISM: Festuca mairei

<400> SEQUENCE: 109
cgaataagga agcattaaag tcaggctgaa ctccatgtgt gcaatatatg gtttgcctag      60
tccagcgaaa tcaagttgta gcagatgttg gcacttatgc ggttgtccta gagaagtaga     120
agaagcttag ataacgagtt ctccggttag ctacactcct ctcagtcttg actgtgttct     180
tacaagagat ggctgcagcg cgtcatagtg cccataaccg tcgtagagaa cacggactgg     240
attatccttg gcatactcct gaccatattc tgctatgatc ctggggccat cagacccctt     300
ggtgtacatg                                                            310

<210> SEQ ID NO 110
<211> LENGTH: 206
<212> TYPE: DNA
<213> ORGANISM: Festuca mairei

<400> SEQUENCE: 110
cgaacaaggc ctgcatctct ctttgcttca catctgacga ccctgctcca atcactatgt      60
ctatgattat caccttccc ccatcctctc ttgaaggaat agctttcttg cagttcttta     120
```

```
gtatcttgac acactcttgg tcgccccagt catgcataac ccacttgagg aagacaacgt    180
ttgccggagg aacgctctca aacatg                                         206

<210> SEQ ID NO 111
<211> LENGTH: 449
<212> TYPE: DNA
<213> ORGANISM: Festuca mairei

<400> SEQUENCE: 111
cgaagaagag tacctgcacg atgacacgca gagggagacg ctcattctga gcggcgtggg     60
tgcaagcctc cagggagagt ttctggcagt ccattacacg gcaaagttct tccttctctg    120
actccgggag atggggatgc gccttcagat agatgtcaac agcacgataa agtccatcgt    180
ctattggccg agcataatct ggtatggcag cagccaaaga cttgaacttt ggcaacttta    240
ggttggcatc tggcgcaact tcagctaggt agccgtcaat caacttagca accatagtta    300
ccggcattag agatggagaa gctaatagtt gcccatcgtc gccaaggcca ggggaagttc    360
caccagtttc ttgatccatt gccaagaagt gtccaagaat cctatggacg caatccacat    420
cgtagagcgt ttcatcagat tcagacatg                                      449

<210> SEQ ID NO 112
<211> LENGTH: 233
<212> TYPE: DNA
<213> ORGANISM: Festuca mairei

<400> SEQUENCE: 112
catgcttgtc caggagcagg acaatgttaa gcgtgtgcag cttgctgaca cttacatgag     60
ccaggcagct ctgggtgatg ctaaccagga tgccacgaag actggttcct tctacggtta    120
gaacactctt catacaccca ccatctctag ctgcatagga ggaggtaaag gagcacaaca    180
aagaactttg cctgtgccgg aaggttgtac cgaccgggaa gccaagaact tcg           233

<210> SEQ ID NO 113
<211> LENGTH: 206
<212> TYPE: DNA
<213> ORGANISM: Festuca mairei

<400> SEQUENCE: 113
cgaacaaggc ctgcatctct ctttgcttca catctgacga ccctgctcca atcactatgt     60
ctatgattat cacctttccc ccatcctctc ttgaaggaat agctttcttg cagttcttta    120
gtatcttgac acactcttgg tcgccccagt catgcataac ccacttgagg aagacaacgt    180
ttgccggagg aacgctctca aacatg                                         206

<210> SEQ ID NO 114
<211> LENGTH: 251
<212> TYPE: DNA
<213> ORGANISM: Festuca mairei

<400> SEQUENCE: 114
catgttgaac agcctttgcc gcgacaagaa caacatggtc ttgctcgcta gcacgaagac     60
tcgggcgatg ttaagcgaat ggttttcgcc atgtgagaac ctagggctgg ctgctgagca    120
cggctatttc ctcaggctga gaggagatgc agagtgggaa acgtgcgctc ctgcgcctga    180
ctctggctgg aagcagattg tggagcctgt gatgaaaacc tacacggaga caaccgacgg    240
gtcaacgatc g                                                         251

<210> SEQ ID NO 115
```

```
<211> LENGTH: 280
<212> TYPE: DNA
<213> ORGANISM: Festuca mairei

<400> SEQUENCE: 115
catgctatcc gatcagagca gcaactcatt tggctctacc gactttgggt gggatgatga    60
ggccatgaca ccggactaca catccgtctt cgttccaaat gctgccatgc cagcatatgg   120
cgggcccgct tacctgcaag gcggagcgcc aaagaggatg aggaacaatt tcggtgtagc   180
tgtgcttcct cagggaaatg atgcgccaca agatgtctgt gcttttgacc atgagatgaa   240
gtattcactg ccttacgttg agagtagctc agacggatcg                          280

<210> SEQ ID NO 116
<211> LENGTH: 199
<212> TYPE: DNA
<213> ORGANISM: Festuca mairei

<400> SEQUENCE: 116
catgtactta ccagctagct gttggtccgg tcgtcgttaa gaagcaatta ccacagcttt    60
aattgaagtg atcgtgacga gtaactaaac caaactaggg taggtagacg dacgggtccg   120
ggacgtccgt ccagcagctc ccggcgttcc agtacgcggc cggcgacgcg tcgtcccga    180 gctcgttcag gactcatcg                                                 199

<210> SEQ ID NO 117
<211> LENGTH: 76
<212> TYPE: DNA
<213> ORGANISM: Festuca mairei

<400> SEQUENCE: 117
catgtgtggt ctctagagga acttgaacag caggcctccg tacgtggcaa agaacggcgc    60
aaacacaagg gattcg                                                    76

<210> SEQ ID NO 118
<211> LENGTH: 309
<212> TYPE: DNA
<213> ORGANISM: Festuca mairei

<400> SEQUENCE: 118
catgcgacag gtagtagtac aaaccaacag actacaagat tagtcaggac aacagctaca    60
gagcgtattc ctactatgta cacatatatg gcaccatcta tacgtagtag taacttaatg   120
tgtgcaatgc atgtccacat caccagccat atacagggtg ctgtacctgg ggaggcagca   180
ggcccatatc agcacggtgt tgttcatcgt agtcacgtgt accaggaatc gcgcctgtag   240
ccaacctgag gacctcacta gaggtcaggc aacgatgcgc aaatgccgat ccactgtcca   300
cgacattcg                                                            309

<210> SEQ ID NO 119
<211> LENGTH: 273
<212> TYPE: DNA
<213> ORGANISM: Festuca mairei

<400> SEQUENCE: 119
catgtggtat ccagggtcca tttatccaca caaatgcaca atcggcaata catacgtaag    60
cacagactgg tcactgggtt cagcgatgaa tactgatcac tgggtttcaa ggctggggca   120
tttgttcagt gcttgtgttt tggcttcttc acaatcatca ccgtgcagtg cgcgtgatgg   180
gtgcagtaat cgctcacact tccaagaaca gccctttaa ttgctccata gccatggttg    240
```

```
cccacaacca acatctccgc gtgatgccgt tcg                                273
```

<210> SEQ ID NO 120
<211> LENGTH: 231
<212> TYPE: DNA
<213> ORGANISM: Festuca mairei

<400> SEQUENCE: 120

```
catgtggtgc tgtctctcca cgaagtgaag gtgaagctga agccaaagcg cttttgacat     60
ggaagtctac tttgatgttc tccgacgtca acggctcttc tccgctctcg tcatgatcac    120
cggccaactc cctctgcaat tcttggtctg gcatcacgtg caacacggct ggccatatcg    180
tggagctcac ggttcccgga gctggtgtcg caggcacgct ggacgccttc g             231
```

<210> SEQ ID NO 121
<211> LENGTH: 128
<212> TYPE: DNA
<213> ORGANISM: Festuca mairei

<400> SEQUENCE: 121

```
cgcagggcaa actgcaagca gatgcaaagg atcctgagac agcactggcc ccaagcattg     60
tagagatctc tccagcacca agtttgtctc tgagtaactc aacactctgg tcataggaag    120
cgagcatg                                                             128
```

<210> SEQ ID NO 122
<211> LENGTH: 103
<212> TYPE: DNA
<213> ORGANISM: Festuca mairei

<400> SEQUENCE: 122

```
catgttaagg cttatagcaa tgtgaacaag tatctactta ctggtaggta cagaaacatc     60
atggacatga acgcaggctt tgggggtttc gctgcagcga tcg                      103
```

<210> SEQ ID NO 123
<211> LENGTH: 256
<212> TYPE: DNA
<213> ORGANISM: Festuca mairei

<400> SEQUENCE: 123

```
catgctaagc gcactgtttc ataaatataa tgttgtgcag acgatgataa atacagtaga     60
tgcaaccaga ggcgactggt aacccagctt cattatccag ggaagtgggc gaacccttgg    120
tcctaaagca gtcgctcact gcttaggaga gtgccaagga tcaatctgat ctcacaggag    180
atgcagaacc ggataagctc ttgctagggc ttctgctcac tgattttcca ggagaggccg    240
aagaaactgg ggatcg                                                    256
```

<210> SEQ ID NO 124
<211> LENGTH: 156
<212> TYPE: DNA
<213> ORGANISM: Festuca mairei

<400> SEQUENCE: 124

```
ccatgatgct gaagggatgg tgaatgttat atctgagaag gaaactgaca gaatcctcgg     60
cgtacacatt atgtcccctg gcgcgggaga gatcatccat gaggctgtgc ttgcgcttca    120
gtatggagct tccagcgagg acattgcccg tacatg                              156
```

<210> SEQ ID NO 125
<211> LENGTH: 120
<212> TYPE: DNA

-continued

<213> ORGANISM: Festuca mairei

<400> SEQUENCE: 125
cgacagcaac ggacagggtg tacagcgggg ccaccttata gtcaactacc agttcgtcaa   60
ctgcggcgac aacgagctgc tgctccagcg cgaagagaaa taagaagcta ccagtacatg  120

<210> SEQ ID NO 126
<211> LENGTH: 306
<212> TYPE: DNA
<213> ORGANISM: Festuca mairei

<400> SEQUENCE: 126
cgaatgagaa cgcggcatcc tccgtcgcca agaccatctc cggtcagccc ccactgaaga   60
taccgatcag gagcgacaac gccgggtcct ggctgctcac aacctacctt gatgacgagc  120
ttagaatctc cagaggagat ggcagcagca tctttgtgct gttcaaggaa gggagcactc  180
tcttaatata ggcttacgtg tatctcttct cagagtagaa tttgggcgaa tccaatagat  240
agttgtggct atgtgtttgt tttgttagcc cgtgcgttta tagttcgttc ttgtgtgttg  300
tgcatg                                                              306

<210> SEQ ID NO 127
<211> LENGTH: 168
<212> TYPE: DNA
<213> ORGANISM: Festuca mairei

<400> SEQUENCE: 127
catgcgtaga attcttcgcg aagtaaacac gacatgatac gtacgtaaag catcacgtat   60
acgtagctaa tctcggttga ttctgtcctc gcaacctaca taaactggct gcaaggacgc  120
ggtactagtt aatttcgcaa aaagtatatc ggccacgtgt acgattcg              168

<210> SEQ ID NO 128
<211> LENGTH: 230
<212> TYPE: DNA
<213> ORGANISM: Festuca mairei

<400> SEQUENCE: 128
cgaactcgtg ccgcagcgtg gcgacccaga acccgacggt ggcgatggcg agcgacttgc   60
cggggcagct ccgcctgccc gacccgaacg gcgccagcct gaggtctgag cccgttatgg  120
agaactcggc ggcgccggcg tgatcccgcg acggtccggc gaggaaccgg tcaggcctga  180
actctgccgg ctcggtccag acggccgggt cgtgcgttat ggcccacatg              230

<210> SEQ ID NO 129
<211> LENGTH: 185
<212> TYPE: DNA
<213> ORGANISM: Festuca mairei

<400> SEQUENCE: 129
cgaagggaag agatagacaa atgtatccat aaagccgatg gcttcattca gagtattcaa   60
agaagtgacg gttcatggta cggctcctgg ggtgtttgtt tcacatatgg gacatggtat  120
gcagtgaggg gattagttgc cgctggaagg acattcaaga actgtcctgc tatcaggaag  180
gcatg                                                              185

<210> SEQ ID NO 130
<211> LENGTH: 201
<212> TYPE: DNA
<213> ORGANISM: Festuca mairei -continued

<400> SEQUENCE: 130

```
cgataattgc tcttatcgtc tgcataccac cagcagttat tattgaaggt ccccaactta    60
tgcagtatgg attaaatgac gcaattgcaa aagtaggtct gacaaagttt gtttcagacc   120
ttttcctggt cggactgttc taccatctgt ataaccagct tgctacaaac acattggagc   180
gggtggcccc tctgacacat g                                             201
```

<210> SEQ ID NO 131
<211> LENGTH: 390
<212> TYPE: DNA
<213> ORGANISM: Festuca mairei

<400> SEQUENCE: 131

```
catgcgtgaa gatggaggtt ttgaagtgat taagaaagca atcctgaacc tttcacttcg    60
tcacgacttg cacataagtg aatatggtga aggaaatgaa cggaggttga cagggttaca   120
tgagacagct agcatatcag acttttcatg gggtgtagca aaccgtggtt gctctattcg   180
ggtggggcga gacactgagg caaaagggaa aggatacctg gaagaccgtc gtccggcctc   240
aaacatggac ccatacactg tgacggccct actggctgaa accacaattc tctgggagcc   300
gacccttgaa gcagaggctc ttgctgccaa gaagctggcg atgaacgtat gaaggactga   360
aaaggatgaa tttctgggga aaataaatcg                                    390
```

<210> SEQ ID NO 132
<211> LENGTH: 69
<212> TYPE: DNA
<213> ORGANISM: Festuca mairei

<400> SEQUENCE: 132

```
catgttcggc ggcggcaagt tcaagaagtg gaagtaatct gccagtagct ttccatagct    60
gatggatcg                                                            69
```

<210> SEQ ID NO 133
<211> LENGTH: 238
<212> TYPE: DNA
<213> ORGANISM: Festuca mairei

<400> SEQUENCE: 133

```
catgcccgcc aacaaccgga acactgactt ctctaggatc aactccaagc acttcagcca    60
caaaggtgtt agccctcgct acatcaagag ttgtcactcc aaggagacgt ttggggcagt   120
aagttccagc cctcttgaaa actttcgccg caatgggac agttgagttc acagggttgc   180
tgatcaaatt cataattgca ttagggcagc tcttggcaac gccctcacag attgatcg     238
```

<210> SEQ ID NO 134
<211> LENGTH: 119
<212> TYPE: DNA
<213> ORGANISM: Festuca mairei

<400> SEQUENCE: 134

```
catgtacacg caagcccccc taatacaggt cgccttcctt gtgggtgtgg atgatgcagt    60
cagacttggg gtatgagacg caggtcagca cgtagccttc ctcctgctgg ttgtcatcg    119
```

<210> SEQ ID NO 135
<211> LENGTH: 122
<212> TYPE: DNA
<213> ORGANISM: Festuca mairei

<400> SEQUENCE: 135

```
catgtaccac actgagcacg agcttctccg ttacctacac aagttgcaaa ccaaggatct    60
ctcactgtgc cacagtatga ttcctcttgg ttcttgcacc atgaaactaa atgctactgt   120
cg                                                                 122
```

\<210> SEQ ID NO 136
\<211> LENGTH: 153
\<212> TYPE: DNA
\<213> ORGANISM: Festuca mairei
\<220> FEATURE:
\<221> NAME/KEY: misc_feature
\<222> LOCATION: (11)..(11)
\<223> OTHER INFORMATION: n is a, c, g, or t

\<400> SEQUENCE: 136

```
cgaaacgggg ngatttcttt ttctttttat ggaggaaaag aacattcaag tgaacaacat    60
cccagcagaa gatggggaga aagagagatg aataagaatt attccgatca ggggaggaac   120
aaacaagctc cctttcttaa ttatgatgac atg                                153
```

\<210> SEQ ID NO 137
\<211> LENGTH: 80
\<212> TYPE: DNA
\<213> ORGANISM: Festuca mairei

\<400> SEQUENCE: 137

```
cgaatcctgg ctgtgcaata ccccggaccg aatctattga cagatcatcc atccttggtt    60
tcttgggaga aggctgcatg                                                80
```

\<210> SEQ ID NO 138
\<211> LENGTH: 473
\<212> TYPE: DNA
\<213> ORGANISM: Festuca mairei

\<400> SEQUENCE: 138

```
catgcatcct taccagcttc ctcagttgtc ctgttgctct ccaatgtaac aactgctgat    60
ttatcacctt cctccaaacc tgcgacccct ttaatctcat tgctatgcca agactcagca   120
ttagcatcac aagctaactg aggctgagaa ttttcagtct tcattttcac ccgccgacca   180
ttctgttcat gcttatcagc aagcacagga gatgaagatc tactcccagt gacagatggg   240
tcgtcaaatg agccaccact cacacttcta gcaggactac gacttggatt tgaaaagcga   300
actatcaatc tatggctatt accattatca ggaggtgtat cacctacttt ctcagacacc   360
attccaggtt gtgatgcttt ttcctggaat gaggaccgat caagtgaagt agatcttccc   420
acggtagctt ctttctttac cccagaacca agacgggcac tgtttgccct tcg          473
```

\<210> SEQ ID NO 139
\<211> LENGTH: 91
\<212> TYPE: DNA
\<213> ORGANISM: Festuca mairei

\<400> SEQUENCE: 139

```
cgacttcacc gggggcatct catcctaccc gctcctcgtc gcccaggtga cccacttcaa    60
gtgcggaggc gtggccctcg gcataggcat g                                   91
```

\<210> SEQ ID NO 140
\<211> LENGTH: 166
\<212> TYPE: DNA
\<213> ORGANISM: Festuca mairei

\<400> SEQUENCE: 140

```
cgatccggtg aagcaatccc tccgccgctt cgccgaagaa aggagaaaag ccattggtga      60
agagatagcc cggctgctcg cagccggctt tatcatggaa gtgctgcccc cagactggtt     120
ggctaaccca gtcctggtct tgaagaagaa tgacacctgg cacatg                    166
```

<210> SEQ ID NO 141
<211> LENGTH: 259
<212> TYPE: DNA
<213> ORGANISM: Festuca mairei

<400> SEQUENCE: 141

```
cgatcgccgt ctccgcactg cagcagctac catggcgtcc accgcgctct ccaccgcctc      60
caaccctacc cagctctgca ggtccagagc ttcgccgtgc aagcccatca agggcctggg     120
catcggccgg gagcgcgtcc cgaggaacat cacatgcatg gccggcagca tctccgccga     180
ccgcgtgccg gacatgagca agagggagac gatgaacctc ctcctgctcg gcgccatctc     240
gctccccacc ttcggcatg                                                   259
```

<210> SEQ ID NO 142
<211> LENGTH: 276
<212> TYPE: DNA
<213> ORGANISM: Festuca mairei

<400> SEQUENCE: 142

```
catgttctct tttgcaggaa gttaggacag gagcgaagcc gaacgtcttt agcttgataa      60
aaaagatgaa gcaaaggaag acgccgcatc ctgagacggg gtccttgtgg gttaacgagc     120
aatccgggac ccagtgtgcg gcgtatgtct tgaagttcaa gcagaagcac ggcgagagct     180
ccaacccaga ggccgaggat tttgacgttg aggttgcggt gcttgcggga gaaggcatga     240
agcatggccg cctatggctt ggtgatgggt gtgtcg                                276
```

<210> SEQ ID NO 143
<211> LENGTH: 399
<212> TYPE: DNA
<213> ORGANISM: Festuca mairei

<400> SEQUENCE: 143

```
cgaagaggtt attcgtgata aggaggccca gttcagcagc cccaacctca atgttgttta      60
ccgcatgaat gtgcgggagt accaggcact aaccccctat gcctccatgc tggaggagaa     120
ctggggcaag gcacctgggc atctcaattc tgatggcgag aacctccttg tctatgggaa     180
gcagtatgga aacatcttca tcggagtgca gcccactttt ggttatgaag gtgatcctat     240
gcggctcctg ttctcaaaat ctgccagccc tcaccatgga tttgcagcat actacaccta     300
tgttgagaag atcttcaagg cagatgctgt tctgcatttc ggcacacacg gatcccttga     360
gttcatgccc gggaaacaag tcgggacgag tgatgcatg                            399
```

<210> SEQ ID NO 144
<211> LENGTH: 204
<212> TYPE: DNA
<213> ORGANISM: Festuca mairei

<400> SEQUENCE: 144

```
catgtataca aaacctggac ctcagaatac aacacatcca gtaataaggt aaaaacaaat      60
taactcttaa caggatggaa aacatcatct atctagctct tggggatgtt cttgccaacg     120
atcttggcag gtgtgatgcg gagaaggttc ccctgcttcc caggaatggc tcccttgatc     180
atcacaactt taagatcgtt atcg                                             204
```

<210> SEQ ID NO 145
<211> LENGTH: 285
<212> TYPE: DNA
<213> ORGANISM: Festuca mairei

<400> SEQUENCE: 145

```
cgatcggact atcctcacca ccaattgcat gaataaccac cgggatgtcg ctcaggtagc      60
gtatcaccag gggcagagcc gctggggcaa catcagcttt cactacgtca tcgctcagca     120
aaactgaatc ggcagcagcg ggaccgccag cctctattgc tcctggttca tctttgtctt     180
cagataacat taactcggat gggttcacca ccactgcgac ttcctcaatt gctatgctac     240
atttgaactg gcttcccctc ctttgggcag gcttgttcct gcatg                     285
```

<210> SEQ ID NO 146
<211> LENGTH: 82
<212> TYPE: DNA
<213> ORGANISM: Festuca mairei

<400> SEQUENCE: 146

```
catgccggcg tgcccttgta atagccacat tcatgagcct gctgtcaccc atgaacccta      60
cagctcctag agggtttgat cg                                               82
```

<210> SEQ ID NO 147
<211> LENGTH: 224
<212> TYPE: DNA
<213> ORGANISM: Festuca mairei

<400> SEQUENCE: 147

```
cgaaatcata cttaacctcc ttcccttgct tgtttatttc tttcaacccc ttcctgaaaa      60
agatcatggc tccacgtggt ccacggagtg acttgtgagt agtggtagta acaacatctg     120
catactcaaa aggagatgga atgacaccag cagcaactag ccactgata tgtgccatgt      180
ctgcgagaag tattgccttc tgcttgttac agatcttccg catg                      224
```

<210> SEQ ID NO 148
<211> LENGTH: 120
<212> TYPE: DNA
<213> ORGANISM: Festuca mairei

<400> SEQUENCE: 148

```
cgaattccat aatgaaatat gttgtaattg ctcatgtgaa cgaatggaga acaggagacc      60
tccatgggcg gcccagaaat tcagcaatga cgcggacctg cgcttccgcc tccaagcatg     120
```

<210> SEQ ID NO 149
<211> LENGTH: 460
<212> TYPE: DNA
<213> ORGANISM: Festuca mairei

<400> SEQUENCE: 149

```
catgtttgaa ggaaatgacg tgtcagatgg tatgggtttc ggaatgctaa ccgagggtga      60
gagatccctg gttgagcgtg taaggcaaga gctgaagcac gagcttaaac aggggtacag     120
agaaaagctt gtggacatta gggaagagat acttcggaag cgaagagccg aaagctccc     180
aggagacaca gcgtctactc tgaaagcctg gtggcaagct catgcaaaat ggccataccc     240
gactgaggag acagggcccg cctggtgca ggaaacaggg ctgcaactga agcagatcaa      300
caattggttc atcaaccaac gcaagcgcaa ctggcacagc aaccccacct catcctcatc     360
agacaagagc aagagaaaaa gaaacaatgc aggtgatggc aacgccgagc ggtcttggta     420
```

```
ggacatggtt ggagaagaac acgcgtgtgt aaacagttcg                              460
```

<210> SEQ ID NO 150
<211> LENGTH: 177
<212> TYPE: DNA
<213> ORGANISM: Festuca mairei

<400> SEQUENCE: 150

```
ccaaccgctc ataccagcat gatgatttgg aggccttgct gatgatatct ctcccccct        60
tcctgttcat ataggaagga tttagtgtac ctattgcccg aatagtgtat ttctggtgca      120
cctgccggtt ccctgggtac tggcttgaat atgtgaatac tgtgcatatg gggcatg         177
```

<210> SEQ ID NO 151
<211> LENGTH: 287
<212> TYPE: DNA
<213> ORGANISM: Festuca mairei

<400> SEQUENCE: 151

```
catgcatgca gcctggggcg tacagattga caggcctatg tgtagctcag ccctcatcag       60
gtagcgatac atggtggtaa ttaagtagtg atgcaagcgg ccagatcata gctcgttgac      120
tgatgatcta gcaggtgcag caggagcagc cacagctggt gctgcagttg cacttgctgc      180
aggggcagcc gccgttctcc gcctccgcgg ccatgtccat cccaccggcg ctcgccttgt      240
gggtggcggc ggcgacgagg aagacgttgc cgttgccggc ggcttcg                    287
```

<210> SEQ ID NO 152
<211> LENGTH: 91
<212> TYPE: DNA
<213> ORGANISM: Festuca mairei

<400> SEQUENCE: 152

```
cgataagaag gacagcgagg aggccaagca ggcgctagac cagctgaagg agctcggctg       60
ggccaagcga tggagctcgc agccctacat g                                      91
```

<210> SEQ ID NO 153
<211> LENGTH: 128
<212> TYPE: DNA
<213> ORGANISM: Festuca mairei

<400> SEQUENCE: 153

```
catgccgggg ctggggaagg agcacgtcaa ggtgtgggcg gagcagaaca gcctggtgat       60
caagggcgag ggcgagaagg actccgagga ggagggcgtc gccgccccga ggtacagcgg      120
ccgtatcg                                                               128
```

<210> SEQ ID NO 154
<211> LENGTH: 132
<212> TYPE: DNA
<213> ORGANISM: Festuca mairei

<400> SEQUENCE: 154

```
catgtagccg atctttgttc caagagatgg taaagctttg ctttcataga tgcacctata       60
tgacctcttc ccaggtggta gtcatcccag gcggcgacga ggtgttcagg ggagaggccc      120
ttggcgcgat cg                                                          132
```

<210> SEQ ID NO 155
<211> LENGTH: 223
<212> TYPE: DNA
<213> ORGANISM: Festuca mairei

<400> SEQUENCE: 155

```
catgcggcaa acaatcttcc cactccttca agttcttctt gatcatggat ctcaacagtt      60
gtgacaatgt tctattcacc acctcagttt gaccatcagt ttggggatga caagtagtgt     120
tgaaaagtag cttcgtcccc agctttctcc aaagcgtctt ccagaagtag ctcatgaact     180
tcacgtcacg atcagaaaca atagtcttcg ggactccatg tcg                       223
```

<210> SEQ ID NO 156
<211> LENGTH: 100
<212> TYPE: DNA
<213> ORGANISM: Festuca mairei

<400> SEQUENCE: 156

```
cgacttgcgc cacaccacct gcgtgtagtg cccgcacacc ttgccggcgt cgcaggtgtt      60
gctgctgagg tggtagttct tcttctcgtc cacccacatg                           100
```

<210> SEQ ID NO 157
<211> LENGTH: 70
<212> TYPE: DNA
<213> ORGANISM: Festuca mairei

<400> SEQUENCE: 157

```
catgttagcc ccgagcagga agcccacggc gagcggcccg atggtgccca cgtggcccct      60
cttggggtcg                                                            70
```

<210> SEQ ID NO 158
<211> LENGTH: 582
<212> TYPE: DNA
<213> ORGANISM: Festuca mairei

<400> SEQUENCE: 158

```
catgttgttg gccagaactt ggcaccacgg agccacgccg cagggaacgc ggcgtactcc      60
ctggagtatg gcttagtcca tgcgtcactc atcaggagtt ggggtgggtg gggagcgccc     120
ttcaggacat tgttgttcac atctgctacg ccattttcta cctgtgcaat ttcttccctg     180
atggaaataa gggcatcaca gaacctgtct agttcagcct tgctttcact ttcagtgggt     240
tcaatcataa gtgtgcctgg aacaggccat gacatggttg gtccatggaa cccatagtcc     300
atcaagcgct tcgccacatc ctcaggctct ataccagcag tcgccttgag ccctcttaaa     360
tcaatgatga attcatgggc aacagttcca ttgactccac ggaaaagaac tgggtagtgt     420
ttctccagac gctttgccat gtagtttgca ttcaagatcg caatctttga agcatcagtg     480
agtccctgag accccatcat ggctatgtat gtataggaaa ttggaagaat caaagcagat     540
ccccatggag cagcagaaat ggaacccagg aggtcggttt tc                        582
```

<210> SEQ ID NO 159
<211> LENGTH: 130
<212> TYPE: DNA
<213> ORGANISM: Festuca mairei

<400> SEQUENCE: 159

```
catgccgctg tactgatcta ccggaagctg cagctggttg cagaacaagc tgctgctgga      60
tctcctcctc ttcatcccat tatacttgtt accagtagcg taatcacggt catctaactg     120
cggcacgtcg                                                            130
```

<210> SEQ ID NO 160
<211> LENGTH: 122
<212> TYPE: DNA

-continued

<213> ORGANISM: Festuca mairei

<400> SEQUENCE: 160

```
catgtggcat caattttaca tcaacctgcc gcagctgtcc tgatcatacg actaattagc      60
cggagaaggt ctggatgatg gtgttgtgcc acgggtcaga caagtgctgg aacaggttct     120
cg                                                                   122
```

<210> SEQ ID NO 161
<211> LENGTH: 166
<212> TYPE: DNA
<213> ORGANISM: Festuca mairei

<400> SEQUENCE: 161

```
catgcggcag catccatcag caatgaagtt gtcggccaag cacgcgcgcg cacgcccgcg      60
ctactgctag agagctgaca aagctcactt tccggggacg aagttggtgg cgaaggccca    120
ggcgttgttg ttgacggggt cggcgaggtg gtcggcgagg ttctcg                   166
```

<210> SEQ ID NO 162
<211> LENGTH: 178
<212> TYPE: DNA
<213> ORGANISM: Festuca mairei

<400> SEQUENCE: 162

```
cgacaaagaa cacggccggc gaccatggca gcagcggttt tggaactgct atactttgaa     60
gtttgaacag cgccttgacc tcagatgctg gtggaattag ctatttgcgt gccaaatgta   120
gcgggtaaaa aatagctgtg gtggttccag gattgtgtat tcggtaccgt gccacatg     178
```

<210> SEQ ID NO 163
<211> LENGTH: 178
<212> TYPE: DNA
<213> ORGANISM: Festuca mairei

<400> SEQUENCE: 163

```
catgcggtac ctcccatcca tggggctgga agacacactg aacgggtgcc actgcaagaa     60
cgacagctcc cgcacttgaa caaagatgaa gctgagagca ctgtaccgga ggcttgctgg   120
ctttgaggag actagctcca cagttccgca ggggcggcag gcagcagaaa caatgtcg     178
```

<210> SEQ ID NO 164
<211> LENGTH: 278
<212> TYPE: DNA
<213> ORGANISM: Festuca mairei

<400> SEQUENCE: 164

```
catgtgtctc tttgtccaaa tcagtttctt gaagaggtgc tttctcagtg gtcttgcttt     60
cttcacaaag ctgctgtggc gtcaccgttg gatcaacagg taaggcagtg cagcttccat    120
ctttctctaa tttctcatct gctgcatcgg tagcgacagg ttcttcatca gtgacagcag   180
cagcagaagc ggatacatct tcagactctt gtttctcagc tggagctgcc tgcttgttct   240
tgccatgcat tgccttgtag gtggcgacgg cgtggtcg                           278
```

<210> SEQ ID NO 165
<211> LENGTH: 278
<212> TYPE: DNA
<213> ORGANISM: Festuca mairei

<400> SEQUENCE: 165

```
catgtgtctc tttgtccaaa tcagtttctt gaagaggtgc tttctcagtg gtcttgcttt     60
```

```
cttcacaaag ctgctgtggc gtcaccgttg gatcaacagg taaggcagtg cagcttccat    120
cttcctctaa tttctcatct gctgcatcgg tagcgacagg ttcttcatca gtgacagcag    180
cagcagaagc ggatacatct tcagactctt gtttctcagc tggagctgcc tgcttgttct    240
tgccatgcat tgccttgtag gtggcgacgg cgtggtcg                            278

<210> SEQ ID NO 166
<211> LENGTH: 215
<212> TYPE: DNA
<213> ORGANISM: Festuca mairei

<400> SEQUENCE: 166
cgacgtactt taatatccgt aaaggcctag acggctccct agacaaggca attaatgctc    60
tttgtgaaga agctgacgct gctgtgcgga gtggttctca acttctggtc ctttctgatc    120
gttctgaagc acttgaacca acacggcctg ccatcccaat acttctagcc gttggtgcca    180
tccaccagca tctgattcaa aatggcctcc gcatg                               215

<210> SEQ ID NO 167
<211> LENGTH: 338
<212> TYPE: DNA
<213> ORGANISM: Festuca mairei

<400> SEQUENCE: 167
catgtaccaa caacgaggcc tgcaacgacg ccattgtccc tgccagccca accggcaaag    60
acgaagagtc ctatcttgcc atagttataa cccatgttga tatcggtaag ccctgtccca    120
taggaattgg cgaatccaag catggggggcg acgacatagg ctataaccac gtagtaccat   180
ttcacctgtc ggaacattat tggcgtggta accactgcaa cagcacttaa caaggcatac    240
ccggtgtacg ccaaccaaga ggggatatgg cccttccgga agatctcgtc gcgctgcaga   300
tcctcaagtg agaccgtatt gtccacatct ttcactcg                           338

<210> SEQ ID NO 168
<211> LENGTH: 167
<212> TYPE: DNA
<213> ORGANISM: Festuca mairei

<400> SEQUENCE: 168
cgacacgctc actgatatct gatggaggtg aattcagctt gacaaatgag caggaaaagt    60
gggttgtaga cattatgctc tcagtaacgc tggtgaaact tgctctagct ttatattgcc    120
gcacattcac caatgaaatt gtcaaggctt atgcgcagga tcacatg                  167

<210> SEQ ID NO 169
<211> LENGTH: 134
<212> TYPE: DNA
<213> ORGANISM: Festuca mairei

<400> SEQUENCE: 169
catgcggagg gaaggatatg aatttatgat tggacctcca aaggtcataa acaagagtgt    60
agatgggaag ctactggagc cgtatgagat agctgctata gaggtaccag aggaatatat   120
gtgatcagct gtcg                                                      134

<210> SEQ ID NO 170
<211> LENGTH: 121
<212> TYPE: DNA
<213> ORGANISM: Festuca mairei

<400> SEQUENCE: 170
```

```
cgactgcggc gtctccatcg gaacgatctt tgggatttac atgatcaaga actttgacac    60
cgtgacccct tgaggaagtgc cgctgcctgg gaaggacatg attgctgctg gatactgcat   120
g                                                                   121
```

<210> SEQ ID NO 171
<211> LENGTH: 201
<212> TYPE: DNA
<213> ORGANISM: Festuca mairei

<400> SEQUENCE: 171

```
catgcatatg ctgcaaatgt ttcttcccac ctagtgtttc tttttttcctt ttaccccgca    60 attgaaccgt gcaaagctca aggctccgat catatatacg ccttcgtatc tagcgacaag   120
agtgaatgag cgcggtaagc tgttatggaa tctccttggc acgtctgatc aatgtacata   180
ctgacactcg catttgtctc g                                             201
```

<210> SEQ ID NO 172
<211> LENGTH: 113
<212> TYPE: DNA
<213> ORGANISM: Festuca mairei

<400> SEQUENCE: 172

```
cgagtcgcag tcgcagacca acgatctgga gtcggacagt ctgcaggtgt acagcttctc    60
cgggctgttc ctcatctgcg gcgtggcgtg cgtgatcacc ctcgccatac atg          113
```

<210> SEQ ID NO 173
<211> LENGTH: 148
<212> TYPE: DNA
<213> ORGANISM: Festuca mairei

<400> SEQUENCE: 173

```
catgtcgttg gacggcagca ccatcaccac atggagagaa aggagccgtt ggacaatctg    60
tgcaggagct cgccgaggca caggatggcg tagaccagca ggatgaactt gaagaggaac   120
gggaagtagt gcgagagccc ggcgctcg                                      148
```

<210> SEQ ID NO 174
<211> LENGTH: 398
<212> TYPE: DNA
<213> ORGANISM: Festuca mairei

<400> SEQUENCE: 174

```
catgcaccca tttgccccta ttgatcaggc tgcaggctat catgaaatgt ttgacaactt    60
gggtgatctg ttgaacacga tcaccggttt tgattccttc tctctgcaac caaatgctgg   120
tgcttcagga gagtatgctg gactgatggt tattcgggcc caccacaggg caagaggaga   180
ccatcaccga aatgtctgca tcattcctgt ctcggcacac ggtacaaatc ctgcaagtgc   240
tgctatgtgt ggaatgaaga ttattactgt cggaactgac tccaaaggta acattaacat   300
tgcggagttg aagaaagctg ctgaagcaaa caaggacaac ctgtctgctc tgatggttac   360
ctatccttca acccatggag tctatgaaga aagcatcg                           398
```

<210> SEQ ID NO 175
<211> LENGTH: 318
<212> TYPE: DNA
<213> ORGANISM: Festuca mairei

<400> SEQUENCE: 175

```
cgacattatg cacaggcaga ggaagctgaa gaggatgatg aaattgagcg gctctttagt    60
```

```
agtaagaaag agaagaagaa tgatcggcca cgagcagata ttggtcttat cgttgagcag    120
ttcattgccg agtttgaagt agcgtctgaa gaagatgcaa acctaaatag gcaatccaaa    180
ccggccatta acaaacttat gaagcttcca ctgctcatag aggttctctc aaagaagaat    240
ctccagcagg aattccttga tcatggaatt ctcactcttc tgaaaaactg gcttgaacct    300
ttacctgatt gaagcatg                                                  318

<210> SEQ ID NO 176
<211> LENGTH: 86
<212> TYPE: DNA
<213> ORGANISM: Festuca mairei

<400> SEQUENCE: 176
catgtacgtg cttcgttgca tcttctgaac agcctcggtg acctccttac gtacgccaag     60
ccatcgcact gagctgagct cagtcg                                          86

<210> SEQ ID NO 177
<211> LENGTH: 116
<212> TYPE: DNA
<213> ORGANISM: Festuca mairei

<400> SEQUENCE: 177
catgcatatc tcgcccggcc ggtggtcgga cggatggcta actcatttaa catccaggag     60
cgaagttggt ggcgaaagcc catgcgttgt tgttgactgg gtcagcaacg cagtcg        116

<210> SEQ ID NO 178
<211> LENGTH: 194
<212> TYPE: DNA
<213> ORGANISM: Festuca mairei

<400> SEQUENCE: 178
cgaccataaa cgccccgtga tcggcggcaa ggagcacccc taccctcgcc gatgccgcac     60
cggtcgccct aaaaccatca ttgactcaga gacggagaag aggagctcac cagtgtatgt    120
gccacgtgac gagcagttct cggacattaa agggcagaca ttcagcgcga cgacactgcg    180
gtctggattg catg                                                      194

<210> SEQ ID NO 179
<211> LENGTH: 290
<212> TYPE: DNA
<213> ORGANISM: Festuca mairei

<400> SEQUENCE: 179
cgacgaccta aaggctcacg cagaatcaaa tgtgactgat aagatgatgt caaatgcaaa     60
gttcatctac ccacacaaca ccccgacaac aaaggaggca tactgttaca gaacgatctt    120
tgagaggttc ttcccccaga actcggcgat cctgacagtg ccaggtggac caagcgtcgc    180
atgcagcacg gcgaaggcgg tagagtggga tgctcagtgg tcggggaacc tggatccctc    240
agggagagca gcgcttggag tccatctctc agcctatgaa caagagcatg               290

<210> SEQ ID NO 180
<211> LENGTH: 170
<212> TYPE: DNA
<213> ORGANISM: Festuca mairei

<400> SEQUENCE: 180
catgcacgta cggggttcgt aacactactc tagcttaatt aatctagacg ttgacaaagg     60
gcgtgccggt gatgaactcg gtgacggcga gcgcgacgag tccgagcatg gcgaagcggc    120
```

```
cgttccagag ctcggcgtcg gcgctccaga cgccgctgga cttgctctcg        170
```

<210> SEQ ID NO 181
<211> LENGTH: 204
<212> TYPE: DNA
<213> ORGANISM: Festuca mairei

<400> SEQUENCE: 181

```
catgttggtg cttacaaata tggcagctgg ggacgaatta agcaaggaag ctgtaatgga    60
tgttattgtt cctcacagat cagatcgcat caagccatct tttgtggtca actttctgca   120
gagcaaggac gaacaattga gagttgcatc tttgtggtgc attcttaact tagcttaccc   180
aaaaagtgat gcttcatcta ctcg                                          204
```

<210> SEQ ID NO 182
<211> LENGTH: 77
<212> TYPE: DNA
<213> ORGANISM: Festuca mairei

<400> SEQUENCE: 182

```
catgcttggg aataggtgtg tcatcttcaa tcacctcgca ttcgtagtca tcaggaacgc    60
cccagggatc ccactcg                                                   77
```

<210> SEQ ID NO 183
<211> LENGTH: 114
<212> TYPE: DNA
<213> ORGANISM: Festuca mairei

<400> SEQUENCE: 183

```
catgctgtcg ttcaggactc atcgtgactg tagactgcgt tcccatgctt tctcctccaa    60
agtgagttgc acatccttca tctcacactg gactgatgcc atttccccgt gtcg         114
```

<210> SEQ ID NO 184
<211> LENGTH: 431
<212> TYPE: DNA
<213> ORGANISM: Festuca mairei

<400> SEQUENCE: 184

```
catgttcctt ctacgttgat atgtacggtg catacacaaa caattatacg tggaactaaa    60
agtaaaaccc ggaaagcgga gttgtcatca aaaactaaac caagagactc cacatggatt   120
cctagctcgc ggcttatgcc ttgccggact cctcacagcc tggtggcttg aaggcgatga   180
agctgacgca ctgcacctga cggatgttgt caaaaccgat gatgcggaca taggcgtcag   240
ggtactcctt cttgacctcc tccacctcct tgaggacctg ggtggcgtct gtgcagccga   300
acatgggcag cttccacatt gtccagtacc tgccgtcgta gtatccggga gtgctgccgt   360
gctcacggaa gatgaagcca accttgctga actccaggca gggaacccat ttggagcgga   420
tcaagaagtc g                                                        431
```

<210> SEQ ID NO 185
<211> LENGTH: 84
<212> TYPE: DNA
<213> ORGANISM: Festuca mairei

<400> SEQUENCE: 185

```
catgcagtgg aatgtcttct gataaacgta ggggagaaca tgactgggga aggacttcgg    60
tggaagctat tttcttgcca gtcg                                           84
```

<210> SEQ ID NO 186

```
<211> LENGTH: 398
<212> TYPE: DNA
<213> ORGANISM: Festuca mairei

<400> SEQUENCE: 186
catgcttgcg cacatagttc atctctactg gctcgtccag ctcagcaacc atctttactg      60
cccggtccag cagattcatc tggttgatga aaagacctct gaacacgccc gagcagttga     120
cgacgacatc aaccctagga cgtccaagct cctcaatgct gacaggctcc acacggttga     180
cacggccaag gccatcagta accggctcca caccaagcat ccaaaacacc tgggccaggg     240
actcgccgta ggtcttgatg ttgtcagtac cccacaagac aagagcaatt gtctcaggat     300
acttgccacc attgtcagcc ttttgccgct ccagcagacg ttccacaaca accttggcac     360
tcttcgtggc cgctgcggtc gggattgact gcgggtcg                             398

<210> SEQ ID NO 187
<211> LENGTH: 231
<212> TYPE: DNA
<213> ORGANISM: Festuca mairei

<400> SEQUENCE: 187
cgacgtccag cgctctcttc tccttcttca ccttgggctg cgtgatcaca gtggcatcac      60
ccggcccaga gaccgccttg cgccgacgt ctgtgcctgg agccgccgtg gaggccatca     120
tcgcccggcg cgccttccgc tgcctgatgc acaagcgtt gcaaagtgac ttggggccac     180
atggaccact cctccacaag ggggttttgg tggtgttgca gtcggagcat g             231

<210> SEQ ID NO 188
<211> LENGTH: 178
<212> TYPE: DNA
<213> ORGANISM: Festuca mairei

<400> SEQUENCE: 188
catgttcaaa ctagattgat acgacaccag gtccacatga tcactgcggt tccgaagagc      60
tgaagatcct acagtgcctt gaggatctcc tcagcaccag agattgtgaa ctggccgccc     120
tcctcaatgt ttgcaacagt gaccttgagg tcatcagcaa ggagagcaaa ccgtctcg      178

<210> SEQ ID NO 189
<211> LENGTH: 232
<212> TYPE: DNA
<213> ORGANISM: Festuca mairei

<400> SEQUENCE: 189
cgagagtact ttgggcttca attttgggtc attcaataga gaatctagtt caccttcatt      60
cagtacagga cttgatagag taacctggtc agcattttca gggccaacct ccaagatgtt     120
gcctcgttta ccaatattaa cttcaagaga catgactaaa ccttctcgga gtggatcaat     180
tgcagggttt gtaacctgtg caaatcgctg cttgaaataa tcaaagagca tg             232

<210> SEQ ID NO 190
<211> LENGTH: 356
<212> TYPE: DNA
<213> ORGANISM: Festuca mairei

<400> SEQUENCE: 190
catgccactt gcccttgtag gcagggttct gcttcgttgg cttcttccat tcaccacatc      60
caggtgcctc ttcgcacttg gggttgtcaa tcttcggtgc ctcccattca ccatcctcct     120
catcatccca gtctttaggc ttagcagcct caggatcgtc aatttcatca ggctcatcat     180
```

```
ccagccatcc ttctggcttg gtggcctcct catccacaat ctctattggg gcatcctcat      240
cccagtcgtc aggcttagta gcatctggat cagggatctt agctctctcg tcccagtcct      300
ctggcttctt gtcgtcaggg tcaggaatcg tctttgatgg aataagtgct gactcg          356

<210> SEQ ID NO 191
<211> LENGTH: 122
<212> TYPE: DNA
<213> ORGANISM: Festuca mairei

<400> SEQUENCE: 191
catgccttca tatctgcaac aactggtcag tagggcaatc acatcagaag ataaattcgt      60
tgatgatgtt ggtccctcca ggcaaacaat aagcaagggt gtcccatcag acaacaatgt     120
cg                                                                    122

<210> SEQ ID NO 192
<211> LENGTH: 390
<212> TYPE: DNA
<213> ORGANISM: Festuca mairei

<400> SEQUENCE: 192
cgactccagc agcaacccga gaagatcgtc gctcgttgct tcgccagctt ttaaggcgtt      60
ctctcttttg gtgatgatcc tcttaggatc ctcccaatct ccgcagcaat ctgcttcatc     120
cttctgttgg ctttggttgg caagaacagg taaccaggga tatgtatctt gttcatggcc     180
tgcatgacga gcaggatctg ctccccctga agctggaata tcctcacgcc ctcaaggtag     240
ctgctgccga atgcggcgcg ggagatgaca tcccctgtca ggttctgcat atcaggccag     300
acatctacct cgcatggcag gtcaccggtg actaaacctt cccatctgtg taccagctcc     360
gtgcaacatt cggcgaaagc cggcaacatg                                      390

<210> SEQ ID NO 193
<211> LENGTH: 400
<212> TYPE: DNA
<213> ORGANISM: Festuca mairei

<400> SEQUENCE: 193
catgctgtca aagtggcagc tgatggctga acaagctagg cagaagcgag caccagtaca      60
gaggccagca catggatctg aaaaggttc ggcagaacag aatgaagctt caagaggag      120 ccattttgca gccttcggaa ctggaggcac gaaaaggcaa ggcaagggtt cattcgctac     180
gcgtcactcg catgggccac aacgaactgt ttccgtgaag gatgtaatct gcgtcctgga     240
gagggagcct cagatgacga aatcacggct aatttatcgg ctgtacgagc gattgcctgg     300
agatttcacc acagattagg ctgaattatg tagtgtaact tatagcgtgt aactgtttgt     360
tgatgcacag cccgtcgctc agactgacgt gttccagtcg                           400

<210> SEQ ID NO 194
<211> LENGTH: 192
<212> TYPE: DNA
<213> ORGANISM: Festuca mairei

<400> SEQUENCE: 194
cgacccatgc cgtgagcggg tcgcggaagt ccttgagccc gatcccgggt ggcgggaaga      60
ggatggggtt ggcggggtgc ttgatccagc tgcggaggag cgggtcggat gggtcggcgg     120
gcacggccag gcactggacc tgcgcgaagg tgtcagtgtt ccccgtgtcg agcaggatca     180
cgcgcccgtc ag                                                         192
```

<210> SEQ ID NO 195
<211> LENGTH: 209
<212> TYPE: DNA
<213> ORGANISM: Festuca mairei

<400> SEQUENCE: 195

```
catgctattg gagaacggtc ccaacgaggc ccaggcaaag aaggcccgcc aggtcctgca    60
ggcctgcggc gataggaaag acggctacca gctgaactac gacttcagga acccgttcgt   120
tgtgtgcggg gcgacctttg tcccgatcta ccgcgggcag aaggacgtct cctgcccta    180 ctgcacttcc cggttcgtgc cctccgtcg                                     209
```

<210> SEQ ID NO 196
<211> LENGTH: 172
<212> TYPE: DNA
<213> ORGANISM: Festuca mairei

<400> SEQUENCE: 196

```
cgagatagac gagcagacct tcctgaccaa cagggagagg gcggtggact acctcaactc    60
cctggacaag gtgttcgtga acgaccagtt cctcaactgg gacccggaga accgcatcaa   120
ggtgcgcatc atctccgcca gggcctacca ctcgctcttc atgcacaaca tg           172
```

<210> SEQ ID NO 197
<211> LENGTH: 109
<212> TYPE: DNA
<213> ORGANISM: Festuca mairei

<400> SEQUENCE: 197

```
cgagagaatc acggagcaag ctggtgtagt gctcactctt gacccaaaac caatccaggg    60
tgactggaat ggagctggct gccacacaaa ttacagcaca aagagcatg               109
```

<210> SEQ ID NO 198
<211> LENGTH: 235
<212> TYPE: DNA
<213> ORGANISM: Festuca mairei

<400> SEQUENCE: 198

```
cgagtcagcg ccactactgt gccattacag ttggagagga tgctgtcgtt tcagcatata    60
ggttatcaga agacagaggc aggtcattag ttggagcaat tttgtcaagg ggtgtagctg   120
caacattttc aacaatatca tctttgtcca aaattctatg gcggagtgaa ccatcaccaa   180
ctaagaagcc acggccaaaa cctcaatcct ttgcaaaaac ttcacctctg acatg        235
```

<210> SEQ ID NO 199
<211> LENGTH: 398
<212> TYPE: DNA
<213> ORGANISM: Festuca mairei

<400> SEQUENCE: 199

```
cgaggttcgc gttttggagt tggagaaacc tggtggacgt tgggagacaa ggtccactat    60
tccaatgcaa ccatttgaaa atgctctgac tgtgcgcatt gttacattac ataacacaac   120
caccaaggaa aatgaaaccc tgatggccat cgggactgct tatgtccaag agaggatgt    180 agctgctaga ggacgggtgc ttctgttctc tttcacgaaa agtgaaaatt ctcaaaatct   240
ggtgacagaa gtctactcaa aagagagtaa aggtgctgta tcagctgttg catcgcttca   300
aggtcatctt gtgatagctt ctggcccaaa aatcacattg aacaaatggt ccggttctga   360
attgacagct gttgcattct atgatgcccc tttgcatg                           398
```

<210> SEQ ID NO 200
<211> LENGTH: 114
<212> TYPE: DNA
<213> ORGANISM: Festuca mairei

<400> SEQUENCE: 200
catgcctcat ctataggcaa gaaggcagta gcctttgact ggatgtccat aaatgcgcca      60
tttgaagtag tcatgaatac tgttccttta atgagtgagc cgatttcagt gtcg          114

<210> SEQ ID NO 201
<211> LENGTH: 90
<212> TYPE: DNA
<213> ORGANISM: Festuca mairei

<400> SEQUENCE: 201
catgttcacg cctagctgga tctgaaccct tactgtgcct ggaagcagga ggtctacttc      60
cccgaatcca gcagcagatg atcgcagtcg                                       90

<210> SEQ ID NO 202
<211> LENGTH: 129
<212> TYPE: DNA
<213> ORGANISM: Festuca mairei

<400> SEQUENCE: 202
catgcttcca tctgcaagtg aggattccac aacactgcat ctgaccaatt tgtatttgag      60
atgacaattt tgtcacccaa tccattgtcc agggtaagct cactcggtgc gccaaggtaa     120
acgcagtcg                                                             129

<210> SEQ ID NO 203
<211> LENGTH: 108
<212> TYPE: DNA
<213> ORGANISM: Festuca mairei

<400> SEQUENCE: 203
catgccatgt gaccatcaca caggatgcgg atgctgatca gatgcttgac aaggtcattg      60
ggtacatcaa ggcagagtac aacatcagtc atgtgaccat tcaggtcg                  108

<210> SEQ ID NO 204
<211> LENGTH: 119
<212> TYPE: DNA
<213> ORGANISM: Festuca mairei

<400> SEQUENCE: 204
cgagacactg gctacagtgc cctcaagctg ctcaaggcgc tactagcact ctctccatag      60
gtagatataa gatagctcgc cggccaatgg atcagtagct gtagttcttg acgaacatg     119

<210> SEQ ID NO 205
<211> LENGTH: 245
<212> TYPE: DNA
<213> ORGANISM: Festuca mairei

<400> SEQUENCE: 205
cgagaagtcc gggcacaggt tcctgtgggt gctgcgtgcg cctcctgcct tcgctgcggc      60
cgccgctgaa ccggatgcgg cgctttctct cctcccagag gggttcttgg cacgaccgc     120 agacaggggc ctcgtggtga ccgcgtcctg ggtgccgcag gtggacgtgc ggcgtcacgc     180
ctccactggt gccttcgtaa cgcactgcgg atggaactca acactggagg caggcgaccg     240
gcatg                                                                 245

<210> SEQ ID NO 206
<211> LENGTH: 345
<212> TYPE: DNA
<213> ORGANISM: Festuca mairei

<400> SEQUENCE: 206

| | |
|---|---|
| cgagtcacga tgagtcctga acgagtgttt tcatcttcat aatggatatg ttgcatggca | 60 |
| tttttcaaag cttttccct caatttgctt cccggccaat gcgacagaac tggtacaaca | 120 |
| aatttgttaa gagcagccca tatgatatct tgtcccagtg gatgtggaca gtacagatcc | 180 |
| tccttagcac attggttccg agccttgtcc caatcaacct catcataggg tactttatag | 240 |
| agctccttcc gtaagttcaa tacaactggt gtaattgggc caacaaacct ctttccatat | 300 |
| acgtaagaca tgggaaagta taccattcgg caatgggacc acatg | 345 |

<210> SEQ ID NO 207
<211> LENGTH: 323
<212> TYPE: DNA
<213> ORGANISM: Festuca mairei

<400> SEQUENCE: 207

| | |
|---|---|
| cgagttacaa ttatatgagt actactgacc agacctgtgt atactggaaa gaactgggtc | 60 |
| gctaagaggc tgctgagaaa gaattaccta caagccgtgg attacatggt gaagattgct | 120 |
| tttatggaga gagaaaaaaa ggagaaaaat cagagatatg tgtatgttat atgtactctc | 180 |
| agcaggggaa caacaaaaac gcagcctccc tgtggatcct cctattctct accagtatga | 240 |
| tcttgtccag cttcgccttg caccactgca gctgctcgct ggtgatcctc ggcatccgca | 300 |
| gcacccgcgc caccagccgc atg | 323 |

<210> SEQ ID NO 208
<211> LENGTH: 357
<212> TYPE: DNA
<213> ORGANISM: Festuca mairei

<400> SEQUENCE: 208

| | |
|---|---|
| catgcacccg gagtggcaag agcaggcaag aaaggaagtg ttgcaccact tcggaagaat | 60 |
| cacaccagac tttgagaact agagtcggct gaagatagta acgatggttc tatatgaggt | 120 |
| tcttaggttg tacccgccag caatctttgt taccagaaga acatacaaga caatggagct | 180 |
| tggtggcatc acatatccgg caggagtgaa ccttatgttg cccattctct ttatccacca | 240 |
| tgaccccaat atatggggaa aagatgcaag cgagttcaat ccacagaggt ttgctgatgg | 300 |
| catctcaagt gccgtgaagc atccggctgc gttcttccca tttggagggg gtcctcg | 357 |

<210> SEQ ID NO 209
<211> LENGTH: 245
<212> TYPE: DNA
<213> ORGANISM: Festuca mairei

<400> SEQUENCE: 209

| | |
|---|---|
| cgactgtcca tgcgattgaa atcggttttgt aacctgacca tggattttct gaattccact | 60 |
| tcttcaatcc atgatccatc aaagtatgtc cggtgcaaat gccctgggtc tcaactctca | 120 |
| caacacccctt cttaaatgtg aagtactcag gatgaactaa ggccgtaaag ctcacaggat | 180 |
| catggaggaa aatcccatgg aagccgtcag acttggtatg ccaatctctg tagaacttgc | 240 |
| acatg | 245 |

<210> SEQ ID NO 210

```
<211> LENGTH: 232
<212> TYPE: DNA
<213> ORGANISM: Festuca mairei

<400> SEQUENCE: 210
catgccataa aggctcatat atcctactac tctacaactt gagctgccta tacaaacgta      60
ttacatctgt ggtctagtct ggactacgta gatcttccca tccttcacta ctccctcaac     120
gtcctgtggt gacccataga gctcctcaat ggcatggcca gcccgtgcaa tgcttgagag     180
aattgagctt cggaatccag agtctgtgat gagagcgtcg gtcgtgtagt cg             232

<210> SEQ ID NO 211
<211> LENGTH: 258
<212> TYPE: DNA
<213> ORGANISM: Festuca mairei

<400> SEQUENCE: 211
catgcctgac atggcgaacc catccaaatt gcaaagagga tttgggaagt ttctgacaac      60
ctttcctgca aatatcttgg tagccacaat gctcaggggg cccaatattg tttgattctt     120
caaagcacct gctaacagtt catgagactc caaggaacgc tcagcttgct tgatcatctc     180
atctaaacat gctttctcct ccaaagtgag ttgcacatcc ttcatctcac actggactga     240
tgccattttc ccgcgtcg                                                   258

<210> SEQ ID NO 212
<211> LENGTH: 161
<212> TYPE: DNA
<213> ORGANISM: Festuca mairei

<400> SEQUENCE: 212
catgtgatcc aggcgccacc cttatgtcca ccttgtaacg aggaggaagg ctccgcatga      60
gcttcacacg taagcaaagg ccaataatag tcgccatact gcaatgctcc actgttgggg     120
tgaaagtaac ccgcacatga ctaagatcat cgctgatctc g                         161

<210> SEQ ID NO 213
<211> LENGTH: 223
<212> TYPE: DNA
<213> ORGANISM: Festuca mairei

<400> SEQUENCE: 213
cgagatctgc agtctattgt gttgtatgat caaaatggta agtttgtggg ggttcgtcgg      60
ccaagctcaa aactccccat tgaaatcaat ggtaatgaaa tactaattga agacgctatt     120
ggcagtactg gtctggatct taagaccgat ccaggaattc ctgtcgtgta tgctggattt     180
ggcgcgctca tgttgacgac ctgcattagc tatctttcgc atg                       223

<210> SEQ ID NO 214
<211> LENGTH: 309
<212> TYPE: DNA
<213> ORGANISM: Festuca mairei

<400> SEQUENCE: 214
catgtgctct ggatgtacca gtgtcgctgg cgaagggaat gcaggccaag cttatcggtg      60
atttcagcag cgttcatggc attaggaaga tcttgtttgt ttgcaaacac cagaagcaca     120
gcatcacgca actcatcctc attgagcatt cggtgaagct catctctggc ctcaacaaca     180
cgctctctgt cgttgctgtc caccacaaaa ataaggccct gggtgttctg gaagtagtgc     240
ctccacaggg gcctgatctt gtcctgaccc ccgacatccc aaactgtgaa actaatgttc     300
```

```
ttgtactcg                                                              309
```

<210> SEQ ID NO 215
<211> LENGTH: 185
<212> TYPE: DNA
<213> ORGANISM: Festuca mairei

<400> SEQUENCE: 215

```
catgtactta ccagctaggt gttggttcgg tcgtcgttaa gaagcattta accacagctt      60
aattgaagtg atcgtgatga gaaagtaagc caaactaggg taggtagacg gatggatccg     120
ggacgtccgt ccagcagctc ccggcgttcc agtacgcggc cggcgacgcg tcgtcgccga     180
gctcg                                                                185
```

<210> SEQ ID NO 216
<211> LENGTH: 254
<212> TYPE: DNA
<213> ORGANISM: Festuca mairei

<400> SEQUENCE: 216

```
ccagggtttg cacccaatgt acgacgaacg tgtgagagac ctccttgatt tcagcatcta      60
cttagacatc agcaatgagg ttaagtttgc atggaaaatt cagagagaca tggcagagcg     120
tgggcacagc cttgaaagca tcaaggctag cattgaagcc aggaaaccaa attttgatgc     180
atttattcgt agtgcctttt tgccatctga aaacaataat tgtttgccat aaacccaact     240
taacatgggg catg                                                      254
```

<210> SEQ ID NO 217
<211> LENGTH: 18
<212> TYPE: DNA
<213> ORGANISM: Artificial Sequence
<220> FEATURE:
<223> OTHER INFORMATION: Synthetic

<400> SEQUENCE: 217

```
gtagactgcg ttcccatg                                                    18
```

<210> SEQ ID NO 218
<211> LENGTH: 17
<212> TYPE: DNA
<213> ORGANISM: Artificial Sequence
<220> FEATURE:
<223> OTHER INFORMATION: Synthetic

<400> SEQUENCE: 218

```
ggaacgcagt ctacgag                                                     17
```

<210> SEQ ID NO 219
<211> LENGTH: 18
<212> TYPE: DNA
<213> ORGANISM: Artificial Sequence
<220> FEATURE:
<223> OTHER INFORMATION: Synthetic

<400> SEQUENCE: 219

```
gtagactgcg ttcccatg                                                    18
```

<210> SEQ ID NO 220
<211> LENGTH: 20
<212> TYPE: DNA
<213> ORGANISM: Artificial Sequence
<220> FEATURE:
<223> OTHER INFORMATION: Synthetic

<400> SEQUENCE: 220
gtagactgcg ttcccatgta                                               20

<210> SEQ ID NO 221
<211> LENGTH: 20
<212> TYPE: DNA
<213> ORGANISM: Artificial Sequence
<220> FEATURE:
<223> OTHER INFORMATION: Synthetic

<400> SEQUENCE: 221
gtagactgcg ttcccatgtt                                               20

<210> SEQ ID NO 222
<211> LENGTH: 20
<212> TYPE: DNA
<213> ORGANISM: Artificial Sequence
<220> FEATURE:
<223> OTHER INFORMATION: Synthetic

<400> SEQUENCE: 222
gtagactgcg ttcccatgtc                                               20

<210> SEQ ID NO 223
<211> LENGTH: 20
<212> TYPE: DNA
<213> ORGANISM: Artificial Sequence
<220> FEATURE:
<223> OTHER INFORMATION: Synthetic

<400> SEQUENCE: 223
gtagactgcg ttcccatgtg                                               20

<210> SEQ ID NO 224
<211> LENGTH: 20
<212> TYPE: DNA
<213> ORGANISM: Artificial Sequence
<220> FEATURE:
<223> OTHER INFORMATION: Synthetic

<400> SEQUENCE: 224
gtagactgcg ttcccatgca                                               20

<210> SEQ ID NO 225
<211> LENGTH: 20
<212> TYPE: DNA
<213> ORGANISM: Artificial Sequence
<220> FEATURE:
<223> OTHER INFORMATION: Synthetic

<400> SEQUENCE: 225
gtagactgcg ttcccatgct                                               20

<210> SEQ ID NO 226
<211> LENGTH: 20
<212> TYPE: DNA
<213> ORGANISM: Artificial Sequence
<220> FEATURE:
<223> OTHER INFORMATION: Synthetic

<400> SEQUENCE: 226
gtagactgcg ttcccatgcc                                               20

<210> SEQ ID NO 227
<211> LENGTH: 20
<212> TYPE: DNA

```
-continued

<213> ORGANISM: Artificial Sequence
<220> FEATURE:
<223> OTHER INFORMATION: Synthetic

<400> SEQUENCE: 227
gtagactgcg ttcccatgcg                                                 20

<210> SEQ ID NO 228
<211> LENGTH: 16
<212> TYPE: DNA
<213> ORGANISM: Artificial Sequence
<220> FEATURE:
<223> OTHER INFORMATION: Synthetic

<400> SEQUENCE: 228
aagtcctgag tagcac                                                     16

<210> SEQ ID NO 229
<211> LENGTH: 15
<212> TYPE: DNA
<213> ORGANISM: Artificial Sequence
<220> FEATURE:
<223> OTHER INFORMATION: Synthetic

<400> SEQUENCE: 229
cgttcaggac tcatc                                                      15

<210> SEQ ID NO 230
<211> LENGTH: 18
<212> TYPE: DNA
<213> ORGANISM: Artificial Sequence
<220> FEATURE:
<223> OTHER INFORMATION: Synthetic

<400> SEQUENCE: 230
cacgatgagt cctgaacg                                                   18

<210> SEQ ID NO 231
<211> LENGTH: 21
<212> TYPE: DNA
<213> ORGANISM: Artificial Sequence
<220> FEATURE:
<223> OTHER INFORMATION: Synthetic

<400> SEQUENCE: 231
cacgatgagt cctgaacgaa a                                               21

<210> SEQ ID NO 232
<211> LENGTH: 21
<212> TYPE: DNA
<213> ORGANISM: Artificial Sequence
<220> FEATURE:
<223> OTHER INFORMATION: Synthetic

<400> SEQUENCE: 232
cacgatgagt cctgaacgaa t                                               21

<210> SEQ ID NO 233
<211> LENGTH: 21
<212> TYPE: DNA
<213> ORGANISM: Artificial Sequence
<220> FEATURE:
<223> OTHER INFORMATION: Synthetic

<400> SEQUENCE: 233
cacgatgagt cctgaacgaa c                                               21
```

<210> SEQ ID NO 234
<211> LENGTH: 21
<212> TYPE: DNA
<213> ORGANISM: Artificial Sequence
<220> FEATURE:
<223> OTHER INFORMATION: Synthetic

<400> SEQUENCE: 234
cacgatgagt cctgaacgaa g                                              21

<210> SEQ ID NO 235
<211> LENGTH: 21
<212> TYPE: DNA
<213> ORGANISM: Artificial Sequence
<220> FEATURE:
<223> OTHER INFORMATION: Synthetic

<400> SEQUENCE: 235
cacgatgagt cctgaacgat a                                              21

<210> SEQ ID NO 236
<211> LENGTH: 21
<212> TYPE: DNA
<213> ORGANISM: Artificial Sequence
<220> FEATURE:
<223> OTHER INFORMATION: Synthetic

<400> SEQUENCE: 236
cacgatgagt cctgaacgat t                                              21

<210> SEQ ID NO 237
<211> LENGTH: 21
<212> TYPE: DNA
<213> ORGANISM: Artificial Sequence
<220> FEATURE:
<223> OTHER INFORMATION: Synthetic

<400> SEQUENCE: 237
cacgatgagt cctgaacgat c                                              21

<210> SEQ ID NO 238
<211> LENGTH: 21
<212> TYPE: DNA
<213> ORGANISM: Artificial Sequence
<220> FEATURE:
<223> OTHER INFORMATION: Synthetic

<400> SEQUENCE: 238
cacgatgagt cctgaacgat g                                              21

<210> SEQ ID NO 239
<211> LENGTH: 21
<212> TYPE: DNA
<213> ORGANISM: Artificial Sequence
<220> FEATURE:
<223> OTHER INFORMATION: Synthetic

<400> SEQUENCE: 239
cacgatgagt cctgaacgac a                                              21

<210> SEQ ID NO 240
<211> LENGTH: 21
<212> TYPE: DNA
<213> ORGANISM: Artificial Sequence
<220> FEATURE:
<223> OTHER INFORMATION: Synthetic -continued

<400> SEQUENCE: 240
cacgatgagt cctgaacgac t                                    21

<210> SEQ ID NO 241
<211> LENGTH: 21
<212> TYPE: DNA
<213> ORGANISM: Artificial Sequence
<220> FEATURE:
<223> OTHER INFORMATION: Synthetic

<400> SEQUENCE: 241
cacgatgagt cctgaacgac c                                    21

<210> SEQ ID NO 242
<211> LENGTH: 21
<212> TYPE: DNA
<213> ORGANISM: Artificial Sequence
<220> FEATURE:
<223> OTHER INFORMATION: Synthetic

<400> SEQUENCE: 242
cacgatgagt cctgaacgac g                                    21

<210> SEQ ID NO 243
<211> LENGTH: 21
<212> TYPE: DNA
<213> ORGANISM: Artificial Sequence
<220> FEATURE:
<223> OTHER INFORMATION: Synthetic

<400> SEQUENCE: 243
cacgatgagt cctgaacgag a                                    21

<210> SEQ ID NO 244
<211> LENGTH: 21
<212> TYPE: DNA
<213> ORGANISM: Artificial Sequence
<220> FEATURE:
<223> OTHER INFORMATION: Synthetic

<400> SEQUENCE: 244
cacgatgagt cctgaacgag t                                    21

<210> SEQ ID NO 245
<211> LENGTH: 21
<212> TYPE: DNA
<213> ORGANISM: Artificial Sequence
<220> FEATURE:
<223> OTHER INFORMATION: Synthetic

<400> SEQUENCE: 245
cacgatgagt cctgaacgag c                                    21

<210> SEQ ID NO 246
<211> LENGTH: 21
<212> TYPE: DNA
<213> ORGANISM: Artificial Sequence
<220> FEATURE:
<223> OTHER INFORMATION: Synthetic

<400> SEQUENCE: 246
cacgatgagt cctgaacgag g                                    21

<210> SEQ ID NO 247
<211> LENGTH: 17
<212> TYPE: DNA

```
<213> ORGANISM: Artificial Sequence
<220> FEATURE:
<223> OTHER INFORMATION: Synthetic

<400> SEQUENCE: 247
ctcgtagact gcgtacc                                                  17

<210> SEQ ID NO 248
<211> LENGTH: 18
<212> TYPE: DNA
<213> ORGANISM: Artificial Sequence
<220> FEATURE:
<223> OTHER INFORMATION: Synthetic

<400> SEQUENCE: 248
aattggtacg cagtctac                                                 18

<210> SEQ ID NO 249
<211> LENGTH: 16
<212> TYPE: DNA
<213> ORGANISM: Artificial Sequence
<220> FEATURE:
<223> OTHER INFORMATION: Synthetic

<400> SEQUENCE: 249
cactgcgtac caattc                                                   16

<210> SEQ ID NO 250
<211> LENGTH: 18
<212> TYPE: DNA
<213> ORGANISM: Artificial Sequence
<220> FEATURE:
<223> OTHER INFORMATION: Synthetic

<400> SEQUENCE: 250
cactgcgtac caattcaa                                                 18

<210> SEQ ID NO 251
<211> LENGTH: 18
<212> TYPE: DNA
<213> ORGANISM: Artificial Sequence
<220> FEATURE:
<223> OTHER INFORMATION: Synthetic

<400> SEQUENCE: 251
cactgcgtac caattcat                                                 18

<210> SEQ ID NO 252
<211> LENGTH: 18
<212> TYPE: DNA
<213> ORGANISM: Artificial Sequence
<220> FEATURE:
<223> OTHER INFORMATION: Synthetic

<400> SEQUENCE: 252
cactgcgtac caattcac                                                 18

<210> SEQ ID NO 253
<211> LENGTH: 18
<212> TYPE: DNA
<213> ORGANISM: Artificial Sequence
<220> FEATURE:
<223> OTHER INFORMATION: Synthetic

<400> SEQUENCE: 253
cactgcgtac caattcag                                                 18
```

```
<210> SEQ ID NO 254
<211> LENGTH: 18
<212> TYPE: DNA
<213> ORGANISM: Artificial Sequence
<220> FEATURE:
<223> OTHER INFORMATION: Synthetic

<400> SEQUENCE: 254
cactgcgtac caattcta                                                18

<210> SEQ ID NO 255
<211> LENGTH: 18
<212> TYPE: DNA
<213> ORGANISM: Artificial Sequence
<220> FEATURE:
<223> OTHER INFORMATION: Synthetic

<400> SEQUENCE: 255
cactgcgtac caattctt                                                18

<210> SEQ ID NO 256
<211> LENGTH: 18
<212> TYPE: DNA
<213> ORGANISM: Artificial Sequence
<220> FEATURE:
<223> OTHER INFORMATION: Synthetic

<400> SEQUENCE: 256
cactgcgtac caattctc                                                18

<210> SEQ ID NO 257
<211> LENGTH: 18
<212> TYPE: DNA
<213> ORGANISM: Artificial Sequence
<220> FEATURE:
<223> OTHER INFORMATION: Synthetic

<400> SEQUENCE: 257
cactgcgtac caattctg                                                18

<210> SEQ ID NO 258
<211> LENGTH: 18
<212> TYPE: DNA
<213> ORGANISM: Artificial Sequence
<220> FEATURE:
<223> OTHER INFORMATION: Synthetic

<400> SEQUENCE: 258
cactgcgtac caattcca                                                18

<210> SEQ ID NO 259
<211> LENGTH: 18
<212> TYPE: DNA
<213> ORGANISM: Artificial Sequence
<220> FEATURE:
<223> OTHER INFORMATION: Synthetic

<400> SEQUENCE: 259
cactgcgtac caattcct                                                18

<210> SEQ ID NO 260
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 260
cactgcgtac caattccc                                                18

<210> SEQ ID NO 261
<211> LENGTH: 18
<212> TYPE: DNA
<213> ORGANISM: Artificial Sequence
<220> FEATURE:
<223> OTHER INFORMATION: Synthetic

<400> SEQUENCE: 261
cactgcgtac caattccg                                                18

<210> SEQ ID NO 262
<211> LENGTH: 18
<212> TYPE: DNA
<213> ORGANISM: Artificial Sequence
<220> FEATURE:
<223> OTHER INFORMATION: Synthetic

<400> SEQUENCE: 262
cactgcgtac caattcga                                                18

<210> SEQ ID NO 263
<211> LENGTH: 18
<212> TYPE: DNA
<213> ORGANISM: Artificial Sequence
<220> FEATURE:
<223> OTHER INFORMATION: Synthetic

<400> SEQUENCE: 263
cactgcgtac caattcgt                                                18

<210> SEQ ID NO 264
<211> LENGTH: 18
<212> TYPE: DNA
<213> ORGANISM: Artificial Sequence
<220> FEATURE:
<223> OTHER INFORMATION: Synthetic

<400> SEQUENCE: 264
cactgcgtac caattcgc                                                18

<210> SEQ ID NO 265
<211> LENGTH: 18
<212> TYPE: DNA
<213> ORGANISM: Artificial Sequence
<220> FEATURE:
<223> OTHER INFORMATION: Synthetic

<400> SEQUENCE: 265
cactgcgtac caattcgg                                                18

<210> SEQ ID NO 266
<211> LENGTH: 10
<212> TYPE: DNA
<213> ORGANISM: Festuca mairei

<400> SEQUENCE: 266
aatcgggctg                                                         10

<210> SEQ ID NO 267
<211> LENGTH: 10
<212> TYPE: DNA
<213> ORGANISM: Festuca mairei
```

```
<400> SEQUENCE: 267
agggtcttg                                                              10

<210> SEQ ID NO 268
<211> LENGTH: 10
<212> TYPE: DNA
<213> ORGANISM: Festuca mairei

<400> SEQUENCE: 268
gaaacgggtg                                                             10

<210> SEQ ID NO 269
<211> LENGTH: 10
<212> TYPE: DNA
<213> ORGANISM: Festuca mairei

<400> SEQUENCE: 269
gtgacgtagg                                                             10

<210> SEQ ID NO 270
<211> LENGTH: 10
<212> TYPE: DNA
<213> ORGANISM: Festuca mairei

<400> SEQUENCE: 270
gttgcgatcc                                                             10

<210> SEQ ID NO 271
<211> LENGTH: 10
<212> TYPE: DNA
<213> ORGANISM: Festuca mairei

<400> SEQUENCE: 271
ccttgacgca                                                             10

<210> SEQ ID NO 272
<211> LENGTH: 10
<212> TYPE: DNA
<213> ORGANISM: Festuca mairei

<400> SEQUENCE: 272
ttcgagccag                                                             10

<210> SEQ ID NO 273
<211> LENGTH: 10
<212> TYPE: DNA
<213> ORGANISM: Festuca mairei

<400> SEQUENCE: 273
gtgaggcgtc                                                             10

<210> SEQ ID NO 274
<211> LENGTH: 10
<212> TYPE: DNA
<213> ORGANISM: Festuca mairei

<400> SEQUENCE: 274
ccgcatctac                                                             10

<210> SEQ ID NO 275
<211> LENGTH: 10
<212> TYPE: DNA
<213> ORGANISM: Festuca mairei
```

<400> SEQUENCE: 275
gatgaccgcc                                                           10

<210> SEQ ID NO 276
<211> LENGTH: 10
<212> TYPE: DNA
<213> ORGANISM: Festuca mairei

<400> SEQUENCE: 276
gaacggactc                                                           10

<210> SEQ ID NO 277
<211> LENGTH: 10
<212> TYPE: DNA
<213> ORGANISM: Festuca mairei

<400> SEQUENCE: 277
gtcccgacga                                                           10

<210> SEQ ID NO 278
<211> LENGTH: 10
<212> TYPE: DNA
<213> ORGANISM: Festuca mairei

<400> SEQUENCE: 278
tggaccggtg                                                           10

<210> SEQ ID NO 279
<211> LENGTH: 10
<212> TYPE: DNA
<213> ORGANISM: Festuca mairei

<400> SEQUENCE: 279
ctcaccgtcc                                                           10

<210> SEQ ID NO 280
<211> LENGTH: 10
<212> TYPE: DNA
<213> ORGANISM: Festuca mairei

<400> SEQUENCE: 280
tgtctgggtg                                                           10

<210> SEQ ID NO 281
<211> LENGTH: 10
<212> TYPE: DNA
<213> ORGANISM: Festuca mairei

<400> SEQUENCE: 281
aaagctgcgg                                                           10

<210> SEQ ID NO 282
<211> LENGTH: 10
<212> TYPE: DNA
<213> ORGANISM: Festuca mairei

<400> SEQUENCE: 282
aagcctcgtc                                                           10

<210> SEQ ID NO 283
<211> LENGTH: 10
<212> TYPE: DNA
<213> ORGANISM: Festuca mairei -continued

```
<400> SEQUENCE: 283
gacggatcag                                                            10

<210> SEQ ID NO 284
<211> LENGTH: 10
<212> TYPE: DNA
<213> ORGANISM: Festuca mairei

<400> SEQUENCE: 284
cacactccag                                                            10

<210> SEQ ID NO 285
<211> LENGTH: 10
<212> TYPE: DNA
<213> ORGANISM: Festuca mairei

<400> SEQUENCE: 285
gttgccagcc                                                            10

<210> SEQ ID NO 286
<211> LENGTH: 10
<212> TYPE: DNA
<213> ORGANISM: Festuca mairei

<400> SEQUENCE: 286
acttcgccac                                                            10

<210> SEQ ID NO 287
<211> LENGTH: 10
<212> TYPE: DNA
<213> ORGANISM: Festuca mairei

<400> SEQUENCE: 287
cttcacccga                                                            10

<210> SEQ ID NO 288
<211> LENGTH: 10
<212> TYPE: DNA
<213> ORGANISM: Festuca mairei

<400> SEQUENCE: 288
gtggcatctc                                                            10

<210> SEQ ID NO 289
<211> LENGTH: 10
<212> TYPE: DNA
<213> ORGANISM: Festuca mairei

<400> SEQUENCE: 289
catcgccgca                                                            10

<210> SEQ ID NO 290
<211> LENGTH: 10
<212> TYPE: DNA
<213> ORGANISM: Festuca mairei

<400> SEQUENCE: 290
acagcctgct                                                            10

<210> SEQ ID NO 291
<211> LENGTH: 10
<212> TYPE: DNA
<213> ORGANISM: Festuca mairei
```

```
<400> SEQUENCE: 291
ggctgcgaca                                                          10

<210> SEQ ID NO 292
<211> LENGTH: 10
<212> TYPE: DNA
<213> ORGANISM: Festuca mairei

<400> SEQUENCE: 292
aaggctcacc                                                          10

<210> SEQ ID NO 293
<211> LENGTH: 10
<212> TYPE: DNA
<213> ORGANISM: Festuca mairei

<400> SEQUENCE: 293
agagccgtca                                                          10

<210> SEQ ID NO 294
<211> LENGTH: 10
<212> TYPE: DNA
<213> ORGANISM: Festuca mairei

<400> SEQUENCE: 294
agcagcgcac                                                          10

<210> SEQ ID NO 295
<211> LENGTH: 10
<212> TYPE: DNA
<213> ORGANISM: Festuca mairei

<400> SEQUENCE: 295
caaacgtggg                                                          10

<210> SEQ ID NO 296
<211> LENGTH: 10
<212> TYPE: DNA
<213> ORGANISM: Festuca mairei

<400> SEQUENCE: 296
gggtctcggt                                                          10

<210> SEQ ID NO 297
<211> LENGTH: 10
<212> TYPE: DNA
<213> ORGANISM: Festuca mairei

<400> SEQUENCE: 297
ggtcgatctg                                                          10

<210> SEQ ID NO 298
<211> LENGTH: 10
<212> TYPE: DNA
<213> ORGANISM: Festuca mairei

<400> SEQUENCE: 298 agtcgcccctt                                                         10

<210> SEQ ID NO 299
<211> LENGTH: 10
<212> TYPE: DNA
<213> ORGANISM: Festuca mairei
```

<400> SEQUENCE: 299
gggccaatgt                                                          10

<210> SEQ ID NO 300
<211> LENGTH: 10
<212> TYPE: DNA
<213> ORGANISM: Festuca mairei

<400> SEQUENCE: 300
gacgtggtga                                                          10

<210> SEQ ID NO 301
<211> LENGTH: 10
<212> TYPE: DNA
<213> ORGANISM: Festuca mairei

<400> SEQUENCE: 301
gtggagtcag                                                          10

<210> SEQ ID NO 302
<211> LENGTH: 10
<212> TYPE: DNA
<213> ORGANISM: Festuca mairei

<400> SEQUENCE: 302
tgagggtccc                                                          10

<210> SEQ ID NO 303
<211> LENGTH: 10
<212> TYPE: DNA
<213> ORGANISM: Festuca mairei

<400> SEQUENCE: 303
agccgtggaa                                                          10

<210> SEQ ID NO 304
<211> LENGTH: 10
<212> TYPE: DNA
<213> ORGANISM: Festuca mairei

<400> SEQUENCE: 304
ctgggcacga                                                          10

<210> SEQ ID NO 305
<211> LENGTH: 10
<212> TYPE: DNA
<213> ORGANISM: Festuca mairei

<400> SEQUENCE: 305
acgccagagg                                                          10

<210> SEQ ID NO 306
<211> LENGTH: 10
<212> TYPE: DNA
<213> ORGANISM: Festuca mairei

<400> SEQUENCE: 306
acgggagcaa                                                          10

INTROGRESSION OF *FESTUCA MAIREI* DROUGHT TOLERANT GENOME INTO *LOLIUM PERENNE* PLANTS

This application claims priority to U.S. provisional patent application Ser. No. 60/899,837, filed Feb. 6, 2007, which is herein incorporated by reference in its entirety.

The present application was funded in part with government support under grant numbers MICL01975, 1230-21000-035-00D, and 1230-21000-045-00D United States Department of Agriculture. The government may have certain rights in this invention.

A Sequence Listing has been submitted on a compact disc, the entire content of which is herein incorporated by reference. The compact disc and its duplicate are labeled Copy 1 and Copy 2, respectively. Each disk contains a file named "13543seq.txt" created on Apr. 24, 2008 that is 286,720 bytes, and each disk is identical to the other.

FIELD OF THE INVENTION

The present inventions relate to compositions and methods for providing drought resistant grass plants comprising *Festuca mairei* plant germplasm. Specifically, the inventions relate to providing compositions and methods for introgressing *Festuca mairei* germplasm and/or specific *Festuca mairei* genes into grass plants, such as *Lolium perenne* plants. Further, the invention relates to methods of grass plant breeding comprising genetic markers for identifying the preferred *Festuca mairei* germplasm introgressed into grass plants, and providing commercially desirable drought resistant cultivars of grass plants.

BACKGROUND OF THE INVENTION

Perennial ryegrass (*Lolium perenne* L.) (Lp) is a cool-season grass (2n=2x=14, LL) that is in wide use as turfgrass and forage grass due to superior quality and rapid establishment of plants. However, lack of drought tolerance makes Lp less persistent and reduces economical advantages of its use during hot and dry summers or dry environments.

One approach for improvement of drought tolerance in perennial ryegrass is introgression of alien genomes from other drought tolerant genera, such as fescue plants (Rie and Mondart 1985, Ames: Iowa State Univ. Press, 1985:241-246; herein incorporated by reference). Thus, plant breeders and geneticists have attempted for several decades to genetically combine perennial ryegrass (*L. perenne* L.) with fescue (*Festuca* spp.) to create novel forage grasses containing both high forage quality and good drought tolerance.

However, a major barrier in *Festuca*×*Lolium* breeding programs for providing commercial cultivars of *L. perenne* plants comprising the desirable traits of *Festuca* is the difficulty in selecting hybrids with the desired alien chromatin or chromosome addition-substitution. Further, *Festuca* germplasm is rapidly loss from subsequent breeding lines when attempting to retain the drought resistant *Festuca* germplasm and the desired agronomic traits of *Lolium* plants.

Therefore, despite exhaustive efforts, especially in light of the potential enormous economic and environmental significance of success, there is still a need for identification and characterization of plant genes that would confer drought tolerance to *Lolium* plants. Further, there remains a need for providing increased drought tolerance in *L. perenne* L. ryegrass plants.

SUMMARY OF THE INVENTION

The present inventions relate to compositions and methods for providing drought resistant grass plants comprising *Festuca mairei* plant germplasm. Specifically, the inventions relate to providing compositions and methods for introgressing *Festuca mairei* germplasm and/or specific *Festuca mairei* genes into grass plants, such as *Lolium perenne* plants. Further, the invention relates to methods of grass plant breeding comprising genetic markers for identifying the preferred *Festuca mairei* germplasm introgressed into grass plants, and providing commercially desirable drought resistant cultivars of grass plants.

The present invention relates to compositions and methods for identifying preferred plant germplasm associated with successful adaptation to drought conditions, such as *Festuca mairei* germplasm, including but not limited to individual nucleic acid sequence associated with drought resistance.

The present invention also relates to the field of plant breeding, specifically to methods of grass plant breeding comprising introgression of preferred drought resistant germplasm into plants. The breeding methods further comprise identifying and using nucleic acid sequence tic markers for identifying germplasm associated with drought resistance in breeding populations. The grass plant breeding methods include but are not limited to natural breeding, artificial breeding, selective breeding involving DNA molecular marker analysis for germplasm associated with drought tolerance and other desired agronomic traits, transgenics, and commercial breeding. Further, the invention relates to new drought resistant grass plants comprising preferred germplasm, including but not limited to populations, cultivars, varieties, lines and methods of breeding the same for commercial use.

The invention further relates to new grass plants that are resistant to drought, and in particular grass plants comprising germplasm that was identified during onset or adaptation to drought stress, methods of breeding drought resistant grass plants, and the resulting new drought resistant grass plant varieties, lines and cultivars developed through traditional plant breeding methods that provide for successful commercialization of the drought resistant germplasm. The present invention is not limited to providing any particular grass plant variety, line, and cultivar having drought resistance activities. The present invention also provides breeding methods comprising DNA marker analysis for identifying *Festuca mairei* plant nucleic acid sequence in grass plants with increased tolerance for drought stress, including but not limited to *Festuca mairei* and *Lolium perenne* grass plants.

Accordingly, in some embodiments, the present invention provides a nucleic acid sequence, wherein said nucleic acid sequence comprises a sequence selected from the group consisting of SEQ ID NOs:1-39 and 93-216. In other embodiments, the nucleic acid sequence comprises a sequence at least 50%, 60%, 70%, 80%, 90%, 95%, 98%, or 99% identical to a sequence selected from the group consisting of SEQ ID NOs:1-39 and 93-216. In other embodiments, the nucleic acid sequence is at least 50%, 60%, 70%, 80%, 90%, 95%, 98%, or 99% identical to a sequence selected from the group consisting of SEQ ID NOs:1-39 and 93-216. In other embodiments, the present invention provides nucleotide sequences at least 90% identical to a sequence selected from the group consisting of SEQ ID NOs:1-39 and 93-216. In one embodiment, the nucleic acid sequence comprises a sequence selected from the group consisting of SEQ ID NOs: 1-39. In one embodiment, the nucleic acid sequence is a sequence selected from the group consisting of SEQ ID NOs:1-39. In other embodiments, the present invention provides nucleotide sequences at least 90% identical to a sequence selected from the group consisting of SEQ ID NOs:1-39. In one embodiment, the nucleic acid sequence comprises a sequence selected from the group consisting of SEQ ID NOs: 93-216. In one embodiment, the nucleic acid sequence is a sequence selected from the group consisting of SEQ ID NOs: 93-216. In other embodiments, the present invention provides nucleotide sequences at least 90% identical to a sequence selected from the group consisting of SEQ ID NOs: 93-216. In one embodiment, the nucleic acid sequence comprises a sequence selected from the group consisting of SEQ ID NOs:1-4, 8-10, 12-19, 25-26, 29-30, and 32-37. In one embodiment, the nucleic acid sequence is selected from the group consisting of SEQ ID NOs: 1-4, 8-10, 12-19, 25-26, 29-30, and 32-37. In one embodiment, the nucleic acid sequence encodes a polypeptide comprising a sequence selected from the group consisting of SEQ ID NOs:40-91. In other embodiments, the polypeptide comprises a sequence at least 50%, 60%, 70%, 80%, 90%, 95%, 98%, or 99% identical to a sequence selected from the group consisting of SEQ ID NOs:40-91. In other embodiments, the polypeptide comprises a sequence at least 90% identical to a sequence selected from the group consisting of SEQ ID NOs:40-91. In one embodiment, the expression of said nucleic acid sequence is altered during drought stress treatment of a *Festuca mairei* plant as compared to a control *Festuca mairei* plant. The present invention is not limited to any particular type of altered expression of a nucleic acid sequence. Indeed, a variety of altered nucleic acid sequence expression is contemplated, including, but not limited to up-regulation, down-regulation, silencing, up-regulation then down-regulation, transient regulation, and differential regulation. In one embodiment, the nucleic acid sequence is up-regulated during drought stress treatment of a *Festuca mairei* plant as compared to a control *Festuca mairei* plant. The present invention is not limited to any particular function category of up-regulated nucleic acid sequence. Indeed, a variety of function categories of up-regulated nucleic acid sequences are contemplated, including, but not limited to subcellular localization, transcription, defense, metabolism, transport, et cetera. The present invention is not limited to any particular sequence of up-regulated nucleic acid sequence. Indeed, a variety of sequences of up-regulated nucleic acid sequences are contemplated, including, but not limited to a nucleic acid sequence comprising a sequence selected from the group consisting of SEQ ID NOs: 94, 95, 99, 102, 105, 109, 113, 114, 116, 119, 122, 124, 126, 134, 140, 156, 157, 182, 192, 203, 209, and 215. In one embodiment, the nucleic acid sequence is selected from the group consisting of SEQ ID NOs: 94, 95, 99, 102, 105, 109, 113, 114, 116, 119, 122, 124, 126, 134, 140, 156, 157, 182, 192, 203, 209, and 215. In one embodiment, the nucleic acid sequence is down-regulated during drought stress treatment of a *Festuca mairei* plant as compared to a control *Festuca mairei* plant. The present invention is not limited to any particular function category of a down-regulated nucleic acid sequence. Indeed, a variety of function categories of down-regulated nucleic acid sequences are contemplated, including, but not limited to subcellular localization, metabolism, transport, energy, et cetera. The present invention is not limited to any particular sequence of a down-regulated nucleic acid sequence. Indeed, a variety of down-regulated nucleic acid sequences are contemplated, including, but not limited to a nucleic acid sequence comprising a sequence selected from the group consisting of SEQ ID NOs: 96, 103, 104, 106, 108, 110, 111, 112, 162, 172, 181, 200, 202, 204, and 208. In one embodiment, the nucleic acid sequence is selected from the group consisting of SEQ ID NOs: 96, 103, 104, 106, 108, 110, 111, 112, 162, 172, 181, 200, 202, 204, and 208. In one embodiment, the nucleic acid sequence is up-regulated then down-regulated during drought stress treatment of a *Festuca mairei* plant as compared to a control *Festuca mairei* plant. The present invention is not limited to any particular function category of up-regulated then down-regulated nucleic acid sequence. Indeed, a variety of function categories of up-regulated then down-regulated nucleic acid sequences are contemplated, including, but not limited to subcellular localization, energy, cell type differentiation, protein fate, et cetera. The present invention is not limited to any particular sequence of up-regulated then down-regulated nucleic acid sequence. Indeed, a variety of sequences of up-regulated then down-regulated nucleic acid sequences are contemplated, including, but not limited to a nucleic acid sequence comprising a sequence selected from the group consisting of SEQ ID NOs: 101, 118, 120, 141, and 185. In one embodiment, the nucleic acid sequence is selected from the group consisting of SEQ ID NOs: 101, 118, 120, 141, and 185. In one embodiment, the nucleic acid sequence comprises a transiently expressed fragment. In one embodiment, the nucleic acid sequence is transiently regulated during drought stress treatment of a *Festuca mairei* plant as compared to a control *Festuca mairei* plant. The present invention is not limited to any particular function category of transiently regulated nucleic acid sequence. Indeed, a variety of function categories of transiently regulated nucleic acid sequences are contemplated, including, but not limited to nucleic acid sequences associated with transport, subcellular localization, encoding a protein with a binding function, defense, metabolism, interaction with the cellular environment, cell type differentiation, et cetera. The present invention is not limited to any particular sequence of transiently regulated nucleic acid sequence. Indeed, a variety of sequences of transiently regulated nucleic acid sequences are contemplated, including, but not limited to a nucleic acid sequence comprising a sequence selected from the group consisting of SEQ ID NOs: 93, 151, 153, and 179. In one embodiment, the nucleic acid sequence is expressed in a drought stressed *Festuca mairei* plant. In one embodiment, the nucleic acid sequence is a differentially expressed fragment. In one embodiment, the nucleic acid sequence is silenced in a drought stressed *Festuca mairei* plant. In one embodiment, the altered nucleic acid sequence provides drought tolerance in a *Festuca mairei* plant as compared to a control *Festuca mairei* plant. In one embodiment, the altered nucleic acid sequence provides increased drought tolerance in a *Festuca mairei* plant as compared to a control *Festuca mairei* plant.

The present invention provides a polypeptide, wherein said polypeptide is encoded by a nucleic acid sequence comprising a sequence selected from the group consisting of SEQ ID NOs: 1-39 and 93-216. In one embodiment, the polypeptide increases drought tolerance in a grass plant.

The present invention provides a polypeptide, wherein said polypeptide comprises an amino acid sequence selected from the group consisting of SEQ ID NOs: 40-91. In other embodiments, the polypeptide comprises a sequence at least 50%, 60%, 70%, 80%, 90%, 95%, 98%, or 99% identical to a sequence selected from the group consisting of SEQ ID NOs: 40-91. In other embodiments, the polypeptide sequence is at least 50%, 60%, 70%, 80%, 90%, 95%, 98%, or 99% identical to a sequence selected from the group consisting of SEQ ID NOs: 40-91. In other embodiments, the present invention provides a polypeptide comprising a sequence at least 90% identical to a sequence selected from the group consisting of SEQ ID NOs: 40-91.

The present invention provides a vector construct comprising at least one nucleic acid sequence from a *Festuca mairei* plant, wherein said nucleic acid sequence comprises a sequence selected from the group consisting of SEQ ID NOs:

1-39 and 93-216. In other embodiments, the present invention provides a nucleotide sequence at least 90% identical to a sequence selected from the group consisting of SEQ ID NOs: 1-39 and 93-216. In one embodiment, the nucleic acid sequence comprises a sequence selected from the group consisting of SEQ ID NOs:1-39. In one embodiment, the nucleic acid sequence comprises a sequence selected from the group consisting of SEQ ID NOs:1-4, 8-10, 12-19, 25-26, 29-30, and 32-37. In one embodiment, the nucleic acid sequence encodes a polypeptide comprising a sequence selected from the group consisting of SEQ ID NOs:40-91. In one embodiment, the nucleic acid sequence is operably linked to an exogenous promoter. The present invention is not limited to any particular type of promoter. Indeed, the use of a variety of promoters is contemplated. In some embodiments, the promoter is a eukaryotic promoter. In some embodiments, the promoter is a constitutive promoter or an inducible promoter. In some embodiments, the eukaryotic promoter is active in a plant. The present invention is not limited to any particular type of vector construct. Indeed, the use of a variety of vector constructs is contemplated. In some embodiments, the vector is a eukaryotic vector. In other embodiments, said eukaryotic vector is a plant vector. In some embodiments, the vector is a binary vector. In some embodiments, the vector is an expression vector. In other embodiments, said vector plant vector comprises a T-DNA vector. In other embodiments, said vector is a prokaryotic vector.

The present invention provides a cultivar of a grass plant comprising at least one heterologous nucleic acid sequence from a *Festuca mairei* plant genome, wherein said nucleic acid sequence comprises a sequence selected from the group consisting of SEQ ID NOs:1-39 and 93-216. In other embodiments, the present invention provides a nucleotide sequence at least 90% identical to a sequence selected from the group consisting of SEQ ID NOs:1-39 and 93-216. In one embodiment, the nucleic acid sequence comprises a sequence selected from the group consisting of SEQ ID NOs:1-39. In one embodiment, the nucleic acid sequence comprises a sequence selected from the group consisting of SEQ ID NOs: 1-39. In one embodiment, the nucleic acid sequence comprises a sequence selected from the group consisting of SEQ ID NOs:1-4, 8-10, 12-19, 25-26, 29-30, and 32-37. In one embodiment, the nucleic acid sequence encodes a polypeptide comprising a sequence selected from the group consisting of SEQ ID NOs:40-91. In one embodiment, the grass plant includes, but not limited to, a ryegrass, bluegrass, Bermuda grass, and zoysiagrass plant. In one embodiment, the grass plant is a perennial ryegrass plant. In one embodiment, the grass plant is selected from the group consisting of *Lolium perenne* species and hybrids thereof. In one embodiment, the grass plant is a hybrid plant is selected from the group of hybrid plants consisting of *Festuca mairei*×*Lolium perenne* species and hybrids thereof. In one embodiment, the grass plant is a *Festuca mairei* plant×Calypso plant or *Festuca mairei* plant×Citation II plant. In one embodiment, the grass plant includes, but is not limited to, a G15 plant or a G30a plant. In one embodiment, the grass plant includes, but is not limited to, a grass plant derived from a G15 or a G30a plant. In one embodiment, the nucleic acid sequence is meiotically stable. In one embodiment, the cultivar is drought resistant. In one embodiment, the cultivar is tolerant to drought stress. In one embodiment, the grass plant remains turgid during drought conditions. In one embodiment, the grass plant is an agronomically desirable plant. In one embodiment, the grass plant is a commercially desirable plant. In one embodiment, the invention provides a seed of the cultivar.

The present invention provides a cultivar of a grass plant grown from a seed, comprising at least one heterologous nucleic acid sequence from a *Festuca mairei* plant. In one embodiment, the nucleic acid sequence comprises a sequence selected from the group consisting of SEQ ID NOs:1-39 (FIG. 7), 93-216 (FIG. 9) and 307-320 (Table 1). In one embodiment, the nucleic acid sequence comprises a sequence selected from the group consisting of SEQ ID NOs:1-39. In one embodiment, the nucleic acid sequence comprises a sequence selected from the group consisting of SEQ ID NOs: 1-4, 8-10, 12-19, 25-26, 29-30, and 32-37.

The present invention provides a seed of a drought resistant grass plant cultivar, wherein said drought resistant grass plant comprises at least one heterologous nucleic acid sequence selected from the group consisting of SEQ ID NOs: 1-39, 93-216 and 307-320.

The present invention provides a plant, comprising the morphological and physiological properties of a grass plant grown from a seed deposited under Budapest Treaty requirements to American Type Culture Collection (ATCC), 10801 University Boulevard, Manassas, Va., 20110-2209, The United States of America, Accession Numbers (i.e. Patent Deposit Designations) selected from the group consisting of G11a deposited under ATCC accession no. PTA-8920, G14 deposited under ATCC accession no. PTA-8921, and G16 deposited under ATCC accession no. PTA-8922.

The present invention provides a method of providing a cultivar of a grass plant comprising: a) providing; i) a grass plant, and ii) a nucleic acid sequence, wherein said nucleic acid sequence comprises a sequence selected from the group consisting of SEQ ID NOs:1-39, 93-216, and sequences at least 90% identical thereto; and b) introgressing said nucleic acid sequence into said grass plant under conditions to produce a progeny grass plant. In other embodiments, the nucleic acid sequence comprises a sequence at least 50%, 60%, 70%, 80%. 90%, 95%, 98%, or 99% identical to a sequence selected from the group consisting of SEQ ID NOs:1-39 and 93-216. In other embodiments, the nucleic acid sequence is at least 50%, 60%, 70%, 80%, 90%, 95%, 98%, or 99% identical to a sequence selected from the group consisting of SEQ ID NOs:1-39 and 93-216. In other embodiments, the present invention provides nucleotide sequences at least 90% identical to a sequence selected from the group consisting of SEQ ID NOs:1-39 and 93-216. In one embodiment, the nucleic acid sequence comprises a sequence selected from the group consisting of SEQ ID NOs:1-39. In one embodiment, the nucleic acid sequence comprises a sequence selected from the group consisting of SEQ ID NOs:1-4, 8-10, 12-19, 25-26, 29-30, and 32-37. In one embodiment, the nucleic acid sequence encodes a polypeptide comprising a sequence selected from the group consisting of SEQ ID NOs:40-91. In one embodiment, the introgressing is breeding or transfecting. The present invention is not limited to any particular type of introgression, including but not limited to natural breeding, artificial breeding, breeding using molecular marker selection, commercial breeding, and transgenics. In one embodiment, the introgressed nucleic acid sequence is meiotically stable. The present invention is not limited to any particular source of *Festuca mairei* nucleic acid sequence. Indeed, a variety of sources are contemplated including but not limited to a hybrid plant, *Lolium perenne* hybrid plant, $F_1$ hybrid plant, $4 \times F_1$ hybrid plant, $3 \times F_1$ hybrid plant, backcross progeny plant, plant parts, and synthetic nucleic acid sequence. In one embodiment, the $F_1$ hybrid plant is selected from the group of hybrid plants consisting of *Festuca mairei*×*Lolium perenne* species and hybrids thereof. In one embodiment, the $F_1$ hybrid plant is a *Festuca mairei* plant×Calypso plant. In one embodiment, the F₁ hybrid plant is a *Festuca mairei* plant×Citation II plant. In one embodiment, the backcross progeny plant is selected from but not limited to the group of G15, G30a, G6, G11b, G14, G27b, G30b, G11a, and G14 plants. In one embodiment, the *Festuca mairei* nucleic acid sequence is provided by a G15 plant or progeny thereof. In one embodiment, the *Festuca mairei* nucleic acid sequence is provided by a G30a plant or progeny thereof. In one embodiment, the *Festuca mairei* nucleic acid sequence is provided by a plant that derives from a G15 or a G30a plant. In one embodiment, the *Festuca mairei* nucleic acid sequence is provided by a plant part. The present invention is not limited to any particular plant part. Indeed, a variety of plant parts are contemplated including but not limited to a pollen grain, ovule, tissue, seed, and a cell. In one embodiment, the *Festuca mairei* nucleic acid sequence is provided by a synthetic *Festuca mairei* nucleic acid sequence. In one embodiment, the *Festuca mairei* nucleic acid sequence is provided by a transgenic nucleic acid sequence. The present invention is not limited to any particular grass plant. Indeed, a variety of grass plants are contemplated for breeding purposes including but not limited to turfgrass plants, forage grass plants, ornamental grass plants, ground cover grass plants, transgenic grass plants and elite grass plants. In one embodiment, the plant is selected from the group including but not limited to ryegrass, bluegrass, Bermuda grass, zoysiagrass plants and cool season grass plants. In one embodiment, an elite grass plant comprises at least one agronomic trait desirable in the progeny grass plant. The present invention is not limited to any particular agronomic trait. Indeed, a variety of agronomic traits are contemplated, including but not limited to drought resistance, heat resistance, microbe resistance, insect resistance, particular color, particular height, particular type of root development, forage quality, and the like. In one embodiment, the ryegrass plant is a *Lolium perenne* plant or hybrid plant thereof. In one embodiment, the ryegrass plant is a Citation II or a Calypso plant. In one embodiment, the grass plant is a hybrid grass plant. The present invention is not limited to any particular hybrid grass plant. Indeed, a variety of hybrid grass plants are contemplated for breeding purpose, including but not limited to *Lolium perenne* species plant hybrids and *Festuca mairei* plant hybrids. In one embodiment, the types of hybrid grass plants include but are not limited to a *Festuca mairei* plant×a grass plant. a *Festuca mairei* plant×*Lolium perenne* species plant or hybrid plant thereof. In one embodiment, the types of hybrid grass plants include but are not limited to F₁ hybrid plants, 4× F₁ hybrid plants, 3× F₁ hybrid plant, and backcross progeny plants.

In one embodiment, the F₁ hybrid plant is selected from the group of hybrid plants consisting of *Festuca mairei*×*Lolium perenne* species and hybrids thereof. In one embodiment, the F₁ hybrid plant is a *Festuca mairei* plant×Calypso plant. In one embodiment, the F₁ hybrid plant is a *Festuca mairei* plant×Citation II plant. In one embodiment, the backcross progeny plant is selected from the group consisting of G15, G30a, G6, G11b, G14, G27b, G30b, G11a, and G14 plants. In a preferred embodiment, the backcross progeny plant is a G15 or a G30a plant. In one embodiment, the ryegrass plant derives from a G15 plant or a G30a plant. In one embodiment, a molecular marker is provided. In one embodiment, the method further comprises a molecular marker and using said molecular marker for identifying at least one *Festuca mairei* nucleic acid sequence in a grass plant or a progeny grass plant.

The present invention is not limited to any particular molecular marker. Indeed, a variety of molecular markers are contemplated, including but not limited to a simple sequence repeat (SSR), microsatellite marker, random amplified polymorphic DNA (RAPD), cDNA-amplified fragment length polymorphism, *Festuca mairei* nucleic acid, and *Festuca mairei* polypeptide. In one embodiment, the cDNA-amplified fragment length polymorphism (AFLP) marker is provided by a linker or primer nucleic acid sequence selected from the group consisting of SEQ ID NOs:217-246 and 247-265. In one embodiment, the random amplified polymorphic DNA (RAPD) marker is provided by a primer sequence selected from the group consisting of SEQ ID NOs:266-306. In one embodiment, the *Festuca mairei* nucleic acid marker comprises a sequence selected from the group consisting of SEQ ID NOs:1-39 and 93-216. In other embodiments, the nucleic acid sequence marker comprises a sequence at least 50%, 60%, 70%, 80%, 90%, 95%, 98%, or 99% identical to a sequence selected from the group consisting of SEQ ID NOs: 1-39 and 93-216. In other embodiments, the nucleic acid sequence marker is at least 50%, 60%, 70%, 80%, 90%, 95%, 98%, or 99% identical to a sequence selected from the group consisting of SEQ ID NOs:1-39 and 93-216. In other embodiments, the present invention provides nucleotide sequence markers at least 90% identical to a sequence selected from the group consisting of SEQ ID NOs:1-39 and 93-216. In one embodiment, the nucleic acid sequence marker comprises a sequence selected from the group consisting of SEQ ID NOs: 1-39. In one embodiment, the nucleic acid sequence marker is a sequence selected from the group consisting of SEQ ID NOs:1-39. In other embodiments, the present invention provides nucleotide sequence markers at least 90% identical to a sequence selected from the group consisting of SEQ ID NOs: 1-39. In one embodiment, the nucleic acid sequence marker comprises a sequence selected from the group consisting of SEQ ID NOs: 93-216. In one embodiment, the nucleic acid sequence marker is a sequence selected from the group consisting of SEQ ID NOs: 93-216. In other embodiments, the present invention provides nucleotide sequence markers at least 90% identical to a sequence selected from the group consisting of SEQ ID NOs: 93-216. In one embodiment, the polypeptide marker comprises an amino acid sequence selected from the group consisting of SEQ ID NOs: 40-91. In one embodiment, the polypeptide marker is an amino acid sequence selected from the group consisting of SEQ ID NOs: 40-91. In other embodiments, the polypeptide marker comprises a sequence at least 50%, 60%, 70%, 80%, 90%, 95%, 98%, or 99% identical to a sequence selected from the group consisting of SEQ ID NOs: 40-91. In other embodiments, the polypeptide marker is at least 50%, 60%, 70%, 80%, 90%, 95%, 98%, or 99% identical to a sequence selected from the group consisting of SEQ ID NOs: 40-91. In other embodiments, the present invention provides a polypeptide marker at least 90% identical to a sequence selected from the group consisting of SEQ ID NOs: 40-91. In one embodiment, the identifying is an assay selected from the group consisting of a simple sequence repeats (SSR), microsatellite marker, random amplified polymorphic DNA (RAPD), cDNA-amplified fragment length polymorphism, microarray, macroarray, Northern, Southern, and Western. In one embodiment, the progeny plant is drought resistant. The present invention is not limited to any particular drought resistant progeny plant. Indeed, a variety of drought resistant progeny plants are contemplated, including but not limited to a drought resistant progeny plant comprising an agronomically desirable trait, a progeny plant that is tolerant to drought stress, a progeny plant that remains turgid during drought stress, a progeny plant that demonstrates increased resistance to drought stress as compared to the grass plant, a progeny plant that is an agronomically desirable plant, a progeny plant that is a commercially desirable plant, and a progeny plant that is a commercially desirable cultivar.

DESCRIPTION OF THE FIGURES

FIG. 4 shows an exemplary distribution of the patterns of differentially expressed fragments (DEFs) revealed by cDNA-AFLP during drought stress treatment in *F. mairei*.

FIG. 7 shows exemplary preferred Fm nucleotide sequences (SEQ ID NOs:1-39).

FIG. 8 shows exemplary translated Fm sequences (SEQ ID NOs:40-91).

FIG. 9 shows an exemplary preferred Fm nucleotide sequences (SEQ ID NOs: 93-216).

FIG. 15 shows an exemplary grouping (classification) of hybrid lines and cultivar plants of the present inventions.

DEFINITIONS

Figure 1:
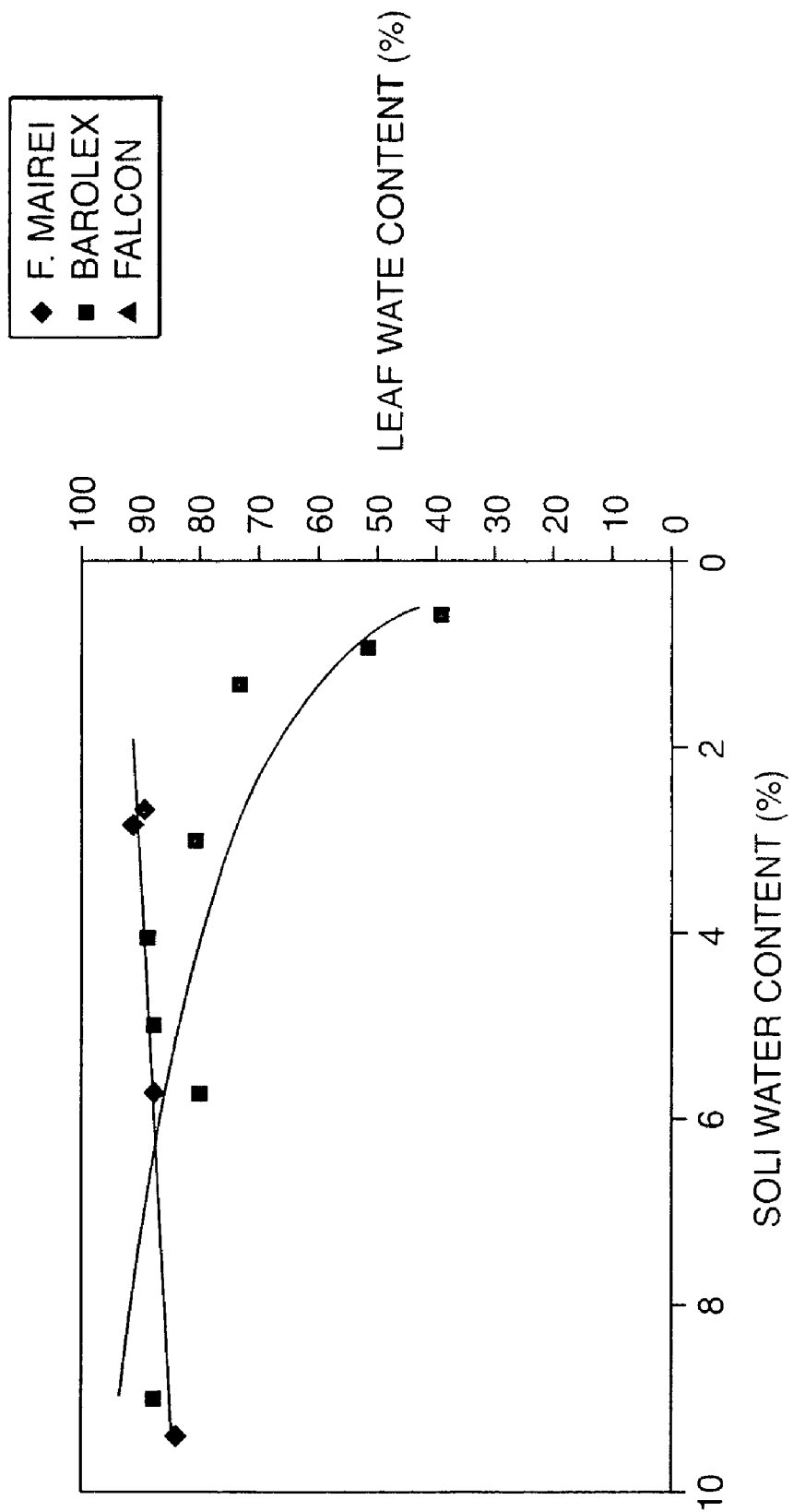
FIG. 1 shows an exemplary relationship between leaf water content and soil moisture content of *Festuca mairei* compared with *Festuca arundinacea* tall fescue cultivars (such as Falcon and Borolex).

To facilitate an understanding of the present invention, a number of terms and phrases are defined below:

The use of the article "a" or "an" is intended to include one or more.

The use of terms defined in the singular are intended to include those terms defined in the plural and vice versa.

The term "drought resistant" or "drought tolerant" in reference to a plant refers in general to a plant that is living and/or thriving in surroundings having persistently low water availability, such as low soil moisture content, for example, a *Festuca mairei* drought tolerant plant growing in the Atlas mountains or a plant of the present invention that continues to live and/or thrive following the lowering of soil moisture content and/or a under conditions of persistently low water availability. On the other hand, a "drought susceptible" plant refers to a plant that loses normal leaf color and/or increases leaf firing and/or wilts during onset or persistent of low water availability.

The terms "drought resistance" or "drought tolerance" or "drought stress resistance" or "drought stress tolerance" refer in general to the response of a plant to a change in water availability, naturally or artificially. An example of a natural change in water availability is a seasonal difference in availability of environmentally derived water. An example of an artificial change of water availability is the lowering of the amount of irrigation water, such that the soil moisture content is lowered. Lowering water availability may be short-term or long-term in time.

As used herein, "tolerant" in relation to "drought stress" and equivalent terms also refers to a plant that is living and/or thriving during time periods of low water availability.

The terms "altered environmental tolerance" and "altering environmental tolerance" in reference to a plant refer to any changes in a plant's ability to tolerate an environmental abiotic stress. The terms "altered abiotic stress" and "altering abiotic stress" refer to any changes in abiotic tolerance such as an increased tolerance to an abiotic stress, such as onset or persistence of "dry conditions" or "drought," heat, cold, "high saline" or "salt."

The terms "altered drought tolerance" and "altering drought tolerance" refer to any changes in drought and tolerance and changes in environmental factors such as lower rainfall and lower soil moisture content. An "altered drought tolerance phenotype" refers to detectable change in the ability of a modified plant to withstand low-water conditions compared to the similar, but non-modified plant. In general, improved (increased) drought tolerance phenotypes (i.e., ability to a plant to survive in low-water conditions that would normally be deleterious to a plant) are of interest.

For the purposes of the present invention, an "increasing" or "increased" or "enhanced" tolerance refers to a higher level of tolerance of a modified plant or plant part over a control plant or plant part, such as a wild-type control plant or plant part or a nonmodified control or plant part, such as when comparing a plant or leaf from a Fm:Lp hybrid grass plant of the present invention to a closely related cultivar of Lp plant or a Lp leaf from an Lp cultivar. Examples include increasing expression of a gene associated with increasing drought tolerance or maintaining turgor under low water conditions, increasing water content of plants under drought conditions, increasing the capability of a plant to continue living and/or growing under environmental conditions such as extreme dryness, such as depriving plants of irrigation water, see, EXAMPLES.

As used herein, the term "drought adaptation" in reference to a plant refers to an adaptation response of a plant during lowering or lowered environmental water access.

As used herein, the term "environmental water access" refers to natural soil moisture content or artificially controlling water access to a plant.

As used herein, the terms "turgid" or "not wilted" or "hydrated" applied to a plant cell, a plant tissue, a plant part and a plant refer to a firm condition of the plant cell, plant tissue, plant part or plant when it is filled with water. A turgid condition of a plant or plant part refers to the opposite condition of wilted plant or plant part. "Turgor" refers to a condition of a cell or tissue or plant such as a turgid cell or turgid tissue or turgid plant that is opposite of a dehydrated cell or dehydrated tissue or dehydrated plant.

As used herein, the term "wilt" refers to a symptom or a disease characterized by a loss of turgidity in a plant (for example, vascular wilt).

As used herein, the term "wilting" refers to a symptom characterized by loss of turgor or dehydration which results in drooping of leaves and/or stems and/or flowers, such as demonstrated when a physiological damaging decrease in turgidity causes wilting.

As used herein, the term "plant" is used in it broadest sense. It includes, but is not limited to, any species of grass (e.g. ryegrass and turfgrass), ornamental or decorative, crop or cereal, fodder or forage, fruit or vegetable, fruit plant or vegetable plant, herb plant, woody plant, flower plant or tree. It is not meant to limit a plant to any particular structure. It also refers to a unicellular plant (e.g. microalga) and a plurality of plant cells that are largely differentiated into a colony (e.g. volvox) or a structure that is present at any stage of a plant's development. Such structures include, but are not limited to, a seed, a tiller, a sprig, a stolen, a plug, a rhizome, a shoot, a stem, a leaf, a flower petal, a fruit, et cetera.

The term "xerophytic plant" refers to a plant adapted for life with a limited supply of water, as opposed to a "hydrophytic plant" or "hydrophyte" in reference to a plant adapted to live in water or in waterlogged soil and a "mesophytic plant" or "mesophyte" in reference to a land plant growing in surroundings having an average supply of water, for example, a moderate amount of moisture, neither too dry nor too wet.

The term "xerophyte" refers to a plant adapted to living in a dry arid habitat, such as a desert plant.

The term "xeromorphic" refers to a plant with morphological and physiological characters that tolerate persistently low water availability, such as succulent plant.

As used herein, the terms "crop" and "crop plant" are used herein its broadest sense. The term includes, but is not limited to, any species of plant or alga edible by humans or used as a feed for animals or fish or marine animals, or consumed by humans, or used by humans (natural pesticides), or viewed by humans (flowers) or any plant or alga used in industry or commerce or education, lawns, engineering, and agricultural uses. Indeed, a variety of crop plants are contemplated, including but not limited to ryegrass, such as and annual ryegrass and perennial ryegrass, turf grass, forage grass, corn, wheat, rice, barley, sorghum, sunflower, herbs and trees. The term includes, but is not limited to any species of plant used as a feed for animals or birds, or fish, or reptiles, or marine animals. In some embodiments of the present invention, transgenic plants are crop plants.

As used herein, the term "grass" in reference to a plant refers to any plant of the Poaceae family or Gramineae family, Cyperaceae family (sedges), and Juncaceae family (rushes). A grass may comprise a hollow, a segmented, and a round stem, bladelike leaf, and extensively branching fibrous root systems, such as any of grasses of the genus *Festuca* species or any of the *Lolium* species. A grass plant may be a cereal grass, a forage grass, a turf grass, an ornamental grass, pasture grass, a hay grass, a cover grass, and a cereal grass, such as wheat, corn, rice, rye, oats, barley, and millet. A grass plant may provide forage for grazing animals, shelter for wildlife, stabilization of soils, such as fire-burned soil, bare soil, etc., construction materials, furniture, utensils, and food for humans. Some grass species are grown as garden ornamentals, cultivated as turf for lawns and recreational areas, or used as cover plants for erosion control.

The term "ground cover" refers to a use of a plant to fill in areas of land (e.g. sunny area, shaded area, and the like).

As used herein, "*Festuca mairei*" or "Fm" or "Atlas Fescue" refers to an ornamental grass plant of the Festuca family as described herein.

As used herein, "ryegrass" in general refers to a perennial ryegrass "*Lolium perenne* L. ssp. Perenne" or "English ryegrass" or "crested ryegrass." Ryegrass may also refer to an annual ryegrass "*Lolium perenne* ssp. multiflorum" also referred to as "Italian ryegrass," and any intermediate species of ryegrass.

As used herein, "common ryegrass" or "*Lolium* species" or "*Lolium* spp." refers to a commercial mixture of ryegrass species, such as a mixture of annual ryegrass species, but may also contain a substantial percentage of a perennial ryegrass species and annual-perennial hybrid species of ryegrass, also referred to as "intermediate ryegrass."

As used herein, "annual ryegrass" in general refers to a "*Lolium multiflorum*" plant that lives for one year or less.

As used herein, "perennial ryegrass" in general refers to a "*Lolium perenne*" plant that lives for more than two years.

As used herein, "intermediate ryegrass" in general refers to a hybrid "*Lolium hybridum*" plant that developed by crossing annual and perennial ryegrass.

The term "haploid" or "n" refers to an organism or cell with no more than one set of chromosomes.

The term "polyploidy" refers to a condition of a cell or organisms containing more than two homologous sets of chromosomes. For example, polyploid types are termed according to the number of chromosome sets in the nucleus: three sets refers to a triploid (3n), four sets refers to a tetraploid (4n), five sets refers to a pentaploid (5n), six sets refers to a hexaploid (6n, such as a *Sequoia sempervirens*), et cetera.

The term "diploid" in reference to a plant refers to a plant with 2 sets of chromosomes (for e.g. the majority of wild-type grass plants).

The term "triploid" in reference to a plant refers to a plant with 3 sets of chromosomes.

The term "tetraploid plant" refers to a plant that has 4 sets of chromosomes per cell. As used herein, the term "tetraploid grasses" refers to grasses that have 4 sets of chromosomes per cell (e.g. tetraploid varieties of grasses such as ryegrass, red clover, lotus, etc.).

The term "allopolyploids" refers to a polyploidy with chromosomes derived from different species, for example, triticale has six chromosome sets, four from wheat (*Triticum turgidum*) and two from rye (*Secale cereale*).

The term "amphidiploid" or "allopolyploid" refers to a polyploid formed from the union of two separate chromosome sets and their subsequent doubling, such as an organism produced by hybridization of two species followed by chromosome doubling. An allotetraploid may appear to be a normal diploid.

The term "autopolyploids" or "autotetraploidy" refers to a polyploidy with chromosomes derived from a single species, such as an autopolyploid can arise from a spontaneous, naturally-occurring genome doubling (for example, potatoes), and as a further example, bananas and apples can be triploid autopolyploids.

The term "plant tissue" includes differentiated and undifferentiated tissues of plants including those present in roots, shoots, leaves, pollen, seeds and tumors, as well as cells in culture (e.g., single cells, protoplasts, embryos, callus, etc.). Plant tissue may be in planta, in organ culture, tissue culture, or cell culture.

As used herein, the term "plant part" as used herein refers to a plant structure or a plant tissue, for example, pollen, an ovule, a tissue, a pod, a seed, a leaf and a cell. Plant parts may comprise one or more of a tiller, plug, rhizome, sprig, stolen, meristem, crown, and the like.

For the purposes of the present inventions, the term "hybrid" in reference to a seed or plant is produced as the result of artificially controlled cross-pollination as opposed to a "non-hybrid" seed produced as the result of natural pollination, such as in a "hybrid seed" or "hybrid plant" produced by introgression methods of the present invention, for example, selective breeding or transgene insertion.

As used herein, the terms "F-generation" and "filial generation" refers to any of the consecutive generations of cells, tissues or organisms, such as a plant, after a biparental cross. The generation resulting from a mating of the a biparental cross (i.e. parents) is the first filial generation (designated as "F1" and "$F_1$") in reference to both a seed and a plant of that generation, while that resulting from crossing of F1 individuals is the second filial generation (designated as "F2" or "$F_2$") in reference to both a seed and a plant of that generation, et cetera.

As used herein, "progeny" refers to a product of any cross between two plants, such as a backcross or outcross, where progeny may trace a pedigree back to the original cross. As used herein, a second plant is derived from a first plant if the second plant's pedigree includes the first plant.

As used herein, the terms "introgress" and "introgressing" refer to incorporating a genetic substance, such as germplasm, loci, allele, gene, DNA, and the like for introducing a trait into an organism, such as a plant, a plant cell, a yeast cell, and the like, for example, incorporating drought resistant transgenic material and/or transgenes into a previously drought susceptible plant variety. Introgression may refer to one of several types of breeding methods for a incorporating a genetic trait, such as drought resistance, provided by expression of a heterologous gene or silencing of an endogenous gene.

The term "variety" refers to a biological classification for an intraspecific group or population, that can be distinguished from the rest of the species by any characteristic (for example morphological, physiological, cytological, etc.). A variety may originate in the wild but can also be produced through selected breeding (for example, see, cultivar).

The terms "cultivar," "cultivated variety," and "cv" refer to a group of cultivated plants distinguished by any characteristic (for example morphological, physiological, cytological, etc.) that when reproduced sexually or asexually, retain their distinguishing features to produce a cultivated variety. In reference to a ryegrass, a cultivar may be a diploid or a tetraploid cultivar, such as "Big Daddy" (1995) and "Jumbo" (2000), released by the University of Florida IFAS (Institute of Food and Agricultural Sciences) Ryegrass Breeding Program.

The term "elite cultivar" refers to a commercial or breeding stock cultivar. In reference to a ryegrass, an elite ryegrass cultivar includes but is not limited to "Citation II," "Calypso," "Florida 80" (1982), "Surrey" (1989), Big Daddy, "Stampede" (1998), "Natchez" (1999), "Fantastic" (1999), "Florlina" (1999), Jumbo, "Passeral Plus" (2000), "King" (2000) and "Graze-N-Gro" (2000) released by the University of Florida IFAS (Institute of Food and Agricultural Sciences) Ryegrass Breeding Program. An elite ryegrass cultivar in reference to ryegrass plants of the present inventions may also refer to a preferred breeding stock such as hybrid ryegrass plants comprising Fm germplasm as described herein.

The term "host cell" refers to any cell capable of replicating and/or transcribing and/or translating a heterologous gene. Thus, a "host cell" refers to any eukaryotic or prokaryotic cell (e.g., plant cells, algal cells such as *C. reinhardtii*, bacterial cells such as yeast cells, *E. coli*, insect cells, etc.), whether located in vitro or in vivo. For example, a host cell may be located in a transgenic plant, or located in a plant part or part of a plant tissue or in cell culture.

As used herein, the term plant cell "compartments" or "organelles" is used in its broadest sense. As used herein, the term includes but is not limited to, the endoplasmic reticulum, Golgi apparatus, trans Golgi network, plastids, sarcoplasmic reticulum, glyoxysomes, mitochondrial, chloroplast, thylakoid membranes and nuclear membranes, and the like.

The terms "leaf" and "leaves" refer to a usually flat, green structure of a plant where photosynthesis and transpiration take place and that grow attached to a stem or branch.

The terms "cotyledon," "true leaf," and "seed leaf" refer to any one of the first leaves to appear after germination (there may be one, such as a monocotyledon, two, such a dicotyledoen or more) and the foliar portion of the embryo as found in the seed. The term "hypocotyl" refers to a part of the stem of an embryo or young seedling below the cotyledons.

As used herein, "aerial" and "aerial parts of *Arabidopsis* plants" refer to any plant part that is above water in aquatic plants or any part of a terrestrial plant part found above ground level.

The terms "radicle" and "radicles" refer to rootlets emerging from the sides and base of the stem and the end of a plant embryo which gives rise to the first root. A radicle may also comprise a "rhizoid" which refers to a cellular outgrowth of a plant that usually aids in anchoring to the surface and increasing surface area to acquire water or nutrients.

The term "lemma" refers to the lower of the two bracts enclosing the flower in the spikelet of grasses.

The term "bract" refers to a leaf from the axil of which a flower arises.

The term "axil" refers to the angle between a branch or leaf and the stem from which it grows.

The term "inflorescence" refers to a flowering part of a plant. The term "meristem" refers to undifferentiated tissue from which new cells are formed, e.g., the tips of roots or stems; the growing tip. The term "meristem cloning" refers to artificial propagation of a plant using cells taken from the meristem of a parent plant and yielding genetically identical offspring.

The term "stem" refers to a main ascending axis of a plant.

The term "seed" refers to a ripened ovule, consisting of the embryo and a casing.

The term "propagation" refers to the process of producing new plants, for example, asexual reproduction or sexual reproduction.

The terms "vegetative propagation" and "asexual reproduction" refer to the ability of plants to reproduce without sexual reproduction, by producing new plants from existing vegetative structures that are clones, i.e., plants that are identical in all attributes to the mother plant and to one another. In other words, vegetative propagation involves using parts of an original plant to make new plants. Plants derived from vegetative propagation may be produced by means such as tissue culture, the division of a plant clump, rooting of root or stem or leaf cuttings, or cutting of mature crowns or involving the rooting or grafting of pieces of one plant onto other pieces of other plants.

The terms "calli" and "callus" refer to a tough, often hairy, swelling at the base or insertion of the lemma.

The term "tiller" refers to a portion of a plant where a lateral stem (or shoot), usually erect, develops from the central crown, often used for propagation of grass plants. Also refers to the branch or shoot that originates at a basal node.

The terms "stolen" and "runner" refer to an elongated horizontal stem (or shoot) that grows above the soil or just under the soil surface that roots at nodes and can form new plants. The term "stoloniferous" in reference to a plant, refers to spreading or growing by means of stolons.

The term "rhizome" refers to a specialized slender or swollen stem with branching close to the soil surface that can produce a root, a stem, a leaf and a flower, along its length and at its apex.

The term "sprig" refers to a small part of a plant comprising a short piece of the stolon or rhizome, roots and leaves, but not soil, (e.g. stolon, used for propagation). The term "plug" refers to a small piece of sod usually two or more inches wide comprising 2 to 3 inches of soil and grass roots.

The term "sod" refers to any one of a plug, square of grass, and strip of grass, with adhering soil that are used in vegetative planting, for example, top few centimeters of soil permeated by and held together with grass roots or grass-legume roots.

The term "sodformer" refers to grass that propagates by seed and vegetatively by rhizomes and/or stolons to form a sod.

As used herein, the term "trait" refers to an observable and/or measurable characteristics of an organism, such as a trait of a plant, for example, resistance to low soil moisture, tolerance to an herbicide, an agronomic trait, and the like.

As used herein, the terms "agronomic trait" or "agronomically desirable trait "or" agronomically significant trait" refers to any selected trait that increases the commercial or economic or utility value of a plant and/or preferred plant part, for example a preferred level of drought resistance or drought tolerance, water resistance, cold weather resistance, hot weather resistance, growth in a particular hardiness zone, yield, nutritional content, protein content, fiber content, root properties, root spreading, oil content, seed protein content, seed size, seed color, seed coat thickness, seed sugar content, seed free amino acid content, seed germination rate, seed texture, seed fiber content, food-grade quality, hilum color, seed yield, and color of a plant part.

As used herein, the term "modified plant" refers to plant modified by man. A modified plant may be plant derived from artificial breeding, such as artificial pollination, or transgenic production, such as *Agrobacterium*-mediated, electroporation, etc. to insert a heterologous gene or a combination of artificial breeding and transgenic methods.

As used herein, the terms "modified" or "altered" regarding a plant trait, refer to a change in the phenotype of a modified plant relative to the similar non-modified plant, such as introgressing a plant trait into a plant lacking that trait, for example increasing drought tolerance in a plant. An "improvement" is a feature that may enhance the utility of a plant species or variety by providing the plant with a unique and/or novel quality.

The terms "ABA" and "abscisic acid" refer to molecules that induce "ABA-responsive proteins" comprising "abscisic acid responsive elements" and "ABA responsive elements" that refer to DNA regions of in the promoter region that bind to ABA of genes that respond to ABA mediated environmental stress.

The term "abiotic stress" refers to a nonliving environmental factors such as drought, salt, cold, excessive heat, high winds, etc., that can have harmful effects upon plants. For the purposes of the present invention, examples of abiotic stress specifically include drought and salt factors.

The terms "eukaryotic" and "eukaryote" are used in its broadest sense. It includes, but is not limited to, any organisms containing membrane bound nuclei and membrane bound organelles. Examples of eukaryotes include but are not limited to plants, yeast, animals, alga, diatoms, and fungi.

The terms "prokaryote" and "prokaryotic" are used in its broadest sense. It includes, but is not limited to, any organisms without a distinct nucleus. Examples of prokaryotes include but are not limited to bacteria, blue-green algae, archaebacteria, actinomycetes and mycoplasma. In some embodiments, a host cell is any microorganism.

As used herein the term "microorganism" refers to microscopic organisms and taxonomically related macroscopic organisms within the categories of yeast, algae, bacteria, and fungi (including lichens).

The term "*Agrobacterium*" refers to a soil-borne, Gram-negative, rod-shaped phytopathogenic bacterium that causes crown gall. *Agrobacterium* is a representative genus of a soil-borne, Gram-negative, rod-shaped phytopathogenic bacterium family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. *Agrobacterium tumefaciens* causes crown gall disease by transferring some of its DNA to the plant host. The transferred DNA (T-DNA) is stably integrated into the plant genome, where its expression leads to the synthesis of plant hormones and thus to the tumorous growth of the cells. A putative macromolecular complex forms in the process of T-DNA transfer out of the bacterial cell into the plant cell. The term "*Agrobacterium*" includes, but is not limited to, the strains *Agrobacterium tumefaciens* (which typically causes crown gall in infected plants), and *Agrobacterium* rhizogens (which causes hairy root disease in infected host plants). Infection of a plant cell with *Agrobacterium* generally results in the production of opines (e.g., nopaline, agropine, octopine etc.) by the infected cell. Thus, *Agrobacterium* strains which cause production of nopaline (e.g., strain GV3101, LBA4301, C58, A208, etc.) are referred to as "nopaline-type" Agrobacteria; *Agrobacterium* strains which cause production of octopine (e.g., strain LBA4404, Ach5, B6, etc.) are referred to as "octopine-type" Agrobacteria; and *Agrobacterium* strains which cause production of agropine (e.g., strain EHA105, EHA101, A281, etc.) are referred to as "agropine-type" *Agrobacteria*.

The term "transgene" refers to a foreign gene that is placed into an organism or host cell by the process of transfection. The term "foreign gene" or heterologous gene refers to any nucleic acid (e.g., gene sequence) that is introduced into the genome of an organism or tissue of an organism or a host cell by experimental manipulations, such as those described herein, and may include gene sequences found in that organism so long as the introduced gene does not reside in the same location, as does the naturally occurring gene.

The terms "transgenic" when used in reference to a plant or leaf or fruit or seed or plant part, for example a "transgenic plant," "transgenic leaf," "transgenic fruit," "transgenic seed," and a "transgenic host cell," refer to a plant or leaf or fruit or seed or part or cell that contains at least one heterologous or foreign gene in one or more of its cells. The term "transgenic plant material" refers broadly to a plant, a plant structure, a plant tissue, a plant seed or a plant cell that contains at least one heterologous gene in one or more of its cells. The term "portion" when used in reference to a protein (as in "a portion of a given protein") refers to fragments of that protein. The fragments may range in size from four amino acid residues to the entire amino sequence minus one amino acid.

The terms "transformants" and "transformed cells" include the primary transformed cell and cultures derived from that cell without regard to the number of transfers. Resulting progeny may not be precisely identical in DNA content, due to deliberate or inadvertent mutations. Mutant progeny that have the same functionality as screened for in the originally transformed cell are included in the definition of transformants.

The terms "tissue culture" and "micropropagation" refer to a form of asexual propagation undertaken in specialized laboratories, in which clones of plants are produced from small cell clusters from very small plant parts (e.g. buds, nodes, leaf segments, root segments, etc.), grown aseptically (free from any microorganism) in a container where the environment and nutrition can be controlled.

The term "gene" refers to a nucleic acid (e.g., DNA or RNA) sequence that comprises coding sequences necessary for the production of an RNA, or a polypeptide or its precursor (e.g., proinsulin). A functional polypeptide can be encoded by a full-length coding sequence or by any portion of the coding sequence as long as the desired activity or functional properties (e.g., enzymatic activity, ligand binding, signal transduction, etc.) of the polypeptide are retained. The term "portion" when used in reference to a gene refers to fragments of that gene. The fragments may range in size from a few nucleotides to the entire gene sequence minus one nucleotide. The term "a nucleotide comprising at least a portion of a gene" may comprise fragments of the gene or the entire gene. The term "cDNA" refers to a nucleotide copy of the "messenger RNA" or "mRNA" for a gene. In some embodiments, cDNA is derived from the mRNA. In some embodiments, cDNA is derived from genomic sequences. In some embodiments, cDNA is derived from EST sequences. In some embodiments, cDNA is derived from assembling portions of coding regions extracted from a variety of BACs, contigs, Scaffolds and the like.

The term "gene" encompasses the coding regions of a structural gene and includes sequences located adjacent to the coding region on both the 5' and 3' ends for a distance of about 1 kb on either end such that the gene corresponds to the length of the full-length mRNA. The sequences which are located 5' of the coding region and which are present on the mRNA are referred to as 5' non-translated sequences. The sequences which are located 3' or downstream of the coding region and which are present on the mRNA are referred to as 3' non-translated sequences.

The term "gene" encompasses both cDNA and genomic forms of a gene. A genomic form or clone of a gene contains the coding region termed "exon" or "expressed regions" or "expressed sequences" interrupted with non-coding sequences termed "introns" or "intervening regions" or "intervening sequences." Introns are segments of a gene that are transcribed into nuclear RNA (hnRNA); introns may contain regulatory elements such as enhancers. Introns are removed or "spliced out" from the nuclear or primary transcript; introns therefore are absent in the messenger RNA (mRNA) transcript. The mRNA functions during translation to specify the sequence or order of amino acids in a nascent polypeptide.

In addition to containing introns, genomic forms of a gene may also include sequences located on both the 5' and 3' end of the sequences that are present on the RNA transcript. These sequences are referred to as "flanking" sequences or regions (these flanking sequences are located 5' or 3' to the non-translated sequences present on the mRNA transcript). The 5' flanking region may contain regulatory sequences such as promoters and enhancers that control or influence the transcription of the gene. The 3' flanking region may contain sequences that direct the termination of transcription, post-transcriptional cleavage and polyadenylation.

The term "derived" in reference to a gene, such as a "gene derived from a *Festuca mairei* plant" refers to a gene comprising a nucleic acid sequence present in *Festuca mairei* germplasm.

The term "germplasm" refers to any genetic material of plants, animals or other organisms containing functional units of heredity. As used herein, germplasm may refer to any hereditary material, such as a nucleotide sequence, gene, linkage group, QTL, chromosome, and groups of chromosomes. As used herein, the term "germplasm" in reference to "drought resistant germplasm" and "drought resistance germplasm" refers to and encompasses hereditary material associated with resistance to drought conditions, such as *Festuca mairei* nucleic acid sequences, linkage groups, chromosomes, quantitative trait loci (QTLs) and the like.

The term "meiotic stability" or "meiotically stable" in reference to genetic material of a plant, such as a gene, linkage group or chromosome, refers to the retention of parental genetic material in a daughter cell following meiotic division. For the purposes of the present inventions, meiotic stability refers to the passage of desired *Festuca mairei* germplasm from parental plants to progeny plants produced by sexual reproduction.

The terms "allele" and "alleles" refer to each version of a gene for a same locus that has more than one sequence. For example, there are multiple alleles for eye color at the same locus. The terms "recessive," "recessive gene," and "recessive phenotype" refer to an allele that has a phenotype when two alleles for a certain locus are the same as in "homozygous" or as in "homozygote" and then partially or fully loses that phenotype when paired with a more dominant allele as when two alleles for a certain locus are different as in "heterozygous" or in "heterozygote." The terms "dominant," "dominant allele," and "dominant phenotype" refer to an allele that has an effect to suppress the expression of the other allele in a heterozygous (having one dominant allele and one recessive allele) condition.

The term "heterologous" when used in reference to a gene or nucleic acid refers to a gene that was manipulated in some way. For example, a heterologous gene includes a gene from one species introduced into another species. A heterologous gene also includes a gene native to an organism that was altered in some way (e.g., mutated, added in multiple copies, linked to a non-native promoter or enhancer sequence, etc.). Heterologous genes may comprise plant gene sequences that comprise cDNA forms of a plant gene; the cDNA sequences may be expressed in either a sense (to produce mRNA) or anti-sense orientation (to produce an anti-sense RNA transcript that is complementary to the mRNA transcript). Heterologous genes are distinguished from endogenous plant genes in that the heterologous gene sequences are typically joined to nucleotide sequences comprising regulatory elements such as promoters that are not found naturally associated with the gene for the protein encoded by the heterologous gene or with plant gene sequences in the chromosome, or are associated with portions of the chromosome not found in nature (e.g., genes expressed in loci where the gene is not normally expressed).

The terms "nucleic acid sequence," "nucleotide sequence of interest" or "nucleic acid sequence of interest" refer to any nucleotide sequence (e.g., RNA or DNA), the manipulation of which may be deemed desirable for any reason (e.g., treat disease, confer improved qualities, etc.), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product (e.g., promoter sequence, polyadenylation sequence, termination sequence, enhancer sequence, etc.). The term "up-regulated" refers to a gene or protein whose expression is increased over a control or before exposure to a condition, such as low soil moisture.

The term "down-regulated" refers to a gene or protein whose expression is decreased over a control or before exposure to a condition, such as low soil moisture.

The term "up-regulated then down-regulated" or "up-then-down-regulated" refers to a gene or protein whose expression is increased over a control or before exposure to a condition, such as low soil moisture, then decreases in expression over time.

The term "differentially expressed" or "differentially regulated" or "DEF" refers to a gene or nucleic acid or protein whose expression is different from that of a control.

The term "transiently expressed" or "transiently regulated" or "TEF" refers to a gene or protein whose expression is temporarily expressed.

As used herein, the term "wild-type" when made in reference to a gene refers to a functional gene common throughout an outbred population. As used herein, the term "wild-type" when made in reference to a gene product refers to a functional gene product common throughout an outbred population. A functional wild-type gene is that which is most frequently observed in a population and is thus arbitrarily designated the "normal" or "wild-type" form of the gene.

As used herein, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. Thus, the terms "variant" and "mutant" when used in reference to a nucleotide sequence refer to an nucleic acid sequence that differs by one or more nucleotides from another, usually related nucleotide acid sequence. A "variation" is a difference between two different nucleotide sequences; typically, one sequence is a reference sequence.

The terms "variant" and "mutant" when used in reference to a polypeptide refer to an amino acid sequence that differs by one or more amino acids from another, usually related polypeptide. The variant may have "conservative" changes, wherein a substituted amino acid has similar structural or chemical properties. One type of conservative amino acid substitution refers to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine. More rarely, a variant may have "non-conservative" changes (e.g., replacement of a glycine with a tryptophan). Similar minor variations may also include amino acid deletions or insertions (i.e., additions), or both. Guidance in determining which and how many amino acid residues may be substituted, inserted or deleted without abolishing biological activity may be found using computer programs well known in the art, for example, DNAStar software. Variants can be tested in functional assays. Preferred variants have less than 10%, and preferably less than 5%, and still more preferably less than 2% changes (whether substitutions, deletions, etc.). Thus, nucleotide sequences of the present invention can be engineered in order to introduce or alter a preferred Fm coding sequence for a variety of reasons, including but not limited to initiating the production of environmental stress tolerance; alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics).

The term "structural" when used in reference to a gene or to a nucleotide or nucleic acid sequence refers to a gene and/or A nucleotide or nucleic acid sequence whose ultimate expression product is a protein (such as an enzyme or a structural protein), an rRNA, an sRNA, a tRNA, and the like.

The term "oligonucleotide" refers to a molecule comprised of two or more deoxyribonucleotides or ribonucleotides, preferably more than three, and usually more than ten. The exact size will depend on many factors, which in turn depends on the ultimate function or use of the oligonucleotide. The oligonucleotide may be generated in any manner, including chemical synthesis, DNA replication, reverse transcription, or a combination thereof.

The term "polynucleotide" refers to refers to a molecule comprised of several deoxyribonucleotides or ribonucleotides, and is used interchangeably with oligonucleotide. Typically, oligonucleotide refers to shorter lengths, and polynucleotide refers to longer lengths, of nucleic acid sequences.

The term "an oligonucleotide (or polypeptide) having a nucleotide sequence encoding a gene" or "a nucleic acid sequence encoding" a specified polypeptide refers to a nucleic acid sequence comprising the coding region of a gene or in other words the nucleic acid sequence which encodes a gene product. The coding region may be present in a cDNA, genomic DNA or RNA form. When present in a DNA form, the oligonucleotide may be single-stranded (i.e., the sense strand) or double-stranded. Suitable control elements such as enhancers/promoters, splice junctions, polyadenylation signals, etc., may be placed in close proximity to the coding region of the gene. When needed to permit proper initiation of transcription and/or correct processing of the primary RNA transcript. Alternatively, the coding region utilized in the expression vectors of the present invention may contain endogenous enhancers, exogenous promoters, splice junctions, intervening sequences, polyadenylation signals, etc., or a combination of both endogenous and exogenous control elements.

As used herein, the term "exogenous promoter" refers to a promoter in operable combination with a coding region wherein the promoter is not the promoter naturally associated with the coding region in the genome of an organism. The promoter which is naturally associated or linked to a coding region in the genome is referred to as the "endogenous promoter" for that coding region.

The terms "complementary" and "complementarity" refer to polynucleotides (i.e., a sequence of nucleotides) related by the base-pairing rules. For example, for the sequence "A-G-T," is complementary to the sequence "T-C-A." Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods that depend upon binding between nucleic acids.

The terms "EST" and "expressed sequence tag" refer to a unique stretch of DNA within a coding region of a gene; approximately 200 to 600 base pairs in length. The term "recombinant" when made in reference to a nucleic acid molecule refers to a nucleic acid molecule that is comprised of segments of nucleic acid joined together by means of molecular biological techniques. The term "recombinant" when made in reference to a protein or a polypeptide refers to a protein molecule that is expressed using a recombinant nucleic acid molecule.

The terms "protein," "polypeptide," "peptide," "encoded product," and "amino acid sequence" are used interchangeably to refer to compounds comprising amino acids joined via peptide bonds and a "protein" encoded by a gene is not limited to the amino acid sequence encoded by the gene, but includes post-translational modifications of the protein. Where the term "amino acid sequence" is recited herein to refer to an amino acid sequence of a protein molecule, the term "amino acid sequence" and like terms, such as "polypeptide" or "protein" are not meant to limit the amino acid sequence to the complete, native amino acid sequence associated with the recited protein molecule. Furthermore, an "amino acid sequence" can be deduced from the nucleic acid sequence encoding the protein. The deduced amino acid sequence from a coding nucleic acid sequence includes sequences which are derived from the deduced amino acid sequence and modified by post-translational processing, where modifications include but not limited to glycosylation, hydroxylations, phosphorylations, and amino acid deletions, substitutions, and additions. Thus, an amino acid sequence comprising a deduced amino acid sequence is understood to include post-translational modifications of the encoded and deduced amino acid sequence. The term "X" may represent any amino acid.

The terms "homolog," "homologue," "homologous," and "homology" when used in reference to amino acid sequence or nucleic acid sequence or a protein or a polypeptide refers to a degree of sequence identity to a given sequence, or to a degree of similarity between conserved regions, or to a degree of similarity between three-dimensional structures or to a degree of similarity between the active site, or to a degree of similarity between the mechanism of action, or to a degree of similarity between functions. In some embodiments, a homologue has a greater than 30% sequence identity to a given sequence. In some embodiments, a homologue has a greater than 40% sequence identity to a given sequence. In some embodiments, a homologue has a greater than 60% sequence identity to a given sequence. In some embodiments, a homologue has a greater than 70% sequence identity to a given sequence. In some embodiments, a homologue has a greater than 90% sequence identity to a given sequence. In some embodiments, a homologue has a greater than 95% sequence identity to a given sequence. In some embodiments, homology is determined by comparing internal conserved sequences to a given sequence. In some embodiments, homology is determined by comparing designated conserved functional and/or structural regions, a low complexity region or a transmembrane region. In some embodiments, homology is determined by comparing designated conserved "motif" regions. In some embodiments, means of determining homology are shown in the Examples.

The term "homology" when used in relation to nucleic acids or proteins refers to a degree of identity. There may be partial homology or complete homology. The following terms are used to describe the sequence relationships between two or more polynucleotides and between two or more polypeptides: "identity," "percentage identity," "identical," "reference sequence," "sequence identity," "percentage of sequence identity," and "substantial identity." "Sequence identity" refers to a measure of relatedness between two or more nucleic acids or proteins, and is described as a given as a percentage "of homology" with reference to the total comparison length. A "reference sequence" is a defined sequence used as a basis for a sequence comparison; a reference sequence may be a subset of a larger sequence, for example, the sequence that forms an active site of a protein or a segment of a full-length cDNA sequence or may comprise a complete gene sequence. Since two polynucleotides or polypeptides may each (1) comprise a sequence (i.e., a portion of the complete polynucleotide sequence) that is similar between the two polynucleotides, and (2) may further comprise a sequence that is divergent between the two polynucleotides, sequence comparisons between two (or more) polynucleotides are typically performed by comparing sequences of the two polynucleotides over a "comparison window" to identify and compare local regions of sequence similarity. A "comparison window," as used herein, refers to a conceptual segment of in internal region of a polypeptide. In one embodiment, a comparison window is at least 77 amino acids long. In another embodiment, a comparison window is at least 84 amino acids long. In another embodiment, conserved regions of proteins are comparison windows. In a further embodiment, an amino acid sequence for a conserved transmembrane domain is 24 amino acids. Calculations of identity may be performed by algorithms contained within computer programs such as the ClustalX algorithm (Thompson, et al. Nucleic Acids Res. 24:4876-4882 (1997)); herein incorporated by reference); MEGA2 (version 2.1) (Kumar, et al. Bioinformatics 17:1244-1245 (2001); herein incorporated by reference); "GAP" (Genetics Computer Group, Madison, Wis.), "ALIGN" (DNAStar, Madison, Wis.), BLAST (National Center for Biotechnology Information; NCBI as described at world wide web.ncbi.nlm.nih.gov/BLAST/BLAST/blast_help.shtml) and MultAlin (Multiple sequence alignment) program (Corpet, Nucl. Acids Res., 16(22): 10881-10890 (1988); herein incorporated by reference, at hypertext transfer protocol site: prodes.toulouse.inra.fr/multalin/multalin.html), all of which are herein incorporated by reference).

For comparisons of nucleic acids, 20 contiguous nucleotide positions wherein a polynucleotide sequence may be compared to a reference sequence of at least 20 contiguous nucleotides and wherein the portion of the polynucleotide sequence in the comparison window may comprise additions or deletions (i.e., gaps) of 20 percent or less as compared to the reference sequence (which does not comprise additions or deletions) for optimal alignment of the two sequences. Optimal alignment of sequences for aligning a comparison window may be conducted by the local homology algorithm of Smith and Waterman (Smith and Waterman, Adv. Appl. Math. 2:482 (1981)) by the homology alignment algorithm of Needleman and Wunsch (Needleman and Wunsch, J. Mol. Biol. 48:443 (1970); herein incorporated by reference), by the search for similarity method of Pearson and Lipman (Pearson and Lipman, Proc. Natl. Acad. Sci. (U.S.A.) 85:2444 (1988); herein incorporated by reference), by computerized implementations of these algorithms (GAP, BESTFIT, FASTA, and TFASTA in the Wisconsin Genetics Software Package Release 7.0, Genetics Computer Group, 575 Science Dr., Madison, Wis.; herein incorporated by reference), or by inspection, and the best alignment (i.e., resulting in the highest percentage of homology over the comparison window) generated by the various methods is selected.

The term "sequence identity" means that two polynucleotide or two polypeptide sequences are identical (i.e., on a nucleotide-by-nucleotide basis or amino acid basis) over the window of comparison. The term "percentage of sequence identity" is calculated by comparing two optimally aligned sequences over the window of comparison, determining the number of positions at which the identical nucleic acid base (e.g., A, T, C, G, U, or I) or amino acid, in which often conserved amino acids are taken into account, occurs in both sequences to yield the number of matched positions, dividing the number of matched positions by the total number of positions in the window of comparison (i.e., the window size), and multiplying the result by 100 to yield the percentage of sequence identity. The terms "substantial identity" as used herein denotes a characteristic of a polynucleotide sequence, wherein the polynucleotide comprises a sequence that has at least 85 percent sequence identity, preferably at least 90 to 95 percent sequence identity, more usually at least 99 percent sequence identity as compared to a reference sequence over a comparison window of at least 20 nucleotide positions, frequently over a window of at least 25-50 nucleotides, wherein the percentage of sequence identity is calculated by comparing the reference sequence to the polynucleotide sequence which may include deletions or additions which total 20 percent or less of the reference sequence over the window of comparison. The reference sequence may be a subset of a larger sequence.

The term "ortholog" refers to a gene in different species that evolved from a common ancestral gene by speciation. In some embodiments, orthologs retain the same function. The term "paralog" refers to genes related by duplication within a genome. In some embodiments, paralogs evolve new functions. In further embodiments, a new function of a paralog is related to the original function.

The term "partially homologous nucleic acid sequence" refers to a sequence that at least partially inhibits (or competes with) a completely complementary sequence from hybridizing to a target nucleic acid and is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence that is completely complementary to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial-degree of identity (e.g., less than about 30% identity); in the absence of non-specific binding the probe will not hybridize to the second non-identical target.

The term "substantially homologous" when used in reference to a double-stranded nucleic acid sequence such as a cDNA or genomic clone refers to any probe that can hybridize to either or both strands of the double-stranded nucleic acid sequence under conditions of low to high stringency as described above.

The term "substantially homologous" when used in reference to a single-stranded nucleic acid sequence refers to any probe that can hybridize (i.e., it is the complement of) the single-stranded nucleic acid sequence under conditions of low to high stringency as described above.

The term "hybridization" refers to the pairing of complementary nucleic acids. Hybridization and the strength of hybridization (i.e., the strength of the association between the nucleic acids) is impacted by such factors as the degree of complementary between the nucleic acids, stringency of the conditions involved, the $T_m$ of the formed hybrid, and the G:C ratio within the nucleic acids. A single molecule that contains pairing of complementary nucleic acids within its structure is said to be "self-hybridized."

The term "$T_m$" refers to the "melting temperature" of a nucleic acid. Melting temperature $T_m$ is the midpoint of the temperature range over which nucleic acids are denatured (e.g. DNA:DNA, DNA:RNA and RNA:RNA, etc.). Methods for calculating the $T_m$ of nucleic acids are well known in the art (see, for e.g., Sambrook, et al. Molecular Cloning: A Laboratory Manual, 2nd ed., Cold Spring Harbor Laboratory Press, New York (1989) pp. 9.50-51, 11.48-49 and 11.2-11.3; herein incorporated by reference).

The term "stringency" refers to the conditions of temperature, ionic strength, and the presence of other compounds such as organic solvents, under which nucleic acid hybridizations are conducted. With "high stringency" conditions, nucleic acid base pairing will occur only between nucleic acid fragments that have a high frequency of complementary base sequences. Thus, conditions of "low" stringency are often required with nucleic acids that are derived from organisms that are genetically diverse, as the frequency of complementary sequences is usually less.

"Low stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.1% SDS, 5×Denhardt's reagent (50×Denhardt's contains per 500 ml:05 g Ficoll (Type 400, Pharmacia):05 g BSA (Fraction V; Sigma)) and 100 µg/ml denatured salmon sperm DNA followed by washing in a solution comprising 5×SSPE, 0.1% SDS at 42° C. when a probe of about 500 nucleotides in length is employed.

"Medium stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 1.0×SSPE, 1.0% SDS at 42° C. when a probe of about 500 nucleotides in length is employed.

"High stringency conditions" when used in reference to nucleic acid hybridization comprise conditions equivalent to binding or hybridization at 42° C. in a solution consisting of 5×SSPE (43.8 g/l NaCl, 6.9 g/l $NaH_2PO_4H_2O$ and 1.85 g/l EDTA, pH adjusted to 7.4 with NaOH), 0.5% SDS, 5×Denhardt's reagent and 100 µg/ml denatured salmon sperm DNA followed by washing in a solution comprising 0.1×SSPE, 1.0% SDS at 42° C. when a probe of about 500 nucleotides in length is employed. It is well known that numerous equivalent conditions may be employed to comprise low stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of low stringency hybridization different from, but equivalent to, the above listed conditions. In addition, the art knows conditions that promote hybridization under conditions of high stringency (e.g., increasing the temperature of the hybridization and/or wash steps, the use of formamide in the hybridization solution, etc.).

As used herein, the term "polymerase chain reaction" and "PCR" refers to the method of K. B. Mullis (U.S. Pat. Nos. 4,683,195; 4,683,202; and 4,965,188; herein incorporated by reference), which describe a method for increasing the concentration of a segment of a target sequence in a mixture of genomic DNA without cloning or purification. This process for amplifying the target sequence consists of introducing an excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified".

The term "reverse-transcriptase" or "RT-PCR" refers to a type of PCR where the starting material is mRNA. The starting mRNA is enzymatically converted to complementary DNA or "cDNA" using a reverse transcriptase enzyme. The cDNA is then used as a "template" for a "PCR" reaction.

"Amplification" is a special case of nucleic acid replication involving template specificity. It is to be contrasted with nonspecific template replication (i.e., replication that is template-dependent but not dependent on a specific template). Template specificity is here distinguished from fidelity of replication (i.e., synthesis of the proper polynucleotide sequence) and nucleotide (ribo- or deoxyribo-) specificity. Template specificity is frequently described in terms of "target" specificity. Target sequences are "targets" in the sense that they are sought to be sorted out from other nucleic acid. Amplification techniques were designed primarily for this sorting out.

As used herein, the term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. When double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

As used herein, the terms "PCR product," "PCR fragment," and "amplification product" refer to the resultant mixture of compounds after two or more cycles of the PCR steps of denaturation, annealing and extension are complete. These terms encompass the case where there was amplification of one or more segments of one or more target sequences. Template specificity is achieved in most amplification techniques by the choice of enzyme. Amplification enzymes are enzymes that, under conditions they are used, will process only specific sequences of nucleic acid in a heterogeneous mixture of nucleic acid. For example, in the case of Q replicase, MDV-1 RNA is the specific template for the replicase (see, for e.g., Kacian et al. Proc. Natl. Acad. Sci. USA, 69:3038-3042 (1972); herein incorporated by reference). Other nucleic acids will not be replicated by this amplification enzyme. Similarly, in the case of T7 RNA polymerase, this amplification enzyme has a stringent specificity for its own promoters (see, for e.g., Chamberlin et al. (1970) Nature, 228:227; herein incorporated by reference). In the case of T4 DNA ligase, the enzyme will not ligate the two oligonucleotides or polynucleotides, where there is a mismatch between the oligonucleotide or polynucleotide substrate and the template at the ligation junction (Wu and Wallace, Genomics, 4:560 (1989); herein incorporated by reference). Finally, Taq and Pfu polymerases, by virtue of their ability to function at high temperature, are found to display high specificity for the sequences bounded and thus defined by the primers; the high temperature results in thermodynamic conditions that favor primer hybridization with the target sequences and not hybridization with non-target sequences (H. A. Erlich (ed.), PCR Technology, Stockton Press (1989); herein incorporated by reference).

The term "amplifiable nucleic acid" refers to nucleic acids that may be amplified by any amplification method. It is contemplated that "amplifiable nucleic acid" will usually comprise "sample template."

The term "sample template" refers to nucleic acid originating from a sample that is analyzed for the presence of "target" (defined below). In contrast, "background template" is used—in reference to nucleic acid other than sample template that may or may not be present in a sample. Background template is most often inadvertent. It may be the result of carryover, or it may be due to the presence of nucleic acid contaminants sought to be purified away from the sample. For example, nucleic acids from organisms other than those to be detected may be present as background in a test sample.

The term "primer" refers to an oligonucleotide, whether occurring naturally as in a purified restriction digest or produced synthetically, which is capable of acting as a point of initiation of synthesis when placed under conditions in which synthesis of a primer extension product which is complementary to a nucleic acid strand is induced, (i.e., in the presence of nucleotides and an inducing agent such as DNA polymerase and at a suitable temperature and pH). The primer is preferably single stranded for maximum efficiency in amplification, but may alternatively be double stranded. When double stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and the use of the method.

The term "linker" refers to a synthetic double-stranded oligonucleotide that carries the sequence for one or more restriction endonuclease sites.

The term "linker fragment" refers to a short synthetic duplex oligonucleotide containing the target site for a restriction enzyme that may be ligated to the end of a DNA fragment prepared by cleavage with some other restriction enzyme during reconstruction of recombinant DNA.

The term "expression" when used in reference to a nucleic acid sequence, such as a gene, refers to the process of converting genetic information encoded in a gene into RNA (e.g., mRNA, rRNA, tRNA, or snRNA) through "transcription" of the gene (i.e., via the enzymatic action of an RNA polymerase), and into protein where applicable (as when a gene encodes a protein), through "translation" of mRNA. Gene expression can be regulated at many stages in the process. "Up-regulation" or "activation" refers to regulation that increases the production of gene expression products (i.e., RNA or protein), while "down-regulation" or "repression" refers to regulation that decrease production. Molecules (e.g., transcription factors) that are involved in up-regulation or down-regulation are often called "activators" and "repressors," respectively.

The term "vector" in reference to nucleic acid sequences refers to nucleic acid molecules that transfer DNA segment (s). Transfer can be into a cell, cell to cell, et cetera. A vector may also refer to a "binary vector" or a "superbinary vector." The term "vehicle" is sometimes used interchangeably with "vector."

The terms "expression vector" or "expression cassette" refer to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals. The term "expression vector" when used in reference to a construct refers to an expression vector construct comprising, for example, a heterologous DNA encoding a gene of interest and the various regulatory elements that facilitate the production of the particular protein of interest in the target cells. In certain embodiments of the present invention, a nucleic acid sequence of the present invention within an expression vector is operatively linked to an appropriate expression control sequence(s) (promoter) to direct mRNA synthesis.

The terms "in operable combination," "in operable order," and "operably linked" refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "regulatory element" refers to a genetic element that controls some aspect of the expression of nucleic acid sequences. For example, a promoter is a regulatory element that facilitates the initiation of transcription of an operably linked coding region. Other regulatory elements are splicing signals, polyadenylation signals, termination signals, and the like.

Transcriptional control signals in eukaryotes comprise "promoter" and "enhancer" elements. Promoters and enhancers consist of short arrays of DNA sequences that interact specifically with cellular proteins involved in transcription (see, for e.g., Maniatis, et al. (1987) Science 236:1237; herein incorporated by reference). Promoter and enhancer elements were isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Maniatis, et al. (1987), supra; herein incorporated by reference).

The terms "promoter element," "promoter," or "promoter sequence" refer to a DNA sequence that is located at the 5' end (i.e. precedes) of the coding region of a DNA polymer. The location of the majority of promoters known to occur in nature precedes the transcribed region. The promoter functions as a switch, activating the expression of a gene. When the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

The term "regulatory region" refers to a gene's 5' transcribed but untranslated regions, located immediately downstream from the promoter and ending just prior to the translational start of the gene.

The term "promoter region" refers to the region immediately upstream of the coding region of a DNA polymer, and is typically between about 500 bp and 4 kb in length, and is preferably about 1 to 1.5 kb in length. Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene and/or A reporter gene expressing a reporter molecule, to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected.

Promoters may be "constitutive" or "inducible." The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to Cauliflower Mosaic Virus (CaMV SD; see, for example, U.S. Pat. No. 5,352,605, incorporated herein by reference), mannopine synthase, octopine synthase (ocs), superpromoter (see for example, WO 95/14098; herein incorporated by reference), ubi3 promoters (see, for example, Garbarino and Belknap, Plant Mol. Biol. 24:119-127 (1994); herein incorporated by reference) other constitutive promoters suitable for use in the present invention are a rice actin promoter and a maize ubiquitin promoter, a maize alcohol dehydrogenase gene (Adh-1) promoter, rice or maize tubulin (Tub A, B or C) promoters; and the alfalfa His 3 promoter. Such promoters were used successfully to direct the expression of heterologous nucleic acid sequences in transformed plant tissue (see, for example, United States Patent Application No. 20060212973; herein incorporated by reference).

In contrast, an "inducible" promoter is one that is capable of directing a level of transcription of an operably linked nucleic acid sequence in the presence of a stimulus (e.g., heat shock, chemicals, light, etc.) that is different from the level of transcription of the operably linked nucleic acid sequence in the absence of the stimulus.

The term "regulatory element" refers to a genetic element that controls some aspect of the expression of nucleic acid sequence(s). For example, a promoter is a regulatory element that facilitates the initiation of transcription of an operably linked coding region. Other regulatory elements are splicing signals, polyadenylation signals, termination signals, and the like.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter. For example, an endogenous promoter in operable combination with a first gene can be isolated, removed, and placed in operable combination with a second gene, therein making it a "heterologous promoter" in operable combination with the second gene. A variety of such combinations are contemplated (e.g., the first and second genes can be from the same species, or from different species).

The term "naturally linked" or "naturally located" when used in reference to the relative positions of nucleic acid sequences means that the nucleic acid sequences exist in nature in the relative positions.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. Molecular Cloning: A Laboratory Manual, 2nd ed., Cold Spring Harbor Laboratory Press, New York (1989) pp. 16.7-16.8; herein incorporated by reference). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence that directs both the termination and polyadenylation of the nascent RNA transcript. Efficient polyadenylation of the recombinant transcript is desirable, as transcripts lacking a poly(A) tail are unstable and are rapidly degraded. The poly (A) signal utilized in an expression vector may be "heterologous" or "endogenous." An endogenous poly(A) signal is one that is found naturally at the 3' end of the coding region of a given gene in the genome. A heterologous poly(A) signal is one, which was isolated from one gene and positioned 3' to another gene. A commonly used heterologous poly(A) signal is the SV40 poly(A) signal. The SV40 poly(A) signal is contained on a 237 bp BamHI/BclI restriction fragment and directs both termination and polyadenylation (Sambrook, supra, at 16.6-16.7).

The term "transfection" refers to the introduction of foreign DNA into cells. Transfection may be accomplished by a variety of means known to the art including calcium phosphate-DNA co-precipitation, DEAE-dextran-mediated transfection, polybrene-mediated transfection, glass beads, electroporation, microinjection, liposome fusion, lipofection, protoplast fusion, viral infection, biolistics (i.e., particle bombardment) and the like.

The terms "stable transfection" and "stably transfected" refer to the introduction and integration of foreign DNA into the genome of the transfected cell. The term "stable transfectant" refers to a cell that has stably integrated foreign DNA into the genomic DNA.

The terms "transient transfection" and "transiently transfected" refer to the introduction of foreign DNA into a cell where the foreign DNA fails to integrate into the genome of the transfected cell. The foreign DNA persists in the nucleus of the transfected cell for several days. During this time the foreign DNA is subject to the regulatory controls that govern the expression of endogenous genes in the chromosomes. The term "transient transfectant" refers to cells that have taken up foreign DNA but have failed to integrate this DNA.

The term "calcium phosphate co-precipitation" refers to a technique for the introduction of nucleic acids into a cell. The uptake of nucleic acids by cells is enhanced when the nucleic acid is presented as a calcium phosphate-nucleic acid co-precipitate. The original technique of Graham and van der Eb in Virol., 52:456 (1973); herein incorporated by reference, was modified by several groups to optimize conditions for particular types of cells. The art is well aware of these numerous modifications.

The terms "infecting" and "infection" when used with a bacterium refer to co-incubation of a target biological sample, (e.g., cell, tissue, etc.) with the bacterium under conditions such that nucleic acid sequences contained within the bacterium are introduced into one or more cells of the target biological sample.

The terms "bombarding," bombardment, and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807; herein incorporated by reference), and are commercially available (e.g. the helium gas-driven microprojectile accelerator (PDS-1000/He, BioRad)).

The term "microwounding" when made in reference to plant tissue refers to the introduction of microscopic wounds in that tissue. Microwounding may be achieved by, for example, particle bombardment as described herein.

The term "selectable marker" refers to a gene which encodes an enzyme having an activity that confers resistance to an antibiotic or drug upon the cell in which the selectable marker is expressed, or which confers expression of a trait which can be detected (e.g., luminescence or fluorescence). Selectable markers may be "positive" or "negative." Examples of positive selectable markers include the neomycin phosphotrasferase (NPTII) gene that confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

The term "reporter gene" refers to a gene encoding a protein that may be assayed. Examples of reporter genes include, but are not limited to, luciferase (See, e.g., deWet et al. Mol. Cell. Biol. 7:725 (1987) and U.S. Pat. Nos. 6,074,859; 5,976, 796; 5,674,713; and 5,618,682; all of which are herein incorporated by reference in their entirety), green fluorescent protein (e.g., GenBank Accession Number U43284; GFP variants commercially available from CLONTECH Laboratories, Palo Alto, Calif.; herein incorporated by reference), chloramphenicol acetyltransferase, β-galactosidase (lacZ gene), alkaline phosphatase, and horse radish peroxidase.

The term "probe" refers to an oligonucleotide (i.e., a sequence of nucleotides), whether occurring naturally as in a purified restriction digest or produced synthetically, recombinantly or by PCR amplification, that is capable of hybridizing to another oligonucleotide of interest. A probe may be single-stranded or double-stranded. Probes are useful in the detection, identification and isolation of particular gene sequences. It is contemplated that any probe used in the present invention will be labeled with any reporter molecule," so that is detectable in any detection system, including, but not limited to enzyme (e.g., ELISA, as well as enzyme-based histochemical assays), fluorescent, radioactive, and luminescent systems. It is not intended that the present invention be limited to any particular detection system or label.

The term "antisense" refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex that is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or mRNA and that blocks the expression of a target gene by interfering with the processing, transport and/or translation of its primary transcript or mRNA. The complementarity of an antisense RNA may be with any part of the specific gene transcript, i.e., at the 5' non-coding sequence, 3' non-coding sequence, introns, or the coding sequence. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein.

The term "RNA interference" or "RNAi" refers to the silencing or decreasing of gene expression by siRNAs. It is the process of sequence-specific, post-transcriptional gene silencing in animals and plants, initiated by siRNA that is homologous in its duplex region to the sequence of the silenced gene. The gene may be endogenous or exogenous to the organism, present integrated into a chromosome or present in a transfection vector that is not integrated into the genome. The expression of the gene is either completely or partially inhibited. RNAi may also be considered to inhibit the function of a target RNA; the function of the target RNA may be complete or partial. In both plants and animals, RNAi is mediated by RNA-induced silencing complex (RISC), a sequence-specific, multicomponent nuclease that destroys messenger RNAs homologous to the silencing trigger. RISC is known to contain short RNAs (approximately 22 nucleotides) derived from the double-stranded RNA trigger, although the protein components of this activity are unknown. However, the 22-nucleotide RNA sequences are homologous to the target gene that is being suppressed. Thus, the 22-nucleotide sequences appear to serve as guide sequences to instruct a multicomponent nuclease, RISC, to destroy the specific mRNAs. Carthew (2001) has reported (Curr. Opin. Cell Biol. 13(2):244-248; herein incorporated by reference) that eukaryotes silence gene expression in the presence of dsRNA homologous to the silenced gene. Biochemical reactions that recapitulate this phenomenon generate RNA fragments of 21 to 23 nucleotides from the double-stranded RNA. These stably associate with an RNA endonuclease, and probably serve as a discriminator to select mRNAs. Once selected, mRNAs are cleaved at sites 21 to 23 nucleotides apart.

The term "siRNAs" refers to short interfering RNAs. In some embodiments, siRNAs comprise a duplex, or double-stranded region, of about 18-25 nucleotides long; often siRNAs contain from about two to four unpaired nucleotides at the 3' end of each strand. At least one strand of the duplex or double-stranded region of a siRNA is substantially homologous to or substantially complementary to a target RNA molecule. The strand complementary to a target RNA molecule is the "antisense strand" the strand homologous to the target RNA molecule is the "sense strand," and is also complementary to the siRNA antisense strand. siRNAs may also contain additional sequences; non-limiting examples of such sequences include linking sequences, or loops, as well as stem and other folded structures. siRNAs appear to function as key intermediaries in triggering RNA interference in invertebrates and in vertebrates, and in triggering sequence-specific RNA degradation during posttranscriptional gene silencing in plants.

The terms "hpRNA" and "hairpin RNA" refer to self-complementary RNA that forms hairpin loops and functions to silence genes (e.g. Wesley et al. (2001) The Plant Journal 27(6):581-590; herein incorporated by reference). The term "ihpRNA" refers to intron-spliced hpRNA that functions to silence genes.

The term "target RNA molecule" refers to an RNA molecule to which at least one strand of the short double-stranded region of a siRNA is homologous or complementary.

Typically, when such homology or complementarity is about 100%, the siRNA is able to silence or inhibit expression of the target RNA molecule. Although it is believed that processed mRNA is a target of siRNA, the present invention is not limited to any particular hypothesis, and such hypotheses are not necessary to practice the present invention. Thus, it is contemplated that other RNA molecules may also be targets of siRNA. Such targets include unprocessed mRNA, ribosomal RNA, and viral RNA genomes.

The terms "posttranscriptional gene silencing" and "PTGS" refer to silencing of gene expression in plants after transcription, and appears to involve the specific degradation of mRNAs synthesized from gene repeats. The term "cosuppression" refers to silencing of endogenous genes by heterologous genes that share sequence identity with endogenous genes.

The term "coexpression" refers to the expression of a foreign gene that has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "overexpression" generally refers to the production of a gene product in transgenic organisms that exceeds levels of production in normal or non-transformed organisms. The terms "overexpression" and "overexpressing" and grammatical equivalents are specifically used in reference to levels of mRNA to indicate a level of expression approximately 3-fold higher than that typically observed in a given tissue in a control or non-transgenic animal. Levels of mRNA are measured using any of a number of techniques known to those skilled in the art including, but not limited to Northern blot analysis. Appropriate controls are included on the Northern blot to control for differences in the amount of RNA loaded from each tissue analyzed (e.g., the amount of 28S rRNA, an abundant RNA transcript present at essentially the same amount in all tissues, present in each sample can be used as a means of normalizing or standardizing the RAD50 mRNA-specific signal observed on Northern blots).

The terms "Southern blot analysis" and "Southern blot" and "Southern" refer to the analysis of DNA on agarose or acrylamide gels in which DNA is separated or fragmented according to size followed by transfer of the DNA from the gel to a solid support, such as nitrocellulose or a nylon membrane. The immobilized DNA is then exposed to a labeled probe to detect DNA species complementary to the probe used. The DNA may be cleaved with restriction enzymes prior to electrophoresis. Following electrophoresis, the DNA may be partially depurinated and denatured prior to or during transfer to the solid support. Southern blots are a standard tool of molecular biologists (Sambrook, et al. Molecular Cloning: A Laboratory Manual, 2nd ed., Cold Spring Harbor Laboratory Press, New York (1989) pp. 9.31-9.58; herein incorporated by reference).

The term "Northern blot analysis," "Northern blot," and "Northern" refer to the analysis of RNA by electrophoresis of RNA on agarose gels to fractionate the RNA according to size followed by transfer of the RNA from the gel to a solid support, such as nitrocellulose or a nylon membrane. The immobilized RNA is then probed with a labeled probe to detect RNA species complementary to the probe used. Northern blots are a standard tool of molecular biologists (Sambrook, et al. (1989) supra, pp 7.39-7.52; herein incorporated by reference).

The term "isolated" when used in relation to a nucleic acid or polypeptide, as in "an isolated oligonucleotide" refers to a nucleic acid sequence that is identified and separated from at least one contaminant nucleic acid with which it is ordinarily associated in its natural source. Isolated nucleic acid is present in a form or setting that is different from that in which it is found in nature. In contrast, non-isolated nucleic acids, such as DNA and RNA, are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs that encode a multitude of proteins. However, isolated nucleic acid encoding a particular protein includes, by way of example, such nucleic acid in cells ordinarily expressing the protein, where the nucleic acid is in a chromosomal location different from that of natural cells, or is otherwise flanked by a different nucleic acid sequence than that found in nature. The isolated nucleic acid or oligonucleotide may be present in single-stranded or double-stranded form. When an isolated nucleic acid or oligonucleotide is to be utilized to express a protein, the oligonucleotide will contain at a minimum the sense or coding strand (i.e., the oligonucleotide may single-stranded), but may contain both the sense and anti-sense strands (i.e., the oligonucleotide may be double-stranded).

The term "purified" refers to molecules, either nucleic or amino acid sequences that are removed from their natural environment isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated. As used herein, the terms "purified" and "to purify" also refer to the removal of contaminants from a sample. The removal of contaminating proteins results in an increase in the percent of polypeptide of interest in the sample. In another example, recombinant polypeptides are expressed in plant, bacterial, yeast, or mammalian host cells and the polypeptides are purified by the removal of host cell proteins; the percent of recombinant polypeptides is therein increased in the sample.

The term "accession" when used herein associated with sequences of genes and proteins refers to a gene or group of similar genes or proteins from these genes or proteins received from a single source at a single time. The term "accession number" when used herein refers to a unique identifier for protein and gene sequences and is assigned when an accession is entered into a database (for example GenBank at NCBI, European Molecular Biology Laboratory (EMBL) and the like).

The term "accession" when used herein associated with sources of plants refers to a plant or group of similar plants or group of seeds from these plants received from a single source at a single time. The term "accession number" when used herein associated with sources of plants, such as the number following PI, refers to a unique identifier for each accession and is assigned when an accession is entered into a plant collection. As used herein "PI" used before an accession number indicates the identity of the genebank or national system that in this case refers to an accession cataloged within the USA system where the term "PI" refers to "plant introductions."

The term "sample" is used in its broadest sense. In one sense it can refer to a plant cell or tissue, such as a leaf. In another sense, it is meant to include a specimen or culture obtained from any source, as well as biological and environmental samples. Biological samples may be obtained from plants or animals and encompass fluids, solids, tissues, and gases. Environmental samples include environmental material such as surface matter, soil, water, salt, and industrial samples. These examples are not to be construed as limiting the sample types applicable to the present invention.

The term "eigenvector" refers to a "vector" which, when acted on by a particular linear transformation, produces a scalar multiple of the original vector. The scalar in question refers to an eigenvalue corresponding to a particular eigenvector. A "vector" in reference to mathematical calculations, such as eigenvector calculations, refers to an "element of a vector space" which can include many mathematical entities.

As used herein, the terms "marker" and "DNA marker" and "molecular marker" in reference to a "selectable marker" refers to a physiological or morphological trait which may be determined as marker for its own selection or for selection of other traits closely linked to that marker, for example, a gene or trait that associates with drought resistance, such as a marker, such as a DNA marker including but not limited to simple sequence repeat (SSR), single nucleotide polymorphism analysis (SNP), random amplified polymorphic DNA analysis (RAPID), amplified fragment length polymorphism analysis (AFLP), and the like that will link phenotype information, such as drought resistance and agronomic traits to a linkage or QTL locus, to provide a genomic map, for example a fingerprint map, and chromosome location and/or map.

As used herein, the term "linkage group" or "LG" refers to a group of two or more genetically or physically mapped loci with observed linkage to a trait, for example, one or more of a SSR, SNP, AFLP, and RAPD marker of the present invention that may map to drought resistant germplasm.

The term "functional category" refers to a classification of cellular function as defined and assigned by criteria on the website of the Munich Information Center for Protein Sequences (MIPS) (website address at mips.gsf.de). Functional categories include but are not limited to metabolism energy, biogenesis of cellular components, subcellular localization, transport, transcription, signal transduction, interaction with the cellular environment, protein synthesis, protein with binding function, defense, development, cell fate, cell cycle and DNA processing, protein fate, cell type differentiation, and protein activity regulation.

The term "metabolic process" refers to a process that causes a chemical change in a living organism, including anabolism and catabolism. A metabolic process may transform a small molecule, alter a macromolecular process such as DNA repair, alter DNA replication, alter protein synthesis or alter protein degradation.

GENERAL DESCRIPTION OF THE INVENTION

The present inventions relate to compositions and methods for providing drought resistant grass plants comprising *Festuca mairei* plant germplasm. Specifically, the inventions relate to providing compositions and methods for introgressing *Festuca mairei* germplasm and/or specific *Festuca mairei* genes into grass plants, such as *Lolium perenne* plants. Further, the invention relates to methods of grass plant breeding comprising genetic markers for identifying the preferred *Festuca mairei* germplasm introgressed into grass plants, and providing commercially desirable drought resistant cultivars of grass plants.

Environmental abiotic stresses such as drought, high salinity, and extreme temperatures can severely impair plant growth and performance. Thus, the response of plant to these abiotic stresses were the focus of study for decades at physiological and genetics levels (Levitt, J. 1980 Academic Press, NY; Quarrie et al., 1994 Theor. Appl. Genet. 89:794-800; all of which are herein incorporated by reference) and recently at molecular and genomics levels (Seki et al., 2001 Plant Cell. 13: 61-72; Ozturk et al., 2002 Plant Mol. Biol. 48: 55 1-573; all of which are herein incorporated by reference). Among these stresses, drought or water deficit is the most severe and complex limiting factor on plant growth and crop production (Seki et al., 2002 Plant J. 30:279-292).

The Michigan Agricultural Statistics Service (MASS) showed that over 1.9 million acres of turfgrass were maintained throughout the state during 2002-2003. Over 84% of this acreage was in the residential sector, while 96,000 acres were intensively managed by golf course superintendents. In addition, 1.8 million acres were used as forage grasses. The contribution of the turf grass industry to Michigan's state economy exceeded $1.8 billion annually and created jobs for over 30,000 full-time employees.

Thus, it is contemplated that drought tolerant cultivars will save the turf grass industry millions of dollars by reducing the irrigation rate, energy input, and more importantly conserving water resources, as such resources become limited throughout the USA and the world. In particular, drought resistant turf grass will especially be cost efficient when grown in regions experiencing increased drought conditions, such as when cities and municipalities declare water emergencies causing restrictions in the watering of landscapes.

I. Perennial Ryegrass (*Lolium perenne* (L.)) Plants, Annual Ryegrass Plants (*Lolium multiflorum*) and Hybrids with *Festuca* Plants:

Perennial ryegrass (*L. perenne* L.) (Lp) is a cool-season turfgrass grass (2n=2x=14, LL) that is widely used as turf and forage with superior quality and rapid establishment of plants, qualities lacking in *Festuca* plants. However, lack of drought tolerance makes *L. perenne* less persistent during hot and dry summers or dry environments unlike drought tolerant *Festuca* plants. One approach for improvement of drought tolerance in perennial ryegrass is introgression of alien genomes from other drought tolerant genera, such as *Festuca* (Riewe et al., 1985, In Heath et al. eds. pp. 241-246; herein incorporated by reference). Intergeneric hybridization followed by backcrossing or by chromosome doubling produced alien chromosome addition, substitution, or translocation in progeny plants (Sharma et al., 1995, Genome 38:406-413; herein incorporated by reference).

Thus, intergeneric hybridization between *Lolium* and *Festuca* was used for developing novel allopolyploids for combining desirable agronomic attributes from two important turf grass and forage grass species. Amphiploids ($LLG_1G_1G_2G_2$, 2n=6x=42) between diploid ryegrass (*L. multiflorum*, LL, 2n=2x=14) and tetraploid tall fescue (*F. arundinacea* var. *glaucescens* gauct. [=*F. arundinacea* subsp. *fenas* (Lag.) Arcang.] ($G_1G_1G_2G_2$, 2n=4x=28) were synthesized to improve palatability of tall fescue by introducing the L genome from annual ryegrass (Cao et al. 1994, Boiss. Sci. Agric. Sin. 27:69-76; herein incorporated by reference). Amphiploids (2n=8x=56) between annual ryegrass and hexaploid tall fescue (*F. arundinacea*, 2n 6×42) were produced to transfer the nutritive quality of annual ryegrass into tall fescue while retaining the adaptive qualities of tall fescue (Buckner et al. 1985, Crop Sci. 25:757-761; Buckner, 1965, Crop Sci. 5:395-397; all of which are herein incorporated by reference).

Amphidiploids between ryegrasses (*L. multiflorum* or *L. perenne*) and meadow fescue (*F. pratensis* Huds.) were selected for better agronomic performance as forage grass (Zwierzykowski et al. 1998, J. of Hered. 89:324-328; herein incorporated by reference) and some are widely used in grasslands, such as 'Elmet' and 'Prior' (Jauhar 1993, In Cytogenetics of the *Festuca-Lolium* complex: Relevance to breeding. Springer-Verlag, Berlin; herein incorporated by reference). Eleven cultivars were developed from these *Lolium* spp.×*F. pratensis* hybrids and seven cultivars from *L. multiflorum*×*F. arundinacea* (Zwierzykowski, 2004, In: Yamada et al. (eds) Development of a novel grass with environmental stress and high forage quality through intergeneric hybridization between *Lolium* and *Festuca*, NARO, Tsukuba, pp: 17-29; herein incorporated by reference). The amphiploids and tetraploid hybrids derived from these ryegrass and fescue hybrids were subjected to extensive cytological analyses and were determined to be good breeding material for improving forage quality of tall fescue (Cao et al. 2003, Crop Sci. 43:1659-1662; Zwierzykowski et al., 2006, Theor. Appl. Genet. 113:539-547; all of which are herein incorporated by reference).

Further, several genes were identified in *Festuca arundinacea* L. germplasm, including dehydrin and a cytosolic-heat shock protein (HSC 70), that associated with a response to drought stress in two tall fescue (*Festuca arundinacea* L.) cultivars, 'Southeast' and 'Rebel Jr.' (Jiang and Huang, 2002, Crop Sci. 42(1):202-207; herein incorporated by reference).

II. *Festuca mairei* Plants:

*Festuca mairei* St. Yves (Fm) is a tetraploid plant (2n=4x=28, $M_1M_1M_2M_2$) species, commonly known as Atlas Fescue, that grows in the Moroccan Atlas mountains. The M genome in *Festuca* is associated with a xerophytic adaptation allowing the plant to survive long summers under drought stress (Marlatt et al., 1997, Neotyphodium/Grass Interactions, Baxon and Hill, Plenum Press, NY; herein incorporated by reference). Fm plants shares it's $M_1M_2$ genomes with *F. arundinacea* var. *atlantigena* ($GiG_1$ $G_2G_2M_1M_1M_2M_2$) a species that also grows near and in the Atlas Mountain ranges of northwest Africa but with a broader environmental range including lowland areas. *F. mairei* tolerates high temperature and drought stress (Borill et al. 1971, Cytologia 36:1-14; herein incorporated by reference) in addition to a high photosynthetic rate (Randall et al., 1985, NY pp: 409-418; herein incorporated by reference).

As described herein, unexpected results were obtained when *Festuca mairei* plants demonstrated a greater capability to withstand drought stress treatment than other species of *Festuca*, including commercial cultivars of *F. arundinacea*, see, FIG. 1). Thus, it is contemplated that breeding programs using *Festuca mairei* germplasm, in particular providing germplasm associated with drought tolerance to grass plants, had the potential to provide superior hybrid drought tolerant grass cultivars. Furthermore, it is contemplated that *F. mairei*'s genome contains unique *Festuca* genetic material and/or expresses a unique combination of genes providing for conserved and highly developed systems for growing under severe drought conditions.

Figure 14A:
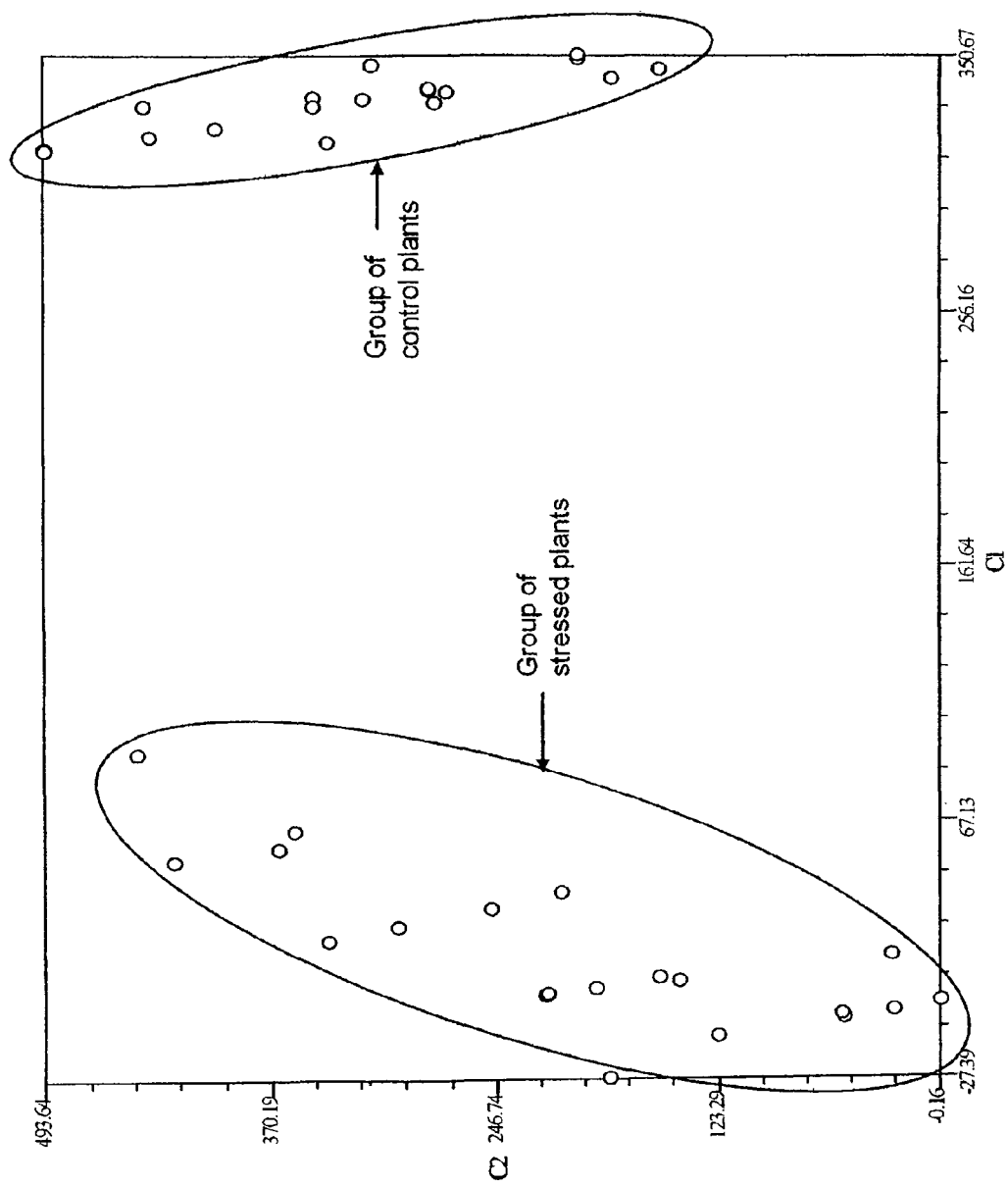
FIG. 14 shows an exemplary principle component analysis of 9 genotypes for both control and stressed plants: a: Three genotype components accounted for 33.4%, 16.4%, and 11.2% of the total variation; and b: Three genotype components accounted for 30.5%, 16.2%, and 11.5% of the total variation.
Figure 14B:
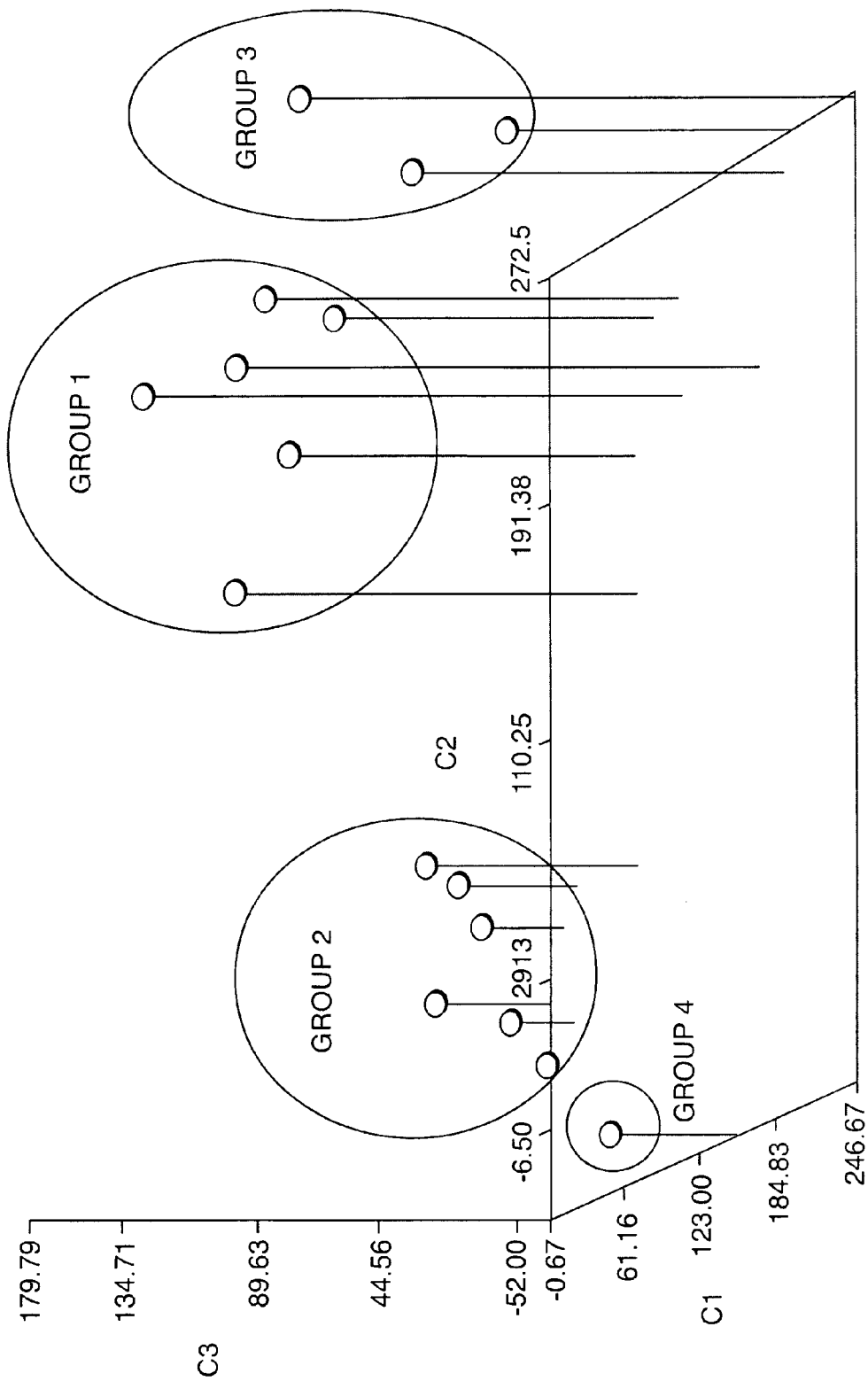

Moreover, additional unexpected results were obtained after evaluation of the hybrid plants developed through plant breeding methods of the present inventions, see, for example, FIG. 14b. These unexpected results demonstrate that a *F. mairei*×*L. perenne* 'Calypso' hybrid plant and backcrossed plants (lines G15 and G30a) of the present invention show superior levels of drought resistance when compared to parental and $F_1$ *F. mairei*×*L. perenne* hybrid plants. In other words, the *F. mairei*×*L. perenne* hybrid backcrossed plants of the present inventions demonstrated unexpected "hybrid vigor" also known as "hybrid superiority," "heterosis" and "transgression" for resisting drought stress. These unexpected results were obtained using PCA-based evaluation methods for drought tolerance of the present inventions, as described herein.

Therefore, the inventor used this polyploidy monocot species, *F. mairei* as a model plant system for providing a genetic study of drought tolerance for providing drought tolerant hybrid grass plants and for comparing drought tolerance mechanisms to other grass species. Further, in some embodiments, this genetic information is used to provide novel grass varieties demonstrating strong vegetative growth and selected agronomic performance, such as for providing novel grass plant cultivars showing a combined enhanced drought resistance with desired characteristics of ornamental grasses, or turf grasses or forage grasses.

III. Genetics of Drought Tolerance:

A. Molecular Regulation:

Drought stress triggers a wide range of plant responses manifested by changes from growth rates, physiological, and metabolic processes to altered gene expression. A stress response is initiated when a plant recognizes stress at the cellular level, which then activates signal transduction pathways to transmit the information within individual cells and throughout the plants. Ultimately, changes in gene expression will occur and are integrated into plant adaptive response to modify growth and development.

Genes involved in many different pathways expressed in response to drought stress in *Arabidopsis* plants, were extensively studied as a model plant that tolerates moderate water deficit. Several hundred *Arabidopsis* genes were shown to be differentially expressed in response to dehydration, as evidenced by transcript profiling (Bockel et al., 1998 J. Plant Physiol. 152: 158-166; herein incorporated by reference). These differentially expressed genes (DEFs) were assigned to diverse metabolic pathways. For example, genes encoding enzymes involved in sugar metabolism and biosynthesis of other compounds acting as compatible solutes were found up-regulated in response to drought (Bohnert et al., 1995 Plant Cell 7: 1099-10111; herein incorporated by reference). The ion and water channel proteins are likely to be important in regulating water flux, which were supported by isolation of channel protein genes from pea (*Pisum sativum*) in response to water deficit (Guerrero et al., 1990 Plant Mol. Biol. 15: 11-26; herein incorporated by reference).

Enzymes required for cell wall lignification processes are increased in drought stressed tissue (Peleman et al., 1989 Plant Cell 1: 81-93; herein incorporated by reference). Genes encoding proteins similar to proteases and enzymes that detoxify active oxygen species were induced by drought (Williams et al., 1994 Plant Mol. Biol. 25: 259-270; Mittler et al., 1994 Plant J. 5: 397 405; all of which are herein incorporated by reference). Although precise function of these genes has not yet been demonstrated, five main groups were summarized by Bartels and Salamini (Bartels et al., 2001 Plant Physiol. 127: 1346-1353; herein incorporated by reference) as genes encoding: (a) proteins with protective properties; (b) membrane proteins involved in transport processes; (c) enzymes related to carbohydrate metabolism; (d) regulatory molecules, such as transcription factors, kinases, or other putative signaling molecules; and (e) open reading frames that show no homologies to known sequences.

The molecular complexity of the process during drought stress response was illustrated by recent microarray experiments (Seki et al., 2002 Plant J. 30:279-292; herein incorporated by reference). These results indicate that a network of signal transduction pathways allows the plant to adjust its metabolism to the demands imposed by water deficit (Shinozaki et al., 2000 Curr. Opin. Plant Biol. 3:217-223; Kirch et al., 2001 In Scheel et al., eds, Vol. II, 2nd ed. Academic press. NY; all of which are herein incorporated by reference). The complex signal transduction cascade is divided into three basic steps: (a) perception of stimulus; (b) signal amplification and integration; and (c) response reaction in the form of de novo gene expression (Ingram et al., 1996 Annu. Rev. Plant Physiol. Plant Mol. Biol. 47: 377-403; herein incorporated by reference).

Several experimental approaches were followed to identify signaling molecules involved in signal transmission process and the activation of gene expression in response to stress. The majority of information was derived from promoter analyses and from differential screening procedures. One molecule that was found as central to dehydration-regulated gene expression is the plant hormone abscisic acid (ABA). Endogenous ABA levels were reported to increase as a result of water deficit in many physiological studies, and therefore ABA is thought to be involved in the signal transduction (Chandler et al., 1994 Annu. Rev. Plant Physiol. Plant Mol. Biol. 45: 113-141; Giraudat et al., 1994 Plant Mol. Biol. 26: 1557-1577; all of which are herein incorporated by reference). Besides the ABA-mediated gene expression, the investigation of drought-induced genes in *A. thaliana* also revealed ABA-independent signal transduction pathways (Yamaguchi-Shinozaki et al., 1994 Plant Cell 6: 251-264; herein incorporated by reference). Both ABA-dependent and -independent stress signaling first modifies constitutively expressed transcription factors, leading to the expression of early response transcriptional activators, which then activate downstream stress tolerance effective genes (Zhu et al., 2001, Trends Plant Sci. 6: 66-71; herein incorporated by reference).

Therefore, even though a large number of drought-induced genes were identified in a wide range of species, the molecular basis for increasing drought tolerance remains unknown (Ingram et al., 1996 Annu. Rev. Plant Physiol. Plant Mol. Biol. 47: 377-403; herein incorporated by reference).

Thus, it is contemplated that the use of whole genomic-related technology for identifying differential gene expression in Fm provides the necessary tools to identify the key genes that are altered during drought stress within large-scale drought stress experiments and for providing grass plant breeding goals.

B. Genomics:

Recently, within the rapidly expanding field of genomics, the creation of a large-scale EST database from various plant species, including the complete sequencing of *Arabidopsis* (Arabidopsis genome initiative [AGI 2000, Nature 408: 796-815; herein incorporated by reference) and rice genome (Yu et al., 2002, Science 296:79-92; herein incorporated by reference) were made public. This genomic information source provides a vast reference database for evaluating the coordinated function and expression of genes identified by using cDNA-AFLP in plants where few genes have been identified or sequenced, such as in *Festuca mairei* plants (see, Wang and Bughrara, 2005, Mol Biotechnol. 29(3):211-20; herein incorporated by reference).

Functional genomics of *Festuca* species lags far behind other plant systems. Molecular genetic mechanisms controlling the expression of drought tolerance in these species also was an unknown field, even though a significant effort were invested into the physiological mechanisms studies (Levitt, 1980, Academic Press, NY; Youngner et al., 1985, In: Gibeault et al., eds., 37-43 Qian et al., 1997, Crop Sci. 37:905-910; all of which are herein incorporated by reference) and developing and evaluating drought resistance in grass species (Aronson et al., 1987, Crop Sci. 27: 1261-1266; Fry et al., 1989, Crop Sci. 29: 1535-1541; all of which are herein incorporated by reference).

It is contemplated that by relating gene regulation to adaptive events occurring during stress using a variety of techniques, such as cDNA-AFLP, provides genetic tools for gaining information on differential gene expression during stress. cDNA amplified fragment length polymorphism (cDNA-AFLP) is an extremely efficient method for isolating differentially expressed fragments (DEFs) or transcript derived fragments (TDFs) in a genome wide scale (Bachem et al., 1996 Plant J. 9: 745-753; herein incorporated by reference). cDNA-AFLP shows high reproducibility and sensitivity, good correlation with northern blot analysis and low set-up cost, even though it requires a comprehensive reference database (Donson et al., 2002 Plant Mol. Biol. 48:75-97; herein incorporated by reference). Therefore, the inventor investigated drought-induced gene expression of *F. mairei* plants in order to facilitate germplasm introduction and gene manipulation for increasing drought tolerance of plants within grass plant breeding programs.

Unlike previous studies where one or two stress time-points were compared with the control, including limited microarray analysis, the inventor provides herein an analysis of more relevant drought stress treatments, such as a nine serial time-point study of the drought stress cycle, which covered the whole course of dynamic changes of the plant adaptive response to drought stress. These studies revealed four separate differential expression patterns detected by the cDNA-AFLP analysis, even though two expression patterns of transient and up-then-down expression patterns were not abundant. The inventor further contemplates that using a complete differential expression pattern that included spatial and temporal regulation patterns would lead to the design of a programmed control of a survival response to drought, and thus, will allow the artificial regulation of a stress response mechanism at the gene level. Thus, the cDNA-AFLP technique provided a means to provide genomic sequence information and functional analysis but also served as a powerful tool for identification of gene regulation and types of differential expression patterns responsible for stress adaptation.

Also unlike previous studies where a large number of genes, such as stress inducible or up-regulated transcripts and proteins, were identified associated with stress responses, the inventor additionally identified herein, down-regulated genes, transiently expressed genes and other types of altered gene expression patterns, such as up-then-down regulation. Thus, down-regulation or other types of gene regulation are contemplated by the inventor to play important roles in responding favorably to drought stress and/or long-term stress tolerance, such as retaining green leaves and turgid tissues.

C. Molecular Identification of *Festuca* Germplasm in Grass Plants:

When combined in hybrid plants, Fm and Lp genomes show a distant relationship according to a low level of homologous chromosome pairing and hence less genetic recombination (Chen et al., 1995 Crop Sci. 35:720-725; Humphreys et al., 1997 New Phytol. 137:55-60; all of which are herein incorporated by reference). When Fm germplasm was identified in Lp hybrids, demonstrating that Fm and Lp genomes could combine, Fm Lp hybrid plants were contemplated to provide an effective means to produce hybrids of high agronomic potential (Cao et al., 2000, Genome 43:398-403; herein incorporated by reference). However, the Lolium×Festuca amphiploids were found to be unstable and oftentimes shifted back towards one of the parent types, particularly Lolium, Humphreys et al., 2003, *Annals of Applied Biology* 143, 1-10; herein incorporated by reference.

Therefore, in some embodiments, the present invention contemplates using molecular markers for identifying *F. mairei* germplasm associated with drought tolerance. In particular, the inventor contemplates identifying meotically stable Fm germplasm on a Lp plant background for choosing plants with increased drought resistance for use in grass plant breeding programs.

Previously, within Fm×Lp hybrid plants, *F. mairei* chromatin was identified in the *L. perenne* genetic background by FISH and RFLP methods (see, for example, Chen and Sleper (1999) Crop Science 39, 1676-1679; PaSakinskien and Jones, 2005, Cytogenet Genome Res 109: 393-399; herein incorporated by reference). While genomic in situ hybridization (GISH) showed homologous chromosome pairing between L and M genomes detected in hybrids from crosses between Fm and Lp plants (Cao et al., 2000 Genome 43:398-403; Morgan et al. (2001) *Theoretical and Applied Genetics* 103, 696-701; all of which are herein incorporated by reference).

Compared to PCR-based molecular markers, the procedure of FISH is more difficult, needs trained personnel, and is relatively expensive. In addition, the amount of information obtained by the FISH procedure is very limited due to fewer genome specific probes. Thus PCR based markers such as simple sequence repeat (SSR) and random amplified polymorphic DNA (RAPD) are important genetic markers for plant genome analysis due to their genome wide distribution, simple assay by PCR, and high levels of polymorphism.

Additional *Festuca* markers contemplated for use in the present inventions include markers used for comparative genome RFLP mapping for meadow and tall fescue (Chen et al., 1995 Crop Sci. 35:720-725; herein incorporated by reference), SSR markers for tall fescue (*Festuca arundinacea* Schreb.) (FA), that were used to generate a large number of SSR markers through mining the FA expressed sequence tag (EST) database, then applied in molecular mapping, comparative genomics, and molecular plant breeding across a wide range of turfgrass species (Saha et al., 2004, Theor. Appl. Genet. 109:783-791; Saha, et al., 2005, Theor. Appl. Genet., 110:323-336; all of which are herein incorporated by reference).

The use of ryegrass markers are also contemplated in methods of the present inventions whereas SSR markers are co-dominantly inherited and were successfully isolated from perennial ryegrass, which constitute a valuable resource of markers for the molecular breeding of ryegrass (Kubik et al., 2001, Crop Sci. 45:1565-1571; Jones et al., et al., 2001, Theor. Appl. Genet. 102:405-415; all of which are herein incorporated by reference) with additional ryegrass markers described in Warnke, et al., 2004, Theor. Appl. Genet. 109: 294-304; and Saha, et al., 2006, Theor Appl Genet. 113(8): 1449-58; all of which are herein incorporated by reference).

RAPD DNA markers are also contemplated for use in the present inventions for routine fingerprinting of germplasm and cultivars, because of the low cost and random marker distribution throughout the genome. Even though RAPD markers are dominantly inherited, they are useful for monitoring genome introgressions from wild donor to cultivated species (Bemabdelmouna et al., 1999 Theor. Appl. Genet. 98:10-17; Siffelova et al., 1997 Biologia Plantarum 40:183-192; all of which are herein incorporated by reference).

Assessment of the genome introgression status in the progeny from intergenic hybridization by using SSR and RAPD markers will be useful in directing breeding programs to develop improved grass cultivars. With the goal of transferring drought tolerance of Fm into Lp, a population comprised of hybrids, amphidiploid, and backcross progeny derived from intergeneric crosses between Fm and Lp were generated Monitoring the Fm and Lp genome compositions in these progeny using molecular markers will assist in identifying individuals with desirable genome combinations to develop new perennial ryegrass cultivars with improved drought tolerance. This reference describes the use of molecular markers for tracing genomic introgression between *Lolium perenne* and *Festuca mairei×L. perenne* in the progeny of a backcross population (Wang et al. (2003) Crop Science 43, 2154-2161; herein incorporated by reference).

Further, desirable agronomic traits are also contemplated for tracking with molecular markers. For example, genetic control of herbage quality variation in perennial ryegrass (*Lolium perenne* L.) was assessed through the use of the molecular marker-based reference (QTL) genetic map of perennial ryegrass (*Lolium perenne* L.). Restriction fragment length polymorphism (RFLP), amplified fragment length polymorphism (AFLP) and genomic DNA-derived simple sequence repeat-based (SSR) framework marker set was enhanced, with RFLP loci corresponding to genes for key enzymes involved in lignin biosynthesis and fructan metabolism. Quality traits such as crude protein (CP) content, estimated in vivo dry matter digestibility (IVVDMD), neutral detergent fiber content (NDF), estimated metabolisable energy (EstME) and water soluble carbohydrate (WSC) content were measured by near infrared reflectance spectroscopy (NIRS) analysis of herbage harvests (see, Cogan et al., 2005, Theor Appl Genet. 1110(2):364-80; herein incorporated by reference).

DETAILED DESCRIPTION OF THE INVENTION

In some embodiments, the present invention relates to compositions and methods for providing drought resistant grass plants comprising *Festuca mairei* plant germplasm. Specifically, the invention relates to providing compositions and methods for introgressing preferred *Festuca mairei* germplasm and/or specific *Festuca mairei* genes into grass plants, such as *Lolium perenne* plants. Further, the invention relates to methods of grass plant breeding comprising genetic markers for identifying the preferred *Festuca mairei* germplasm introgressed into grass plants, and providing commercially desirable drought resistant cultivars of grass plants.

In some embodiments, the present invention further relates to methods of breeding Lp hybrid plants comprising Fm preferred germplasm further comprising compositions and methods for using DNA markers for identifying the Fm germplasm including but not limited to simple sequence repeat (SSR), single nucleotide polymorphism analysis (SNP), random amplified polymorphic DNA (RAPD), amplified fragment length polymorphism analysis (AFLP), DNA fingerprinting, and the like, for identifying introgressed drought resistance germplasm into a formerly drought-susceptible plant variety, for example, certain elite ryegrass plant varieties.

In some embodiments, the present invention additionally provides comparative methods for identifying superior drought resistant plants.

In some embodiments the present invention relate to compositions and methods utilizing genes derived from *Festuca mairei* (Fm) plant genomes. Thus, in some embodiments, the present invention provides compositions comprising Fm genes, Fm nucleic acid sequences, Fm coding sequences, and Fm polypeptides, and in particular to plants and expression vectors comprising any one of SEQ ID NOs:1-39 and 93-216 for encoding Fm polypeptides (see, e.g., polypeptides comprising any one of SEQ ID NOs:40-91) and related genes associated with onset, adaptation, and maintenance of drought resistance in plants, see, for e.g., related genes in Tables 3-6. In some embodiments, the nucleic acid sequences are at least 50%, 60%, 70%, 80%, 90%, 95%, 98%, or 99% identical to the aforementioned sequences.

In some embodiments, the present invention also provides breeding methods for using Fm genes, Fm nucleic acid sequences, and Fm polypeptides; such methods include but are not limited to use of these genes to produce drought resistance grass plants for providing breeding and commercial cultivars through artificial breeding and/or transgenic plant production, to produce Fm nucleic acid sequences and/or Fm protein in a plant, to increase levels of Fm nucleic acid sequences and/or Fm protein in a plant, to transiently express Fm nucleic acid sequences and/or Fm protein in a plant, to decrease Fm nucleic acid sequences and/or Fm protein in a plant, to silence Fm nucleic acid sequences and/or Fm protein in a plant, to alter environmental stress tolerance of a plant, to alter environmental stress plant phenotypes of a plant, and for controlled production of drought tolerance in plants. It is not meant to limit the present invention to alterations in Fm expression. In some embodiments, an Fm nucleotide or Fm protein alters Lp gene expression and/or Lp gene activity and/or Lp protein expression and/or Lp protein activity. In some embodiments, Fm genes and/or polypeptides are overexpressed in modified plants, modified plant tissue, modified leaves, and modified host cells. It may be desirable to integrate the nucleic acid sequence of interest into a plant genome. Introduction of the nucleic acid sequence of interest into a plant cell genome may be achieved by, for example, by artificial breeding or heterologous recombination using *Agrobacterium*-derived sequences, such as described herein.

In some embodiments, the present invention also provides methods for inhibiting Fm nucleic acid sequences and/or Fm polypeptides; such methods include but are not limited to use of these genes in antisense constructs to produce transgenic plants, to inhibit Fm protein in a plant, to decrease Fm protein in a plant, to alter levels of endogenous Lp protein in a plant, to alter environmental stress tolerance of a plant, to alter environmental stress phenotypes of a plant, and for controlled production of drought tolerance. Introduction of the inhibitory nucleic acid sequence of interest, such as an Fm antisense nucleic acid sequence, into a plant cell genome may be achieved by, for example, heterologous recombination using *Agrobacterium*-derived sequences.

In some embodiments, the invention provides an expression vector, comprising a first nucleic acid sequence encoding a nucleic acid product that interferes with the expression of a second nucleic acid sequence comprising a sequence set forth in any one of SEQ ID NOs:96, 103, 104, 106, 108, 110, 111, 112, 162, 172, 181, 200, 202, 204, 208, 101, 118, 120, 141, and 185. In some embodiments, the second nucleic acid sequence encodes a polypeptide comprising a sequence set forth in any one of SEQ ID NOs:40-91. In some embodiments, the nucleic acid or polypeptide sequences are at least 50%, 60%, 70%, 80%, 90%, 95%, 98%, or 99% identical to the aforementioned sequences. The present invention is not limited to any particular nucleic acid product that interferes with the expression of a second nucleic acid sequence. Indeed a variety of types of nucleic acid products are contemplated. In some embodiments, said nucleic acid product that interferes is an antisense sequence. In some embodiments, said nucleic acid product that interferes is a dsRNA that mediates RNA interference. In some embodiments, said nucleic acid product that interferes is a siRNA sequence. In some embodiments, said nucleic acid product that interferes is a hpRNA sequence. In some embodiments, the expression vector silences the gene in a plant.

Alternatively, the responsiveness of a plant or plant cell to a stress condition, such as water deprivation, or a return to an irrigated condition, can be modulated by use of a suppressor construct containing a dominant negative mutation for any of the stress-regulated sequences described herein. In particular, a suppressor construct would suppress a silenced Fm gene found to be up-then-down-regulated during adaptation to low water conditions. Expression of a suppressor construct containing a dominant mutant mutation generates a mutant transcript that, when coexpressed with the target transcript inhibits the action of the target transcript. Methods for the design and use of dominant negative constructs are well known (see, e.g., in Herskowitz, (1987) Nature 329:219-222; Lagna and Hemmati-Brivanlou, (1998) Curr. Topics Devel. Biol. 36:75-98; all of which are herein incorporated by reference).

Thus, in some embodiments, the present invention provides compositions comprising Fm and Fm related (homologous) genes, nucleic acids sequences, and coding sequences, Fm polypeptides and Fm homologous polypeptides, and in particular to expression vectors providing Fm nucleic acid sequences and Fm genes encoding Fm polypeptides, related genes and their encoded polypeptides, associated with providing for drought tolerance and increasing drought tolerance in a plant.

In some embodiments, the present invention also provides methods for using Fm related genes, and Fm related polypeptides (see, for examples, Tables 3-6); such methods include but are not limited to use of these genes to produce new grass plants, to alter environmental stress tolerance in grass plants, to alter grass plant phenotypes, and for controlled production of drought resistance in plants. It may be desirable to target the nucleic acid sequence of interest to a particular locus on the plant genome. As such, the identification of Lp linkage groups comprising Fm germplasm in grass plants with superior drought resistance may find use in breeding methods of the present inventions, see, for example, Table 8.

In some embodiments, Fm genes and polypeptides are overexpressed in hybrid grass plants, in nontransgenic plants, in transgenic plants, transgenic tissue, transgenic leaves, transgenic seeds, transgenic host cells. In some embodiments, Fm polypeptides are underexpressed in hybrid grass plants, in nontransgenic plants, in transgenic plants, transgenic tissue, transgenic leaves, transgenic seeds, transgenic host cells. In some embodiments, Fm genes and polypeptides are overexpressed then underexpressed in hybrid grass plants, in nontransgenic plants, in transgenic plants, transgenic tissue, transgenic leaves, transgenic seeds, transgenic host cells. In some embodiments, Fm genes and polypeptides are transiently expressed in hybrid grass plants, in nontransgenic plants, in transgenic plants, transgenic tissue, transgenic leaves, transgenic seeds, transgenic host cells.

The present invention is not limited to any particular mechanism of action of genes for providing drought tolerance. Indeed, an understanding of the mechanism of action is not needed to practice the present invention. The descriptions provided herein, are provided merely to describe pathways involved in regulating environmental stress, with an emphasis on controlling drought tolerance, Fm gene expression, protein production or controlling Fm protein activity. In some embodiments, the present invention provides methods for identifying genes involved in providing or controlling Fm gene activity, and of Fm mutants and related Fm genes discovered through use of these methods. Further, using the sequences and methods of the present invention, additional genes, nucleic acid sequences, and amino acid sequences related to regulating drought tolerance are identified and contemplated for use in the methods of the present inventions. This description also provides methods of identifying and characterizing and using Fm genes and their encoded proteins. In addition, the description provides specific, but not limiting, illustrative examples of embodiments of the present invention.

In some embodiments, methods of the invention can be performed with respect to identifying a functional pathway involving any of the Fm stress-regulated genes, such as a sequence set forth in any one of SEQ ID NOs: 1-39 (FIG. 7), 93-216 (FIG. 9) and 307-320 (Table 1), and/or polypeptides as encoded by a polypeptide comprising a sequence set forth in any one of SEQ ID NOs:40-92 (FIG. 8), including for example, functions such as a stress-regulated transcription factor, metabolism, energy, biogenesis of cellular component, subcellular localization, transport, transcription, signal transduction, interaction with the cellular environment, protein synthesis, protein with binding function, defense, development, cell fate, cell cycle and DNA processing, protein fate, and cell type differentiation, see, for example, Tables 2-6. In some embodiments, the nucleic acid sequences are at least 50%, 60%, 70%, 80%, 90%, 95%, 98%, or 99% identical to the aforementioned sequences. Functions are defined by The Gene Ontology project (GO) at the public website world wide web.geneontology.org/index.shtml. Pathways in which the disclosed stress-regulated genes and/or polypeptides are involved are contemplated to be identified herein, for example, a nucleotide with a homolog, such as *Arabidopsis thaliana* gi|25090853| identified as a homolog of Fm sequence SSBII-D09, involved in electron transport, and Fm sequences SSBI-B09 identified a *Hordeum vulgare* homolog gi|28866019|, farnesylated protein 3 involved in metal ion transport, by searching UniProt (Universal Protein Resource at world wide web.pir.uniprot.org/) and the EBI (European Molecular Biology Laboratory) Gene Ontology website (e.g. QuickGO at the UniProt site) at European Bioinformatics Institute (2006) or the Munich Information Center for Protein Sequences (MIPS) *Arabidopsis thaliana* database (MATDB at hypertext transfer protocol site: mips.gsf.de/projects/plants).

In some embodiments, the present invention provides methods of modulating the activity of a biological pathway, such as a pathway identified herein, in a plant cell, wherein the pathway involves a stress-regulated Fm gene and/or Fm polypeptide. As used herein, reference to a pathway that "involves" a stress-regulated polypeptide means that the polypeptide is required for normal function of the pathway. For example, plant stress-regulated Fm polypeptides as disclosed herein include those acting as transcription factors or as protein binding elements or affecting drought induced and/or mediated stress responses, which are well known to be involved in metabolic pathways. As such, a method of the invention provides a means to modulate a biological pathway involving plant stress-regulated Fm polypeptides, for example, by altering the expression of the Fm polypeptides in response to a stress condition or in response to changes in soil moisture content or irrigation water. Thus, a method of the invention can be performed, for example, by introgressing an Fm polynucleotide portion of a plant stress-regulated Fm gene into the plant cell, therein modulating the activity of the biological pathway.

In some embodiments, the present invention also provides methods of identifying a polynucleotide that modulates a stress response in a plant cell. Such methods are contemplated to be performed, for example, by contacting an array of probes representative of a plant cell genome, such as an Fm genechip array, and nucleic acid molecules expressed in plant cell exposed to a particular stress; such as drought stress, detecting a nucleic acid molecule that is expressed at a level different from a level of expression in the absence of the stress; introducing the nucleic acid molecule that is expressed differently into a plant cell; and detecting a modulated response of the plant cell containing introgressed nucleic acid molecule to a stress, therein identifying a polynucleotide that modulates a stress response in a plant cell. The contacting is under conditions that allow for selective hybridization of a nucleic acid molecule with probe having sufficient complementarity, for example, under stringent hybridization conditions.

In some embodiments, the present invention also provides methods of using a polynucleotide portion of a plant stress-regulated gene, such as an Fm polynucleotide, to confer a selective advantage on a plant cell. In some embodiments, such methods are performed by introducing a plant stress-regulated regulatory element into a plant cell, for example, a regulatory element for a gene sequence described herein, wherein, upon exposure of the plant cell to a stress condition to which the regulatory element is responsive, a nucleotide sequence operatively linked to the regulatory element is expressed, such as an up-regulated Fm nucleotide as described herein. In another embodiment, the stress-regulated element is operably linked to a reporter molecule, such as luciferase, therein identifying a drought stress regulatory element. The operatively linked nucleotide sequence can be, for example, a transcription factor for an Fm gene described herein, the expression of which induces the further expression of polynucleotides involved in a stress response, therein enhancing the response of a plant to the stress condition for resisting drought. In another embodiment, a coding sequence of a plant stress-regulated Fm gene as disclosed herein is introgressed into the cell, therein providing the plant with a selective advantage in response to a stress condition. In still another embodiment, the method results in the knock-out of a plant stress-regulated gene, such as a down-regulated Fm nucleotide, as disclosed herein, in a first population of plants, therein providing a selective advantage to a stress condition in the knock-out population of plants.

In some embodiments, the present invention provides methods of identifying an agent, such as a nucleic acid or polypeptide, that modulates the activity of a stress-regulated regulatory element of a gene. In some embodiments, methods are provided for identifying an agent that alters the activity of a response to an abiotic stress, such as drought stress, such that a composition comprising an agent to be tested is contacted with a responsive regulatory element, preferably an element associated with regulating, e.g., a nucleic acid sequence comprising any one of a sequence as set forth in SEQ ID NOs:1-39 and 93-216, and determining the effect of the agent on the ability of the regulatory sequence to regulate Fm or Lp gene transcription. In some embodiments, the nucleic acid sequences are at least 50%, 60%, 70%, 80%, 90%, 95%, 98%, or 99% identical to the aforementioned sequences. In further embodiments, the regulatory elements are associated with particular stresses or combination of stresses such as drought stress and heat stress. In one embodiment, the regulatory element can be operatively linked to a heterologous polynucleotide encoding a reporter molecule, and an agent that modulates the activity of the stress-regulated regulatory element can be identified by detecting a change in expression of the reporter molecule due to contacting the regulatory element with the agent. Such a method can be performed in vitro in a plant cell-free system, or in a plant cell in culture or in a plant in situ. In another embodiment, the agent is contacted with a transgenic plant containing an introgressed plant stress-regulated regulatory element, and an agent that modulates the activity of the regulatory element is identified by detecting a phenotypic change in the transgenic plant. The methods of the invention can be performed in the presence or absence of the stress condition to which the particularly regulatory element is responsive, in particular to drought stress.

In some embodiments, the present invention provides nucleotide probes useful for detecting an abiotic stress in a plant, such as a drought stress response in plants, the probes comprising a nucleotide sequence of at least 15, 25, 50 or 100 nucleotides that hybridizes under stringent, preferably highly stringent, conditions to a sequence comprising a sequence set forth in any one of SEQ ID NOs:1-39 and 93-216. In some embodiments, the nucleic acid sequences are at least 50%, 60%, 70%, 80%, 90%, 95%, 98%, or 99% identical to the aforementioned sequences. Also provided are nucleotide probes comprising at least 15, 25, 50 or 100 nucleotides in length that hybridize under stringent, preferably highly stringent conditions, to at least one gene associated with a particular stress, for example drought stress a sequence comprising a sequence set forth in any one of SEQ ID NOs:1-39 and 93-216.

I. *Festuca mairei* (Fm) Plant Genes and Polypeptides:

The present invention provides plant Fm genes and proteins including their homologues, orthologs, paralogs, variants and mutants, all of which are identified in relation to Fm and/or Fm genes and proteins of the present inventions. In some embodiments, an isolated nucleic acid sequence comprising a sequence set forth in any one of SEQ ID NOs:1-39 and 93-216 is provided. In some embodiments, the nucleic acid sequences are at least 50%, 60%, 70%, 80%, 90%, 95%, 98%, or 99% identical to the aforementioned sequences. Some embodiments of the present inventions provide polynucleotide sequences that comprise at least one sequence set forth in any one of SEQ ID NOs:1-39 and 93-216. In some embodiments, a sequence encoding a Fm polypeptide comprises a sequence set forth in any one of SEQ ID NOs:40-91.

Some embodiments of the present invention provide polynucleotide sequences that do not encode polypeptides. In some embodiments, the Fm polynucleotide encodes a polypeptide that shows 0 homology or results equivalent to "No significant similarity" to known plant polypeptides in publicly accessible sequence databanks using methods comprising publicly available search engines, such as BLASTX at a NCBI website (world wide web.ncbi.nlm.nih.gov/BLAST/Blast.cgi). Other embodiments of the present invention provide polynucleotide sequences encoding polypeptides comprising a sequence set forth in any one of SEQ ID NOs:40-92. In yet further embodiments, the present invention provides Fm polypeptide homologues; see, for nonlimiting examples, Tables 3-6. In other embodiments, the Fm polynucleotide encodes a polypeptide at least, 3.00E-33, 2.00E-44, 3.00E-51, 1.00E-108 (or more) identical to any of exemplary polypeptides encoded by nucleotide sequences comprising SEQ ID NOs: 93-216, such as a polypeptide obtained by a BLASTX search. These sequences include nucleotide sequences comprising Fm DNA sequences, with or without genomic sequences.

II. Additional Genes and Polypeptides Associated with Onset and Adaptation to Drought Tolerance:

The methods of the present invention are not limited to the use of germplasm from Festuca plants. Indeed, the germplasm of a variety of plants are contemplated for use in methods for altering drought tolerance of any plant, including but not limited to eukaryotes, such as Plantae and Protista, monocotyledon and dicotyledon plants, and in particular, Commelinidae plants, such as *Festuca* spp.; xeromorphic plants of Restionaceae; and the like. In further embodiments, germplasm comprising homologes of Fm nucleic acid sequences are provided. Such germplasm includes but is not limited to *Lolium perenne; Lolium rigidum* (annual ryegrass; Wimmera ryegrass); *Poa pratensis* (Kentucky Bluegrass); *Oryza sativa* (rice); *Triticum aestivum* (wheat); *Avena sativa* (oats); *Spinacia oleracea* (spinach); *Apium graveolens* (celery); and *Flaveria trinervia* (clustered yellowtops); *Brassica* sp. (e.g., *Arabidopsis thaliana, B. napus, B. oleracea*, etc.), *Zea mays* (corn), *Hordeum vulgare* (barley), *Mesembryanthemum crystallinum* (common iceplant); *Gossypium barbadense* (cotton); *Chlamydomonas reinhardtii* (green alga) and the like.

Thus, the present invention provides nucleic acid sequences comprising additional plant genes and polypeptides for use in compositions and methods for altering drought tolerance in plants, for example, GenBank Accessions *Zea mays*' AY588275 and gi|465606602|, plant sequences as described in Tables 2-6, and the like). Some embodiments of the present invention provide additional polynucleotide sequences that are homologous to at least one of exemplary Fm SEQ ID NOs:1-39 and 93-216, such as *Zea mays*' gi|46560602. As such, in some embodiments, the nucleic acid sequences are at least 50%, 60%, 70%, 80%, 90%, 95%, 98%, or 99% identical to the aforementioned sequences. In some embodiments, the additional Fm polynucleotides provide sequences that are at least, 3.00E-33, 2.00E-44, 3.00E-51, 1.00E-108 (or more) identical to any of exemplary polypeptides encoded by nucleotide sequences comprising SEQ ID NOs: 93-216. In some embodiments, the Fm polynucleotides are at least, 3.00E-33, 2.00E-44, 3.00E-51, 1.00E-108 (or more) identical to any of exemplary polypeptides encoded by nucleotide sequences comprising SEQ ID NOs: 1-39. Other embodiments of the present invention provide homologes of polynucleotide sequences encoding polypeptides that are homologous to at least one of exemplary polypeptide comprising a sequence set forth in any one of SEQ ID NOs:40-91.

A polynucleotide sequence of a stress-regulated gene as disclosed herein is contemplated to be particularly useful for performing the methods of the invention on a variety of plants, including but not limited to plants described herein.

III. Alleles of Fm Genes:

In some embodiments of the present invention, alleles of Fm gene sequences comprising a sequence set forth in any one of SEQ ID NOs: 1-39 and 93-216 are provided. In some embodiments, the alleles are at least 50%, 60%, 70%, 80%, 90%, 95%, 98%, or 99% identical to the aforementioned sequences. Any given gene may have none, one or many allelic forms. Common mutational changes that give rise to alleles are generally ascribed to deletions, additions, or insertions, or substitutions of nucleic acids. Each of these types of changes may occur alone, or in combination with the others, and at the rate of one or more times in a given sequence. Mutational changes in alleles also include rearrangements, insertions, deletions, additions, or substitutions in upstream regulatory regions.

In some embodiments, alleles result from a mutation, (i.e., a change in the nucleic acid sequence) and generally produce altered mRNAs or polypeptides whose structure or function may or may not be altered. In preferred embodiments, the invention provides alleles resulting from a mutation for producing altered mRNAs or polypeptides whose structure or function increase tolerance to abiotic stress, such as drought stress.

In some embodiments of the present invention, the polynucleotide sequence encoding a Fm nucleotide sequence is extended utilizing the nucleotide sequences (e.g., SEQ ED NOs:1-39 and 93-216 in various methods known in the art to extend sequences, such as to obtain coding and noncoding gene sequences, such as to detect upstream and/or downstream sequences such as promoters and regulatory elements. For example, it is contemplated that for some Fm, or related Fm sequences, the sequences upstream and/or downstream are identified using RACE or Fm genomic information. For other Fm sequences for which a similar sequence is identified and a database is available, the sequences upstream or downstream of the identified Fm genes can be identified. For other Fm genes for which a public genomic database is not available, or not complete, it is contemplated that polymerase chain reaction (PCR) finds use in the present invention, such as Rapid Amplification of cDNA Ends (RACE) assays and assays described below.

In another embodiment, inverse PCR is used to amplify or extend sequences using divergent primers based on a known region (see, e.g., Triglia et al. (1988) Nucleic Acids Res., 16:8186; herein incorporated by reference). In yet another embodiment of the present invention, capture PCR (see, for e.g., Lagerstrom et al. PCR Methods Applic., 1:111-19 (1991); herein incorporated by reference) is used. In still other embodiments, walking PCR is utilized. Walking PCR is a method for targeted gene walking that permits retrieval of unknown sequence (see, for e.g., Parker et al. Nucleic Acids Res., 19:3055-60 (1991); herein incorporated by reference). The PROMOTERFINDER kit (Clontech) uses PCR, nested primers and special libraries to "walk in" genomic DNA. This process avoids the need to screen libraries and is useful in finding intron/exon junctions. In yet other embodiments of the present invention, add TAIL PCR is used as a preferred method for obtaining flanking genomic regions, including regulatory regions (see, for e.g., Liu and Whittier, (1995) Genomics, 25(3):674-81; Liu et al. (1995) Plant J., (3):457-63; all of which are herein incorporated by reference). Preferred libraries for screening for full-length cDNAs include libraries that have been size-selected to include larger cDNAs. Also, random primed libraries are preferred, in that they contain more sequences that contain the 5' and upstream gene regions. A randomly primed library may be particularly useful in cases where an oligo d(T) library does not yield full-length cDNA. Genomic Libraries are useful for obtaining introns and extending 5' sequence.

IV. Variant Fm Genes and Polypeptides:

In some embodiments, the present invention provides isolated variants of the disclosed nucleic acid sequences encoding Fm genes and the polypeptides encoded therein; these variants include mutants, fragments, fusion proteins, homologes, and functional equivalents of genes and gene protein products.

Thus, nucleotide sequences of the present invention are contemplated for engineering in order to introduce or alter a Fm coding sequence for a variety of reasons, including but not limited to initiating the production of abiotic stress tolerance, such as drought stress; augmenting or increasing stress tolerance, such as drought stress, alterations that modify the cloning, processing and/or expression of the gene product (such alterations include inserting new restriction sites and changing codon preference), as well as varying the protein function activity (such changes include but are not limited to differing binding kinetics to nucleic acid and/or protein or protein complexes or nucleic acid/protein complexes, differing binding inhibitor affinities or effectiveness, differing reaction kinetics, varying subcellular localization, and varying protein processing and/or stability).

A. Homologues: In some embodiments, the present invention provides isolated variants of the disclosed nucleic acid sequence encoding Fm nucleotides, or related plant genes, and the polypeptides encoded therein; these variants include mutants, fragments, fusion proteins or functional equivalents genes and protein products.

Some homologues or variants of encoded Fm products are contemplated to have an intracellular half-life dramatically different than the corresponding wild-type protein. For example, the altered protein is rendered either more stable or less stable to proteolytic degradation or other cellular process that result in destruction of, or otherwise inactivate the encoded Fm product. Such homologues, and the genes that encode them, can be utilized to alter the activity of the encoded Fm and/or Fm products by modulating the half-life of the protein. For instance, a short half-life can give rise to more transient biological effect, such as to mimic the up then down regulated or transiently regulated nucleotides, or to turn on genes for upregulation or turn off genes for down regulation. Other homologues have characteristics that are either similar to wild type Fm, or which differ in one or more respects from wild-type Fm.

In some embodiments of the present invention, the amino acid sequences for a population of Fm nucleic acid product homologues are aligned, preferably to promote the highest homology possible. Such a population of variants can include, for example, Fm gene homologues from one or more species, such as rice, oats, maize, barley, cotton, or Fm gene homologues from the same species, such as *Festuca*, but which differ due to mutation. Amino acids that appear at each position of the aligned sequences are selected to create a degenerate set of combinatorial sequences.

In a preferred embodiment of the present invention, the combinatorial Fm gene library is produced by way of a degenerate library of genes encoding a library of polypeptides that each include at least a portion of candidate encoded Fm-protein sequences. For example, a mixture of synthetic oligonucleotides is enzymatically ligated into gene sequences such that the degenerate set of candidate Fm sequences are expressible as individual polypeptides, or alternatively, as a set of larger fusion proteins (e.g., for phage display) containing the set of Fm sequences therein.

There are many ways by which the library of potential Fm homologues can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential Fm sequences. The synthesis of degenerate oligonucleotides is well known in the art (see, e.g., Narang, (1983) Tetrahedron Lett. 39(1):3-22; Itakura et al. Recombinant DNA, in Walton (ed.), Proceedings of the 3rd Cleveland Symposium on Macromolecules, Elsevier, Amsterdam, pp 273-289 (1981); Itakura et al. (1984) Annu. Rev. Biochem. 53:323; Itakura et al. (1977) Science 198:1056; Ike et al. (1983) Nucl. Acid Res., 11:477; all of which are herein incorporated by reference in their entirety. Such techniques have been employed in the directed evolution of other proteins (See e.g., Scott et al (1990) Science, 249:386-390; Roberts et al. (1992) Proc. Natl. Acad. Sci. USA, 89:2429-2433; Devlin et al (1990) Science, 249:404-406; Cwirla et al (1990) Proc. Natl. Acad. Sci. USA, 87:6378-6382; in addition to U.S. Pat. Nos. 5,223,409, 5,198,346, and 5,096,815; all of which are herein incorporated by reference in their entirety).

Functional homologues can be screened for by expressing the homologues in an appropriate vector (described in more detail below) in a plant cell and analyzing the level of drought tolerance of a plant derived from the cell.

B. Mutants: In some embodiments, the present invention provides nucleic acid sequences encoding mutant forms of Fm proteins, (i.e., mutants), and the polypeptides encoded therein. In some embodiments of the present invention, mutations in up-regulated nucleic acid sequences of Fm genes are provided, (see, Table 4). In some contemplated embodiments, mutations in upregulated genes result in altered abiotic stress tolerance, such as increased drought stress tolerance, and drought stress phenotypes, such as maintaining leaf color and less firing compared to control plants. In some embodiments of the present invention, isolated nucleic acid sequences comprising downregulated genes are provided, (see, Table 5). In some embodiments, mutations in downregulated genes result in altered abiotic stress tolerance, such as drought stress tolerance, and drought stress phenotypes, such as maintaining leaf color and less firing compared to control plants. In some embodiments, mutations in nucleic acid sequences comprising upregulated-then-downregulated genes are provided, (see, Table 6). In some contemplated embodiments, mutations in upregulated-then-downregulated genes result in altered abiotic stress tolerance, such as drought stress, and abiotic stress tolerance, such as drought stress, phenotypes, such as maintaining leaf color and less firing compared to control plants. In some contemplated embodiments, mutations in isolated nucleic acid sequences comprising transiently regulated genes are provided, (see, Table 6). In some contemplated embodiments, mutations in transiently regulated genes result in altered abiotic stress tolerance, such as drought stress, and abiotic stress tolerance, such as drought stress, phenotypes, such as maintaining leaf color and less firing compared to control plants.

In preferred embodiments, mutants result from mutation of the coding sequence, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

Mutants of Fm genes can be generated by any suitable method well known in the art, including but not limited to EMS (ethyl methanesulfonate) induced mutagenesis, site-directed mutagenesis, randomized "point" mutagenesis, and domain-swap mutagenesis or fusion proteins in which portions of Fm cDNA are "swapped" with the analogous portion of Fm encoding cDNAs (Back and Chappell, (1996) PNAS 93: 6841-6845; herein incorporated by reference).

It is contemplated that is possible to modify the structure of a peptide having an activity (e.g., such as a drought resistance activity, such as activity for leaf elongation), for such purposes as increasing synthetic activity or altering the affinity of the Fm protein for a binding partner or a kinetic activity. Such modified peptides are considered functional equivalents of peptides having an activity of an Fm function as defined herein. A modified peptide can be produced in which the nucleotide sequence encoding the polypeptide has been altered, such as by substitution, deletion, or addition. In some preferred embodiments of the present invention, the alteration increases or decreases the effectiveness of the Fm gene product to exhibit a phenotype caused by altered abiotic stress tolerance production, such as drought stress. In other words, construct "X" can be evaluated in order to determine whether it is a member of the genus of modified or variant Fm genes of the present invention as defined functionally, rather than structurally. Accordingly, in some embodiments the present invention provides nucleic acids comprising an Fm sequence that complements the coding regions of any of SEQ ID NOs: 1-39 and 93-216, as well as the polypeptides encoded by such nucleic acids. In some embodiments, the nucleic acid sequences are at least 50%, 60%, 70%, 80%, 90%, 95%, 98%, or 99% identical to the aforementioned sequences.

Moreover, as described above, mutant forms of Fm proteins are also contemplated as being equivalent to those peptides that are modified as set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule.

Accordingly, some embodiments of the present invention provide nucleic acids comprising sequences encoding variants of Fm gene products disclosed herein containing conservative replacements, as well as the proteins encoded by such nucleic acids. Conservative replacements are those that take place within a family of amino acids that are related in their side chains. Genetically encoded amino acids can be divided into four families: (1) acidic (aspartate, glutamate); (2) basic (lysine, arginine, histidine); (3) nonpolar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., Biochemistry, pg. 17-21, 2nd Ed, WH Freeman and Co., 1981; herein incorporated by reference). Whether a change in the amino acid sequence of a peptide results in a functional homologue can be readily determined by assessing the ability of the variant peptide to function in a fashion similar to the wild-type protein. Peptides having more than one replacement can readily be tested in the same manner.

More rarely, a mutant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.; herein incorporated by reference in its entirety). Accordingly, other embodiments of the present invention provide nucleic acids comprising sequences encoding variants of Fm gene products disclosed herein containing non-conservative replacements where the biological activity of the encoded protein is retained, as well as the proteins encoded by such nucleic acids.

V. Plant Breeding Methods:

The present invention also relates to the field of plant breeding, specifically to methods of grass plant breeding and the resulting grass plant s and grass plant lines for commercial distribution. The grass plant breeding methods include but are not limited to natural breeding, artificial breeding, molecular marker selection, commercial breeding, and transgenics. More particularly, the invention relates to producing drought resistant grass plants, populations, cultivars, varieties, lines and methods of breeding the same, the methods further comprising DNA molecular marker analysis.

Plants are crossed by either natural or artificial techniques for introgressing germplasm from one plant into another plant. Plants, in particular grass plants, are reproduced sexually by seed (sexual reproduction) or via vegetative propagation (asexually), for example, by cultivation of tillers which arise from buds on culm nodes, rhizomes, and stolons. Natural pollination occurs in fields through transfer of pollen to stamens by wind (grasses) or insects (plants in general). Artificially directed pollination can be effected either by controlling the types of pollen that can blow onto the flowers (ovaries) or by pollinating by hand. Grass plants are crossed mechanically using artificial pollination techniques, for example, by collection of pollen in pollination bags that are then tied over the flowers of the receiving plants.

Backcross breeding was used to transfer germplasm by introgressing a heritable trait into a desirable homozygous cultivar or inbred line, called the recurrent parent. The source of the trait to be transferred is called the donor parent (e.g., Fm plants). The resulting plant, progeny plant, is expected to have the attributes of the recurrent parent (e.g., cultivar) and the desirable trait transferred from the donor parent. After the initial cross, individuals possessing the phenotype of the donor parent are selected and repeatedly crossed (backcrossed) to the recurrent parent. The resulting progeny are expected to have the attributes of the original recurrent parent (e.g., cultivar) and the desirable trait transferred from the donor parent.

Near-isogenic lines (NIL) are created by numerous backcrosses to produce an array of individuals that are nearly identical in genetic composition except for the trait or genomic region under interrogation that can be used in a mapping population for identifying the genetics of a desirable trait.

The methods of the present invention are not limited to altering drought tolerance in any particular plant. Indeed, a variety of plant classifications, plants, and types of plant are contemplated for use including but not limited to monocotyledon and dicotyledon plants, Classes Liliopsida and Magnoliopsida of flowering plants, and plants such as grasses, grains, vegetables, flowers, herbs, ornamentals, plants for use as ground covers, plants for use as water covers, plants for use in erosion control, plants for use in slope stabilization, plants for use in shore stabilization, bushes, and trees. For example, plant Liliopsida plants include but are not limited to Commelinidae, further including, for example, the grass family Poaceae (also known Gramineae), the sedges Cyperaceae (such as papyrus), the bur-reeds (Sparganiaceae); pipeworts (Eriocaulaceae), the Cattail Family or perennial marsh plants (Typhaceae), the rushes (Juncaceae), the yellow-eyed grass family (Xyridaceae; such as American marsh plants), succulent herb family (Commelinaceae), Amaranthaceae, Asteraceae, and the ginger family (Zingiberaceae or Zingiberidae), such as *Costus speciosus* or 'crepe' ginger. For another example, Magnoliopsida plants include but are not limited to *Gossypium barbadense* (cotton). Preferred forage and turf grass for use in the methods of the invention include perennial ryegrass, intermediate ryegrass, annual ryegrass, and tall fescue. In particular, the following plants are contemplated for use in the present inventions: wheat (*Triticum*), rice (*Oryza* spp.), corn (*Zea Mays*), oats (*Avena* spp.), alfalfa (e.g., *Medicago sativa, Medicago* spp., etc.), rye (e.g., *Secale cereale*, spp., etc.), sorghum (e.g., *Sorghum bicolor, Sorghum vulgare*, etc.), millet (e.g., pearl millet (*Pennisetum glaucum*), proso millet (*Panicum miliaceum*), foxtail millet (*Setaria italica*), finger millet (*Eleusine coracana*), etc.), Melilotus, e.g., clover, *Lotus*, trefoil, lentil, hemp, buckwheat, cotton (e.g., *Gossypium barbadense, Gossypium hirsutum*, etc.), sugarcane (e.g., *Saccharum* spp., etc.), oats (e.g., *Aveneae* spp., such as *Avena sativa*), barley (*Hordeum* spp.), sugar cane (*Saccharum* spp.); bead grass (*Paspalum* spp.), bluegrass (*Poa* spp.), bluestem (*Andropogon, Dichanthium* spp.), fescue (*Festuca* spp.), gramma grass (*Bouteloua* spp.), timothy (*Phleum* spp.), wheatgrass (*Agropyron, Elytrigia, Elymus* spp.), and zoysia (*Zoysia* spp.); little bluestem (*Schizachyrium* spp.), Indian grass (*Sorghastrum* spp.), fountain grass (*Pennisetum* spp.), hair grass (*Deschampsia* spp.), *Miscanthus* spp., *Andropogon* spp., and *Panicum virgatum*.

A. Selection of Parents to Produce Superior Transgressive Segregants:

The goal of plant breeding in general is to produce progeny that exceed their parents in performance for one or more traits. The inventor discovered grass lines, G15 and G30a that demonstrated superior drought resistance when compared to groups of plants segregating for drought resistant levels comprising the parental plants. Thus the inventor contemplates the use of such superior plants for identifying the DNA markers for germplasm that provides drought resistance and use these superior plants as a basis for selection of parents and progeny that comprise a similar complement of desired Fm genes. For example, when examining the marker genotypes of G15 and G30a (Table 8), it is apparent that these two lines differ in genotype at least 7 out of 13 SSR loci tested (Table 8). Therefore, in one embodiment, the inventor contemplates crossing G15 and G30a and select inbred progeny plants that contain the desired alleles within the 7 loci. The desired alleles will contribute to drought tolerance performance in some additive and/or epistatic fashion, and it will be likely that such progeny will be agronomically superior to either parent.

1. Selection of Superior Lines from Segregating Populations:

DNA markers used to select breeding parents that will be used in crosses are contemplated for use in screening progeny from such crosses. For example, in a G15 and G30a cross, progeny plant lines at various stages of inbreeding will be screened for the favorable allele at least 7 loci that are segregating. The breeder will select progeny that contain as many of the favorable alleles as possible. The best possible transgressive segregant or "ideal segregant" will be the one that contains the favorable alleles at segregating loci (for example, Table 8).

2. Selection of Superior Hybrids:

In addition to selection of parents that will produce superior drought resistant recombinant inbred plants, complementation at QTL's affecting desirable agronomic traits are contemplated for use in predicting and providing superior hybrid agronomic performance. The inventors' methods will be used to identify selected agronomic traits in drought resistant plants, in particular ryegrass plants (see, for example, Yamada et al., (2004) Crop Sci. 44:925-935; Bert et al., (1999) Theor. Appl. Genet. 99:445-452; all of which are herein incorporated by reference).

3. Selection for and Maintenance of Fm Germplasm:

In some embodiments, the inventor contemplates plants comprising meoitically stable Fm germplasm. In some embodiments, meotically stable germplasm remains stable during under green house growing conditions. In some embodiments, meotically stable germplasm remains stable during environment interactions under field growing conditions. For example, in the case of a locus "A" where allele "A1" is necessary for maximum drought resistance in one type of environment and allele "A2" is necessary for maximum drought resistance in another type of environment, for example, a field of ryegrass grown in a greenhouse or a field of ryegrass located in the United States Midwest or a field of ryegrass located in the southern region of the United States. In such cases, a population that is heterogeneous for these alleles also retains and shows drought resistance trait stability over both types of environments. The inventors' methods will allow the breeder to select for and maintain such heterogeneity.

A method of confirming whether intra-line heterogeneity at a specific locus will be beneficial for agronomic performance, comprises: 1) identify lines that are heterogeneous for the locus in question; 2) develop sub-populations of the line that are homogeneous for one or the other allele based on selection with DNA markers; 3) field test the original heterogeneous line along with each of derived homogeneous lines over a number of defined environments; and 4) determine whether the heterogeneous line will perform, (such as provide an economical yield) greater than either homogeneous line when averaged over test environments.

4. Use of Genetic Markers for Linkage Groups and Quantitative Trait Loci (QTLs) to Select Superior Plants:

The inventor contemplates using linkage groups and/or QTL's affecting agronomic performance for selecting superior breeding plants. For example, a plant breeder would use a method to for selecting a parental plant comprising: 1) identify parents that will produce superior transgressive segregants; 2) identify superior lines from crosses that are segregating at a DNA marker or loci; 3) identify parents that will produce superior hybrid progeny; 4) identify heterogeneous lines to fix favorable alleles; and 5) identify plants maintaining desirable heterogeneity.

Genetic linkage of marker molecules can be established by a gene mapping model such as, without limitation, the flanking marker model reported by Lander and Botstein, Genetics, 121:185-199 (1989), and the interval mapping, based on maximum likelihood methods described by Lander and Botstein, Genetics, 121:185-199 (1989), and implemented in the software package MAPMAKER/QTL (Lincoln and Lander, Mapping Genes Controlling Quantitative Traits Using MAPMAKER/QTL, Whitehead Institute for Biomedical Research, Massachusetts, (1990); herein incorporated by reference. Additional software includes Qgene, Version 2.23 (1996), Department of Plant Breeding and Biometry, 266 Emerson Hall, Cornell University, Ithaca, N.Y.); herein incorporated by reference.

A maximum likelihood estimate (MLE) for the presence of a marker is calculated, together with an MLE assuming no QTL effect, to avoid false positives. A $\log_{10}$ of an odds ratio (LOD) is then calculated as: LOD=$\log_{10}$ (MLE for the presence of a QTL (MLE given no linked QTL).

The LOD score essentially indicates how much more likely the data are to have arisen assuming the presence of a QTL than in its absence. The LOD threshold value for avoiding a false positive with a given confidence, say 95%, depends on the number of markers and the length of the genome. Graphs indicating LOD thresholds are set forth in Lander and Botstein, Genetics, 121:185-199 (1989); herein incorporated by reference, and further described by Ars and Moreno-Gonzlez, Plant Breeding, Hayward, Bosemark, Romagosa (eds.) Chapman & Hall, London, pp. 314-331 (1993); herein incorporated by reference.

Additional models can be used. Many modifications and alternative approaches to interval mapping have been reported, including the use of non-parametric methods (Kruglyak and Lander, Genetics, 139:1421-1428 (1995); herein incorporated by reference). Multiple regression methods or models can be also be used, in which the trait is regressed on a large number of markers (Jansen, Biometrics in Plant Breed, van Oijen, Jansen (eds.) Proceedings of the Ninth Meeting of the Eucarpia Section Biometrics in Plant Breeding, The Netherlands, pp. 116-124 (1994); Weber and Wricke, Advances in Plant Breeding, Blackwell, Berlin, 16 (1994); all of which are herein incorporated by reference). Procedures combining interval mapping with regression analysis, whereby the phenotype is regressed onto a single putative QTL at a given marker interval, and at the same time onto a number of markers that serve as 'cofactors,' have been reported by Jansen and Stam, Genetics, 136:1447-1455 (1994); Zeng, Genetics, 136:1457-1468 (1994); all of which are herein incorporated by reference. Generally, the use of cofactors reduces the bias and sampling error of the estimated QTL positions (Utz and Melchinger, Biometrics in Plant Breeding, van Oijen, Jansen (eds.) Proceedings of the Ninth Meeting of the Eucarpia Section Biometrics in Plant Breeding, The Netherlands, pp. 195-204 (1994); herein incorporated by reference, thereby improving the precision and efficiency of QTL mapping (Zeng, Genetics, 136:1457-1468 (1994); herein incorporated by reference). These models can be extended to multi-environment experiments to analyze genotype-environment interactions (Jansen et al., (1995) Theo. Appl. Genet. 91:33-37; herein incorporated by reference).

Backcross populations (e.g., generated from a cross between a successful variety (recurrent parent) and another variety (donor parent) carrying a trait not present in the former) can be utilized as a mapping population. A series of backcrosses to the recurrent parent can be made to recover most of its desirable traits. Thus a population is created consisting of individuals nearly like the recurrent parent but each individual carries varying amounts or mosaic of genomic regions from the donor parent. Backcross populations can be useful for mapping dominant markers if all loci in the recurrent parent are homozygous and the donor and recurrent parent have contrasting polymorphic marker alleles (Reiter et al., Proc. Natl. Acad. Sci. (U.S.A.) 89:1477-1481 (1992); herein incorporated by reference). Backcross populations, however, are more informative (at low marker saturation) when compared to RELs as the distance between linked loci increases in RIL populations (i.e., about 0.15% recombination). Increased recombination can be beneficial for resolution of tight linkages.

B. Marker-Assisted Trait Selection and Plant Breeding

In one embodiment, the present invention provides a method for marker-assisted selection. Marker-assisted selection involves the selection of plants having desirable phenotypes based on the presence of particular nucleotide sequences "markers," such as SSR, RAPD, cDNA AFLP and the like, or for transformed plants, an expressed product is a marker, such as GUS or GFP. The use of markers allows plants to be selected by genotype for breeding superior grass lines. The use of markers also allows plants to be selected early in development, often before a desired phenotype would normally be manifest. Because it allows for early selection, marker-assisted selection decreases the amount of time need for selection and thus allows more rapid genetic progress. Briefly, marker-assisted selection involves obtaining nucleic acid from a plant to be selected. The nucleic acid obtained is then identified, or not, with probes that selectively hybridize under stringent, preferably highly stringent, conditions to a nucleotide sequence or sequences associated with the desired phenotype. In one embodiment, the probes hybridize to any of the stress-responsive genes or regulatory regions disclosed herein, for example, any one SEQ ID NOs:1-39 and 93-216 or homologs thereof as described above. The presence of any hybridization products formed is detected, or not, and plants are then selected on the presence or absence of the desired hybridization products.

An additional aspect provides a method for marker-assisted breeding to select plants having an altered resistance to abiotic stress tolerance, such as drought stress tolerance, comprising obtaining nucleic acid molecules from the plants to be selected; contacting the nucleic acid molecules with one or more markers or probes that selectively hybridize under stringent, preferably highly stringent, conditions to a nucleic acid sequence selected from any of sequences set forth in SEQ ID NOs:217-246 and 247-265. Such that the detecting the hybridization of the one or more probes to the nucleic acid sequences, for example using PCR amplification of hybridized probes or Southern or Northern gels or micro/macroarrays, wherein the presence of the hybridization indicates the presence of a gene associated with altered resistance to abiotic stress tolerance, such as drought tolerance; and selecting plants on the basis of the presence or absence of such hybridization. Marker-assisted selection can also be accomplished using one or more probes which selectively hybridize under stringent, preferably highly stringent conditions, to a nucleotide sequence comprising a polynucleotide expressed in response associated with a particular stress, for example, a nucleotide sequence comprising any of sequences set forth in SEQ ID NOs:217-246 and 247-265. In each case marker-assisted selection can be accomplished using a probe or probes to a single sequence or multiple sequences or as fusion sequences. In one embodiment, marker assisted selection is by using a PCR primer or linker for amplifying a marker or as a marker. If multiple sequences, such as PCR primers, are used they can be used simultaneously or sequentially. Non-limiting examples of such primers are any of RAPD markers as set forth in SEQ ID NOs:266-306, any of AFLP markers, such as primers or linkers as set forth in SEQ ID NOs:217-265, or an Lp SSR primer, or a *Festuca* EST-SSR primer, and the like. The use of such markers, primers, and linkers is provided in the Examples.

C. Generation of Drought Tolerant Grass Plant Lines Using Transgenic Grass Plants:

The breeding methods of the present inventions further comprise introgressing a heterologous transgene from a transgenic plant. Thus in one embodiment, the inventor contemplates traditional plant breeding methods comprising a transgenic perennial ryegrass (*Lolium perenne* L.) plant for introgressing a transgene into a drought resistant plant of the present inventions. A purpose of such introgression is to provide a desired agronomic trait. In one embodiment, the transgenic ryegrass plant is an established plant. For one example, the use of an established plant of a salt-tolerant transgenic perennial ryegrass (*Lolium perenne* L.) is contemplated for providing increased salt tolerance in a plant of the present invention provided by a rice vacuolar Na[+]/H[+] antiporter transgene, OsNHX1 (Wu, et al., 2005, Plant science, 169, (1):65-73). In another embodiment, the inventor contemplates introgressing a heterologous transgene of a novel transgenic plant of the present invention. For example, a traditional breeding methods comprising a novel transgenic ryegrass plant of the present inventions comprising a Fm gene, such as a gene comprising a nucleic acid sequence set forth in any of SEQ ID NOs:1-39 and 93-216. In some embodiments, the nucleic acid sequences are at least 50%, 60%, 70%, 80%, 90%, 95%, 98%, or 99% identical to the aforementioned sequences. Another purpose for using transgenic ryegrass plants in breeding methods of the present inventions, in addition to introgression of the transgene, is to introgress germplasm for desired agronomic traits of the transgenic plant into a drought resistant plant of the present inventions.

D. Regeneration of Plants:

Plants may be regenerated from plant cells and plant parts, such as seeds, stems, and cultured plant tissue, using well-known methods for regenerating whole plants. Specifically, after selecting for a modified plant comprising Fm germplasm demonstrating desired drought resistant traits or selecting a transformed plant, such as a plant that expresses a heterologous Fm gene encoding a Fm protein or variant thereof, a whole plant is regenerated. It is known that many plants can be regenerated from cultured cells or tissues, including but not limited to all major species of grass, including but not limited to perennial ryegrass (for example, Folling et al., 1995 Plant science 108:229-239; herein incorporated by reference), oats, barley (for example, Nobre et al., 1995, Barley Genetics Newsletter 25:46-50; herein incorporated by reference), rice (for example, Fujimura, et al. (1985) Plant Tissue Culture Lett. 2:74-75; herein incorporated by reference), *Zea Mays* (for example, Shillito et al. (1989) Bio/Technology 7:581-587; herein incorporated by reference), sugarcane, cotton, legumes, vegetables, and monocots.

Methods for regeneration of plants vary from species to species of plants. In one embodiment, a suspension of transformed protoplasts comprising copies of the heterologous gene is provided. Plant regeneration from cultured protoplasts is described in Evans et al. Handbook of Plant Cell Cultures, Vol. 1: (MacMillan Publishing Co., New York, 1983); and Vasil (ed.), Cell Culture and Somatic Cell Genetics of Plants, Acad. Press, Orlando, Vol. I, 1984, and Vol. III, 1986; herein incorporated by reference. A protoplast suspension may be used to form embryogenic callus from which shoots and roots may be induced to form plants.

Alternatively, embryo formation can be induced from a protoplast suspension. These embryos can germinate and form mature plants. The culture media of the protoplast suspension will generally contain various amino acids and hormones, such as auxin and cytokinins. Efficient regeneration will depend on the type of cultures medium, or the genotype, or the history of the culture. The reproducibility of regeneration depends on the control of these variables.

VI. Evaluation of Stress Tolerance, Such as Drought Stress:

The modified plants and grass plant lines are tested for the effects of the Fm gene or Fm transgene on abiotic stress tolerance, such as a drought stress phenotype. For example, the parameters evaluated for drought stress tolerance, are compared to those in control (irrigated) plants, or unmodified plants and plant lines. Parameters evaluated include measures of leaf elongation, leaf water content, leaf water potential, root biomass, root length, flowering, reproduction, and the like, in response to water deprivation, including responses to additional abiotic stresses such as high or low salt, changes in light exposure, heat, cold, and the like. Differences in levels of capability to resist abiotic stress, such as a level of response to drought stress, can be expressed as a distance of leaf elongation, weight as in root biomass, a unit of time, or in a particular tissue, such a leaf color, or as a developmental state, such as stage of flowering; for example, comparative levels of drought stress capabilities in *Festuca* and grass plant hybrids was measured in leaves and roots, see, Examples and Figures. These tests may be conducted both in the greenhouse and in the field.

A further aspect provides a method for monitoring a population of plants comprising providing at least one sentinel plant comprising a recombinant polynucleotide, wherein the polynucleotide comprises a stress responsive sequence comprising a sequence set forth in any one of SEQ ID NOs:1-39 and 93-216 operatively linked to a nucleotide sequence encoding a detectable marker, for example, a fluorescent protein. In some embodiments, the nucleic acid sequences are at least 50%, 60%, 70%, 80%, 90%, 95%, 98%, or 99% identical to the aforementioned sequences.

It should be recognized that one or more polynucleotides, which are the same or different can be introgressed into a plant, therein providing a means to obtain a genetically modified plant containing multiple copies of a single transgenic sequence, or containing two or more different transgenic sequences, either or both of which can be present in multiple copies. Such transgenic plants can be produced, for example, by simply selecting plants having multiple copies of a single type of transgenic sequence; by cotransfecting plant cells with two or more populations of different transgenic sequences and identifying those containing the two or more different transgenic sequences; or by crossbreeding transgenic plants, each of which contains one or more desired transgenic sequences, and identifying those progeny having the desired sequences.

VII. Transgenic Plants Seeds and Plant Parts:

Plants of the present invention are transformed with at least one heterologous gene encoding an Fm or Fm related gene, or encoding a sequence designed to increase Fm or Fm related gene expression, according to any procedure well known or developed in the art. In some embodiments, the heterologous gene may introduce Fm or Fm gene expression and protein activity of the expressed protein. In some embodiments, expression of the heterologous gene may decrease endogenous Fm or Fm expression. In some embodiments, the heterologous gene may replace endogenous homologues of Fm or Fm gene expression. It is contemplated that these heterologous genes, or nucleic acid sequences of the present invention and of interest, are utilized to increase the level of the polypeptide encoded by heterologous genes, or to decrease the level of the protein encoded by endogenous genes. It is contemplated that these heterologous genes, or nucleic acid sequences of the present invention and of interest, are utilized augment and/or increase the level of the protein encoded by endogenous genes. It is also contemplated that these heterologous genes, or nucleic acid sequences of the present invention and of interest, are utilized to provide a polypeptide encoded by heterologous genes.

Introduction of the nucleic acid sequence of interest into the plant cell genome may be achieved by, for example, heterologous recombination using *Agrobacterium*-derived sequences and other plant transformation methods. Transgenic grass plant lines are contemplated to be developed from transgenic plants by tissue culture propagation. The presence of nucleic acid sequence of a heterologous Fm gene and/or an encoded a Fm polypeptide or mutants or variants thereof may be transferred from a transgenic plant to related varieties by traditional plant breeding techniques. Examples of transgenic lines are described herein. Transgenic lines are contemplated for establishment from transgenic plants by tissue culture propagation.

Transgenic lines over-expressing Fm genes of drought resistant cultivars may be utilized for evaluation of drought resistant activity. These transgenic lines are then contemplated for evaluation of abiotic stress tolerance, such as drought stress tolerance, and agronomic traits such as phenotype, color, pathogen resistance and other desired agronomic traits.

A. Expression Cassettes:

The methods of the present invention contemplate the use of at least one heterologous gene encoding a Fm gene and/or Fm related gene, or encoding a sequence designed to decrease or increase a Fm genes or Fm related gene expression, as described herein. Heterologous genes include but are not limited to naturally occurring coding sequences, as well variants encoding mutants, variants, truncated proteins, and fusion proteins, as described above. Heterologous genes may be used alone or in combination with a selected agronomic trait (such as yield, etc.). Heterologous genes intended for expression in plants are first assembled in expression cassettes comprising a promoter. Methods which are well known to or developed by those skilled in the art may be used to construct expression vectors containing a heterologous gene and appropriate transcriptional and translational control elements. These methods include in vitro recombinant DNA techniques, synthetic techniques, and in vivo genetic recombination. Exemplary techniques are widely described in the art (see e.g., Sambrook et al. (1989) Molecular Cloning, A Laboratory Manual, Cold Spring Harbor Press, Plainview, N.Y., and Ausubel, F. M. et al. (1989) Current Protocols in Molecular Biology, John Wiley & Sons, New York, N.Y.; herein incorporated by reference).

In general, these vectors comprise a nucleic acid sequence encoding a Fm gene and/or Fm related gene, or encoding a sequence designed to decrease Fm gene and/or Fm related gene expression, (as described herein) operably linked to a promoter and other regulatory sequences (e.g., enhancers, polyadenylation signals, etc.) required for expression in a plant.

Promoters include but are not limited to constitutive promoters, tissue specific promoters, organ specific promoters, developmentally specific promoters, inducible promoters and stress response promoters. Examples of promoters include but are not limited to: rice actin1 promoter, maize ubiquitin promoter (for example, Dalton et al., 1999, Plant Cell Reports, 18(9): 721-726), fructosyltransferase (LpFT1) promoter (for example, Chalmers, et al., 2005, Plant Biotechnology Journal 3(5):459, constitutive promoter 35S of cauliflower mosaic virus; a wound-inducible promoter from tomato, leucine amino peptidase ("LAP," see, e.g., Chao et al. (1999) Plant Physiol 120: 979-992; herein incorporated by reference); a chemically-inducible promoter from tobacco, Pathogenesis-Related 1 (PR1) (induced by salicylic acid and BTH (benzothiadiazole-7-carbothioic acid S-methyl ester)); a tomato proteinase inhibitor II promoter (PIN2) or LAP promoter (both inducible with methyl jasmonate); a heat shock promoter (see, e.g. U.S. Pat. No. 5,187,267; herein incorporated by reference); a tetracycline-inducible promoter (see, e.g. U.S. Pat. No. 5,057,422; herein incorporated by reference); and seed-specific promoters, such as those for seed storage proteins (e.g., phaseolin, napin, oleosin, and a promoter for soybean beta conglycin (see, e.g., Beachy et al. (1985) EMBO J. 4: 3047-3053; herein incorporated by reference).

The expression cassettes may further comprise any sequences required for expression of mRNA. Such sequences include, but are not limited to transcription terminators, enhancers such as introns, viral sequences, and sequences intended for the targeting of the gene product to specific organelles and cell compartments.

A variety of transcriptional terminators are available for use in expression of sequences using the promoters of the present invention. Transcriptional terminators are responsible for the termination of transcription beyond the transcript and its correct polyadenylation. Appropriate transcriptional terminators and those which are known to function in plants include, but are not limited to, the CaMV 35S terminator, the tml terminator, the pea rbcS E9 terminator, and the nopaline and octopine synthase terminator (see, for examples, Odell et al. (1985) Nature 313:810; Rosenberg et al. (1987) Gene, 56:125; Guerineau et al. (1991) Mol. Gen. Genet. 262:141; Proudfoot (1991) Cell 64:671); Sanfacon et al. (1991) Genes Dev., 5:141; Mogen et al. (1990) Plant Cell, 2:1261; Munroe et al. (1990) Gene 91:151; Ballas et al. (1989) Nucleic Acids Res. 17:7891; Joshi et al. (I 987) Nucleic Acid Res., 15:9627, all of which are incorporated herein by reference in their entirety).

In addition, in some embodiments, constructs for expression of the gene of interest include one or more of sequences found to enhance gene expression from within the transcriptional unit. These sequences can be used in conjunction with the nucleic acid sequence of interest to increase expression in plants. Various intron sequences have been shown to enhance expression, particularly in monocotyledonous cells. For example, the introns of the maize Adh1 gene have been found to significantly enhance the expression of the wild-type gene under its cognate promoter when introgressed into maize cells (see, e.g., Callis et al. (1987) Genes Develop. 1:1183; herein incorporated by reference). Intron sequences have been routinely incorporated into plant transformation vectors, typically within the non-translated leader.

In some embodiments of the present invention, the construct for expression of the nucleic acid sequence of interest also includes a regulator such as a nuclear localization signal (see, e.g., Kalderon et al. (1984) Cell 39:499; Lassner et al. (1991) Plant Molecular Biology 17:229; all of which are herein incorporated by reference), a plant translational consensus sequence (see, e.g., Joshi (1987) Nucleic Acids Research 15:6643; all of which are herein incorporated by reference), an intron (see, e.g., Luehrsen and Walbot (1991) Mol. Gen. Genet. 225:81; all of which are herein incorporated by reference), and the like, operably linked to the nucleic acid sequence encoding a Fm gene.

In preparing the construct comprising the nucleic acid sequence encoding a Fm gene, or encoding a sequence designed to decrease Fm gene expression, various DNA fragments can be manipulated, so as to provide for the DNA sequences in the desired orientation (e.g., sense or antisense) orientation and, as appropriate, in the desired reading frame. For example, adapters or linkers can be employed to join the DNA fragments or other manipulations can be used to provide for convenient restriction sites, removal of superfluous DNA, removal of restriction sites, or the like. For this purpose, in vitro mutagenesis, primer repair, restriction, annealing, resection, ligation, or the like is preferably employed, where insertions, deletions or substitutions (e.g., transitions and transversions) are involved.

Numerous transformation vectors are available for plant transformation. The selection of a vector for use will depend upon the preferred transformation technique and the target species for transformation. For certain target species, different antibiotic or herbicide selection markers are preferred. Selection markers used routinely in transformation include the nptII gene which confers resistance to kanamycin and related antibiotics (see, e.g., Messing and Vierra, (1982) Gene 19: 259; Bevan et al. (1983) Nature 304:184; all of which are incorporated herein by reference), the bar gene which confers resistance to the herbicide phosphinothricin (see, e.g., White et al. (1990) Nucl Acids Res. 18:1062; Spencer et al. (1990) Theor. Appl. Genet. 79:625; all of which are incorporated herein by reference), the hph gene which confers resistance to the antibiotic hygromycin (see, e.g., Blochlinger and Diggelmann (1984) Mol. Cell. Biol. 4:2929; herein incorporated by reference), and the dhfr gene, which confers resistance to methotrexate (see, e.g., Bourouis et. al. EMBO J., 2:1099 (1983); herein incorporated by reference).

In some preferred embodiments, the Ti (T-DNA) plasmid vector is adapted for use in an *Agrobacterium* mediated transfection process (see e.g., U.S. Pat. Nos. 5,981,839; 6,051,757; 5,981,840; 5,824,877; and 4,940,838; all of which are herein incorporated by reference in their entirety). Construction of recombinant Ti and Ri plasmids in general follows methods typically used with the more common vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The use of T-DNA as a flanking region in a construct for integration into a Ti- or Ri-plasmid has been described in EPO No. 116,718 and PCT Application Nos. WO 84/02913, 02919 and 0292; all of which are herein incorporated by reference in their entirety). See, for further examples, Herrera-Estrella (1983) Nature 303:209-213; Fraley et al. (1983) Proc. Natl. Acad. Sci, USA 80:4803-4807; Horsch et al. (1984) Science 223:496-498;

and DeBlock et al. (1984) EMBO J. 3:1681-1689, all of which are herein incorporated by reference).

The second system is called the "binary" system or "binary vector" in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. In some embodiments of the invention, the nucleic acid sequence of interest is targeted to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (see, e.g. U.S. Pat. No. 5,501,967; herein incorporated by reference). One of skill in the art knows that homologous recombination may be achieved using targeting vectors that contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

*Agrobacterium tumefaciens* is a common soil bacterium that causes crown gall disease by transferring some of its DNA to the plant host. The transferred DNA (T-DNA) is stably integrated into the plant genome, where its expression leads to the synthesis of plant hormones and thus to the tumorous growth of the cells. In yet other embodiments, the nucleic acids such as those disclosed herein is utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted heterologous polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

B. Vectors for Expressing a Fm and/or a Fm Gene

The nucleic acid sequences of the present invention may be employed for producing polypeptides by recombinant techniques. Thus, for example, the Fm nucleic acid sequence may be included in any one of a variety of expression vectors for expressing a polypeptide. In some embodiments of the present invention, vectors include, but are not limited to, chromosomal, nonchromosomal and synthetic DNA sequences (for example, derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). It is contemplated that any vector may be used as long as it is replicable and viable in the host plant cell or microbe.

In particular, some embodiments of the present invention provide recombinant constructs comprising one or more of the nucleic sequences as broadly described above (for example, SEQ ID NOs:1-39 and 93-216 and sequences that are at least 50%, 60%, 70%, 80%, 90%, 95%, 98%, or 99% identical to the aforementioned sequences.). In some embodiments of the present invention, the constructs comprise a vector, such as a plasmid or viral vector, into which a nucleic acid sequence of the invention has been inserted, in a forward or reverse orientation. In preferred embodiments of the present invention, the appropriate nucleic acid sequence is inserted into the vector using any of a variety of procedures. In general, the nucleic acid sequence is inserted into an appropriate restriction endonuclease site(s) by procedures known in the art.

Large numbers of suitable vectors are known to those of skill in the art, and are commercially available. Such vectors include, but are not limited to, the following vectors: 1) Bacterial—pQE70, pQE60, pQE-9 (Qiagen), pBS, pD10, phagescript, psiX174, pbluescript SK, pBSKS, pNH8A, pNH16a, pNH18A, pNH46A (Stratagene); ptrc99a, pKK223-3, pKK233-3, pDR540, pRIT5 (Pharmacia); and 2) Eukaryotic—pWLNEO, pSV2CAT, pOG44, PXT1, pSG (Stratagene), pSVK3, pBPV, pMSG, and pSVL (Pharmacia). Any other plasmid or vector may be used as long as they are replicable and viable in the host. In some preferred embodiments of the present invention, plant expression vectors comprise an origin of replication, a suitable promoter and enhancer, and also any necessary ribosome binding sites, polyadenylation sites, splice donor and acceptor sites, transcriptional termination sequences, and 5' flanking nontranscribed sequences. In some embodiments, DNA sequences derived from the SV40 splice, and polyadenylation sites may be used to provide the required nontranscribed genetic elements.

In some embodiments of the present invention, a heterologous nucleic acid sequence of interest is introgressed directly into a plant. One vector useful for direct gene transfer techniques in combination with selection by the herbicide Basta (or phosphinothricin) is a modified version of the plasmid pCIB246, with a CaMV 35S promoter in operational fusion to the *E. coli* GUS gene and the CaMV 35S transcriptional terminator (Intl. Publication No. WO 93/07278; herein incorporated by reference).

C. Generating Transgenic Plants: Transformation Techniques

Introduction of the nucleic acid sequence of interest into the plant cell genome may be achieved by, for example, heterologous recombination using *Agrobacterium*-derived sequences and other plant transformation methods. Examples of such transgenic plants are provided in an over-expressed transgene in ryegrass plants (see, for example, Hisano, et al., 2004, Plant science, 167, (4):861-868; herein incorporated by reference), and ryegrass transformed with an antisense construct for providing a down-regulated (silenced) gene, (Bhalla, et al., 1999, PNAS, 96(20): 11676-11680; herein incorporated by reference). Transgenic grass plant lines are contemplated to be developed from transgenic plants by tissue culture propagation. The presence of nucleic acid sequence of a heterologous Fm gene and/or an encoded a Fm polypeptide or mutants or variants thereof may be transferred from a transgenic plant to related varieties by traditional plant breeding techniques. Examples of transgenic lines are described herein. Transgenic lines are contemplated for establishment from transgenic plants by tissue culture propagation.

Transgenic lines over-expressing Fm genes of drought resistant cultivars may be utilized for evaluation of drought resistant activity. These transgenic lines are then contemplated for evaluation of abiotic stress tolerance, such as drought stress tolerance, and agronomic traits such as phenotype, color, pathogen resistance and other desired agronomic traits. A nucleic acid sequence encoding a Fm gene operatively linked to an appropriate promoter and inserted into a suitable vector for the particular transformation technique utilized (e.g., one of the vectors described herein), the recombinant DNA is introgressed into the plant cell in a number of art-recognized ways. Those skilled in the art will appreciate that the choice of method might depend on the type of plant targeted for transformation. In some embodiments, the vector is maintained episomally. In some embodiments, the vector is integrated into the genome. In one embodiment, a method of the present invention is performed by introducing a polynucleotide portion of a plant stress-regulated gene into the plant. A polynucleotide can be introgressed into a cell by a variety of methods well known to those of ordinary skill in the art. For example, the polynucleotide can be introgressed into a plant cell using a direct gene transfer method such as electroporation or microprojectile mediated transformation, or using *Agrobacterium* mediated transformation. Non-limiting examples of methods for the introduction of polynucleotides into plants are provided in greater detail herein.

In addition to direct transformation, in some embodiments, the vectors comprising a nucleic acid sequence encoding a Fm gene are transferred using *Agrobacterium*-mediated transformation (see, e.g., Hinchee et al. (1988) Biotechnology, 6:915; Ishida et al. (1996) Nature Biotechnology 14:745, all of which are herein incorporated by reference). Introduction of the nucleic acid sequence of interest into the plant cell genome may be achieved by, for example, heterologous recombination using *Agrobacterium*-derived sequences and other plant transformation methods. Transgenic grass plant lines are contemplated to be developed from transgenic plants by tissue culture propagation. The presence of nucleic acid sequence of a heterologous Fm gene and/or an encoded a Fm polypeptide or mutants or variants thereof may be transferred from a transgenic plant to related varieties by traditional plant breeding techniques. Examples of transgenic lines are described herein. Transgenic lines are contemplated for establishment from transgenic plants by tissue culture propagation.

Transgenic lines over-expressing Fm genes of drought resistant cultivars may be utilized for evaluation of drought resistant activity. These transgenic lines are then contemplated for evaluation of abiotic stress tolerance, such as drought stress tolerance, and agronomic traits such as phenotype, color, pathogen resistance and other desired agronomic traits. *Agrobacterium* is a representative genus of the gram-negative family Rhizobiaceae. Its species are responsible for plant tumors such as crown gall and hairy root disease. In the dedifferentiated tissue characteristic of the tumors, amino acid derivatives known as opines are produced and catabolized. The bacterial genes responsible for expression of opines are a convenient source of control elements for chimeric expression cassettes. Heterologous genetic sequences (e.g., nucleic acid sequences operatively linked to a promoter of the present invention) can be introgressed into appropriate plant cells, by means of the Ti plasmid of *Agrobacterium tumefaciens*. The Ti plasmid is transmitted to plant cells on infection by *Agrobacterium* and is stably integrated into the plant genome (Schell (1987) Science, 237: 1176; herein incorporated by reference). Species which are susceptible infection by *Agrobacterium* may be transformed in vitro.

In particular, examples of methods for transformation techniques for overexpressing nucleic acids include but are not limited to providing transgenic forage plants are described in U.S. Patent Appln. Pub. Nos. 20020019997A1; 20020023279A1; and U.S. Pat. No. 5,985,666; all of which are herein incorporated by reference; alfalfa (Galili et al. (2000) Transgenic Res 9, 137-144; Trieu et al. (2000) Plant Journal 22, 531-541; all of which are herein incorporated by reference); fescue (Wang et al. (2000) Plant Cell Rep 20, 213-219; herein incorporated by reference); and an herb (Niu et al. (2000) Plant Cell Rep 19, 304-310; herein incorporated by reference).

In some embodiments, direct transformation into the plastid genome is used to introduce the vector into the plant cell (See e.g., U.S. Pat. Nos. 5,451,513; 5,545,817; 5,545,818; PCT application WO 95/16783, all of which are incorporated herein by reference). The basic technique for chloroplast transformation involves introducing regions of cloned plastid DNA flanking a selectable marker together with the nucleic acid encoding the RNA sequences of interest into a suitable target tissue (e.g., using biolistics or protoplast transformation with calcium chloride or PEG). The 1 to 1.5 kb flanking regions, termed targeting sequences, facilitate homologous recombination with the plastid genome and thus allow the replacement or modification of specific regions of the plastome. Initially, point mutations in the chloroplast 16S rRNA and rps12 genes conferring resistance to spectinomycin and/or streptomycin are utilized as selectable markers for transformation (see, e.g., Svab et al. (1990) PNAS, 87:8526; Staub and Maliga, (1992) Plant Cell, 4:39; all of which are herein incorporated by reference). The presence of cloning sites between these markers allowed creation of a plastid targeting vector introduction of foreign DNA molecules (see, e.g., Staub and Maliga (1993) EMBO J., 12:601; herein incorporated by reference). Substantial increases in transformation frequency are obtained by replacement of the recessive rRNA or r-protein antibiotic resistance genes with a dominant selectable marker, the bacterial aadA gene encoding the spectinomycin-detoxifying enzyme aminoglycoside-3'-adenyl-transferase (Svab and Maliga (1993) PNAS, 90:913; herein incorporated by reference). Other selectable markers useful for plastid transformation are known in the art and encompassed within the scope of the present invention. Plants homoplasmic for plastid genomes containing the two nucleic acid sequences separated by a promoter of the present invention are obtained, and are preferentially capable of high expression of the RNAi encoded by the DNA molecule.

In some embodiments, vectors useful in the practice of the present invention are microinjected directly into plant cells by use of micropipettes to mechanically transfer the recombinant DNA (see, e.g., Crossway (1985) Mol. Gen. Genet, 202:179; herein incorporated by reference). In still other embodiments, the vector is transferred into the plant cell by using polyethylene glycol (see, e.g., Krens et al. (1982) Nature, 296:72; Crossway et al. (1986) BioTechniques, 4:320; all of which are herein incorporated by reference); fusion of protoplasts with other entities, either minicells, cells, lysosomes or other fusible lipid-surfaced bodies (see, e.g., Fraley et al. (1982) Proc. Natl. Acad. Sci., USA, 79:1859; herein incorporated by reference); protoplast transformation (see, e.g., EP 0 292 435; herein incorporated by reference); direct gene transfer (see, e.g., Paszkowski et al. (1984) EMBO J., 3:2717); Hayashimoto et al. (1990) Plant Physiol. 93:857; all of which are herein incorporated by reference).

In still further embodiments, the vector may also be introgressed into the plant cells by electroporation (see, e.g., Fromm, et al. (1985) Pro. Natl Acad. Sci. USA 82:5824; Riggs et al. (1986) Proc. Natl. Acad. Sci. USA 83:5602; all of which are herein incorporated by reference). In this technique, plant protoplasts are electroporated in the presence of plasmids containing the gene construct. Electrical impulses of high field strength reversibly permeabilize biomembranes allowing the introduction of the plasmids. Electroporated plant protoplasts reform the cell wall, divide, and form plant callus.

In yet other embodiments, a vector comprising nucleotides of the present invention is introgressed through ballistic particle acceleration using devices (e.g., such as those devices, available from Agracetus, Inc., Madison, Wis. and Dupont, Inc., Wilmington, Del.); (see, e.g., U.S. Pat. No. 4,945,050; and McCabe et al. Biotechnology 6:923 (1988); all of which are herein incorporated by reference). Other examples of transformation techniques of vectors for introgression of drought resistant genes into plants are See, for further examples, Sato et al. 2006 Grassland Science, 52(2):95 (ryegrass); Murray et al. Mol Gen Genet. (1992) 233(1-2):1-9 (ryegrass); Klein et al. Proc. Natl. Acad. Sci. USA, 85:4305 (1988) (maize); Klein et al. Bio/Technology, 6:559 (1988) (maize); Klein et al. Plant Physiol., 91:4404 (1988) (maize); Fromm et al. Bio/Technology, 8:833 (1990); and Gordon-Kamm et al. Plant Cell, 2:603 (1990) (maize); Koziel et al. Biotechnology, 11:194 (1993) (maize); Hill et al. Euphytica, 85:119 (1995) and Koziel et al. Annals of the New York Academy of Sciences 792:164 (1996); Shimamoto et al. Nature 338: 274 (1989) (rice); Christou et al. Biotechnology, 9:957 (1991) (rice); Datta et al. Bio/Technology 8:736 (1990) (rice); European Application EP 0 332 581 (orchardgrass and other Poaceae); Vasil et al. Biotechnology, 11: 1553 (1993) (wheat); Weeks et al. Plant Physiol., 102: 1077 (1993) (wheat); Wan et al. Plant Physiol. 104: 37 (1994) (barley); Jahne et al. Theor. Appl. Genet. 89:525 (1994) (barley); Knudsen and Muller, Planta, 185:330 (1991) (barley); Umbeck et al. Bio/Technology 5: 263 (1987) (cotton); Casas et al. Proc. Natl. Acad. Sci. USA 90:11212 (1993) (sorghum); Somers et al. Bio/Technology 10:1589 (1992) (oat); Torbert et al. Plant Cell Reports, 14:635 (1995) (oat); Weeks et al. Plant Physiol., 102:1077 (1993) (wheat); Chang et al. WO 94/13822 (wheat) and Nehra et al. The Plant Journal, 5:285 (1994) (wheat); all of which are herein incorporated by reference in their entirety.

In general, advances in understanding the drought tolerance mechanism were obtained from studies on the mild drought tolerant model species, *Arabidopsis* plants. However, those studies were not sufficient to explain the adaptation of plants, such as *Festuca* species, to severe drought stress, such as long-term severe drought conditions. The inventor's research on the *F. mairei* plant and Fm genome uncovered a large number of novel genes associated with onset of drought stress and adaptation to drought, for example, low soil moisture growing conditions. The combination of data from studies on a genetic model *F. mairei* plant and on diverse plant species should help us have a better understand of underlying mechanism of thought tolerance in plant. Existence of variety of drought responsive genes suggests complex processes of a plants response to the stress. The genes are involved in thought stress tolerance and stress responses. Although more work is necessary to define gene functions and dissect the complex regulation of gene expression, the genes isolated and characterized to data give us many intriguing insights into the protective mechanisms that determine desiccation tolerance.

EXPERIMENTAL

The following examples are provided in order to demonstrate and further Illustrate certain preferred embodiments and aspects of the present invention and are not to be construed as limiting the scope thereof.

In the experimental disclosure which follows, the following abbreviations apply: M (molar); mM (millimolar); µM (micromolar); nM (nanomolar); mol (moles); mmol (millimole); µmol (micromole); nmol (nanomole); gm (gram); mg (milligram); µg (microgram); pg (picogram); L (liter); ml (milliliter); µl (microliter); cm (centimeter); mm (millimeter); µm (micrometer); nm (nanometer); ° C. (degrees Centigrade or Celsius), d (day), s (second), v (volt), h and hr (hour), and wk (week).

Example I

Materials and Methods

A. Experimental Procedures for Demonstrating the Superior Drought Tolerance of *F. Mairei* Plants Over Other *Festuca* Plants and for Demonstrating Hybrid Vigor.
Plant Materials and Drought Treatments:
Twelve Weeks of Drought Treatment:

A comparison of four *Festuca* grasses, a selection of Atlas fescue originally collected from Morocco and three commercial tall fescue cultivars used as entries for turf and forage grass plants to compare levels of drought resistance (soft-leaf tall fescue, *Festuca arundinacea* Schreb., 'Barolex, turf-type tall fescue, *Festuca arundinacea* 'Falcon II,' and tall fescue, *Festuca arundinacea*, cultivar 'Kentucky 31'. A single tiller of each entry was used to vegetatively propagate a mature donor plant in the greenhouse. From each plant, two vegetative tillers were transplanted into each of six polyvinyl chloride (PVC) tubes (100 cm deep×34 cm diameter). The tubes were lined with a sleeve of heavy duty plastic to facilitate moving the root system and soil from the tube at the end of the experiment. Tubes were filled with the same weight (11.8 kg) of a recommended substrate for athletic fields consisting of 85% sand and 15% field soil. The transplanted tillers were established for 15 weeks in the greenhouse during the fall with natural lighting, regular irrigation, fertilizer and trimming. Greenhouse temperature was 25±3° C., with an average 13-hour photoperiod.

After trimming the plants to leave stubble of 7.5 cm for equal size plants, a pre-conditioning drought was applied by withholding water for 2 weeks. Plants were allowed to recover by irrigation for one week before being trimmed again to 7.5 cm. Then, three tubes of each entry were randomly allocated to the drought treatment and the control. Drought stress was gradually imposed by progressively applying decreasing amounts of water from 200 ml/day for week one (up to 100% soil capacity in the tube), to 150 ml, 100 ml, and 50 ml/day for weeks 2, 3, and 4, respectively. Water was not applied during the remainder of the 12-week drought period. Control plants were irrigated regularly during this period. The PVC tubes were re-randomized weekly during this drought period to minimize effects of possible environmental gradients within the greenhouse.
Soil Water Content (SWC) Measurement:

Polyvinyl chloride (PVC) tubes were weighed every week at the same time (1:00 p.m.) to determine gravimetric soil water content (SWC) from water loss. The mass of soil mixture was measured for each tube at the beginning of the experiment, which also ensured the same weight of substrate (11.8 kg) in each tube. The moisture of the soil mixture was estimated by weighing 10 samples, first fresh and then after oven drying at 80° Celsius.
Leaf Water Content (LWC) Measurement:

An upper fully developed leaf of the drought stressed plants was detached weekly (for long-term experiments, e.g. weeks) for leaf water content (LWC) measurement or for shorter drought tests as described herein. Control plants were sampled in weeks 3, 6, and 9 during the drought period or for shorter tests the same day as the test leaf.

The fresh weight (FW) (weight of the leaf immediately after detachment), turgor weight (TW) (weight of the leaf after soaking in milliQ water for 24 hr at room temperature), and dry weight (DW) (weight of the leaf after oven drying at 80° C. for 24 hr) of the leaf were measured. Relative leaf water content (LWC) was calculated according to Slavik (1974, Direct methods of water content determination. p. 121-156, In B. Slavik (ed.) Methods of studying plant water relations. Springer-Verlag, Berlin; herein incorporated by reference) and White et al., (1992, Crop Sci. 32: 25 1-2563; herein incorporated by reference) as LWC (%)=(FW-DW)/(TW-DW)×100.

Leaf Water Potential ($\Psi$w) Measurement:

Plants were covered by a black plastic sheet in the evening for one night to imitate a pre-dawn condition of closed stomata and low respiration. The following morning, duplicate fully-emerged, undamaged leaf blades in each tube were removed and immediately subjected to leaf water potential ($\Psi$w) measured immediately by using a pressure chamber (Soil Moisture Equipment Corp., Santa Barbara, Calif.). Measurements were conducted at 22-25° C. within 2 hours in the greenhouse. Data were eliminated when the $\Psi$w of the control was greater than −0.6 MPa.

Leaf Elongation (LE) Measurement:

After 15 weeks establishment, three tillers in each tube were randomly chosen and labeled with wires of different color. Length of the top two emerging leaves on each tiller were measured from the tip of each lamina to the ligule of the next oldest leaf (Norris and Thomas, 1982, Wales J. Agric. Sci. 99:547-553; herein incorporated by reference) every week until leaf growth of drought-stressed plant ceased.

Root Length (RL) and Biomass (RM) Measurement:

At the end of the experiment, the heavy-duty plastic sleeve containing the soil and root system was slid out of each tube. The soil substrate was gently washed from the root system by flowing water. Length of the root system (RL) was measured using a ruler. Root biomass (RM) was weighed after blotting with a paper towel and air-drying at room temperature for about 6 hr to remove surface moisture.

Soil Water Content (SWC) Measurement:

The PVC tubes were weighed every week at the same time (1:00 p.m.) to determine gravimetric soil water content (SWC) from water loss. The mass of soil mixture was measured for each tube at the beginning of the experiment, which also ensured the same weight of substrate (11.8 kg) in each tube. The moisture of the soil mixture was estimated by weighing 10 samples, first fresh and then after oven drying at 80° Celsius.

Statistical Analyses:

The data of LE, LWC, SWC, and $\Psi$w, were subjected to analysis of variance (ANOVA), using repeated measurements in time by SAS program (SAS Institute Inc. 2003). Comparisons were made within the four entries by one-way ANOVA and between drought and control treatments by the student-I test at each specified week. Mean separations were performed by a least significant difference (LSD) procedure where the F-value was significant at the 0.05 probability level. Data for RL and RM were subjected to one-way ANOVA analysis to compare within the four entries and between stressed and control plants. Relationships between parameters were fitted to appropriate nonlinear regression models using Microsoft Office Excel (Microsoft Co., 2002).

B. Experimental Procedures for Identification of *F. mairei* (Fm) Germplasm Associated with Xerophytic Adaptation (See Also, Wang, et al., 2005, Molecular Biotechnology, 29(3):211-220; Herein Incorporated by Reference in its Entirety).

Plant Materials and Drought Treatment for Identifying Preferred Fm Germplasm:

Nine Days of Drought Treatment:

Ten plants of a *F. mairei* clone (Fm1, originally collected from Morocco) were transplanted into polyethylene pots (20.32 cm diameter at the top, 15.24 cm diameter at the bottom, and 35.56 cm height) filled with 90% sand and 10% silt and clay. The plants were established (grown) for three months with regular irrigation and fertilization in a uniform greenhouse environment condition. After establishment (three months), five *F. mairei* plants were deprived of water until they were severely stressed (dehydrated) and passed the permanent wilting point (nine days).

The five control plants, referred to as a "treatment control," were watered daily (irrigated) throughout the drought stress period of the five drought stressed plants. During the drought stress treatment, leaf samples from both the stressed and the control *F. mairei* plants were collected at noon of each day to eliminate the possible gene expression variation from occurring during the day. Leaf samples were immediately frozen in liquid nitrogen and stored in −80° C. for subsequent RNA isolation.

Relative Leaf Water Content Measurements:

As described above, a fully extended leaf of *F. mairei* plant was detached during the drought stress treatment. Leaf water content (LWC) was measured daily (see, FIG. 2).

RNA Isolation and cDNA Synthesis:

Total RNA was isolated with plant RNA purification reagent (Invitrogen Life Technologies, Carlsbad, Calif.) and then quantified using a spectrophotometer at a wavelength 260 nm. Quality of the RNA was checked by running 2 µg of the total RNA on 1.2% agarose gel with 2.5% formaldehyde in 40 mM MOPS (3-(N-morpholino) propane sulfonic acid) running buffer for 2.5 hours. Poly (A)+ RNA was isolated from the total RNA by using PolyATract mRNA isolation systems III (Promega, Madison, Wis.). Double-stranded (ds) cDNA was synthesized from Poly(A)+ RNA using the Universal RiboClone cDNA Synthesis System (Promega) and purified with an equal volume of Tris-EDTA (TE, 10 mM Tris-Cl, pH 7.5 1 mM EDTA):saturated phenol:chloroform:isoamyl alcohol (25:24:1). The ds cDNA was quantified using Hoechst 33258 (bisbenzimide) dye on DyNA quant 200 fluorometer (Hoefer Pharmacia Biotech, Inc., San Francisco, Calif.).

cDNA-AFLP Analysis:

The cDNA-AFLP procedure was conducted as described by Bachem et al. (1998, Plant Mol. Biol. Rep. 16, 157-173; herein incorporated by reference) with some modifications. Briefly, AFLP is a method for genotyping individuals for a large number of loci using a minimal number of PCR reactions. This method is based on Vos et al. 1995 (Nucleic Acids Research 23: 4407-14; herein incorporated by reference). In brief; 1. DNA is cut, with restriction enzymes and then linkers are ligated onto the cut ends. Typically this involves a combination of two restriction enzymes: a 4 base cutter (such as MseI) and a 6 base cutter (such as EcoRI); 2. Pre-selective PCR is performed using primers that match the linkers. These primers have a two base overhang. Selective PCR is performed using primers with three base overhangs. For any given pre-selective amplification, there were 16 possible selective primer combinations. The EcoRI primer is labeled so that fragments that contain an EcoRI site are exclusively detected. PCR products are then analyzed by gel or capillary electrophoresis. Fragments are combined and then analyzed for fingerprint similarity with other samples.

Specifically, 30 nanograms of cDNA were digested with 5 U NspI at 37° C. for 2.5 hours, and then immediately digested with 5 U of TaqI at 65° C. for 2.5 hours followed by heat inactivation at 80° C. for 20 minutes. The two steps of digestion were conducted in NEbuffer 2 (New England Biolabs, Beverly, Mass.) in a total volume of 30 μl. The digestion mix (20 μl) was ligated to 0.5 mM NspI adapter and 2.5 mM TaqI adapter using 1 U of T4 ligase supplemented with T4 DNA ligase buffer (Promega). Oligonucleotide (adapters, linkers, and primers) used during the development of the present inventions, were synthesized by MWG Biotech, Inc. (Charlotte, N.C.) (see, Table 1A and B for sequences).

A PCR reaction solution (20 μl) for pre-amplification contained 1 μl digestion mix, 0.5 μM of each primer, 0.3 mM dNTP mix, 1.5 mM $Mg^{2+}$, and 0.5 U Taq polymerase (Promega). The PCR reaction was conducted on a PTC-225 machine at: 72° C., 2 min; 94° C., 1 min; 15 cycles of 94° C., 30 sec; 56° C., 30 sec; and 72° C., 1 min; then followed by 10 min at 72° C. for a final extension. For selective amplification, the PCR solution included 1 μl of 5× diluted pre-amplification product, 0.4 μM of each selective primer, 1.5 mM $Mg_{2+}$, 0.3 mM dNTP mix, and 0.4 U Taq polymerase in 15 μl total reaction volume. The PCR reaction was performed following the program: 10 cycles: 94° C., 30 s; 65° C. (−0.7° C./cycle), 30 sec; 72° C., 1 min and 25 cycles: 94° C., 30 sec; 56° C., 30 sec; 72° C., 1 min; followed by a final extension step of 10 min at 72° Celsius.

The selective PCR product (15 μl) was denatured at 96° C. for 6 min after adding 9 μl of 98% formamide loading buffer. The denatured PCR product (6 μl) was loaded into a 5% denatured polyacrylamide sequencing gel with 45.4% urea for fractionation by electrophoresis at 90 W for 2.5 hours. The fractionated fragments on the gel were then detected by using the Silver Sequence DNA Sequencing System (Promega). The gel on the back plate was allowed to dry overnight at room temperature for scoring on a light box. For recovery of TDFs from the polyacrylamide gel, silver staining had advantages over radioactive fingerprints by being directly visualized and excised from the gel.

TABLE 1A

Sequences of the linkers and primers used for cDNA-AFLP synthesized by MWG Biotech Inc.

| Restriction Enzyme | Primers | linkers | Lab No. | SEQ ID No:XX | Sequences (5'-3') |
|---|---|---|---|---|---|
| NspI | | linker 1 | | 217 | GTAGACTGCGTTCCCATG |
| NspI | | linker 2 | | 218 | GGAACGCAGTCTACGAG |
| NspI | pre-amplification primer | | | 219 | GTAGACTGCGTTCCCATG |
| NspI | selective amplification primer | | N1 | 220 | GTAGACTGCGTTCCCATGTA |
| NspI | selective amplification primer | | N2 | 221 | GTAGACTGCGTTCCCATGTT |
| NspI | selective amplification primer | | N3 | 222 | GTAGACTGCGTTCCCATGTC |
| NspI | selective amplification primer | | N4 | 223 | GTAGACTGCGTTCCCATGTG |
| NspI | selective amplification primer | | N5 | 224 | GTAGACTGCGTTCCCATGCA |
| NspI | selective amplification primer | | N6 | 225 | GTAGACTGCGTTCCCATGCT |
| NspI | selective amplification primer | | N7 | 226 | GTAGACTGCGTTCCCATGCC |
| NspI | selective amplification primer | | N8 | 227 | GTAGACTGCGTTCCCATGCG |
| TaqI | | linker 1 | | 228 | AAGTCCTGAGTAGCAC |
| TaqI | | linker 2 | | 229 | CGTTCAGGACTCATC |

TABLE 1A-continued

Sequences of the linkers and primers used for cDNA-AFLP synthesized by MWG Biotech Inc.

| Restriction Enzyme | Primers | Lab linkers | SEQ ID No:XX | Sequences (5'-3') |
|---|---|---|---|---|
| TaqI | pre-amplification primer | | 230 | CACGATGAGTCCTGAACG |
| TaqI | selective amplification primer | T1 | 231 | CACGATGAGTCCTGAACGAAA |
| TaqI | selective amplification primer | T2 | 232 | CACGATGAGTCCTGAACGAAT |
| TaqI | selective amplification primer | T3 | 233 | CACGATGAGTCCTGAACGAAC |
| TaqI | selective amplification primer | T4 | 234 | CACGATGAGTCCTGAACGAAG |
| TaqI | selective amplification primer | T5 | 235 | CACGATGAGTCCTGAACGATA |
| TaqI | selective amplification primer | T6 | 236 | CACGATGAGTCCTGAACGATT |
| TaqI | selective amplification primer | T7 | 237 | CACGATGAGTCCTGAACGATC |
| TaqI | selective amplification primer | T8 | 238 | CACGATGAGTCCTGAACGATG |
| TaqI | selective amplification primer | T9 | 239 | CACGATGAGTCCTGAACGACA |
| TaqI | selective amplification primer | T10 | 240 | CACGATGAGTCCTGAACGACT |
| TaqI | selective amplification primer | T11 | 241 | CACGATGAGTCCTGAACGACC |
| TaqI | selective amplification primer | T12 | 242 | CACGATGAGTCCTGAACGACG |
| TaqI | selective amplification primer | T13 | 243 | CACGATGAGTCCTGAACGAGA |
| TaqI | selective amplification primer | T14 | 244 | CACGATGAGTCCTGAACGAGT |
| TaqI | selective amplification primer | T15 | 245 | CACGATGAGTCCTGAACGAGC |
| TaqI | selective amplification primer | T16 | 246 | CACGATGAGTCCTGAACGAGG |

TABLE 1B

Sequences of the linkers and primers used for cDNA-AFLP synthesized by MWG Biotech., Inc.

| Restriction Enzyme | Primers/ linkers | Lab SEQ ID No. | SEQ ID No:XX | Sequence (5'-3') |
|---|---|---|---|---|
| EcoRI, | linker | | 247 | CTCGTAGACTGCGTACC |
| EcoRI | linker 2 | | 248 | AATTGGTACGCAGTCTAC |
| EcoRI | pre-amplification primer | | 249 | CACTGCGTACCAATTC |
| EcoRI | selective amplification primer 1 | E1 | 250 | CACTGCGTACCAATTCAA |
| EcoRI | selective amplification primer 2 | E2 | 251 | CACTGCGTACCAATTCAT |
| EcoRI | selective amplification primer 3 | E3 | 252 | CACTGCGTACCAATTCAC |
| EcoRI | selective amplification primer 4 | E4 | 253 | CACTGCGTACCAATTCAG |
| EcoRI | selective amplification primer 5 | E5 | 254 | CACTGCGTACCAATTCTA |
| EcoRI | selective amplification primer 6 | E6 | 255 | CACTGCGTACCAATTCTT |
| EcoRI | selective amplification primer 7 | E7 | 256 | CACTGCGTACCAATTCTC |
| EcoRI | selective amplification primer 8 | E8 | 257 | CACTGCGTACCAATTCTG |
| EcoRI | selective amplification primer 9 | E9 | 258 | CACTGCGTACCAATTCCA |
| EcoRI | selective amplification primer 10 | E10 | 259 | CACTGCGTACCAATTCCT |
| EcoRI | selective amplification primer 11 | E11 | 260 | CACTGCGTACCAATTCCC |
| EcoRI | selective amplification primer 12 | E12 | 261 | CACTGCGTACCAATTCCG |
| EcoRI | selective amplification primer 13 | E13 | 262 | CACTGCGTACCAATTCGA |
| EcoRI | selective amplification primer 14 | E14 | 263 | CACTGCGTACCAATTCGT |
| EcoRI | selective amplification primer 15 | E15 | 264 | CACTGCGTACCAATTCGC |
| EcoRI | selective amplification primer 16 | E16 | 265 | CACTGCGTACCAATTCGG |

Identification of Differentially Expressed Fragments (DEFs) and Fragment Recovery from Polyacrylamide Gel:

For each primer combination, the final PCR products from a series of days of drought stress were loaded in order into lanes next to each other in the sequencing gel for comparison of band density for bands of the same size. When the density of the bands showed an increase from lane to lane gradually across the time points, the bands were identified as up-regulated differentially expressed fragments. When the band density showed a gradual decrease over time, the bands were identified as down-regulated DEFs (for example, see, Bachem et al., 1996, Plant J. 9:745-753; herein incorporated by reference). When a band appeared at a specific time point, those bands were identified as a transient expressed DEF. A few bands were also identified as an up-then-down regulated DEF, which meant the density of the bands increased at first several lanes and then decreased at the last several lanes.

The four types of DEFs were then excised from a polyacrylamide gel with a sterile surgical blade. DNA was eluted by soaking the excised gel in 50 µl water for 12 h and was then used as the template to re-amplify the DNA fragment using the same PCR condition as used for selective amplification. The re-amplified product was run on a 1% agarose gel in 1×TBE buffer for confirmation of the target fragment and separation from possible DNA contamination. DNA fragments of the target size were purified from the agarose gel with a QIAquick gel extraction kit (QIAGEN, Inc., Valencia, Calif.) and eluted in 50 µl sterile water.

Macroarray Hybridization and Data Analysis:

Double stranded cDNA samples from control and stressed plants at different time points were labeled with DIG-dUTP by using a PCR DIG probe synthesis kit (Roche Applied Science, Penzberg, Germany). The labeled product was purified with a high pure PCR product purification kit (Roche).

Ten microliters of both the recovered DEF DNA samples and control samples were denatured with 10 µl denature solution (0.4 N sodium hydroxide, 0.01 M EDTA, pH=8.0) at 37° C. for 15 minutes and then neutralized with 10 µl 2 M ammonium acetate (pH=7.0).

Controls included a negative control, which contained sterile water but no DNA, and a housekeeping control, which contained only DNA fragments with the same expression level (constitutively expressed) throughout the control and the different days of the stressed plant. Denatured solutions of the DEF and controls, described above, were spotted onto a nylon membrane (115×76 mm) (Nalge Nunc International, Naperville, Ill.) with two replications using the Beckman BioMek® 2000 laboratory automation workstation (see, example method, Dilks et al. 2003; J Neurosci Methods. 123(1):47-54; herein incorporated by reference).

The controls were spotted in different sections of the membrane to compensate for variable background levels. Identical nylon arrays were prepared serially and then subjected to separate hybridization with labeled ds cDNA probes, including control and stressed probes. The hybridization and washing were performed by using DIG high prime DNA labeling and detection starter kit II (Roche). The luminescent signal on the membrane was exposed to Lumi-Film Chemiluminescent detection film (Roche).

The array image on the film was scanned and saved as an individual ".TIFF" file and analyzed with BIORAD® Quantity One Software 4.2.3 (Bio-Rad Laboratories, Hercules, Calif.). For each array image, the spots were delimitated with the same size circles, which could include 100% of the pixels in the spot. The average volume (=pixel intensity×area of the circled spot) of negative control spots on the array image was subtracted from the volume of each of the other spots to eliminate background effect.

The average volume of housekeeping control spots on the array image was used to normalize the spots of unidentified DEFs between array images. The ratio of the average volume of housekeeping spots between images was applied as a scaling factor for the volume of unknown DEF spots, which were compared to its counterpart between membranes to confirm the differential expression pattern.

DNA Fragment Sequencing and Sequence Analysis:

The DEFs were recovered from the polyacrylamide gel whose differential expression patterns were confirmed with macroarray analysis, cloned into pGEM-T easy vector (Promega), and transformed into JM109 component cells (Promega) by heat shock. Plasmid DNA was extracted from successful transformants using the Wizard plus SV minipreps DNA purification system (Promega), and plasmid inserts were sequenced using an ABI PRISM 3100 genetic analyzer (Applied Biosystems, Foster City, Calif.) at The Genomics Technology Support Facility (Michigan State University).

The sequences of the DEFs were searched against the AGI (Arabidopsis Genome Initiative) protein database using BLASTX (website address at world wide web.arabidopsis.org/Blast/). Additional analysis using BLASTX against the GenBank plant protein database and TBLASTX against the GenBank plant dbEST were performed for DEFs with zero matches or low similarity (E value greater than 1E-6) in AGI protein database. A tool of the "Blast 2 sequences", which can be found at: world wide web.ncbi.nlm.nih.gov/blast/b12seq/wblast2.cgi, was used for sequence comparisons, for example, see, Table 3 below.

C. Breeding Methods for Providing Plants of the Present Inventions.

1. Plants Used in Plant Breeding Methods:

A Fm plant (Fm1) was chosen as a founder plant from a Fm population collected in Morocco. This Fm population was adapted to the hot and dry summers of Northwest Africa (Borill et al. 1971, Cytologia 36:1-14; herein incorporated by reference). Another Fm plant line, Fm2, was obtained from a plant introduction, PI 283313, United States Department of Agriculture (USDA) germplasm database. Two Lp plant lines from elite turfgrass cultivars 'Citation II' (Lp1) and 'Calypso' (Lp2), respectively, were also used as founder plants. The initial parental crosses were made by Chen (1996, Ph.D dissertation, Univ. of Missouri-Columbia, Columbia, Mo.; herein incorporated by reference) and the scheme for producing initial backcross derivatives was presented by Chen and Sleper (1999, Crop Sci. 39:1676-16793; herein incorporated by reference) (see, for example, FIG. 10). Plants used during the development of the present inventions, included, but were not limited to, parental plants (Fm1, Lp1 and Lp2), two $F_1$ hybrids: a 4× $F_1$ (Fm1×Lp2) and a 3× $F_1$ (Lp2×Fm2), 13 backcross plants, and an amphidiploid (2n 6x=42) that was obtained from a triploid $F_1$ hybrid of Fm1×Lp1 by Chen (1996, Ph.D dissertation, University of Missouri-Columbia; herein incorporated by reference). Fm1 and Fm1 derived plants were used in developing the majority of plants of the present inventions. See, exemplary crossing schematic, FIG. 10.

2. Identifying Intergeneric Hybridization of *Festuca* Germplasm in *Lolium* Plants.

DNA Isolation:

Total plant genomic DNA samples were extracted from young growing leaves. Plant cells were lysed using the extraction buffer (0.1M Tris-HCl, 0.05M EDTA-Na, 0.25M NaCl, pH=8.0 and 0.04M dodecyl sulfate (SDS)). Potassium acetate (5M) was used for deproteinization and recovery of DNA. Nucleic acid was precipitated by isopropanol followed by RNase treatment to degrade the RNA. The DNA concentration was measured by spectrophotometer readings at 260 nm and the purity was determined by the ratio of the absorptions at 260 nm and 280 nm. DNA quality was checked by loading 100 ng DNA in a 1% agarose gel followed by electrophoresis at 72 V for 2 hours.

RAPD Screening Protocol:

DNA samples from plants, in particular progeny plants, were used as templates for RAPD analyses with these 41 polymorphic primers. Forty-one decamer RAPD oligonucleotides (see, Table 7) were synthesized using C and Y kits (Operon Technologies Inc., Alameda, Calif., and used in screening and detecting maximum polymorphism between the Fm and Lp parents and a $F_1$ hybrid. (See, for examples, Charmet et al. 1997, Theor. Appl. Genet. 94:1038-1046; Siffelova et al. 1997, Biologia Plantarum 40:183-192; all of which are herein incorporated by reference). A 25 µl RAPD reaction mixture contained 10 mM Tris-HCl (pH=8.3), 4 mM $MgCl_2$, 0.24 mM of each dNTP, 1.2 µM of primers, 30 ng of template DNA, and 1 U Taq DNA polymerase (Promega, Madison, Wis.). Amplification conditions were as follows: 3 pre-amplification cycles (94° C. for 1 mm, 35° C. for 1 mm and 72° C. for 2 mm). After initiation of the reaction, 35 amplification cycles were conducted (94° C. for 20 s, 40° C. for 20 s, and 72° C. for 2 mm). The last cycle was followed by 5 mm at 72° C. to ensure that primer extension reactions proceeded to completion. RAPD profiles were generated in 2% agarose gels with 0.003% ethidium bromide subjected to electrophoresis at 72 V for 3.5 hours. A 1 Kb ladder was used to mark the size of the fragments. RAPD images were obtained through an Eagle Eye II still video system V3.2 (Stratagene, La Jolla, Calif.).

SSR Screening Protocol:

Seventy-six tall fescue EST-SSR primer pairs (NFFA series) developed at the Samuel Roberts Noble Foundation (Saha et al. 2004, Theor. Appl. Genet. 109:783-791; herein incorporated by reference), and 32 Lp SSR primer pairs developed from ryegrass (Kubik et al. 2001, Crop Sci. 45:1565-1571; Jones et al. 2001, Theor. Appl. Genet. 102: 405-415; all of which are herein incorporated by reference) were tested on the Fm and Lp parents, then test plant materials, for example, hybrid progeny. The primer combinations that produced polymorphic bands between parents were utilized to test plant materials.

An ethidium bromide detection protocol was used for ryegrass and 19 tall fescue EST-SSR primer pairs and the silver staining protocol was used for screening of the remaining primer pairs. In the ethidium bromide detection protocol, 10 µl PCR reaction mixture contained 10 mM Tris-HCl (pH=8.3), 3 mM $MgCl_2$, 0.25 mM of each dNTP, 0.2 µM of forward and reverse primers, 10 ng of template DNA, and 1 U Taq polymerase (Gibco Invitrogene, Grand Island, N.Y.). PCR amplification was conducted in a PTC-100 programmable thermal controller (MJ Research, Waltham, Mass.). Amplification conditions were as follows: initial denaturation at 95° C. for 5 min., 40 amplification cycles [95° C. for 50 s, 42-approximately 60° C. (the optimum annealing temperature for each primer pair) for 50 s, and 72° C. for 90 s], and the final extension of the reaction at 72° C. for 10 min. SSR profiles were generated by running PCR products in a 6% non-denaturing polyacrylamide gel for 2.5 h at 350V. TBE buffer with 0.002% ethidium bromide filled in the positive node tank was prerun one hour for visualizing bands under UV light.

In a silver staining protocol, 20 ng of DNA was used as a template for each PCR reaction. Ten ul PCR reactions consisted of one U of AmpliTaq Gold® with GeneAmp PCR buffer II (Applied Biosystems/Roche, Branchburg, N.J.), 3 mM $MgCl_2$, 0.2 mM of dNTPs, and 0.2 µM of each primer. PCR amplification conditions were same as in ethidium bromide detection protocol. PCR products were resolved on 6% polyacrylamide denaturing gels (Gel Mix 6, Invitrogen Life Technologies). Gels were silver stained using Silver Sequence Kit (Promega, Madison, Wis.) for SSR band detection.

Data Analysis:

Intense (dark) and repeatable bands in RAPD profiles were scored as 0 and 1 for absence and presence, respectively. In SSR profiles, the intense bands within the expected size range were scored as 0 and 1 for absence and presence, respectively. The Fm genome introgression levels in the progeny from SSR data equaled the number of loci showing Fm alleles in the backcross individual divided by total number of polymorphic SSR loci. Similarly, the Fm genome introgression levels in the progeny from RAPD data were calculated as follows: the number of Fm-specific markers present in the backcross individual/total number of the Fm-specific markers. Parental Fm/Lp genome specific band ratios (Fm/Lp genome ratio) of the Fm-Lp hybrids and backcross progeny were calculated as the ratio of the percentage of Fm-specific-bands to that of Lp-specific bands with an assumption that all markers were randomly dispersed in the whole genome. The correlation analysis of genome introgression levels between SSR and RAPD data was conducted with SAS system V8 (SAS Institute, Cary, N.C.). A SAS Proc Corr procedure was run to obtain the correlation coefficient and the P value. Dice coefficient (Dice et al., 1945 Ecology 26:297-302; herein incorporated by reference) similarity matrices for both SSR and RAPD data were calculated by running similarity for the qualitative data module in numerical taxonomy and multivariate analysis system (NTSYSpc version 2.1, Exeter software, Setauket, N.Y.; herein incorporated by reference).

D. Evaluating Progeny Plants and Identification of Superior Drought Resistant Hybrid Plants.

Plants:

Nineteen genotypes of plants were evaluated that included Atlas Fescue plants originally collected from Morocco; two perennial ryegrass cultivars 'Citation II' (Lp1) and 'Calypso' (Lp2); two $F_1$ hybrids from crosses of Atlas fescue and perennial ryegrass; 12 second-generation backcross progeny; an amphidiploid generated from a triploid $F_1$ hybrid by colchicine treatment; and a tall fescue cultivar, Kentucky 31, which was used as a drought tolerant control plant. The plants were bred using methods described above.

A single tiller of each plant was propagated vegetatively in the greenhouse to provide experimental plant material. From each plant genotype, two tillers were transplanted into each of six PVC tubes (100 cm deep×34 cm in diameter) that was filled with 11.8 kg of a mixed soil substrate, 85% sand and 15% field soil of the type recommended for use in athletic fields. Prior to planting, a heavy duty plastic sleeve was placed inside each tube, between the inner surface and the substrate, to facilitate removing the root system from the tube at the end of the experiment. Transplanted tillers were established by growing for 15 weeks in the greenhouse. Grass plants were clipped to leave a 7.5 cm stubble every week and irrigated daily. The greenhouse temperature was 25±3° C., with an average photoperiod of 13 hours.

A pre-conditioning drought was applied by withholding water for 2 weeks. Plants were then irrigated daily for one week and then trimmed to the same height (around 8 cm). Three tubes of each genotype were randomly allocated to the drought treatment; the other three were allocated to the irrigated control.

Drought stress (treatment) was imposed by withholding water progressively from plants in the drought treatment group by supplying 200 ml (up to 100% soil capacity in the tube), 150 ml, 100 ml, and 50 ml water weekly in the first four weeks respectively and then stopping irrigation completely during the remaining 12-week drought period. The plants in the control treatment were irrigated regularly during this period. The PVC tubes were re-randomized weekly during this drought period to minimize effects of possible environmental gradients within the greenhouse Measurements of physiological parameters are described previously (see, Wang et al., (2003) Crop Sci. 43:2154-2161; herein incorporated in its entirety by reference).

Eigenvector Diagrams Generated by Principle Component Analysis (PCA):

Principle component analysis (PCA) was conducted by using the numerical taxonomy and multivariate analysis system (NTSYSpc version 2.1, Exeter Software, Setauket, N.Y.). A correlation matrix was calculated from a standardized data matrix that included 14 wks of leaf elongation, 12 wks of leaf water content, and 14 wks of leaf water potential.

Eigenvalues and eigenvectors (the principal component axes) of the matrix were computed using EIGEN module. Eigenvectors were plotted using the Matrix plot module. The PROJ module was used to project the genotypes onto the principal component axes and displayed by the Mod3D plot module. Analysis of variance (ANOVA) was conducted by Proc mixed model in the SAS program (SAS Institute, Inc., 2003). Relationships between parameters were fitted to appropriate nonlinear regression models using Microsoft Office Excel (Microsoft Co., 2002).

Example II

*Festuca mairei* Plants Show Superior Drought Resistance Over Plants from Other *Festuca* Species in Response to Drought Stress Treatment Turfgrass plant cultivars vary in drought resistance (White et al., 1992, Crop Sci. 32: 25 1-256; Carrow, 1996, Crop Sci. 36: 687-694; all of which are herein incorporated by reference). Of the grass plants, tall fescue is recognized for its exceptional drought tolerance (Norris and Thomas, 1982, J. Agric. Sci. Camb. 98: 623-628; Fry and Butler, 1989, Crop Sci. 29:1536-1541; all of which are herein incorporated by reference). Tall fescue originated from North Africa and is now a popular turfgrass and forage grass plant species that grows in cool and transition zone regions. In particular, the tall fescue cultivars of *F. arundinacea* Schreb. named 'Kentucky 31' and 'Falcon II' were previously identified as having good drought tolerance (Huang and Gao, 1999, HortScience 34: 897-901; Huang, 2001, HortScience 36:148-152; all of which are herein incorporated by reference). 'Barolex' is a new tall fescue forage-type cultivar and its comparative level of drought tolerance was unknown. Atlas fescue species (*Festuca mairei*) was originally found restricted to the Atlas Mountain ranges of northwest Africa. There were no reports of relative drought tolerance capabilities of Atlas fescue, although it is known for it's xerophytic adaptation to survive long, dry summers in its Mediterranean climate (Marlatt et al., 1997, Investigations on xerophytic *Festuca* species from Morocco and their associated endophytes, In: Bacon, G. W.; Hill, N. S. ed. Neotyphodium/grass interactions, New York, Plenum Pres, p. 73-75; herein incorporated by reference).

Morphological and physiological drought responses of these Fescue plants were compared, in particular leaf elongation, leaf water content, leaf water potential, root biomass and root length, for determining the relative capability of Fescue plants to provide germplasm associated with drought resistance for providing drought tolerance to plants in plant breeding programs.

The inventor shows herein that when the drought resistance of *Festuca mairei* (Fm) plants was compared to other species of *Festuca* plants, the Fm plants retained normal levels of leaf water content while the other species of *Festuca* rapidly dehydrated over the 12 week drought period. These comparisons were made on plants grown under greenhouse conditions and deprived of irrigation water. Thus unlike the large percentage of leaf water loss in Falcon II and Barolex under drought conditions, the *Festuca mairei* plants retained leaf water content and remained green. See, for example, FIG. 1. The results for the other parameters that demonstrate higher levels of drought resistance in Atlas plants are described below.

Soil Water Content and Leaf Water Potential:

At full water capacity, SWC was 9.33%, after which it declined significantly (P<0.001) starting at week 2 of the drought treatment (FIG. 1). The rate of soil water depletion was similar among the grasses except for that of Atlas fescue, which was slower. Specifically, SWC of Atlas fescue was significantly higher than the other entries from week 4 to week 8, indicating that it extracted less soil water.

The imposed drought stress had a significant effect on $\Psi w$, an indicator of plant stress, of the grasses studied. In irrigated plants, $\Psi w$ was similar (P=0.086) among the grasses, and remained relatively high across the 12-week period. In contrast, $\Psi w$ of stressed plants showed significant differences from the irrigated ones after 4 (Falcon II), 5 (Kentucky 31), 6 (Barolex), and 8 (Atlas fescue) weeks. Further, $\Psi w$ of stressed plants decreased differently among the four grasses. Atlas fescue maintained $\Psi w$ at the level of control plants longer into the drought period than did the three cultivars. Variation of $\Psi w$ was highly dependent on SWC with a similar pattern for the four grasses, i.e., $\Psi w$ gradually decreased but remained below −1 Mpa as SWC decreased from 9.33 to about 2.8%. The results reflected that soil water was readily available and kept sufficient for the plants in the SWC range from 9.33 to 2.8%. The critical SWC of 2.8% was basically in agreement with the threshold of SWC for initial stomatal closure due to drought stress in tobacco (*Nicotiana tabacum* L.) (Riga and Vartanian, 1999, Australian Journal of Plant Physiology 26(3) 211-220; herein incorporated by reference). The three cultivars showed a more rapid decrease in $\Psi w$ as the soil dried below a SWC of 1.5-1.8%, whereas $\Psi w$ of Atlas fescue did not decrease steeply until SWC was near 1%. This shows that Atlas fescue is less sensitive to soil water deficits than the other Fescue cultivars.

Leaf Elongation Rate:

Atlas fescue showed a lower LE than Barolex and Kentucky 31 in the first week. As the stress gradually increased there was a negative effect on LE of all grasses (P<0.001) when compared with the control. However, the mean LERs were similar for irrigated Atlas fescue, Barolex, and Kentucky 31 across the 12-week period, and significantly greater than that of Falcon II. These results revealed that irrigated Falcon II grew relatively slower than other grasses, and Atlas fescue initially had a low LE but it increased in later weeks during the drought stress period.

Between weeks 8 and 10, LE of the irrigated plants was greater than during the first 7 weeks of the drought treatment period. At week 10, LE of irrigated plants of Kentucky 31 dropped dramatically, when the plants started to bloom and vegetative growth was switched to reproductive growth. In drought-treated plants, the average LB for four grasses across the whole drought stress period was not significantly different (P=0.5078). For the three tall fescue cultivars, the LE of stressed plants started to decrease to below the level of irrigated plants at week 5 or 6 of the stress treatment, whereas for Atlas fescue, LE started to decrease later, at week 7 of stress. The LE of drought-treated plants in Barolex and Falcon II ceased after 9 weeks of treatment, while in Atlas fescue and Kentucky-31 LB lasted longer, up to week 10.

The relation between LE and SWC was fitted to a second order polynomial function. When SWC was near full soil capacity (8-9.33%), the LE of Barolex and Kentucky 31 were higher than those of Falcon II and Atlas fescue, indicating that Barolex and Kentucky 31 were growing faster at a high SWC. As the SWC was declining, LE decreased differently among the four grasses. Falcon II and Atlas fescue showed a relatively slow decreasing rate compared with Barolex and Kentucky 31, because the slopes of trend line for Falcon II and Atlas fescue were less steep, suggesting that the growth of Falcon II and Atlas fescue was less sensitive to the declining SWC.

The LE responded to the decreasing $\Psi w$ following a polynomial function. As $\Psi w$ was declining and becoming more negative, the LE decreased for all grasses, but at different rates. The decrease in rate of LE of Atlas fescue and Falcon II was less than that of Barolex and Kentucky 31 indicating that, on a relative basis, LEs of Atlas fescue and Falcon II were less sensitive to the increasing severity of drought stress.

Leaf Water Content:

Drought stress treatment had a significant (P<0.001) effect on LWC of the grasses. The LWC of irrigated plants remained constant at about 87.7% during the whole experimental period. In plants subjected to drought, LWC decreased differently among the four grasses. For the tall fescue cultivars, LWC of stressed plants was at the level of irrigated plants during the first 3 or 4 weeks of growth, whereas for Atlas fescue, LWC of stressed plants maintained the same level as irrigated plants up to 8 weeks. The LWC of Atlas fescue was significantly higher than that of the cultivars between week 6 and week 9 in the drought stress treatment. The results imply that Atlas fescue may accumulate or conserve water in leaf tissue and maintain turgor as a stress avoidance mechanism through adapted leaf and root morphology.

The relationship of LWC in response to SWC showed three stages. When SWC was high (8-9.33%), LWC of all grasses was maintained at a high level (between 80 and 90%). In the second stage, as SWC decreased from 8% to about 4%, LWC showed a slightly increasing trend, more so in Atlas fescue than the cultivars. In the third stage, when the SWC was decreasing from 4% to near 0%, the LWC decreased dramatically for all the grasses. It was notable, however, that with SWC was decreasing from 6% to 2%, a medium drought stress status, LWC of Atlas fescue remained higher than that of the other grasses, and then decreased most rapidly.

The association of LWC with $\Psi w$ was described by a polynomial function. As $\Psi w$ became more negative, specifically between −1 and −2.5 MPa, the LWC of grasses declined, but at a much slower rate for Atlas fescue than the cultivars, especially between $\Psi w$ of −1.2 and −2.4 Mpa. This again suggested that Atlas fescue had an adaptation ability to accumulate or conserve water in leaf tissue under drought stress.

Root Length and Biomass:

The RL among grasses ranged from 115 to 132 cm and varied significantly (P=0.034). Barolex had the longest root system, while Kentucky 31 had the shortest. The RL of Falcon II was negatively affected by the drought treatment, whereas there was no significant difference in RL between irrigated and drought-treated plants of Atlas fescue, Barolex, and Kentucky 31. No significant difference was found in RM among the grasses when the irrigated and drought stress treatments were avenged (P=0.072). However, the drought treatment had a significant (P=0.003) effect on RM. Stressed plants of Atlas fescue, Barolex, and Falcon had significantly less RM than did their irrigated controls, but not for Kentucky 31). The results suggested that control plants of Barolex and Atlas fescue with longer roots might be more adaptive to drought stress than Kentucky 31. However, the RM of Kentucky 31 was not reduced by severe drought stress suggesting that Kentucky 31 may tolerate the drought stress through maintenance of viable roots capable of extracting available water, even though it had a shorter root. In summary, drought stress reduced LE, LWC, $\Psi$w, root biomass, and root length of the grasses. Thus Festuca species avoid drought stress through changes in leaf and root morphology and through osmotic adjustment to maintain sufficient turgor pressure in the growing zone for leaf elongation.

Unlike annual plants that escape drought by maturing before stress becomes severe, perennial grasses do not escape drought completely by early flowering. Indeed, a few of the control plants but no drought stressed plants flowered indicating that plant maturity was delayed and/or reproductive growth was inhibited by the imposed drought stress. Further, the four grasses maintained leaf elongation until a very low SWC (1.2%), showing that active growth rather than dormancy occurred during the drought stress period. However, while the leaves of the grasses rolled initially, as SWC decreased further, the leaf tip showed firing and lower leaves became bleached. These symptoms show that these grasses employ an escape strategy to reduce the transpiration surface area and close stomata to limit plant water loss similar to tobacco plants (Nicotiana tabacum L.) (Riga and Vartanian, 1999).

Additionally, in contrast to previous studies on drought stress responses where the root system was chosen as a selection trait in breeding programs to improve drought tolerance of fescue (Torvert et al., 1990, Appl. Agric. Res. 5: 18 1-187; herein incorporated by reference), the results described herein show the benefits of using leaf water content measurements in breeding methods of the present inventions. In particular, LE measured weekly during the drought stress period was a major indicator of the status of plant response to drought. Cell expansion was acknowledged as the most sensitive trait in plants (Boyer, 1988, Physiol. Plant. 73: 311-316; herein incorporated by reference) and is reduced by drought before other physiological processes (Wardlaw, 1969, Aust. J. Biol. Sci. 22: 1-16; herein incorporated by reference). In the present studies LE of Atlas fescue and Kentucky 31 declined significantly one week earlier than $\Psi$w, which was previously shown to be an effective measurement of the maximum soil water potential available to roots (Tardieu and Simonneau, 1998, J. Exp. Bot. 49: 419-432; herein incorporated by reference). These results confirmed that LE is a sensitive parameter for drought tolerance evaluation in plants. In addition, it is difficult to make measurements of $\Psi$w on severely drought-stressed leaves, however LE is measured at any time and water condition.

Further, the slower decrease in LE, LWC, and $\Psi$w for Atlas fescue during the drought-stress period demonstrated its greater capability for drought tolerance and the value for introgressing this characteristic into a plant breeding program.

Therefore, Festuca mairei plants demonstrated a greater capability to resist drought, in other words a higher level of drought resistance, than the Festuca species and their representative commercial plant cultivars that were previously used for providing drought tolerant germplasm to grass plants, including Lolium species.

Example III

Identifying Fm Germplasm in Festuca mairei Plants Associated with Drought Stress See, for Example, Wang et al., 2005, Molecular Biotechnology, 29(3):211-220; Herein Incorporated by Reference in its Entirety A. Plant Performance During Nine Days of Extreme Drought Stress.

A complete drought response was completed in nine days. Of the nine days, eight days were actual drought stress plus the day before withholding irrigation water, was considered to be a whole drought stress period because it covered the range of dynamic changes of the plants responding to drought stress, as described below.

Figure 2:
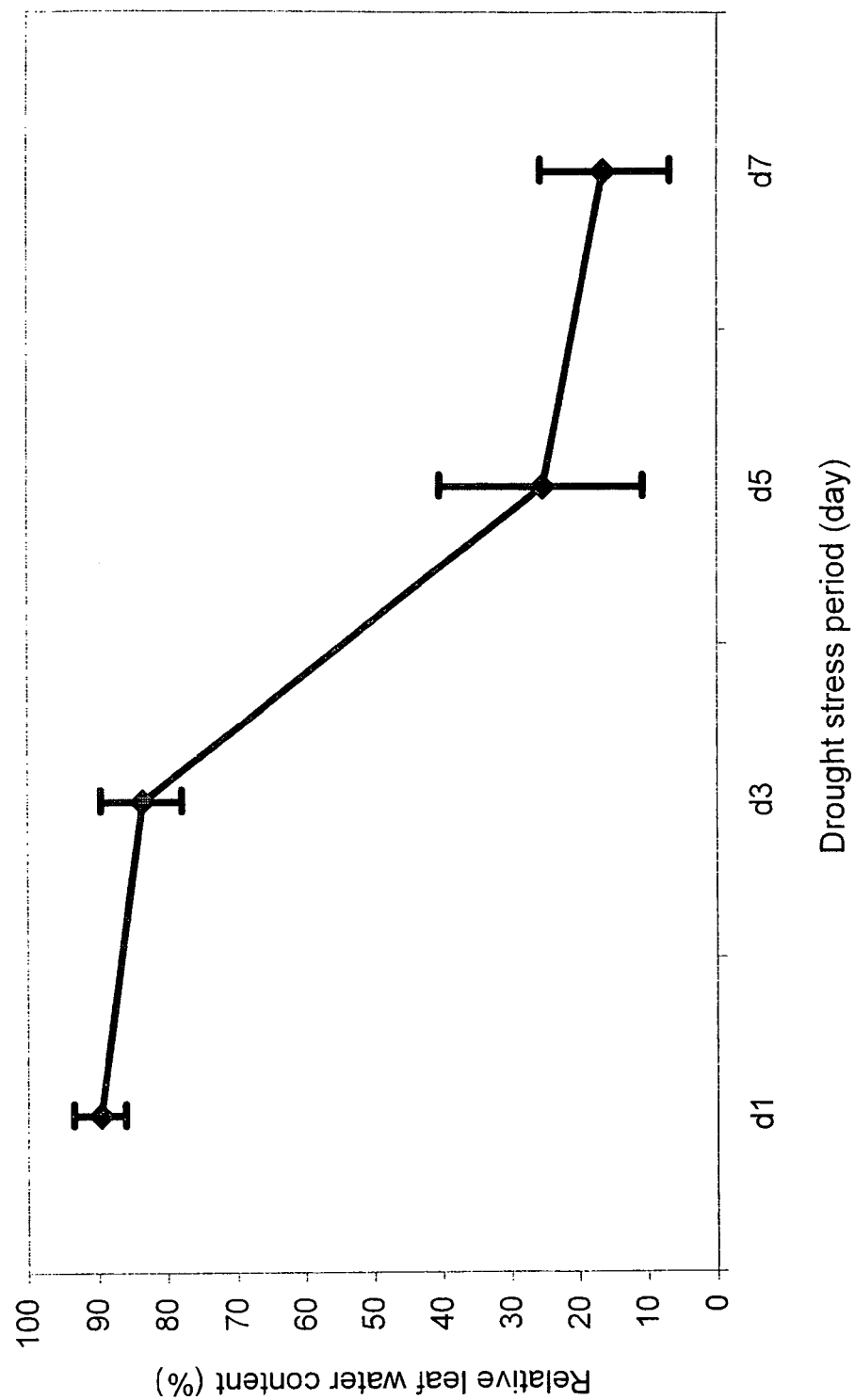
FIG. 2 shows an exemplary chart of relative leaf water content of *Festuca mairei* during an extreme drought stress period.

During the nine days of treatment, control F. mairei plants maintained green and survived throughout the stress treatment period. The F. mairei plants under stress remained green during the first three days after water deprivation. However, on the 4th day after water deprivation the treated plants began discoloring and firing, an indication of tissue injury due to stress. Specifically, the RWC of leaves from the stressed plants decreased dramatically from 83% to 26% between the 3rd and 5th day of drought stress (FIG. 2).

On the 8th day of drought stress, the leaves of the stressed plants were completely fired with a RWC of 17%. Therefore, the 4th day under these extreme stress conditions was critical for the evaluation of information for identifying phenotypical and physiological changes significant of water deprivation.

B. cDNA-AFLP Analysis.

The inventor noticed that in the majority of previous drought tolerance studies, a large number of identified genes, transcripts and proteins related to drought were induced by stress (inducible) or up-regulated. However, there were few reported down-regulated genes and no transient or other types of altered genes reported that would contribute to drought adaptation. Further, low numbers of time points during the onset and duration of drought stress were reported, for example, one or two time-points during stress periods were compared with the control, especially by microarray analysis. Therefore, some genes, such as transiently expressed genes, and up or down regulated genes, would not be identified. However, because the plant response to stress is a complicated procedure, down-regulation or other types of regulation may also play important roles in drought response or even drought tolerance.

The inventor found during the development of the present inventions, that investigation of the systemic and dynamic changes of gene expression on a daily basis during induction of stress provided more complete information for understanding the molecular mechanism of stress response. Thus in contrast to previous studies, four different differential expression patterns were detected by cDNA-AFLP analysis as described herein, even though the third and fourth patterns, transient and up-then-down expression, was not abundant. Further study on genes with these four differential expression patterns, further including spatial and temporal regulation patterns, should lead to a programmed control of the drought stress response, and thus the inventor contemplates regulating a stress response mechanism at the gene regulation level. The cDNA-AFLP technique used by the inventor not only provided an approach to generate genomic sequence information and functional analysis but also served as a powerful tool for the identification of genes with additional kinds of differential expression patterns for a plant's stress response.

Further, in contrast to other studies, the inventor obtained information during the development of the present inventions, which covered the whole dynamic change of the plant responding to the stress. This dynamic change was covered in the nine days (with three later days as reference) during a drought stress treatment of complete water depravation as described below.

C. A Functional Approach to Identify Stress Response Genes:

Control Plants: DEFs induced by regular plant development and any changes of greenhouse conditions during the drought stress treatment were investigated by cDNA-AFLP analysis performed on the control plants of *F. mairei* over nine days using four randomly picked primer combinations (NspI-CC/TaqI-TC, NspI-TG/TaqI-GT, NspI-TG/TaqI-CC, and NspI-TC/TaqI-AG, see, Table 1A). DEFs were not detected across the nine days in control plants (FIG. 3a), which suggested that both plant development and/or greenhouse conditions did not affect gene expression in *F. mairei* plants during the application of the drought stress treatment.

Figure 3B:
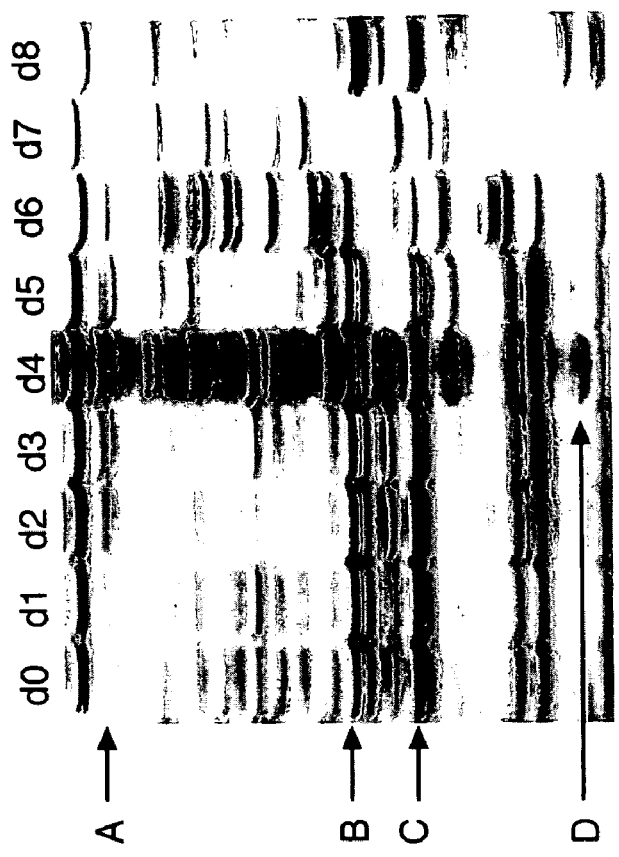
FIG. 3 shows an exemplary comparison of cDNA-AFLP profiles of *Festuca mairei* plants under specific environmental growth conditions: a: cDNA-AFLP (NspI-CC/TaqI-TC) profile on treatment control plants. Transcript derived fragments (TEFs) were constitutively expressed at the same level. b: cDNA-AFLP (NspI-TC/TaqI-TG) profile on stress treated plants: A, up-regulated DEF from day 0 to day 4; B, constitutively expressed fragment from day 0 to day 5; C, down-regulated DEF from day 0 to day 5; D, transiently expressed DEF on day 4. Stressed leaf samples of day 6, 7 and 8 were did not yield sufficient mRNA for evaluation, likely due to the dry and highly fibrous leaf condition. Therefore, DEFs were scored based on the first six lanes of the cDNA-AFLP profile of stress treated plants while the last three lanes were used as reference.
Figure 3A:
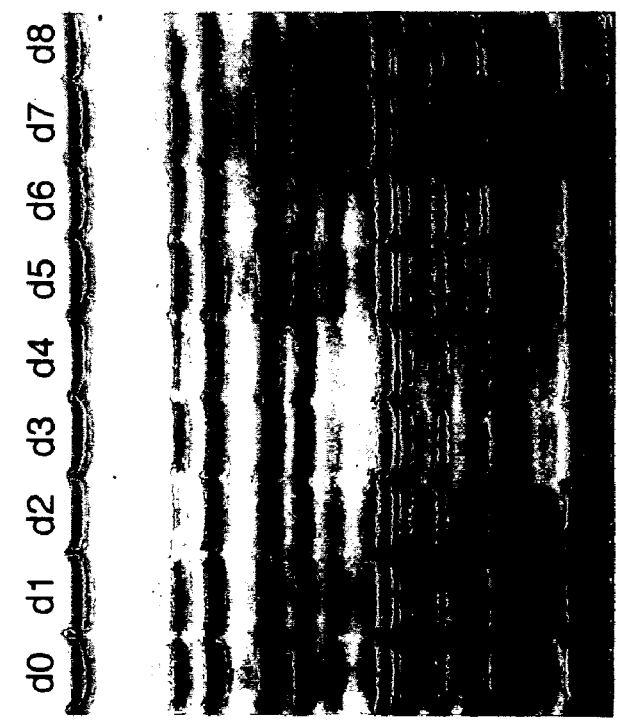

Drought Stressed Plants: cDNA-AFLP analysis was conducted using all of the 128 primer combinations over nine days of the stressed *F. mairei* plants and revealed 11,346 transcript derived fragments (TDFs) with an average of 89 fragments obtained per primer pair. The size of the observed fragments ranged from 50 to 1000 bp. Of these TDFs, 464 fragments (4.1%) were identified as being differentially expressed across the nine days during the drought stress treatment, indicating the gene expression had been altered by the drought conditions (FIG. 3b).

The expression pattern of these DEFs included up-regulated (138, 29.7%), down-regulated (252, 54.3%), transient-expressed (57, 12.3%), and up-then-down-regulated (17, 3.7%) (FIG. 4). Of these 464 DEFs, 434 (94%) fragments were recovered from acrylamide gel and isolated as genes potentially related with plant response to drought stress. Thus the inventor provided isolated nucleic acids for SEQ ID NOs: 1-39 and 93-216.

Figure 6:
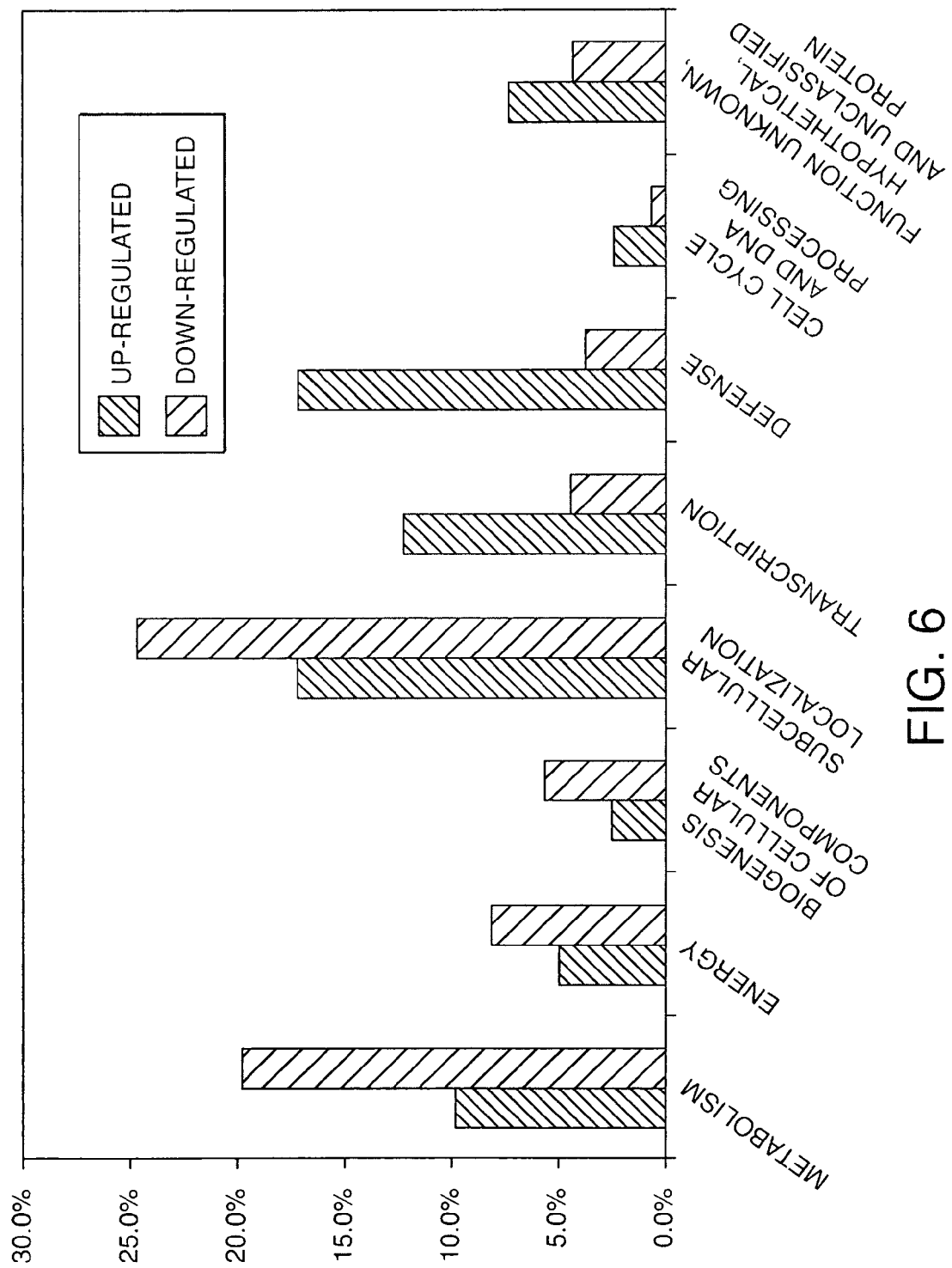
FIG. 6 shows an exemplary comparison of functional categories between up-regulated and down-regulated differentially expressed fragments (DEFs) during drought stress treatment in *Festuca mairei*. Each DEF was searched against the GenBank plant protein database by BLASTX. The functional category was assigned based on function classification criteria on the website of the Munich Information Center for Protein Sequences (MIPS) (website address at mips.gsf.de).

Upon analysis, the majority of the identified proteins fell into one or more statistical significant functional category, thus each of those categories were counted in the analysis. In comparison between the functional categories of the up-regulated and the down-regulated DEFs (FIG. 6), the down-regulated genes were primarily involved in metabolism and cellular biogenesis, such that they were found to be nearly twice that of the up-regulated DEFs. On the other hand, more than two times the amounts of the up-regulated DEFs were involved in transcription, defense, cell cycle and DNA processing compared to down-regulated DEFs.

These results generally indicated that during drought stress there was a decrease in metabolic function and biogenesis of cellular components during the plants degenerative drying (and dying) process. Up-regulated genes were associated with the cell cycle and DNA synthesis that would be involved with increasing activity of growth particularly in specific guard cells that function in stress defense. However, the transiently expressed DEFs were primarily involved in subcellular localization, defense, and heavy metal carriers for transport. The inventor contemplates that the TEFs function to meet the temporary need for turning on and/or regulating sets of genes that are expressed in stress defense, transport and subcellular localization during a plant response to drought stress. In contrast, the up-then-down regulated DEFs were mostly involved in transport, subcellular localization, and energy. Thus the inventor contemplated that genes necessary for electron/hydrogen transport, subcellular localization, and photosynthesis were first stimulated by a drought stress signal, and then inactivated by the continued or severe stress conditions leading to death. Thus the inventor contemplated that the plant system appeared to save energy while at the same time providing for new gene transcription, in particular transcription of genes related to stress defense.

Figure 5B:
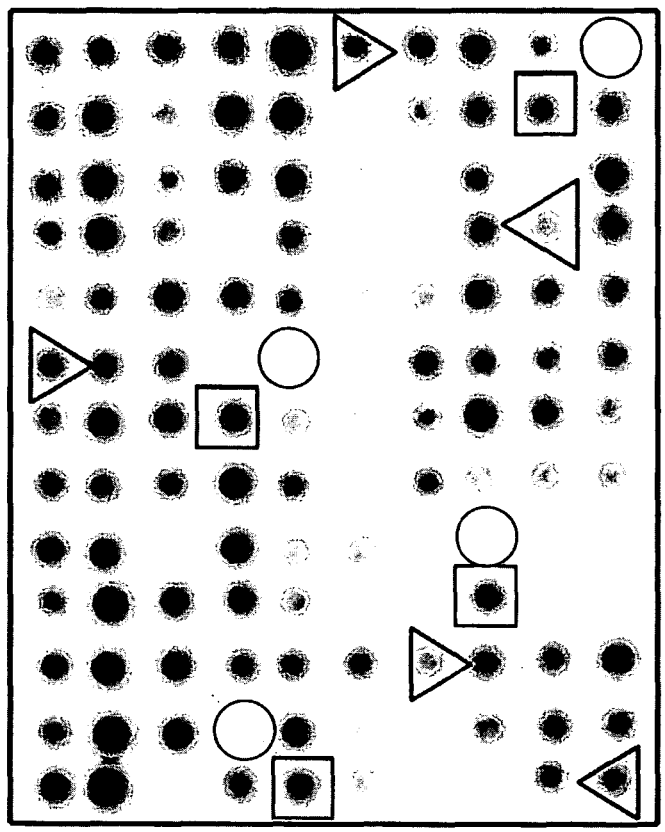
FIG. 5 shows an exemplary portion of a hybridized macroarray. The differentially expressed fragments (DEFs) from cDNA-AFLP were arrayed in duplicate on nylon membranes A and B. Membranes were separately hybridized to treatment control (A) and 5 days stress treated (B) cDNA probes, respectively. Spots in the squares indicated the housekeeping controls used for normalization between arrays before comparing gene expression). Spots in the circles indicated the negative controls used to eliminate the background effect. Spots in the up-triangles are examples of up-regulated DEFs. Spots in the down-triangles are examples of down-regulated DEFs.
Figure 5A:
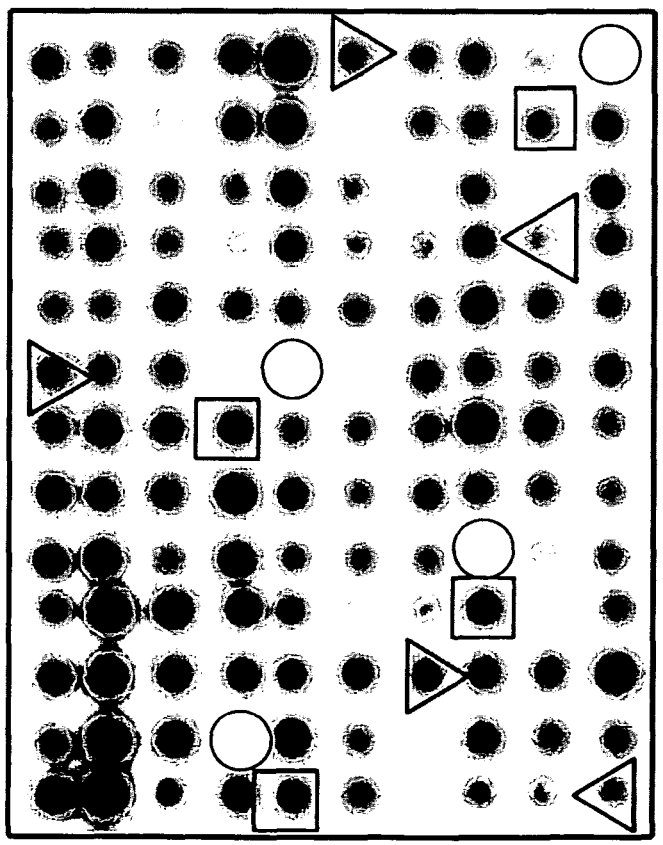

D. Macroarray Hybridization Analysis:

In addition to 13 positive and 13 negative nucleic acid controls, 406 samples of 434 recovered DEFs were printed on a membrane with two replications. Twenty-eight DEFs with small sizes of less than 100 bp were not included in the macroarray analysis. The dot intensity volume of two or three identical membrane arrays hybridized with cDNA probes from different days respectively were compared for confirmation of the differential expression pattern of the 406 DEFs (as described herein). FIG. 5 shows an exemplary image of a portion of the hybridized macroarray. The comparison results revealed that 54 of 128 (42.2%) up-regulated, 97 of 210 (46.2%) down-regulated, 14 of 51 (27.5%) transiently expressed, and 6 of 17 (35.3%) up-then-down regulated DEFs showed a consistent differential expression pattern. In total, the expression pattern of 171 (42.1%) of DEFs were confirmed. These 171 DEFs were cloned as drought responsive gene fragments also referred to herein as preferred Fm germplasm.

After comparing cDNA-AFLP results with microarray results, 42% of DEFs were considered to be consistently expressed by plants. The inconsistency between the two techniques could be due to (1) the subjective evaluation on the DEF in the cDNA-AFLP gel; or (2) the different macroarray hybridization intensities and or background between the membranes compared; or (3) possible cross hybridization of closely related sequences in macroarray; and/or (4) low expression genes in the probe for macroarray hybridization (Miller et al., 2002, BioTechniques 32:620-625; herein incorporated by reference). Therefore, the inventor excluded more than half (58%) of the DEF from subsequent sequence analysis. Additionally, a few of the drought inducible DEFs identified by cDNA-AFLP coupled with macroarray as described herein, were previously reported as stress-inducible genes in other species. These discoveries showed that methods of the present inventions for the analysis system functioned properly to discover stress-inducible genes of plants.

E. DEF Sequence Analysis and Assignment of Functional Category:

One hundred seventy-one DEFs were sequenced and an expected size sequence was obtained for 166 of these sequences. Of the 166 sequences, three pairs of fragments showed above 98% similarity to each other after sequence alignment. Therefore one of each pair was excluded from further analysis, for 163 sequences. Of the 163 sequences, 92 were down-regulated, 50 were up-regulated, 15 were transiently expressed, and 6 were up-then-down-regulated (for example, Tables 3-6). One hundred twenty-four sequences were deposited to the GenBank EST database with accession numbers of DW248995 through DW249118 (SEQ ID NOs: 93-216).

BLASTX analysis was conducted against the GenBank protein database for SEQ ID NOs:1-39 and 93-216. The results revealed that 101 DEFs (62.0%) showed significant homology to protein sequences in the database (E value less than 1E-6). The other 62 DEFs (38.0%) showed zero matches (no hits found) or no significant homology (E value higher than 1E-6). When the entire GenBank EST database was screened for the presence of sequences similar to the 62 DEFs (TBLASTX analysis), 23 DEFs showed statistically significant degrees of similarity to the public available ESTs. The remaining 39 DEFs were defined as novel sequences (SEQ ID NOs:1-39), which are not identified in other organisms. Translation of SEQ ID NOs:1-39 into amino acid sequences SEQ ID NOs:40-91 (FIG. 8) was done via ExPASY (at webite ca.expasy.org/tools/dna.html. For several sequences, more than one predicted amino acid sequence was identified according to different read frames, and a few were not read completely through because of a stop codon.

The 39 novel DEFs included 13 down-regulated, 6 transiently expressed, and 20 up-regulated sequences. Therefore, 40% of the 50 up-regulated, 15 transiently expressed DEFs respectively and 14.1% of the 92 down-regulated DEFs were found to be novel in the genome of *F. mairei* plants under drought stress treatment.

The predicted function for the 101 DEFs was subdivided into 17 functional categories while 4.8% of these DEFs were functionally unknown, hypothetical or an unclassified protein based on function classification criteria defined at the website of MPS (Munich Information Center for Protein Sequences) (hypertext transfer protocol site: mips.gsf.de) (see, Table 2).

TABLE 2

Distribution of the differentially expressed fragments (DEFs) during drought stress cycle in *F. mairei* by functional categories. Classification was performed for 101 DEFs with strong statistical similarity to GenBank plant protein sequence (E values lower than 1.00E−06) by BLASTX search. The functional category was assigned based on function classification criteria in the website of Munich Information Center for Protein Sequences (MIPS) (hypertext transfer protocol site: mips.gsf.de).

| Function category | In general (%) | Up-regulated (%) | Down-regulated (%) | Transiently expressed (%) | Up-then down regulated (%) |
|---|---|---|---|---|---|
| Metabolism | 16.45 | 9.76 | 19.63 | 9.09 | 6.25 |
| Energy | 7.36 | 4.88 | 7.98 | 0.00 | 12.5 |
| Biogenesis of cellular components | 4.76 | 2.44 | 5.52 | 0.00 | 6.25 |
| Subcellular localization | 22.94 | 17.07 | 24.54 | 27.27 | 18.75 |
| Transport | 10.39 | 9.76 | 9.20 | 9.09 | 25 |
| Transcription | 5.19 | 12.20 | 4.29 | 0.00 | 0 |
| Signal transduction | 2.60 | 0.00 | 3.07 | 0.00 | 6.25 |
| Interaction with the cellular environment | 3.90 | 4.88 | 3.68 | 9.09 | 0 |
| Protein synthesis | 1.73 | 2.44 | 1.84 | 0.00 | 0 |
| Protein with binding function | 5.63 | 4.88 | 4.91 | 18.18 | 6.25 |
| Defense | 6.93 | 17.07 | 3.68 | 18.18 | 6.25 |
| Development | 2.16 | 2.44 | 2.45 | 0.00 | 0 |
| Cell fate | 1.30 | 2.44 | 1.23 | 0.00 | 0 |
| Cell cycle and DNA processing | 0.87 | 2.44 | 0.61 | 0.00 | 0 |
| Protein fate | 2.16 | 0.00 | 2.45 | 0.00 | 6.25 |
| Cell type differentiation | 0.43 | 0.00 | 0.00 | 9.0 | 9 0 |
| Protein activity regulation | 0.43 | 0.00 | 0.61 | 0.0 | 0 0 |
| Function unknown, hypothetical, and unclassified protein | 4.76 | 7.32 | 4.29 | 0.00 | 6.25 |

Comparing the functional categories between up-regulated and down-regulated DFEs (FIG. 7 and Tables 3 and 4), the inventor found that down-regulated genes involved in metabolism and cellular biogenesis were nearly twice of the up-regulated. On the other hand, more than two times of the percentage of up-regulated DEF was involved in transcription, defense, and cell cycle and DNA processing compared to down-regulated DEF. The results reflected that during the drought stress generally more metabolic function and biogenesis of cellular components in the plant were under degenerative processes. The plant system seemed to save the energy for new genes transcription and stress defense. More genes involved in cell cycle and DNA synthesis that were up-regulated may suggest the increasing activity of growth in some specific guard cell for stress defense. The transiently expressed DEFs were basically involved in subcellular localization, defense, or acted as heavy metal carrier for transport reflecting the temporary needs for sets of gene in defense, transport and subcellular localization during plant response to drought. The up-then-down regulated DEFs were primarily involved in transport, subcellular localization, and energy indicating that some genes for electron-hydrogen transport, subcellular localization, and photosynthesis were stimulated by drought stress signal firstly and then inactivated by the continued or severe stress.

F. Drought Inducible Genes:

Functional analyses of the stress-inducible genes are important for manipulation of molecular mechanisms of stress response and for stress tolerance improvement of crops. At least 200 drought inducible genes were reported in plants (Seki et al., 2002, Plant J. 30:279-292, Ozturk et al., 2002, Plant Mol. Biol. 48: 55 1-573; all of which are herein incorporated by reference), and some were transferred successfully into several crops to improve the stress tolerance of plants (Bajaj et al., 1999, Molecular Breeding 5: 493-503; herein incorporated by reference). However, because of differences between various crop plant species which are reflected in their germplasm, and the need for further improvement in specific types of stress tolerance, such as drought tolerance, the identification of additional drought-inducible genes would provide improved drought resistant plants and provide a larger picture of the genes involved in stress tolerance and cis-acting promoter elements that function in drought specific gene expression (Seki et al., 2001, Plant Cell. 13: 61-72; herein incorporated by reference).

During the development of the present inventions, 50 drought inducible gene fragments were identified from the drought adaptive monocot plant, F. mairei. 22 (44%) had hits with significant similarity in the protein database and were assigned functions. Several of them have been reported as up-regulated by stress in Arabidopsis such as zinc finger and MYB family transcription factors, raffinose synthases and trehalose-6-phosphate synthase, heat-shock protein, auxin-regulated protein, etc. (Seki et al., 2002, Plant J. 30:279-292; herein incorporated by reference). The remaining 28 (56%) either had hits with no significant similarity in the protein database, or had significant hits in the EST database with unknown function, or had no hits in either database and were defined as novel drought-inducible gene fragments. Functional analysis of such novel DEFs might be informative to follow up in later experiments based on more natural drying plants in the field.

TABLE 3

Relationship of DEFs to known sequences provided by BLASTX searches.

| SEQ ID NO: XX | sequence | plant protein BLASTX | nr BLASTX | Plant EST TBLASTX | | | | Size kb |
|---|---|---|---|---|---|---|---|---|
| 01 | SSBI-A12 | No hits found | No hits found | No hits found | 228 | N5T8-100u-2 | 125 III | 85 |
| 02 | SSBI-A2 | gi|15292985| | No hits found | Low | 020 | N8T1-200t | 230 II | 188 |
| 03 | SSBI-A3 | No hits found | No hits found | Low | 053 | N7T2-100u | 165 II | 122 |
| 04 | SSBI-A6 | gi|34903618| | Low | Low | 104.5 | N4T4-100u | 170 | 132 |
| 05 | SSBI-C1 | No hits found | No hits found | Low | 002 | N1T1-100u | 135 III | 101 |
| 06 | SSBI-C3 | gi|50905077| | Low | Low | 056 | N8T2-300d | 385 II | 328 |
| 07 | SSBI-C8 | gi|50908947| | Low | Low | 155 | N5T6-300d | 310 II | 275 |
| 08 | SSBI-E1 | gi|13568486| gi|51459300|ref|XP_498769.1| | 3.00E−26 | Low | 006 | N2T1-300t-2 | 330 II | 291 |
| 09 | SSBI-E5 | No hits found | No hits found | Low | 009 | N4T4-100u | 110 III | 75 |
| 10 | SSBI-F11 | gi|45181461| | No hits found | Low | 211 | N1T8-100u-3 | 110 III | 77 |
| 11 | SSBI-F3 | No hits found | Low | Low | 060 | N8T2-100u-1 | 198 II | 162 |
| 12 | SSBI-F7 | No hits found | Low | Low | 133 | N7T5-200t | 220 II | 186 |
| 13 | SSBI-F8 | No hits found | No hits found | Low | 163 | N8T6-100d-1 | 155 II | 113 |
| 14 | SSBI-G1 | gi|18406088| | No hits found | Low | 012 | N4T1-100u | 120 II | 81 |
| 15 | SSBI-G11 | No hits found | No hits found | Low | 222 | N4T8-100u | 175 II | 138 |
| 16 | SSBI-G2 | No hits found | No hits found | Low | 041 | N5T2-100u-2 | 118 II | 78 |
| 17 | SSBI-G3 | No hits found | No hits found | Low | 061 | N8T2-100u-2 | 105 III | 69 |
| 18 | SSBI-G4 | gi|50898902| | Low | Low | 082 | N6T3-200u | 290 II | 166 |
| 19 | SSBI-G7 | No hits found | No hits found | Low | 134 | N7T5-100d | 155 II | 116 |
| 20 | SSBI-G8 | gi|50939069| | Low | Low | 165 | N1T7-500t | 570 II | 545 |
| 21 | SSBI-H11 | gi|31431423| | Low | Low | 227 | N5T8-100u-1 | 198 II | 165 |
| 22 | SSBI-H9 | gi|50905401| | Low | Low | 182 | N5T7-200d | 250 II | 211 |
| 23 | SSBII-A10 | gi|33285910| | No hits found | Low | 428 | N1T15-100u-2 | 168 II | 126 |
| 24 | SSBII-A9 | No hits found | No hits found | Low | 415 | N5T14-100u-1 | 190 III | 153 |
| 25 | SSBII-B10 | gi|50912857| | Low | Low | 433 | N1T15-50u | 99 III | 68 |
| 26 | SSBII-B11 | gi|34910006| | Low | Low | 220 | 100d | 135 II | 97 |
| 27 | SSBII-B3 | gi|34902330| | Low | Low | 310 | N4T10-100t-2 | 185 II | 147 |
| 28 | SSBII-B7 | No hits found | No hits found | Low | 388 | N4T13-100d-3 | 160 III | 119 |
| 29 | SSBII-B9 | No hits found | No hits found | Low | 418 | N6T14-100u-1 | 148 III | 108 |
| 30 | SSBII-C4 | No hits found | No hits found | Low | 339 | N4T11-100u | 145 III | 101 |
| 31 | SSBII-C5 | gi|40538965| | Low | Low | 360 | N6T12-300d | 340 I | 299 |
| 32 | SSBII-C6 | gi|5853329| | No hits found | Low | 375 | N8T12-100d-1 | 199 II | 169 |
| 33 | SSBII-C9 | No hits found | Low | Low | 419 | N6T14-100u-2 | 110 III | 71 |

TABLE 3-continued

Relationship of DEFs to known sequences provided by BLASTX searches.

| SEQ ID NO: XX | sequence | plant protein BLASTX | nr BLASTX | Plant EST TBLASTX | | | | Size kb |
|---|---|---|---|---|---|---|---|---|
| 34 | SSBII-D6 | No hits found | No hits found | Low | 377 | N2T13-200d-1 | 240 II | 204 |
| 35 | SSBII-E10 | No hits found | No hits found | No hits found | 455 | N2T16-50u | 80 III | 23 |
| 36 | SSBII-E8 | gi|50908607| | Low | Low | 409 | N2T14-200t | 208 II | 177 |
| 37 | SSBII-F9 | No hits found | No hits found | Low | 424 | N7T14-100d | 120 III | 88 |
| 38 | SSBII-G5 | gi|34896478| | No hits found | Low | 366 | N6T12-100d | 192 III | 161 |
| 39 | SSBII-H1 | No hits found | No hits found | Low | 285 | N8T9-300d | 380 II | 335 |

The products of the stress-inducible genes can be classified into two groups: (1) those that directly protect against environmental stresses; and (2) those that regulate gene expressions and signal transductions in stress response (Seki et al., 2002, Plant J. 30:279-292; herein incorporated by reference). The proteins in the first group have the ability to function in stress tolerance. The raffinose synthases and trehalose-6-phosphate synthase were osmoprotectant biosynthesis-related proteins for adjusting the osmotic pressure under stress conditions. The heat-shock proteins have been reported to be involved in protecting macromolecules such as enzymes and lipids (Shinozaki et al., 1999, In Molecular Responses to Cold, Drought, Heat and Salt Stress in Higher Plants, pp. 11-28; herein incorporated by reference). The fibrillin and fiber proteins might contribute to cell wall structure modification. The type-1 pathogenesis-related protein is considered to be a protein with antifungal activity (Antoniw et al., 1980, J. Gen. Virol. 47: 79-87; herein incorporated by reference) that may have multiple stress-related roles even though the function is still unknown. Tonoplast intrinsic protein (aquaporin) functions as a water channel to transport water through plasma membrane and tonoplast to adjust the osmotic pressure under stress conditions (Daniels et al., 1994, Plant Physiol. 106: 1325-1333; herein incorporated by reference). The transporters for anion and zinc may function in adjustment of ion homeostasis. The second group contains regulatory proteins involved in regulation of signal transduction and gene expression in stress responses. The zinc finger and MYB family transcription factors may function in the regulation of stress-inducible gene expression. The peptide chain release factor induced by drought stress reflected that the post-transcriptional regulatory mechanism also affected the gene expression. Ankyrin protein kinase is thought to be involved in signal transduction and in further regulating the functional genes under stress conditions. The auxin-regulated gene was identified as drought-inducible suggesting a link between auxin and drought stress signaling pathways. Some DEFs annotated to the same functional genes were probably derived from the same gene or from redundant homologous genes. However, the functions of the majority of these genes are not known.

Some DEFs annotated to the same functional genes were probably derived from the same gene or from redundant homologous genes. Currently the functions of the majority of these genes are not fully understood. Moreover, 56% of the drought inducible gene fragments discovered during the development of the present inventions, were still functionally unknown and remain to be elucidated. Functional analysis of such set of DEFs might be informative to follow up in later experiments based on more natural drying plants in the field.

G. Predicted Function of Up-Regulated DEFs.

Twenty two DEFs up-regulated or induced by drought stress in *F. mairei* had significant similarity with protein sequences in the GenBank database (Table 4). The majority had the highest similar hits in the monocot species such as rice (*Oryza sativa*), maize (*Zea mays*), and wheat (*Triticum aestivum*). SSBII-H2, SSBI-B6, and SSBI-C09 encoded enzymes, respectively, involved in biosynthesis of purine nucleotide, raffinose, which has also been induced by water stress in *Cicer arietinum* (Romo et al., 2001, Plant Physiol. Biochem. 39: 1017-10263; herein incorporated by reference), and trehalose, the most effective osmoprotectant sugar in terms of minimum concentration required (Crowe et al., 1992, Annu. Rev. Physiol. 54: 579 599; herein incorporated by reference). The SSBI-D11 encoding of an enzyme for C-compound and carbohydrate utilization has been identified as a transcript differentially expressed in response to high salinity in the mangrove, *Bruguiera gymnorrhiza* (Banzai et al., 2002, Plant Sci. 162: 499-505; herein incorporated by reference).

The farnesylated protein encoded by SSBI-B9 has been found in *Hordeum vulgare* to be a nuclear protein involved in stress response and leaf senescence (Barth et al., 2004 Physiol. Plantarum 121: 282-293; herein incorporated by reference). SSBI-D4, SSBI-D9, SSBII-A3, and SSBI-A4 encoded a fiber protein Fb19, a dehydration-responsive family protein, a type-1 pathogenesis-related protein, and a DNAJ heat shock N-terminal domain-containing protein, respectively, which have been widely studied in association with stress response. SSBI-E2 encoded a 34 kD fibrillin-like protein, the major constituent of elastin-associated extracellular microfibrils, and has been recently identified in a network of rice genes associated with stress response (Cooper et al., 2003, Proc Natl Acad Sci USA. 4945-4950; herein incorporated by reference). SSBI-A5 encoded a brown planthopper susceptibility protein and shared similarity with the sequence of a rice gene induced in response to herbivore grazing. Several DEFs encoded proteins involved in heavy metal ion transport, electron/hydrogen transport, and membrane channel, reflecting the plant actively adjusted the ion and water status for homeostasis. The DEFs encoding proteins for transcription and translation regulation were induced such as zinc finger protein, MYB transcription factor, and peptide chain release factor suggesting certain stress-responsive genes are activated by these factors for positive stress defense.

TABLE 4

Function annotation and size of the differentially expressed fragments
(DEFs) up-regulated by drought stress in *F. mairei*.

| SEQ ID NO: XX | sequence | DEF Top hit in GenBank | E-value* | Description Organism | Size (bp) |
|---|---|---|---|---|---|
| 209 | SSBII-H02 | gi\|46560602\| | 2.00E−44 | putative inosine-uridine preferring nucleoside hydrolase [*Zea mays*] | 245 |
| 102 | SSBI-B06 | gi\|50540754\| | 7.00E−44 | putative raffinose synthase or seed imbibition protein [*Oryza sativa*] | 248 |
| 105 | SSBI-B09 | gi\|28866019\| | 3.00E−40 | farnesylated protein 3 [*Hordeum vulgare*] | 263 |
| 114 | SSBI-C09 | gi\|50252610\| | 1.00E−33 | putative trehalose-6-phosphate synthase/phosphatase [*Oryza sativa*] | 251 |
| 94 | SSBI-A04 | gi\|52353404\| | 1.00E−29 | DNAJ heat shock N-terminal domain-containing protein [*Oryza sativa*] | 194 |
| 126 | SSBI-E02 | gi\|50898740\| | 1.00E−25 | putative chloroplast drought-induced stress protein, 34 kD/fibrillin-like protein [*Oryza sativa*] | 306 |
| 95 | SSBI-A05 | gi\|33771376\| | 2.00E−25 | putative brown planthopper susceptibility protein Hd002A [*Oryza sativa*] | 228 |
| 113 | SSBI-C07 | gi\|49328143\| | 2.00E−24 | putative peptide chain release factor subunit 1 (eRF1) [*Oryza sativa*] | 172 |
| 124 | SSBI-D11 | gi\|34894800\| | 6.00E−19 | putative dihydrolipoamide dehydrogenase precursor [*Oryza sativa*] | 156 |
| 119 | SSBI-D04 | gi\|38016525\| | 9.00E−19 | fiber protein Fb19/universal stress protein USP1-like protein [*Gossypium barbadense*] | 273 |
| 109 | SSBI-C02 | gi\|56784864\| | 8.00E−18 | auxin-regulated protein-like [*Oryza sativa*] | 310 |
| 140 | SSBI-F09 | gi\|53749298\| | 8.00E−16 | putative polyprotein/GAG-POL precursor [*Oryza sativa*] | 166 |
| 156 | SSBII-A03 | gi\|3702665\| | 1.00E−13 | type-1 pathogenesis-related protein [*Triticum aestivum*] | 100 |
| 99 | SSBI-B02 | gi\|50919725\| | 2.00E−13 | Putative anion transporter [*Oryza sativa*] | 114 |
| 122 | SSBI-D09 | gi\|51469000\| | 3.00E−13 | Ankyrin protein kinase-like/dehydration-responsive protein-like [*Poa pratensis*] | 103 |
| 203 | SSBII-G04 | gi\|30420736\| | 4.00E−13 | zinc transporter [*Oryza sativa*] | 108 |
| 134 | SSBI-E11 | gi\|168473\| | 9.00E−13 | ferredoxin [*Zea mays*] | 119 |
| 182 | SSBII-D09 | gi\|25090853\| | 2.00E−09 | NADH-ubiquinone oxidoreductase18 kDa subunit, mitochondrial precursor [*Arabidopsis thaliana*] | 77 |
| 215 | SSBII-H09 | gi\|4996646\| | 1.00E−08 | Dof zinc finger protein [*Oryza sativa*] | 185 |
| 116 | SSBI-C11 | gi\|4996646\| | 1.00E−08 | Dof zinc finger protein [*Oryza sativa*] | 199 |
| 157 | SSBII-A04 | gi\|32879770\| | 5.00E−07 | tonoplast intrinsic protein [*Oryza sativa*] | 70 |
| 192 | SSBI-F02 | gi\|51572282\| | 5.00E−07 | MYB transcription factor [*Triticum aestivum*] | 80 |

*E-value <1.00E−06 means the significant similarity with the protein sequences in the Genbank database.

H. Drought Repressible Genes.

The analysis of drought-repressible genes is as important as analysis of drought-inducible genes in understanding the molecular mechanism of plant response to stress. During the development of the present inventions, many photosynthesis-related genes were found such as chlorophyll a/b binding protein, ribulose-1,5-isphosphate carboxylase, high molecular mass early light-inducible protein HV58, etc., all reflecting that photosynthesis was inhibited by the water deficit. This can be due to a reduction in light interception as leaf senesce, or to a reduction of intercellular $CO_2$ concentration as closure of stomata (Bartels et al., 2001, Plant Physiol. 127: 1346-1353; herein incorporated by reference). The benefit of the depressed photosynthesis appears to be the switch toward another carbohydrate utilization pathway, which leads to the production of valuable stress tolerance molecules (Pattanagul et al., 1999, Plant Physiol. 121: 987-993; herein incorporated by reference). Bockel & Bartels proposed that down-regulation of photosynthesis-related genes possibly contributed to reduced photooxidative stress.

Lipoxygenase, glutamate synthase, malate dehydrogenase up-regulated under drought in barley (Ozturk et al., 2002, Plant Mol. Biol. 48:551-573; herein incorporated by reference) were down-regulated in this study. Some clones have been up-regulated by drought in *Arabidopsis* encoding protein products the same as protein encoded by down-regulated clones, e.g. Cytochrome P450 protein and malate dehydrogenase have shown in both up-regulated and down regulated groups (Seki et al., 2002, Plant J. 30:279-292; herein incorporated by reference). This distinct behavior has also been found in barley and rice (Kawasaki et al., 2001, Plant Cell 13: 889-906; herein incorporated by reference). Their role and importance in tolerance or sensitivity is impossible to judge based on the experiments alone under controlled environment conditions. But these DEFs, at least, provide clues about the genes differentially expressed with a reference database for comparison later on with data from natural field drought conditions.

I. Predicted Function of Down-Regulated DEFs.

In total, 70 down-regulated DEFs showed significant similarity to previously identified proteins (Table 5). A much larger quantity of down-regulated DEFs than up-regulated were isolated in *F. mairei* during drought stress indicating that the plant was mainly under degenerative processes imposed by the stress. Down-regulated genes were involved in a number of basic metabolic or biosynthetic functions and systemic development or growth, such as photosynthesis (light-inducible protein HV58, SSBII-D7), respiration (chlorophyll A-B binding family protein, SSBI-B10), amino acid metabolism (victorin binding protein, SSBI-B12), oligopeptide synthesis (GTP-binding protein type A, SSBII-C2), carbohydrate metabolism (UDP-glycosyltransferase 88B1, SSBII-G7), tissue development (homeobox protein knotted-7, SSBI-H3), DNA cell division (helicase, SSBI-G10) and so on. In addition, some proteins for transport facilitation were down-regulated, such as ADP-ribosylation factor for vesicular transport (SSBII-H8), iron-phytosiderophore transporter protein for aligopeptide transport (SSBII-B8), ferric reductase for electron transport (SSBII-B2), cation diffusion facilitator for ion transport (SSBII-C1), and triose phosphate translocator for c-compound transport (SSBI-E7). Moreover, several proteins involved in transcription and signal transduction were also down-regulated indicating some pathways for signaling and basic biosynthesis or metabolism were turned down in the plant during drought stress. Those proteins included cleavage and polyadenylation specificity factor (SSBII-F10), homeobox gene knotted 7 (SSBI-H3), TATA-binding protein associated factor (SSBII-F3), SEUSS transcriptional co-regulator (repressor) (SSBI-B7), EREBP1 transcription factor (SSBI-C10), zinc finger protein (SSBII-E5), and phosphatidylinositol-4-phosphate 5-kinase (SSBII-G2).

TABLE 5

Functional annotation and size of the differentially expressed fragments (DEFs) down-regulated by drought stress in *F. mairei*.

| SEQ ID NO: XX | DEF | Top hit in GenBank | E-value | Description Organism | Size (bp) |
|---|---|---|---|---|---|
| 158 | SSBII-A05 | gi\|710308\| | 1.00E−108 | victorin binding protein/glycine dehydrogenase P protein [*Avena sativa*] | 582 |
| 111 | SSBI-C05 | gi\|50940811\| | 2.00E−75 | putative non-phototropic hypocotyl 3 (NPH3)/phototropic response protein [*Oryza sativa*] | 449 |
| 143 | SSBI-G05 | gi\|14861035\| | 2.00E−71 | protoporphyrin IX Mg-chelatase subunit XANTHA-F [*Hordeum vulgare*] | 399 |
| 116 | SSBII-C11 | gi\|710308\| | 5.00E−71 | victorin binding protein/glycine dehydrogenase P protein [*Avena sativa*] | 398 |
| 210 | SSBI-H03 | gi\|33333542\| | 1.00E−70 | knotted 7/homeobox gene [*Hordeum vulgare*] | 460 |
| 190 | SSBII-E09 | gi\|1181331\| | 9.00E−69 | calnexin [*Zea mays*] | 356 |
| 186 | SSBII-E04 | gi\|86199\| | 1.00E−68 | protoporphyrin IX Mg-chelatase subunit precursor [*Hordeum vulgare*] | 398 |
| 199 | SSBII-F10 | gi\|50921909\| | 3.00E−65 | OSJNBa0032B23.5/cleavage and polyadenylation specificity factor (CPSF) [*Oryza sativa*] | 398 |
| 208 | SSBII-G10 | gi\|13661772\| | 2.00E−64 | putative cytochrome P450 [*Lolium rigidum*] | 357 |
| 131 | SSBI-E08 | gi\|68599\| | 2.00E−59 | glutamate-ammonia ligase precursor, chloroplast - barley [*Hordeum vulgare*] | 390 |
| 214 | SSBII-H08 | gi\|86205\| | 3.00E−55 | ADP-ribosylation factor [*Chlamydomonas reinhardtii*] | 309 |
| 184 | SSBII-E02 | gi\|6409335\| | 7.00E−54 | ribulose-1,5-bisphosphate carboxylase small subunit [*Avena clauda*] | 431 |
| 138 | SSBI-F05 | gi\|50912639\| | 4.00E−51 | putative serine-threonine rich antigen [*Oryza sativa*] | 473 |
| 206 | SSBII-G08 | gi\|18147771\| | 3.00E−49 | cycloartenol synthase [*Costus speciosus*] | 345 |
| 175 | SSBII-D01 | gi\|54290318\| | 1.00E−48 | unknown protein/IWS1 C-terminus family protein [*Arabidopsis thaliana*] [*Oryza sativa*] | 318 |
| 167 | SSBII-B08 | gi\|40888826\| | 1.00E−46 | iron-phytosiderophore transporter protein yellow stripe 1 [*Oryza sativa*] | 338 |
| 192 | SSBII-F02 | gi\|21842139\| | 1.00E−43 | cytochrome P450 monooxygenase CYP72A28 [*Zea mays*] | 390 |
| 133 | SSBI-E10 | gi\|32251039\| | 3.00E−38 | glyoxysomal malate dehydrogenase [*Triticum aestivum*] | 238 |
| 193 | SSBII-F03 | gi\|49388196\| | 4.00E−37 | putative TATA-binding protein associated factor (IID (TFIID) component TAF4 family) [*Oryza sativa*] | 400 |
| 198 | SSBII-F08 | gi\|51091645\| | 2.00E−35 | rab3-GAP regulatory domain-like [*Oryza sativa*] | 235 |
| 213 | SSBII-H07 | gi\|50872458\| | 1.00E−34 | putative c-type cytochrome synthesis protein [*Oryza sativa*] | 223 |

TABLE 5-continued

Functional annotation and size of the differentially expressed fragments (DEFs) down-regulated by drought stress in *F. mairei*.

| SEQ ID NO: XX | DEF | Top hit in GenBank | E-value | Description Organism | Size (bp) |
|---|---|---|---|---|---|
| 155 | SSBII-A02 | gi\|4325354\| | 1.00E−34 | contains similarity to retrovirus-related polyproteins and to CCHC zinc finger protein/gag-pol polyprotein [*Arabidopsis thaliana*] | 223 |
| 147 | SSBI-H01 | gi\|14334888\| | 1.00E−34 | putative glycine hydroxymethyltransferase [*Arabidopsis thaliana*] | 224 |
| 189 | SSBII-E07 | gi\|2072727\| | 1.00E−34 | ferredoxin-dependent glutamate synthase [*Oryza sativa*] | 232 |
| 103 | SSBI-B07 | gi\|18033922\| | 2.00E−34 | SEUSS transcriptional co-regulator (Repressor) [*Arabidopsis thaliana*] | 286 |
| 115 | SSBI-C10 | gi\|50726040\| | 3.00E−34 | putative transcription factor EREBP1/BTH-induced ERF transcriptional factor 1 [*Oryza sativa*] | 280 |
| 195 | SSBII-F05 | gi\|45357045\| | 5.00E−34 | coatomer alpha subunit [*Hordeum vulgare*] | 209 |
| 162 | SSBII-A11 | gi\|2072727\| | 7.00E−31 | ferredoxin-dependent glutamate synthase [*Oryza sativa*] | 215 |
| 166 | SSBII-B06 | gi\|2072727\| | 7.00E−31 | ferredoxin-dependent glutamate synthase [*Oryza sativa*] | 215 |
| 194 | SSBII-F04 | gi\|20153218\| | 9.00E−31 | putative sucrose:sucrose 1-fructosyltransferase [*Lolium perenne*] | 192 |
| 128 | SSBI-E04 | gi\|50948231\| | 1.00E−30 | putative cytochrome p450 (CYP78A9) [*Oryza sativa*] | 230 |
| 130 | SSBI-E07 | gi\|13195734\| | 2.00E−30 | triose phosphate translocator [*Triticum aestivum*] | 201 |
| 178 | SSBII-D04 | gi\|34922538\| | 1.00E−28 | Lipoxygenase 2.3, chloroplast precursor [*Hordeum vulgare*] | 194 |
| 216 | SSBII-H10 | gi\|21839\| | 2.00E−28 | phosphoribulokinase; ribulose-5-phosphate kinase [*Triticum aestivum*] | 254 |
| 205 | SSBII-G07 | gi\|54290956\| | 1.00E−27 | putative UDP-glycosyltransferase 88B1 [*Oryza sativa*] | 245 |
| 110 | SSBI-C04 | gi\|51451358\| | 3.00E−27 | putative o-methyltransferase ZRP4 [*Oryza sativa*] | 206 |
| 145 | SSBI-G09 | gi\|50912885\| | 8.00E−26 | putative Ribosomal RNA processing protein/S1 self-incompatibility locuslinked pollen G211 protein [*Oryza sativa*] | 285 |
| 196 | SSBII-F06 | gi\|13785467\| | 9.00E−26 | phosphoenolpyruvate carboxykinase (ATP-dependent) [*Flaveria trinervia*] | 172 |
| 164 | SSBII-B02 | gi\|47169677\| | 2.00E−25 | ferric reductase [*Oryza sativa*] | 178 |
| 210 | SSBII-H03 | gi\|39750999\| | 1.00E−24 | unnamed protein product/Alpha-glucan water dikinase, chloroplast precursor (Starch-related R1 protein) [*Lolium perenne*] | 232 |
| 108 | SSBI-B12 | gi\|710308\| | 1.00E−23 | victorin binding protein [*Avena sativa*] | 166 |
| 129 | SSBI-E06 | gi\|50905199\| | 1.00E−23 | cycloartenol synthase [*Oryza sativa*] | 185 |
| 112 | SSBI-C06 | gi\|32481061\| | 1.00E−23 | Rubisco activase alpha form precursor/ribulose-bisphosphate carboxylase activase [*Deschampsia antarctica*] | 233 |
| 212 | SSBII-H06 | gi\|38347077\| | 9.00E−23 | OSJNBa0006A01.18/unknown protein [*Oryza sativa*] | 161 |
| 187 | SSBII-E05 | gi\|50906397\| | 1.00E−22 | zinc finger protein-like/GATA-1 zinc finger protein [*Oryza sativa*] | 231 |
| 168 | SSBII-C01 | gi\|56784641\| | 4.00E−21 | putative cation diffusion facilitator 9 [*Oryza sativa*] | 167 |
| 165 | SSBII-B04 | gi\|51964240\| | 3.00E−19 | PREDICTED P0666E12.10 gene product [*Oryza sativa*] | 278 |
| 202 | SSBII-G03 | gi\|48716905\| | 2.00E−18 | apospory-associated protein C-like [*Oryza sativa*] | 129 |
| 135 | SSBI-E12 | gi\|710308\| | 2.00E−17 | victorin binding protein [*Avena sativa*] | 122 |
| 207 | SSBII-G09 | gi\|50251471\| | 3.00E−17 | unknown protein [*Oryza sativa*] | 323 |
| 154 | SSBI-H08 | gi\|50907447\| | 6.00E−17 | unknown protein [*Oryza sativa*] | 132 |
| 169 | SSBII-C02 | gi\|50906979\| | 1.00E−15 | putative GTP-binding protein typA (tyrosine phosphorylated protein A)/elongation factor family protein [*Oryza sativa*] | 134 |

TABLE 5-continued

Functional annotation and size of the differentially expressed fragments
(DEFs) down-regulated by drought stress in *F. mairei*.

| SEQ ID NO: XX | DEF | Top hit in GenBank | E-value | Description Organism | Size (bp) |
|---|---|---|---|---|---|
| 180 | SSBII-D07 | gi\|119284\| | 1.00E−15 | High molecular mass early light-inducible protein HV58, chloroplast precursor (ELIP) [*Hordeum vulgare*] | 170 |
| 197 | SSBII-F07 | gi\|121343\| | 2.00E−15 | Glutamine synthetase shoot isozyme, chloroplast precursor (Glutamate--ammonia ligase) [*Oryza sativa*] | 109 |
| 121 | SSBI-D06 | gi\|53749331\| | 1.00E−13 | putative 2-oxoglutarate/malate translocator [*Oryza sativa*] | 128 |
| 170 | SSBII-C03 | gi\|119748\| | 7.00E−13 | Fructose-1,6-bisphosphatase, cytosolic (D-fructose-1,6-bisphosphate 1-phosphohydrolase) (FBPase) [*Spinacia oleracea*] | 121 |
| 204 | SSBI-G06 | gi\|50905143\| | 7.00E−12 | putative 50S ribosomal protein L3 [*Oryza sativa*] | 204 |
| 188 | SSBII-E06 | gi\|11761654\| | 2.00E−11 | peroxiredoxin/thioredoxin peroxidase CATP [*Oryza sativa*] | 178 |
| 196 | SSBI-F06 | gi\|32400293\| | 7.00E−11 | hydroxyanthranilate hydroxycinnamoyltransferase 2 [*Avena sativa*] | 91 |
| 173 | SSBII-C10 | gi\|12060390\| | 2.00E−10 | response regulator 7 [*Zea mays*] | 148 |
| 152 | SSBI-H06 | gi\|38345616\| | 4.00E−10 | OSJNBb0003B01.8 (BAC clone)/unknown protein [*Oryza sativa*] | 91 |
| 161 | SSBII-A08 | gi\|1769849\| | 3.00E−09 | photosystem II type I chlorophyll a/b binding protein [*Apium graveolens*] | 166 |
| 181 | SSBII-D08 | gi\|15223823\| | 2.00E−08 | armadillo/beta-catenin repeat family protein/unknown protein [*Arabidopsis thaliana*] | 204 |
| 96 | SSBI-A07 | gi\|82619\| | 6.00E−08 | ribulose-bisphosphate carboxylase [*Triticum aestivum*] | 212 |
| 201 | SSBII-G02 | gi\|50915986\| | 2.00E−07 | putative phosphatidylinositol-4-phosphate 5-kinase [*Oryza sativa*] | 90 |
| 104 | SSBI-B08 | gi\|31323256\| | 2.00E−07 | photosystem II type I chlorophyll a/b binding protein [*Brassica oleracea*] | 116 |
| 146 | SSBI-G10 | gi\|50911901\| | 2.00E−07 | putative DNA helicase/DNA-binding protein [*Oryza sativa*] | 82 |
| 106 | SSBI-B10 | gi\|2196772\| | 4.00E−07 | chlorophyll a/b-binding protein [*Mesembryanthemum crystallinum*] | 116 |
| 172 | SSBII-C08 | gi\|50928287\| | 6.00E−07 | OSJNBa0013K16.8/putative glutamate receptor [*Oryza sativa*] | 113 |
| 200 | SSBII-G01 | gi\|133872\| | 2.00E−06 30S | ribosomal protein S1, chloroplast precursor (CS1) [*Spinacia oleracea*] | 114 |

[1]E-value <1.00E−06 means the significant similarity with the protein sequences in the Genbank database.

J. Predicted Function of Up-then-Down Regulated and Transiently Expressed DEFs.

Five up-then-down regulated and four transiently expressed DEFs were identified sharing significant similarity with proteins in the public database (Table 6). The rieske Fe-S precursor protein (SSBI-F10), a chlorophyll a/b-binding protein (SSBII-D5), digalactosyldiacylglycerol synthase (SSBI-D3), and a disease resistance protein (SSBI-D5) were up-regulated at the earlier stress period and then turned down with the stress continuing, indicating that these proteins may have a positive response to the mild stress but were not retained during the severe stress. The glutamine-dependent asparagine synthase, plasma membrane H+ ATPase, small heat shock protein Hsp23.5, and type 2 metallothioneine were temporally expressed at approximately day 4 stress suggesting the transient regulation of these proteins might be critical for drought stress response. Predicted function of up-then-down regulated and transiently expressed DEF.

K. Transiently Expressed and Up-then-Down-Regulated.

DEFs including the novel ones should be analyzed with breeding lines under more natural drought conditions to further confirm the correlation of expression pattern of the transcripts with drought tolerance. The particular functions of these DEFs need to be studied by using knock-out mutants and transgenics, such as over-expression, antisense suppression, and double-stranded RNA interference (RNAi). It has been found that some genes induced by drought stress have no effect on drought tolerance in transgenic plants (Karakas et al., 1997, Plant cell and Environment. 20:609-616). Therefore, a challenge for future research is to distinguish between gene products with a potential in osmoprotection and those that are only involved in secondary reaction. The combination of quantitative transcript profiles with an appropriate QTL analysis could possibly lead to the identification of candidate genes for agronomically valuable traits. Reverse genetic approach as well as classical genetics will become more important to understand not only functions of stress-inducible genes but also the complex signaling process in environmental stress response.

TABLE 6

Functional annotation and size of the differentially expressed fragments (DEFs) transiently expressed (T) and up-then-down-regulated (UD) during drought stress in *F. mairei*.

| SEQ ID NO: XX | DEF | Representative examples of similarity hits in GenBank | E-value | Representative examples of Description Organism Expression | Pattern | Size (bp) |
|---|---|---|---|---|---|---|
| 179 | SSBII-D05 | gi\|53680379\| | 3.00E−51 | glutamine-dependent asparagine synthetase [*Triticum aestivum*] | T | 290 |
| 93 | SSBI-A10 | gi\|20302435 | 1.00E−33 | plasma membrane H+ ATPase [*Oryza sativa*] | T | 222 |
| 153 | SSBI-H07 | gi\|4138869\| | 9.00E−16 | small heat shock protein Hsp23.5 [*Triticum aestivum*] | T | 128 |
| 151 | SSBI-H05 | gi\|23954355\| | 8.00E−15 | metallothioneine type2 [*Hordeum vulgare*] | T | 287 |
| 141 | SSBI-F10 | gi\|32394644\| | 3.00E−33 | putative Rieske Fe—S precursor protein [*Triticum aestivum*] | UD | 259 |
| 101 | SSBI-B05 | gi\|82682\| | 4.00E−31 | chlorophyll a/b-binding protein precursor [*Zea mays*] | UD | 197 |
| 118 | SSBI-D03 | gi\|50252668\| | 1.00E−21 | putative digalactosyldiacylglycerol synthase [*Oryza sativa*] | UD | 309 |
| 120 | SSBI-D05 | gi\|50943213\| | 5.00E−12 | putative disease resistance protein [*Oryza sativa*] | UD | 231 |
| 185 | SSBII-E03 | gi\|50912463\| | 8.00E−07 | unknown protein [*Oryza sativa*] | UD | 84 |

In summary, over one hundred DEFs identified from cDNA-AFLP analysis were confirmed by macroarray hybridization analysis. Thus the inventor showed that cDNA-AFLP technique coupled with macroarray hybridization analysis was an efficient procedure in detecting differentially expressed genes associated with responding to drought stress. The DEFs provided herein are the first transcripts derived from an Atlas fescue plants's response to drought stress. The use of the methods of the present inventions demonstrated the presence of a variety of drought responsive gene responses showing a comprehensive molecular regulation level in Atlas fescue plants that responded to drought stress.

Further, predicted functions of the sequences were subdivided into 17 functional categories. Some DEFs discovered in Atlas fescue are novel genes, which in combination with their superior capability to resist drought effects showed that Atlas fescue plants comprise novel compositions and mechanisms as a defense against adverse effects of drought stress. The inventor contemplated that the novel sequences provide a valuable resource for future compositions and methods for use in specific types of drought tolerant gene regulation in plants. During drought stress treatment in Atlas fescue, increased metabolic function and biogenesis of cellular components in the plant undergo a degenerative process potentially causing the plant system to save energy for new gene transcription and stress defense. The genes isolated and characterized herein provide compositions and methods for increasing protective mechanisms against desiccation tolerance in plants. In particular for use in breeding programs of grass plants for providing agronomically and/or economically desirable grass plant cultivars.

Example IV

Breeding Methods for Providing Lp Plants Comprising Fm Germplasm

Figure 10:
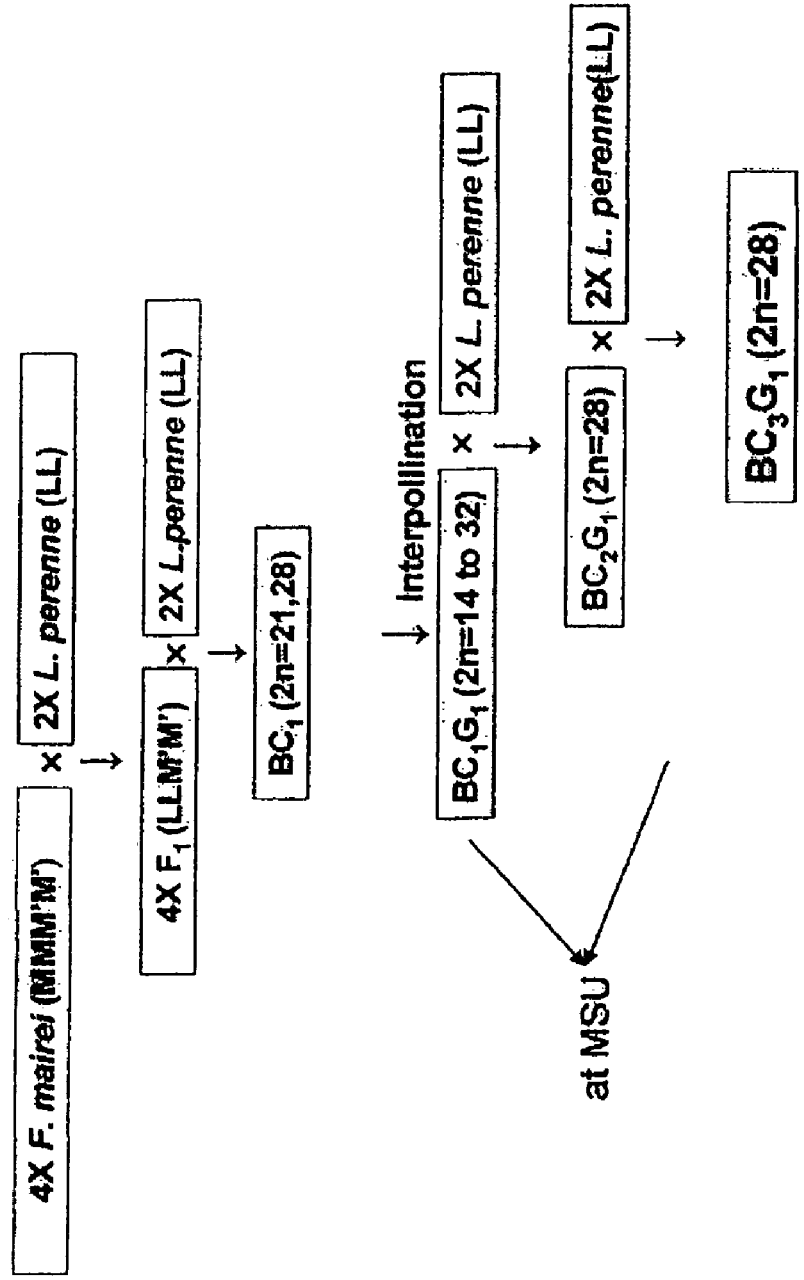
FIG. 10 shows an exemplary schematic for cross-breeding scheme for introgression of *Festuca mairei* germplasm into *Lolium perenne* plants.
Figure 11:
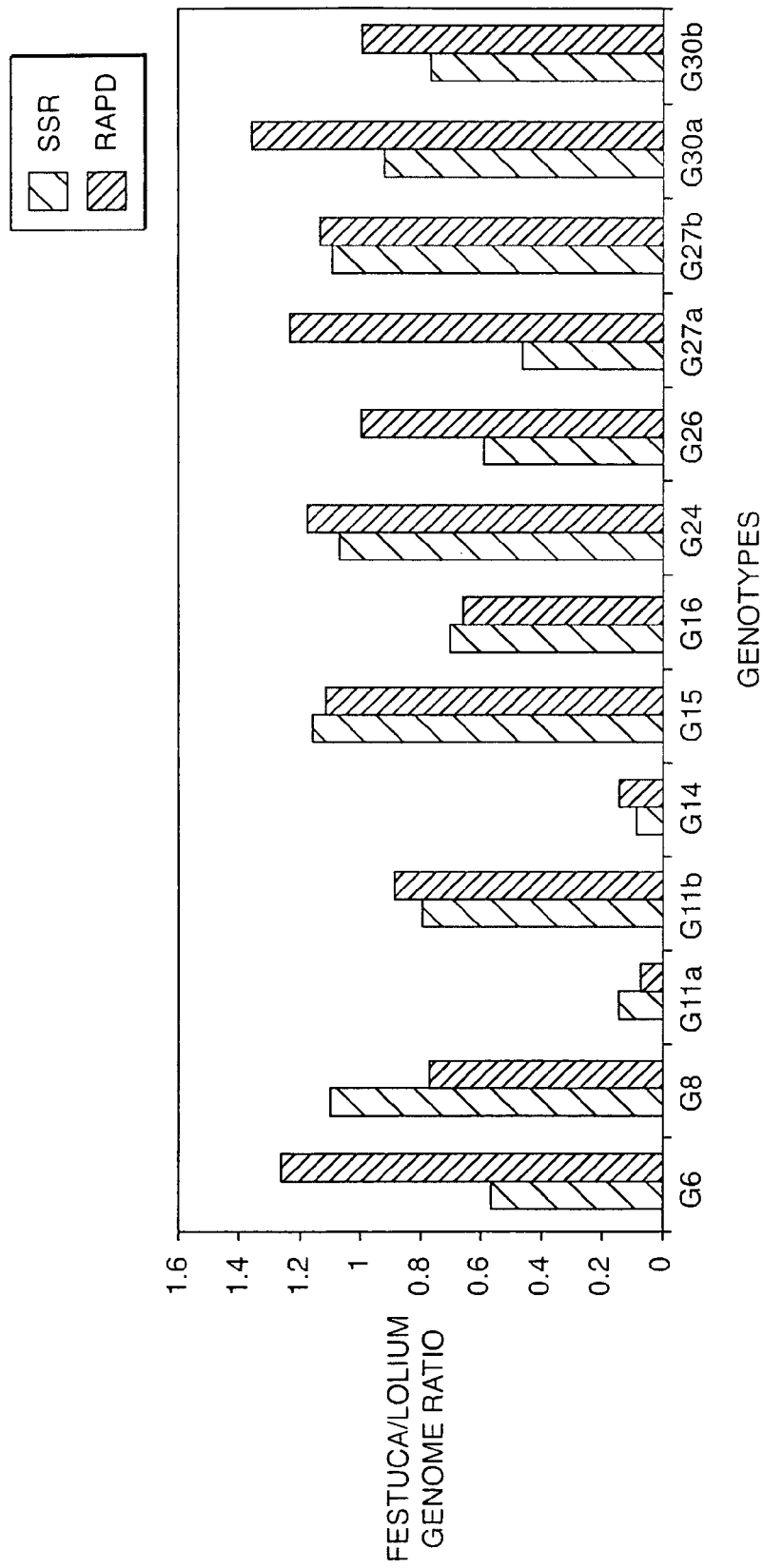
FIG. 11 shows exemplary *Festuca mairei/Lolium perenne* genome ratios of backcross progenies from *Festuca mairei* and perennial ryegrass assessed by using SSR and RAPD markers.
Figure 12A:
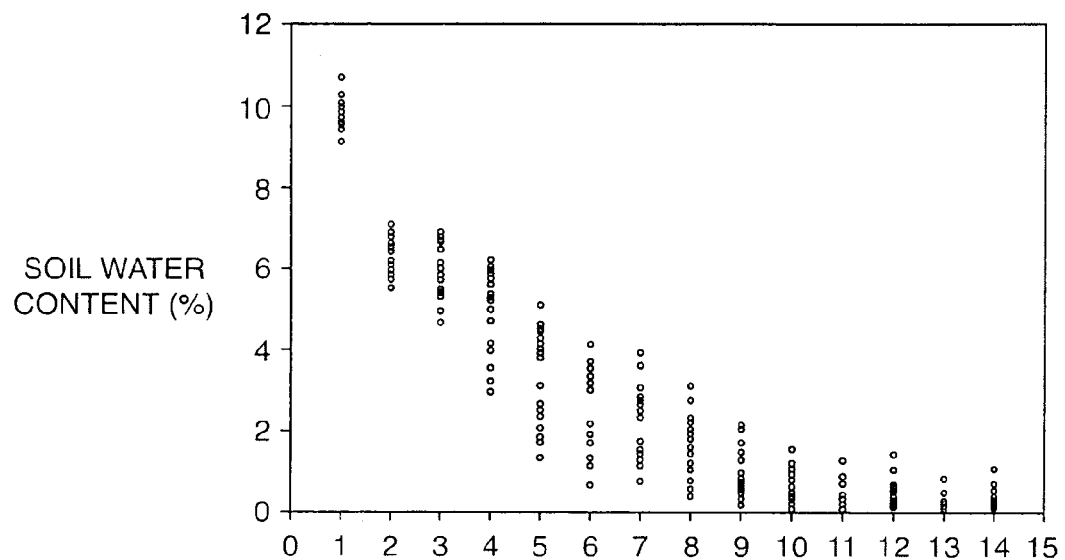
FIG. 12 shows an exemplary variation of soil water content (a), leaf water potential (b), leaf elongation (c), and leaf water content (d) among genotypes of Atlas fescue, perennial ryegrass, and their progeny in control (filled dots) and stressed (opened dots) plants during the drought stress period.
Figure 12B:
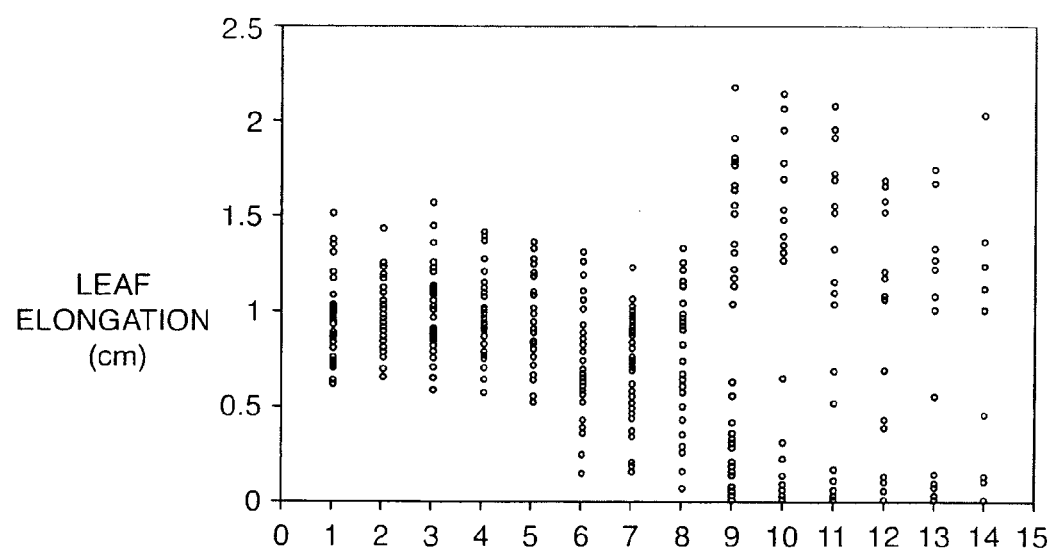
Figure 12C:
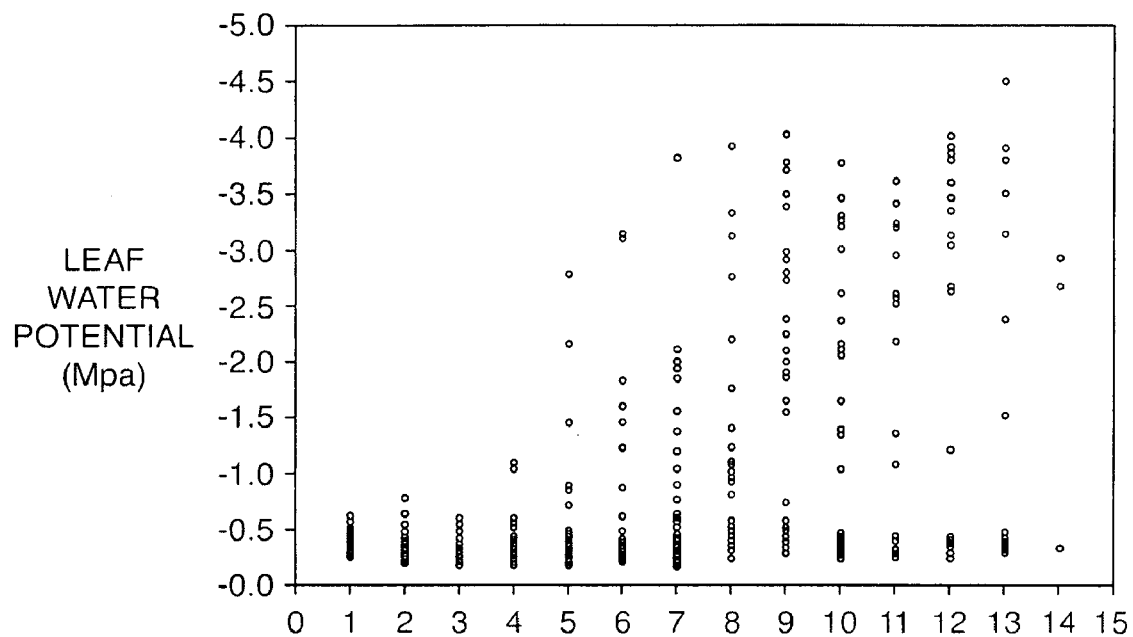
Figure 12D:
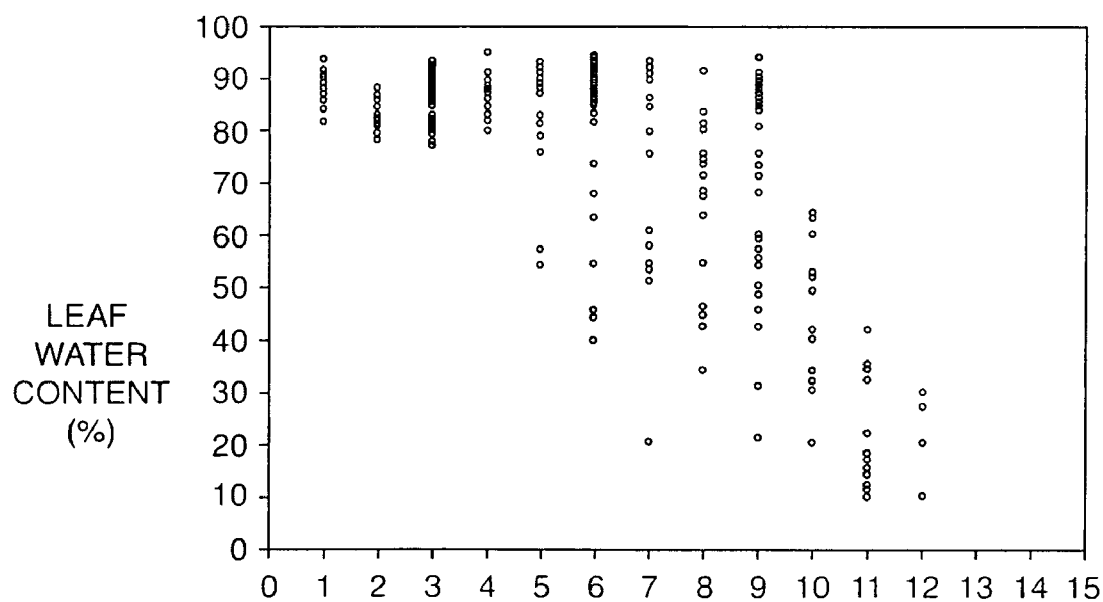

An exemplary schematic for a breeding strategy for providing drought resistant plants of the present inventions is shown in FIG. 10. In particular, 4× Fm1 plants were crossed with 2× Lp plants to provide 4× $F_1$ hybrid progeny plants for subsequent breeding programs, including the plants provided herein. Backcrosses were made in order to restore the desired agronomic traits of the Lp grass plants while retaining drought resistant germplasm from Fm plants. The introgression of germplasm was tracked, (FIG. 11) by identifying ratios of Fm/Lp germplasm using the RAPD and Lp SSR methods as described herein.

The capability of molecular markers, such as RAPD and SSR markers, primers and linkers, to discriminate between *Lolium* and *Festuca* DNA in hybrid and backcross plant progeny in combination with locating these markers on a linkage map enabled the creation of introgression maps. Thus combining genetic mapping and desired physiological traits for identifying and using these methods in breeding methods for providing drought tolerance in grass plants (see, for example, Humphreys et al., 1997 New Phytol. 137:55-60; Humphreys et al., 2005 Theor. Appl. Genet. 110:579-597; all of which are herein incorporated by reference). Markers associated with desired or undesirable trait components are contemplated for application to assist in drought tolerant progeny selection and decrease the time of the breeding process to provide desired plant cultivars.

The inventor discovered that Fm-Lp plant progeny successfully combined germplasm form both Fm and Lp plants and further that progeny showed desirable agronomic traits in initial greenhouse evaluation. Further, evaluation of Lp hybrid plants using morphological criteria for demonstrating drought resistance showed that certain hybrid plants showed superior levels of drought resistance. These elite progeny, such as line G15 and G30a, are contemplated as the basis of new cultivar release and for use in more specific development of marker(s) associated with drought tolerance.

Example V

Hybrid Superiority of *Festuca mairei*×*Lolium Perenne* Plants

This example is provided to show that the inventor unexpectedly identified hybrid plants demonstrating superior drought resistance traits using Principle Component Analysis (PCA) and plots of the comparative eigenvectors comprising morphological and physiological information from drought stressed plants.

Evaluation of eigenvector plots demonstrated that when grass plants of the present inventions, including parental Fm, drought tolerant Fescue species, and backcrossed Lp plants comprising Fm germplasm, were grouped by their ability to resist drought stress, several hybrid grass lines, specifically 2 backcrossed Lp plant lines comprising Fm germplasm, provided a group of plants that showed a higher level of drought tolerance when compared to grouped levels of drought resistance of parental grass plants, FIGS. 12-20, specifically lines G15, G30a and a $F_1$ hybrid of Atlas fescue×Calypso (Lp cultivar).

A $F_1$ hybrid from Atlas fescue×'Calypso' was used as a female parent for backcrossing as described herein. The higher drought tolerance of this $F_1$ hybrid and the existence of a drought-tolerant backcross progeny evidenced that this hybrid contained drought tolerance genes from Atlas fescue. Grouping of Plants Based Upon Drought Response Measurements:

First the irrigated and drought stressed plants fell into two distinct groups by PCA based on leaf elongation, leaf water content, and leaf water potential during the treatment period (FIG. 14a). One group included all of the control plants and the other group included the drought stress treated plants, indicating the successful treatment application and parameters' utility for such grouping methods.

Figure 13:
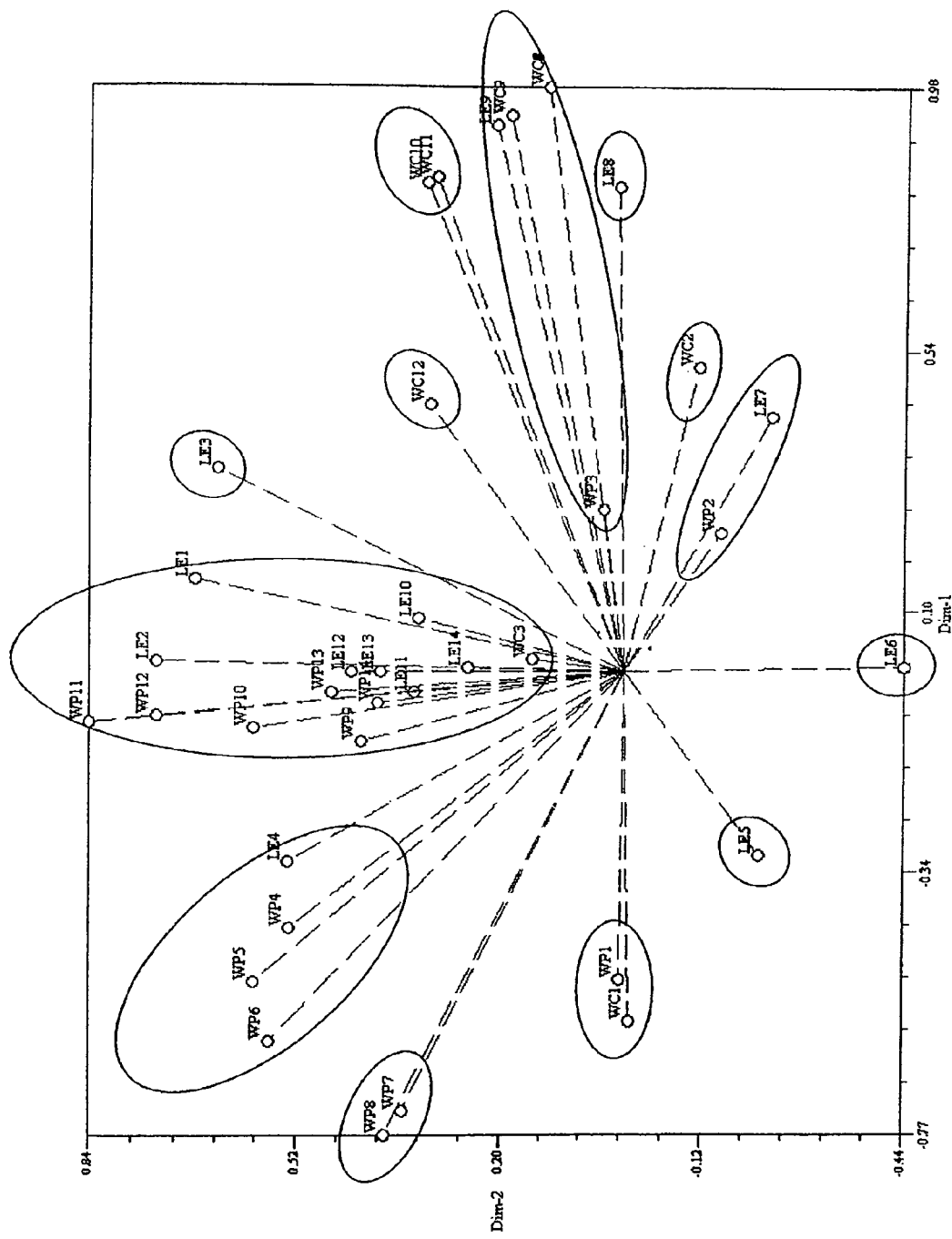
FIG. 13 shows an exemplary plot of eigenvectors. LE, leaf elongation; Ψw, leaf water potential; WC, leaf water content. The numbers after LE, Ψw, and WC represent the week number during the drought stress period.

Genotypes of both irrigated control and non-irrigated plants (19 plants) varied dramatically in response to drought treatment in terms of soil water content, leaf elongation, leaf water content, and leaf water potential (see, for example, FIG. 13). Forty drought responsive variables, including 14 (week 1 to 14) variables of leaf elongation, 14 variables of leaf water potential, and 12 variables leaf water content, were used in PCA to classify the 19 plant genotypes. The plot of the eigenvectors showed that leaf elongation of week 3, 5, 6, and 8, and leaf water content at week 2 and 12 were relatively independent because they were relatively divergent and separated by large angles in terms of closeness of angles from the origin. The other variables were positively and closely correlated to one or more variables by showing relative small angles between or among them. For example, leaf elongation data of weeks 1, 2, 10, 11, 12, 13, and 14, and leaf water potential data of weeks 9, 10 11, 12, 13, and 14, and leaf water content data for week 3 were positively and closely correlated showing relatively 8 small differences in angles. Leaf water potential data of weeks 7 and 8 were also highly correlated.

The PCA based on the plant responses to the drought treatment revealed four groups of all genotypes. The first three principal components accounted for 59% of variation. Group 1 included Kentucky 31, Atlas fescue founder plants, an $F_1$ hybrid, an amphiploid, and five backcross progeny. Group 2 included two perennial ryegrass parents and four backcross progeny. Group 3 contained an $F_1$ hybrid and two backcross progeny. Group 4 had only one backcross progeny, G24 (FIG. 15).

Figure 16:
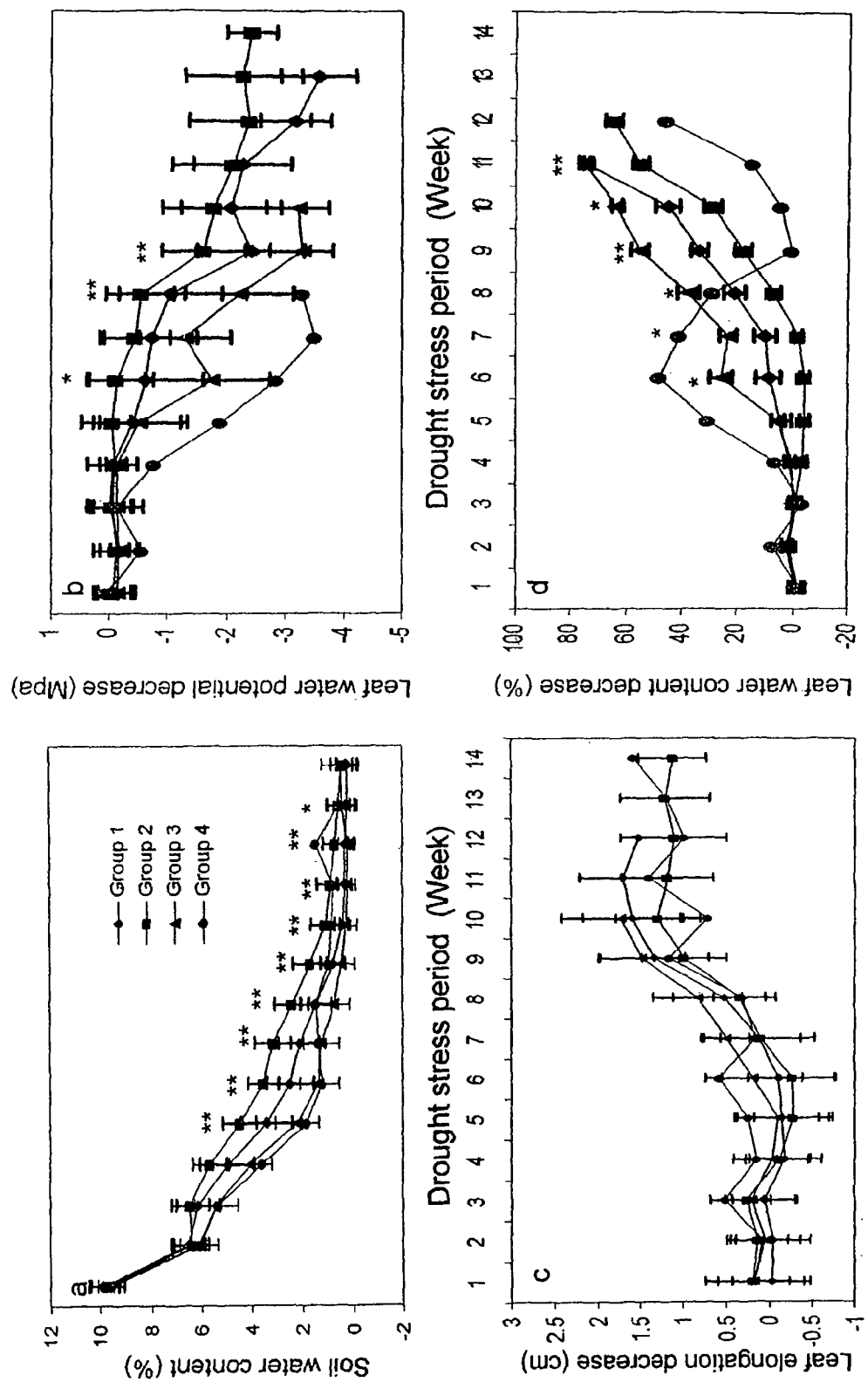
FIG. 16 shows an exemplary soil water content (a), leaf water potential decrease (b), leaf elongation decrease (c), and leaf water content decrease (d) of the four classified groups during the drought stress period. Error bars indicate standard errors. *, ** shows significantly different means among the three groups at certain weeks at P≦0.05 and 0.01 respectively.
Figure 17:
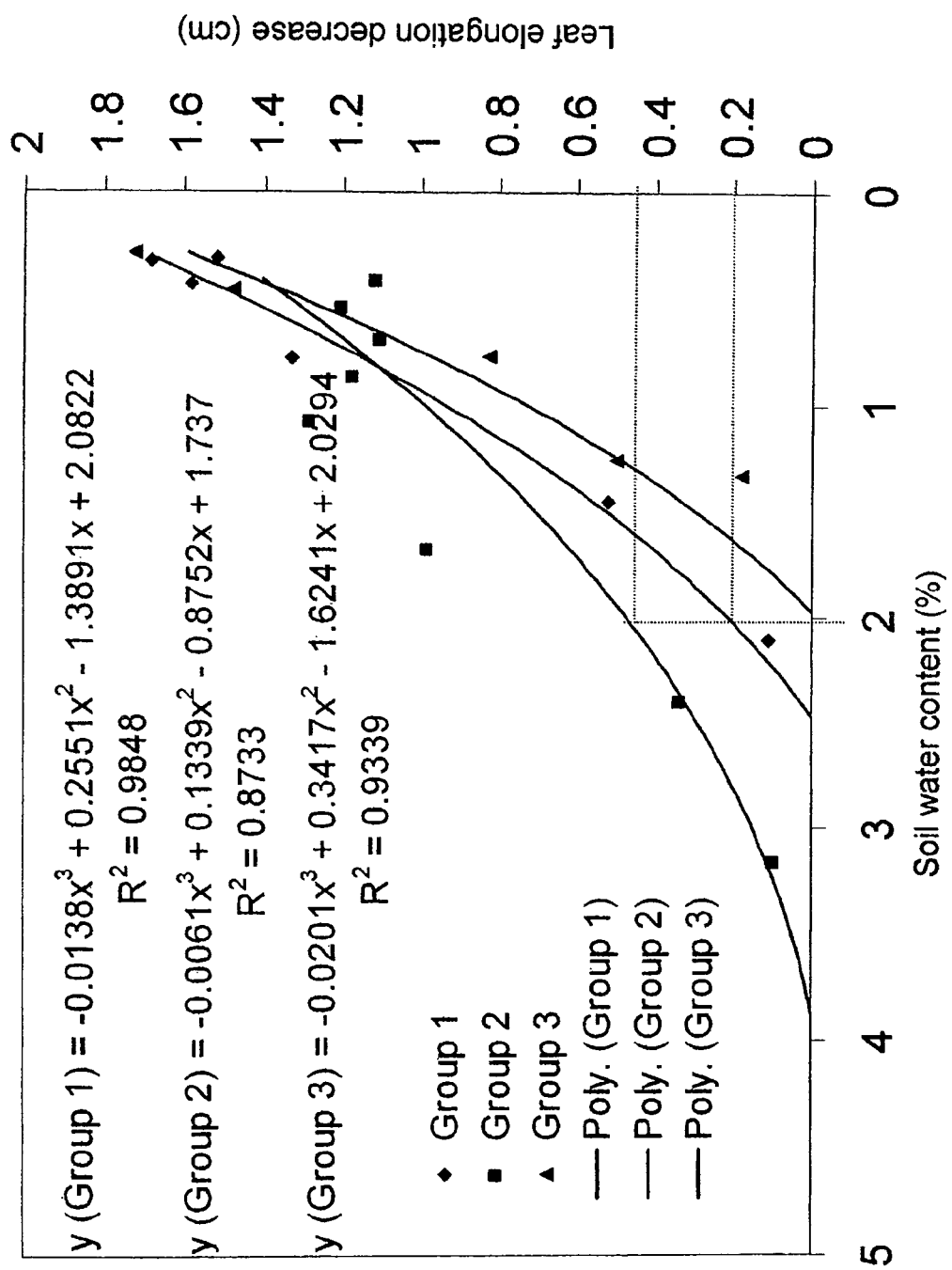
FIG. 17 shows an exemplary relationship between leaf elongation decrease and soil water content.
Figure 18:
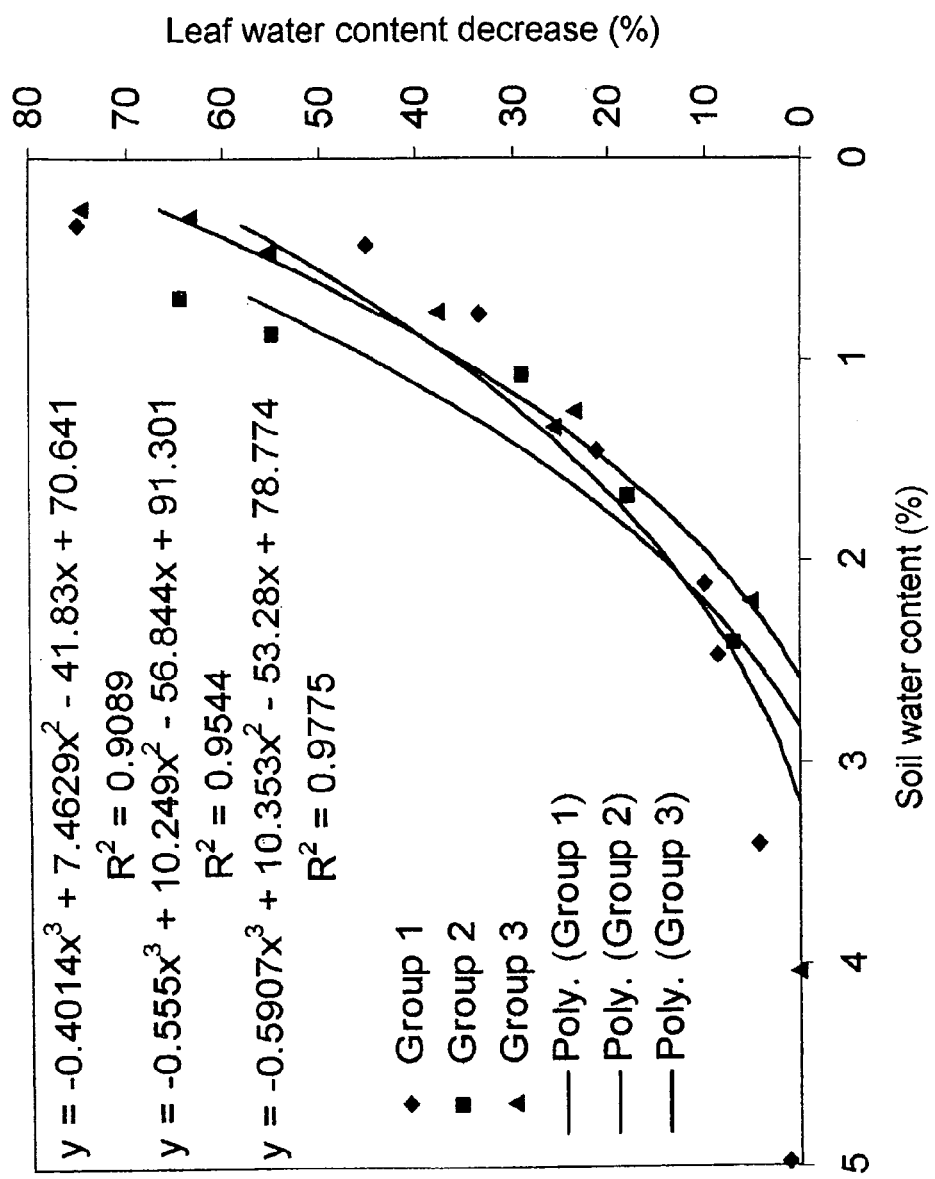
FIG. 18 shows an exemplary relationship between leaf water content decrease and soil water content.
Figure 19:
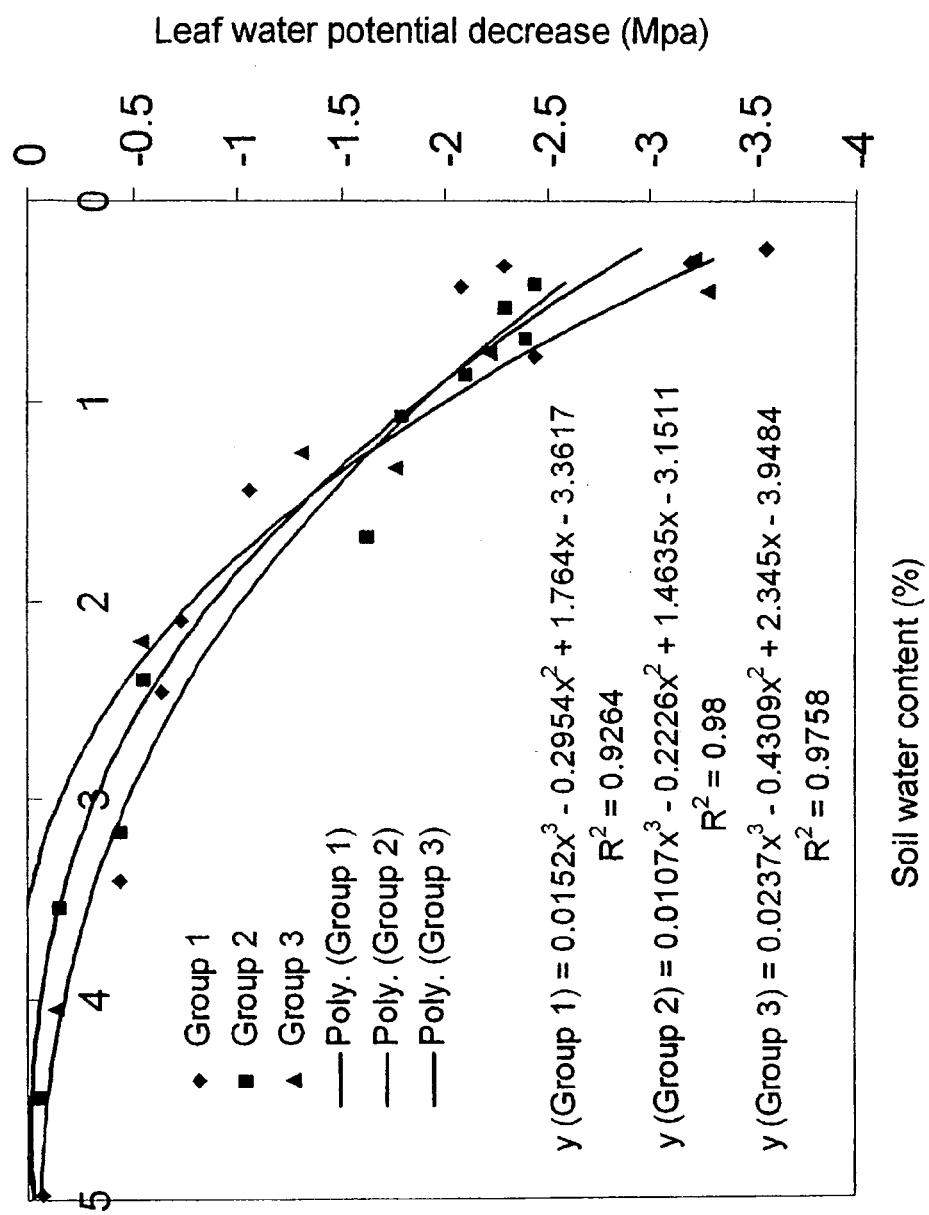
FIG. 19 shows an exemplary relationship between leaf water potential decrease and soil water content.

Morphological-Physiological Responses:

The soil water content of three groups declined steadily during the 14-wk drought stress treatment (FIG. 16), but the effect of drought duration, differed (P<0.05) among groups for weeks 5 to 13 as the soil dried faster for Group 3 than for Group 2 with Group 1 being intermediate to the others. Leaf water content decrease (FIGS. 16 and 18) tended to be inversely related to soil water content during the treatment indicating the drought responses of the three groups varied with drought treatment duration and was reflected similarly by both soil and leaf water content. Even though a difference among the three groups was noted in both soil and leaf water content there was no significant difference among leaf elongation rates (FIGS. 16 and 17). Leaf water potential, among the three groups responded to the drought treatment similarly except in weeks 6, 8, and 9 (FIGS. 16 and 19). Thus data were evaluated at common soil water contents for group comparisons.

The regression analyses showed that the leaf elongation of Group 2 decreased below the controls when the soil water content was reduced to 3.8%, while leaf elongation of Groups 1 and 3 decreased until soil water content decrease to 2.5 and 1.98%, respectively (FIG. 17). At the soil water content of 2%, the leaf elongation of Group 3 had not begun to decrease, while Group 1 was decreased about 0.21 cm/d and Group 2 decreased 0.44 cm/d. These results suggest that genotypes in Group 2 were more sensitive to drought stress in terms of leaf elongation, while Group 3 had the most drought tolerance and Group 1 had moderate drought tolerance. Leaf water potential showed no major differences among the three groups as the soil water content declined (FIG. 19).

Group 4 was represented by only one genotype (G24). Leaf water potential and especially leaf water content of Group 4, compared with the other three groups, showed that G24 responded to the 14-wk drought stress treatment in an aberrant way (FIG. 16). This line was dropped from the majority of studies.

Soil Water Content Estimates of Water Depletion Rate:

Monitoring of the soil water content revealed a different water depletion rate among the three groups (FIG. 16). Group 2 showed the lowest water depletion rate suggesting that the genotypes in Group 2 consumed water slower, which was probably due to a shallow root system and small plant size as they were observed. Regardless of relative drought tolerance, the water content and water potential may decline more rapidly for larger versus smaller genotypes (Cregg, 2004, In: Fernandes et al., (ed.) Pro Celsius. XXVI IHC-Nursery Crops, Can. Int. Dev. Agency; herein incorporated by reference). Thus, interpretations were based on common levels of soil water that were highly correlated with leaf water content. Unexpected Finding of Higher Tolerance to Drought in Hybrid Plants:

Genetic differences in water use might affect the rate of stress development, which can be reduced by growing the plants together (Thomas, 1987, J. Exp. Bot. 38:115-125; herein incorporated by reference) for an accessibility to the same soil volume and soil water to control the uniformity of water stress development (White et al., 1992, Crop Sci. 32: 25 1-256; herein incorporated by reference). Leaf elongation, as a sensitive parameter, was compared among the three groups at the same soil water content (FIG. 17) and was an indicator of the order of drought tolerance, Group 3>Group 1>Group 2. However, no significant differences were found in leaf water potential and leaf water content among the three groups. These results implied that the three groups exhibited similarly in terms of leaf water content and leaf water potential as the stress condition was becoming severe, suggesting (1) the other two parameters were not sensitive enough to significantly discriminate groups, or most likely (2) the three groups applied a similar mechanism related to leaf water status to respond to the drought stress treatment. Using leaf elongation measurements Genotypes in Group 3 showed better drought tolerance than Atlas fescue, the drought tolerant parent, which was in Group 1. These results supported the discovery that Group 3 plants showed hybrid superiority.

Root System Development:

Drought stress significantly reduced the root biomass (FIG. 20) especially in Group 2, the drought sensitive group, by 51%, and only 36% for drought tolerant Group 3. Reduction of root biomass may be associated with root death and desiccation. Even though the physiological factors influencing root death under drought stress are not yet understood, considerable root death from drought stress was reported in various plant species (Smucker et al., 1991, Ecol. 1:1-5; Stasovski and Peterson, 1991, Can. J. Bot. 69:1170-1178; Huang and Nobel, 1992, J. Exp. Bot. 43:1441-1449; all of which are herein incorporated by reference. Some species exhibit more tolerance to drought with little root death (Kosola and Eissenstat, 1994, I Exp. Bot. 45:1639-1645; herein incorporated by reference). In this study, a lesser amount of reduced root biomass in Group 3 further indicated that the genotypes in Group 3 had better drought tolerance. Noticeably, even though root length of Group 2 was enhanced, root biomass was significantly reduced by drought. The results suggested that the Group 2 root system responded to drought by producing a secondary thinner root with less biomass, and may be subject to severe root death and loss of the stronger primary root.

Figure 20A:
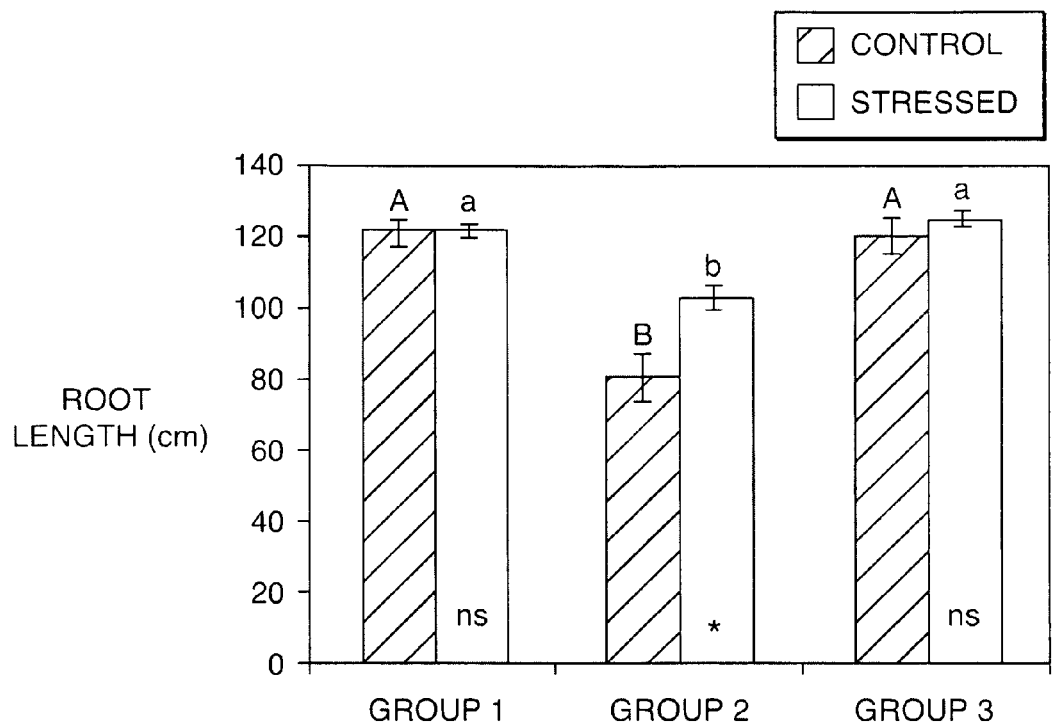
FIG. 20 shows an exemplary comparison of root length (a) and biomass (b) between control (hydrated) and drought-stressed (water deprived) plants. Bars indicate standard errors. Data for group with the same letter (capitalized letter for comparison among the groups in control plants and small letter for comparison among groups in stressed plants) are no significant differences among groups at P≦0.05. ns, * and ** indicate no significant, significantly different means between control and stressed plants within group at P≦0.05 and ≦0.01, respectively.
Figure 20B:
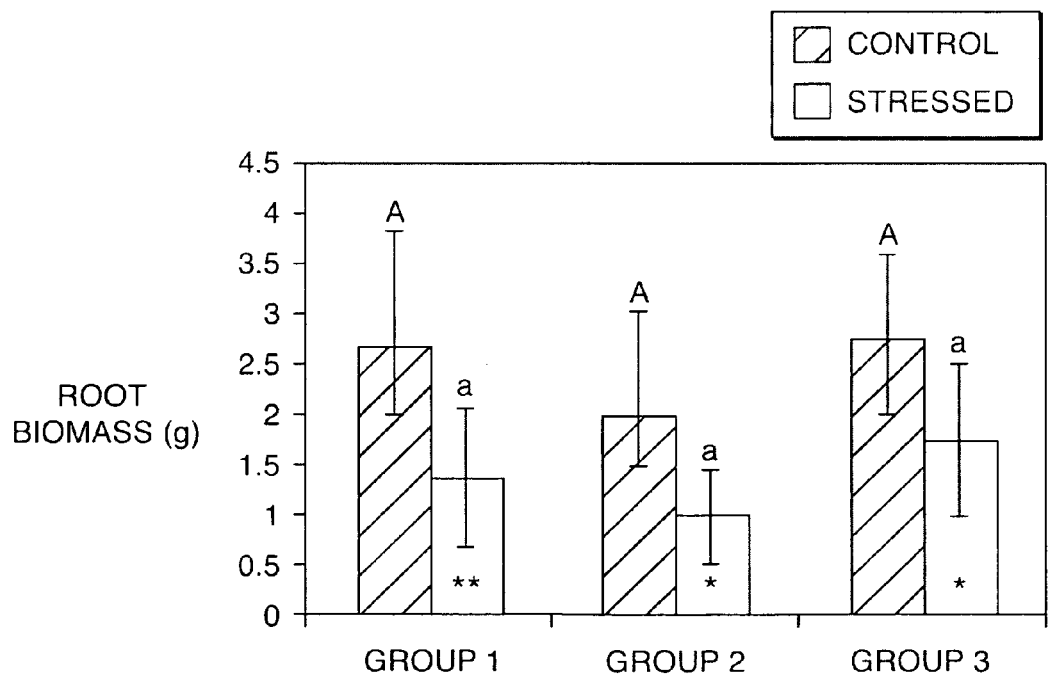

Large root systems help increase water uptake and can increase water-use efficiency. Both the irrigated and non-irrigated plants in Groups 1 and 3 had a significantly longer root system (around 120 cm for both irrigated and non-irrigated plants) than Group 2 (around 82 cm for irrigated and 102 cm for non-irrigated plants) (FIG. 20). Root length responded differently to drought. When comparing the non-irrigated to the irrigated plants in each group, minimal change in root length was noted in Groups 1 and 3. However, in Group 2 the root length of stressed plants was significantly increased by 24%. Measurements of root biomass were more variable, yet stressed plants of each group had less root mass (P<0.05) for all groups (FIG. 20). The drought treatment decreased root biomass by 48% for Group 1, 51% for Group 2, and 36% for Group 3. When stressed, plants maintain or actually increase root growth in length, but have thinner root with less biomass. This response was most noticeable in Group 2.

The longer root system in Groups 1 and 3 (FIG. 20) suggested these genotypes in Groups 1 and 3 are more capable to extract available water, therefore are more tolerant to drought stress than Group 2. In Group 2, the root of non-irrigated plants was significantly longer than the irrigated plant, indicating that the smaller root system of genotypes in Group 2 was triggered for a secondary growth by drought stress. The root re-growth during drought stress implied that the genotypes in Group 2 applied root phenotypic adaptation to avoid drought stress. Enhanced root growth during drought stress has been considered as an important adaptation mechanism to improve efficiency of plant water uptake (Gallardo et al., 1996, Plant Cell Environ. 19:1169-1178; herein incorporated by reference). A reduction of root growth caused merely by soil drying also results in low water uptake rates (Huang and Gao, 2000, Crop Sci. 40:196-203; herein incorporated by reference).

Root growth of genotypes of Groups 1 and 3 (FIG. 20) was not enhanced. This might be due to a long root system that has occupied much of the volume in the pot (100 cm high PVC tube). Kentucky 31 a moderate drought tolerant plant and identified as a good drought resistant cultivar (Huang and Gao, 1999, HortSci. 34:897-901; herein incorporated by reference) was found to have a Group 1 level of drought tolerance. IN a previous study, soil drying increased root length of Kentucky 31 by 10% in the deep soil layer (Huang and Gao, 2000, Crop Sci. 40:196-203; herein incorporated by reference). The study of Huang and Gao (1999, 2000, supra) suggested that Kentucky 31 showed a great potential for enhanced growth during drought stress. Therefore, Groups 1 and 3 in this study might also have potential to increase root length during drought, which may have been limited by little available space for secondary growth in the small one meter PVC tube.

Principle component analysis (PCA) involved a mathematical procedure that transformed a set of correlated response variables into a smaller set of uncorrelated variables (for example, Johnson 1998, In: Applied multivariate methods for data analysts. Brooks/Cole Publishing Co. Pacific Grove, Calif.; herein incorporated by reference). PCA analysis of the data obtained during the course of the development of the present inventions showed that a large portion of the response to drought provided variables that were correlated or duplicated up to a certain point, while some of the variables stood by themselves and had a greater weight to evaluate the drought response of the genotypes. Of three parameters measured, leaf elongation was more typical of drought responses, because seven variables (during weeks 3 to 9) out of the 14 variables (during weeks 1 to 14) were relatively independent from each other (see, for example, FIG. 11). Whereas, for leaf water content, four (weeks 1, 2, 3, and 12) of 12 variables were independent and for leaf water potential, three (weeks 1, 2, and 3) of 14 variables were independent of each other. Leaf elongation is mainly caused by turgor pressure of enlarging cells (Matyssek et al., 1988, Plant Physio. 86:1163-1167; herein incorporated by reference). Cell expansion, which directly contributes to the leaf elongation, was reported as the most sensitive trait (Boyer, 1988, Physiol. Plant. 73:311-316; herein incorporated by reference) and is reduced by drought before any other physiological process (Wardlaw, 1969, Aust. J. Biol. Sci. 22:1-16; herein incorporated by reference). Additionally, results of this study confirmed the value of using leaf elongation as a parameter for drought tolerance evaluation in methods for identifying plant for breeding programs described herein. Due to its sensitivity and high variability, thus allowing greater distinctions and thus comparisons between plants for drought resistance.

In summary, drought stress reduced leaf elongation, leaf water content, and leaf water potential. Leaf elongation was a sensitive and typical parameter for screening drought tolerant plants during drought stress. The drought tolerance of Atlas fescue was inherited in the progeny derived from intergeneric hybridization between ryegrass and Atlas fescue. Some progeny groups expressed higher levels of drought tolerance than groups comprising comparable levels of drought tolerance of the parental Atlas fescue plants.

Example VI

The Use of Molecular Markers, Primers, and Linkers for Identifying Plants for Use in Breeding Programs. This Example is Provided to Demonstrate the Capability of SSR and RAPD Markers to Identify Fm Germplasm within Lp Hybrid Plants RAPD and SSR markers, primers, and linkers were used to overcome the problems in identifying specific genomic segments that are found when using methods comprising fluorescence in situ hybridization (FISH), which utilizes chromosome-specific DNA probes and genomic in situ hybridization (GISH). Further, restriction fragment length polymorphism (RFLP) based markers do not detect alien DNA in a hybrid when a small portion of a chromosome or a few chromosomes are transferred (Chen and Sleper, 1999, Crop Science 39:1676-1679; herein incorporated by reference).

A. The Use of *Festuca* EST-SSR Markers for Identifying Fm Germplasm in Plants for Use in Plant Breeding Methods of the Present Inventions.

Simple sequence repeats (SSR) or microsatellite markers developed from Fescue and *Lolium perenne* L. and random amplified polymorphic DNA (RAPD) markers of Fescue were used to assess genomic introgression of *Festuca mairei* St. Yves (Fm) into *L. perenne* (Lp) as briefly described in EXAMPLE I and below.

Seventy-six tall fescue EST-SSR primer pairs, including but not limited to NFFA005; NFFA007; NFFA012; NFFA013; NFFA015; NFFA017; NFFA019; NFFA021; NFFA022; NFFA024; NFFA029; NFFA031; NFFA032; NFFA033; NFFA034; NFFA036; NFFA037; NFFA039; NFFA041; NFFA047; NFFA048; NFFA050; NFFA052; NFFA057; NFFA059; NFFA061; NFFA062; NFFA066; NFFA068; NFFA069; NFFA071; NFFA072; NFFA073; NFFA074; NFFA075; NFFA076; NFFA077; NFFA084; NFFA087; NFFA090; NFFA091; NFFA092; NFFA094; NFFA095; NFFA096; NFFA098; NFFA100; NFFA103; NFFA108; NFFA109; NFFA113; NFFA114; NFFA120; NFFA123; NFFA125; NFFA126; NFFA129; NFFA131; NFFA132; NFFA135; NFFA13; NFFA140; NFFA142; NFFA143; NFFA146; NFFA147; NFFA149; NFFA150; NFFA151; NFFA155; and NFFA157; and 32 Lp SSR primer pairs developed from ryegrass were first tested on the Fm and Lp parents. Preliminary screening showed that eight out of 32 ryegrass primer pairs and 27 of 76 tall fescue EST-SSR primer pairs demonstrated polymorphic bands (used as markers) between parental plants.

Specifically, amplification of ryegrass genomic SSRs and tall fescue EST-SSRs in a preliminary screening panel showed 127 polymorphic bands scored from the 3.5 SSR primer pairs. The primer combinations that produced polymorphic bands between parents were then utilized to test plant materials. The 127 bands segregated among the Fm-Lp progeny. More than half of the alleles of both parents (Fm1 and Lp 1/Lp2) were combined in the 4×$F_1$ hybrid (Fm1×Lp2) and the amphiploid derived from a 3×$F_1$ (Fm 1×Lp1) crosses, indicating successful wide crosses. In backcross plants, different levels of alleles of both Fm and Lp parents were present in each individual plant which demonstrated segregation of alleles from both parents during backcrossing. Among the 127 bands, 23 (18%) were present in the Fm-Lp progeny but not in the three parents (Fm1, Lp1, and Lp2). A relative higher Fm1/Lp genome ratio showed that more Fm genome was introgressed into the progeny than Lp. Progeny that showed an Fm/Lp genome ratios above zero indicated that the Fm genome was successfully introgressed into those individuals. However, the ratios varied widely from 0.09(014) to 1.95 (Fm1×Lp2) indicating that the Fm genome had been retained in these progeny at various extents.

Therefore, 27 EST-SSR primers pairs and 8 Lp SSR primers demonstrated usefulness in analyzing progeny plants for introgression of Fm germplasm.

B. The Use of RAPD Markers for Identifying Fm Germplasm in Plants for Use in Plant Breeding Methods of the Present Inventions (See, Wang et al., (2003) Crop Sci. 43:2154-2161; Herein Incorporated by Reference in its Entirety).

Forty-one RAPD primers were chosen to detect genome introgression of the backcross progeny. A total of 188 parent-specific markers were obtained. Ninety-two (49%) were Fm-specific markers. The 13 backcross progenies showed a range of introgression of Fm-specific markers (5.4-60.9%).

Two-hundred and twenty two polymorphic bands were generated from 41 RAPD primers. The number of polymorphic bands scored for each primer ranged from 1 to 11. Distribution of the 222 RAPD bands among the parents was similar to that of the SSR markers. Thirty-six bands (15.7%) were present in the progeny but not in the three parents indicating the contribution of the Fm2 genome. Ninety-six (41.9%) were Fm-specific and 87 (38.0%) were Lp-specific bands including the Lp 1- and Lp2-specific bands and the bands common to both parents. Similar to the SSR results, a higher number of common bands between Lp1 and Lp2 (41, 17.9%) suggested a relatively close relationship between Lp1 and Lp2, and a lower number of common bands between Fm and Lp (Lp1, 4.5%; Lp2, 3.0%) suggested a distant relationship between Fm and Lp.

RAPD results were consistent with SSR results as both parent-specific bands were inherited in the $F_1$ hybrids and amphiploid, and various ratios of segregation occurred in backcross progeny. Fm1 Lp genome ratios of these Fm-Lp progeny ranged from 0.08 (G11a) to 1.79 (Fm1×Lp2). This result confirmed that all progeny retained the Fm genome at different levels. The correlation coefficient (r=0.80) of the Fm/Lp genome ratios assessed by SSR and RAPD markers was highly significant (P 0.0004), which reflected upon the reliability of the two marker systems in assessing genome introgression.

TABLE 7

The sequence of 41 RAPD primers and the number of fragments amplified (see, Wang et al., (2003) Crop Sci. 43:2154-2161; herein incorporated by reference in its entirety).

| Primer | SEQ ID NO:XX | Sequence; 5'- 3' | Number of polymorphic fragments scored |
|---|---|---|---|
| OPA-04 | 266 | AATCGGGCTG | 7 |
| OPA-05 | 267 | AGGGGTCTTG | 4 |
| OPA-07 | 268 | GAAACGGGTG | 6 |
| OPA-08 | 269 | GTGACGTAGG | 6 |
| OPA-20 | 270 | GTTGCGATCC | 4 |
| OPB-12 | 271 | CCTTGACGCA | 9 |
| OPC-01 | 272 | TTCGAGCCAG | 9 |
| OPC-02 | 273 | GTGAGGCGTC | 5 |
| OPC-04 | 274 | CCGCATCTAC | 2 |

TABLE 7-continued

The sequence of 41 RAPD primers and the number of fragments amplified (see, Wang et al., (2003) Crop Sci. 43:2154-2161; herein incorporated by reference in its entirety).

| Primer | SEQ ID NO:XX | Sequence; 5'- 3' | Number of polymorphic fragments scored |
|---|---|---|---|
| OPC-05 | 275 | GATGACCGCC | 11 |
| OPC-06 | 276 | GAACGGACTC | 3 |
| OPC-07 | 277 | GTCCCGACGA | 5 |
| OPC-08 | 278 | TGGACCGGTG | 11 |
| OPC-09 | 279 | CTCACCGTCC | 9 |
| OPC-10 | 280 | TGTCTGGGTG | 5 |
| OPC-11 | 281 | AAAGCTGCGG | 7 |
| OPC-13 | 282 | AAGCCTCGTC | 7 |
| OPC-15 | 283 | GACGGATCAG | 7 |
| OPC-16 | 284 | CACACTCCAG | 4 |
| OPC-19 | 285 | GTTGCCAGCC | 3 |
| OPC-20 | 286 | ACTTCGCCAC | 6 |
| OPE-09 | 287 | CTTCACCCGA | 4 |
| OPY-01 | 288 | GTGGCATCTC | 2 |
| OPY-02 | 289 | CATCGCCGCA | 10 |
| OPY-03 | 290 | ACAGCCTGCT | 6 |
| OPY-05 | 291 | GGCTGCGACA | 7 |
| OPY-06 | 292 | AAGGCTCACC | 5 |
| OPY-07 | 293 | AGAGCCGTCA | 4 |
| OPY-09 | 294 | AGCAGCGCAC | 1 |
| OPY-10 | 295 | CAAACGTGGG | 4 |
| OPY-13 | 296 | GGGTCTCGGT | 1 |
| OPY-14 | 297 | GGTCGATCTG | 5 |
| OPY-15 | 298 | AGTCGCCCTT | 3 |
| OPY-16 | 299 | GGGCCAATGT | 4 |
| OPY-17 | 300 | GACGTGGTGA | 6 |
| OPY-18 | 301 | GTGGAGTCAG | 2 |
| OPY-19 | 302 | TGAGGGTCCC | 5 |
| OPY-20 | 303 | AGCCGTGGAA | 5 |
| OPX-01 | 304 | CTGGGCACGA | 11 |
| OPX-06 | 305 | ACGCCAGAGG | 4 |
| OPX-13 | 306 | ACGGGAGCAA | 3 |
| Total | | | 222 |

RAPD results demonstrated that RAPD could be equally effective and informative in monitoring the introgression of alien DNA fragments, as compared to SSR markers. Random amplified polymorphic DNA markers are also efficient in detecting genome introgression because of its small tissue sample requirements, rapid analysis, low cost, no previous knowledge of DNA sequence requirement, and easy establishment. The potential for genome labeling and chromosome tagging are contemplated for further increases in sensitivity of detecting specific regions of DNA by converting RAPD markers into sequence characterized amplified regions (SCARs) (Paran and Michelmore, 1992, Theor. Appl. Genet. 8 5 985-993; herein incorporated by reference in its entirety).

C. The Use of Lp SSR Markers for Identifying Fm Germplasm in Plants for Use in Plant Breeding Methods of the Present Inventions (See, Wang et al., (2003) Crop Sci. 43:2154-2161; Herein Incorporated by Reference in its Entirety).

Additionally, mapping Lp SSR markers in hybrid plants is provided for use in methods for determining meiotic stability in plants comprising Fm germplasm. Forty Lp SSR primer pairs were used to detect polymorphism between the Lp and Fm parents. Of these, 19 primer pairs failed to produce a detectable amplification product. Three primer pairs did not show distinguishable differences between species with this method due to showing similarly sized amplified products. Four SSR primers showed shared alleles between the parents thus Fm was not fully distinguishable from Lp. Amplification of the same size bands in both Fm and Lp parents indicated a close relationship or certain homology between these two genomes. One marker was unscorable in this test.

The remaining 13 markers covering seven linkage groups (Table 8) fully discriminated Fm and Lp by amplifying completely different sizes of SSR products from the parents. nine markers detected that the Fm genome had introgressed in at least one place of the genomes of the backcross individuals, because each of the nine markers amplified the Fm-specific alleles in one or more back-cross individuals. Out of the 13 backcross individuals analyzed, 11 showed that the Fm genome fragments were introduced and that the introgression levels ranged from 0 to 66.7%. This demonstration showed significant DNA structural differentiation in the genomes of the two species on the basis of these Lp SSR markers. The 13 SSR markers were then used to test for Fm genome introgression in additional progeny plant lines derived from hybridization between Fm and Lp.

During the development of the present inventions, the Lp SSR markers tested for a particular linkage group did not completely detect simultaneous genome introgression into the individual progeny. For example, at linkage group 7, three SSR primer pairs (LPSSRK15F05, LPSSRK11E11, and LPSSK14F07) (Table 8) were used to identify Fm germplasm, however only one primer (LPSSRK11E11) revealed the Fm fragment in G8. Two primers (LPSSRK11E11 and LPSSRK14F07) showed a Fm allele in G15, but not all of the three markers detected Fm alleles in G8 and G15. Such introgression suggested that the mechanism of alien chromosome segments transmission is due to genetic recombination through crossover rather than substitution of whole or large segments of chromatin from Fm. Otherwise, the SSR markers for the same linkage group should have detected the Fm genome introgression in the same individual at the same time.

During the development of the present inventions, it was discovered that the introgression levels detected by Lp SSR and RAPD markers were significantly correlated. In particular, the introgression levels of the backcross progeny revealed by Lp SSR and RAPD markers were significantly correlated at $P \leq 0.0116$.

TABLE 8

Lp SSR markers that revealed F. mairei genome introgression into the backcross progeny (see, Wang et al., (2003) Crop Sci. 43: 2154-2161; herein incorporated by reference in its entirety).

| SSR markers (see, Jones et al., 2001, Theoretical And Applied Genetics 102 (2-3): 405-415). | Lp linkage group | Expected alleles in $F_1$ | Progeny with Fm alleles |
|---|---|---|---|
| LPSSRK03G05 | 3 | | G27a, G30b |
| LPSSRK10B07 | 6 | none | none |
| LPSSRK15F05 | 7 | | G27a, G27b |
| LPSSRK12E06 | 2 | | none |
| LPSSRK10F08 | 1 | | G8, G11b, G15, G24, G26, G27a, G27b, G30a, G30b |
| LPSSRH10G02 | 5 | | G15 |
| LPSSRK08A09 | 3 | | G11b, G15, G24, G27b, G30a |
| LPSSRH02H05 | 6 | none | none |
| LPSSRH03A08 | 2 | | none |
| LPSSRK02D08 | 4 | | G14, G16, G24, G26, G27a |
| LPSSRK11E11 | 7 | | G8, G11b, G15, G24, G30a, G30b |
| LPSSRK14F07 | 7 | | G11b, G15, G27a, G27b |
| LPSSRH02D10 | 2 and 6 (two loci) | | G11b, G15, G24, G27a, G27b, G30a, G30b |

The ability of molecular markers to discriminate between *Lolium* and *Festuca* DNA in hybrids and backcross progeny enables introgression maps to be created when these markers were localized on a linkage map. By combining the genetic mapping approach and physiological complex trait dissection, it should be possible to identify and localize the importance of trait components that contribute to drought tolerance (Humphreys et al, 1997, New Phytol. 137:55-60; Humphreys et al., 2005, Theor. Appl. Genet. 110:579-597; herein incorporated by reference). Markers associated with trait components are contemplated for application to assist in drought tolerant progeny selection and speed up the breeding process. During the development of the present inventions, a number of Fm-Lp progeny successfully combined both genomes from Fm and Lp and some of those progeny showed desirable agronomic traits during initial greenhouse evaluation. The results described herein demonstrate that Fm-Lp progeny plants of the present invention are useful for new grass plant cultivar release, plant breeding methods, and for the development of marker(s) associated with drought tolerance.

D. Combining Lp SSR and RAPD Results for Evaluating Grass Plant Progeny and Application of Fm-Lp Ratios in Grass Plant Progeny for Use in Turfgrass Breeding.

Genome introgression levels of Fm and Lp determined by SSR and RAPD ratios (FIG. 11) were favorably consistent with morphological characteristics (FIGS. 14*b* and 15). These results demonstrated that the two molecular techniques were efficient in assessing alien genome introgression.

Specifically, backcross progeny plants tested using RAPD and SSR markers showed different introgression levels of Fm DNA fragments that were consistent with morphological characteristics. For example, in G27a, which resembled Fm with rigid, long leaves as compared to Lp with softer and shorter leaves, Fm DNA segments were introgressed at five SSR loci out of the nine loci tested. Fm genome introgression level was measured up to 66.7%. More than half of 92 RAPD markers (introgression level at 60.9%) revealed Fm chromatin introgressed in G27a. While in G11a, which resembled Lp with soft and short leaves, none of the Fm genome was introgressed at the nine SSR loci, and only five out of 92 RAPD markers (5.4% introgression level) showed introgression of Fm chromatin.

Fm-Lp Genome Recombination in the 4× $F_1$:

The partially fertile 4× $F_1$ hybrid was found to be useful in a backcross-breeding program to develop a diploid perennial ryegrass, which was then tested for inheritance of drought tolerance from Fm. Although 3× $F_1$ hybrid plants were sterile, fertility was largely restored through chromosome doubling and therefore has potential use in developing new cultivars.

With several generations of backcrossing and selection for meiotic stability and turf quality, several drought tolerant cultivars were developed. In particular, progeny G11a plants and G14 plant lines recovered the majority of the Lp genome within one generation of backcrossing to Lp. They were then tested for drought tolerance and meiotic stability to evaluate the potential for a new cultivar release. The drought resistance level of the line G14 grouped with the parental Atlas plants. The other backcross plants required additional generations of backcrossing to Lp to recover desired perennial ryegrass attributes.

An example of an application of SSR and RAPD analysis of chromosomal integration in hybrid plants is provided. In a 4× $F_1$ hybrid plant derived from Fm1×Lp1, 84.3 and 90.6% of Fm-specific SSR and RAPD bands were inherited, respectively. The inventor contemplated that at these loci, the genotype of Fm, as an autotetraploid, is Aaaa, AAaa, AA.Aa or AAAA while the Lp genotype is aa. As a result, the band ratios of $F_1$ are expected be 1:1 for Aaaa×aa, 5:1 for AAaa×aa, 1:0 for AAAa×aa and 1:0 AAAA×aa. When the four Fm genotypes among these loci showed the same ratio, then on average, the $F_1$ plant was estimated to comprise at least 83.2% Fm-specific bands.

The Chi-squared test ($X^2$) test was used to test the significance of consistency of observed Fm-specific bands presented in the 4× $F_1$ with the expected results. The analysis revealed that, for both SSR and RAPD data, the observations were consistent with the expectation (P=0.8 and P=0.05 for SSR and RAPD data, respectively). Fm was considered an autotetraploid or at least a partial allotetraploid because the genomes of $M_1$ and $M_2$ are closely related and readily paired in the $F_1$ hybrid plants of Fm×Lp (Chen et al. 1995, Crop Sci. 35:720-725; herein incorporated by reference).

The inventor's results supported the finding of autotetraploidy in Fm plants. The genome of the other founder parent, Lp1 was transferred into the 4× $F_1$ by 75% and 53% dominant alleles detected by SSR and RAPD, respectively. Lp1 was transferred to the $F_1$ through 2n pollen and the relatively high rate of dominant alleles transferred suggested that the 2n pollen were produced through first division restitution (FDR) (Chen et al. 1997, Crop Sci. 462 37:76-80; herein incorporated by reference).

Fm-Lp Genome Recombination in Progeny Plants.

Improvement of any plant depends on the ability to introgress the desirable genomes of source plants into cultivated varieties (Prakash et al., 2002 Euphytica 124:265-271; herein incorporated by reference). This strategy is largely facilitated by precise monitoring of alien and cultivated genome combinations at the molecular level. In backcross progeny detected in this study, dominant alleles from both Fm and Lp parents were present in each individual at various levels suggesting segregation of alleles of both parents during backcrossing. The results were in agreement with the finding that L chromosomes of Lp could pair with $M_1$ and $M_2$ chromosomes from Fm (Cao et al., 2000 Genome 43:398-403; herein incorporated by reference). The pairing of homologous chromosomes would cause segregation of alleles of both parents. Of the 27 polymorphic EST-SSR loci, 15 were mapped to ryegrass linkage groups (LGs) (Wanke et al., 2004 Theor. Appl. Genet. 109:294-304). Three groups of these marker loci were uniquely mapped on both male and female maps (NFFA031 and NFFA075 on LG 1; NFFA015, 036, and 048 on LG 6; NFFA019 and NFFA069 on LG 7).

To investigate the event of chromosome crossover between M and L genomes, the co-segregation of markers on each of the three LGs was assessed among the Fm-Lp hybrids and backcross individuals. The results indicated that the linked markers were not co-inherited into the hybrids or backcross individuals. The separation of the linked markers demonstrated the crossover of homologous chromosomes and genome recombination between M and L in the progeny from intergeneric hybridization. The mapped EST-SSR markers on ryegrass LGs showed a great applicable value in assessment of the homologous chromosome crossover and genome recombination in the intergeneric hybrid, which is usually tested by sophisticated cytogenetic studies. In addition, the map location of EST-SSRs derived from transcripts with known function would provide functional genetic markers for direct characterization of the QTLs for putatively correlated traits (Saha et al., 2005 Theor. Appl. Genet. 110:323-336; herein incorporated by reference).

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be within the scope of the following claims.

I claim:

1. A plant produced by growing the seed of a perennial ryegrass *Lolium perenne* L. variety selected from the group consisting of G11a deposited under ATCC Accession No. PTA-8920, G14 deposited under ATCC Accession No. PTA-8921, and G16 deposited under ATCC Accession No. PTA-8922.

2. A plant produced by growing the seed of a perennial ryegrass *Lolium perenne* L. variety selected from the group consisting of G11a deposited under ATCC Accession No. PTA-8920, G14 deposited under ATCC Accession No. PTA-8921, and G16 deposited under ATCC Accession No. PTA-8922, wherein said plant is capable of expressing all the physiological and morphological characteristics of said perennial ryegrass *Lolium perenne* L. plant variety selected from the group consisting of G11a, G14, and G16.

3. A plant produced by growing the seed of a perennial ryegrass *Lolium perenne* L. variety selected from the group consisting of G11a deposited under ATCC Accession No. PTA-8920, G14 deposited under ATCC Accession No. PTA-8921, and G16 deposited under ATCC Accession No. PTA-8922, wherein said plant is capable of expressing drought tolerance characteristics of said perennial ryegrass Lolium perenne L. plant variety selected from the group consisting of G11a, G14, and G16.

4. A plant part of the plant of claim 1.

5. The plant part of claim 4, wherein said plant part is selected from the group consisting of pollen, ovule, tissue, seed, cell, and germplasm.

6. A method of producing perennial ryegrass *Lolium perenne* L. seed, comprising: a) providing: i) a first plant of perennial ryegrass *Lolium perenne* L. variety, and ii) a second plant of perennial ryegrass *Lolium perenne* L. variety, wherein one or both of said first and second plants is the plant of claim 1, and b) crossing said first plant with said second plant to produce a progeny seed.

7. The method of claim 6, wherein said first plant is *Lolium perenne* L. variety G11a, and said second plant is selected from the group consisting of *Lolium perenne* L. variety G14 and variety G16.

8. The method of claim 6, wherein said first plant is *Lolium perenne* L. variety G14, and said second plant is selected from the group consisting of *Lolium perenne* L. variety G11a and variety G16.

9. The method of claim 6, wherein said first plant is *Lolium perenne* L. variety G16, and said second plant is selected from the group consisting of *Lolium perenne* L. variety G11a and variety G14.

10. The method of claim 6, wherein the produced seed is an $F_1$ hybrid perennial ryegrass *Lolium perenne* L. seed.

11. The method of claim 10, further comprising step c) growing said $F_1$ seeds into $F_1$ plants and step e) crossing $F_1$ plants for producing $F_2$ hybrid perennial ryegrass *Lolium perenne* L. seed.

12. A method of producing a perennial ryegrass *Lolium perenne* L. plant, comprising: a) providing: i) a first plant of claim 1, ii) a second perennial ryegrass *Lolium perenne* L. plant, and iii) a third perennial ryegrass *Lolium perenne* L. plant, b) crossing said first plant with said second plant to produce a first progeny plant, and c) crossing said first progeny plant with itself or with said third perennial ryegrass *Lolium perenne* L. plant to produce a second progeny plant.

13. The method of claim 12, further comprising step d) crossing said second progeny plant with itself or with a fourth perennial ryegrass *Lolium perenne* L. plant to produce a third progeny plant.

* * * * *